(12) United States Patent
Mitsuyama et al.

(10) Patent No.: US 9,072,734 B2
(45) Date of Patent: Jul. 7, 2015

(54) QUATERNARY AMMONIUM SALT COMPOUNDS

(75) Inventors: Etsuko Mitsuyama, Tokyo (JP); Takayuki Hara, Yamaguchi (JP); Junji Igarashi, Tokyo (JP); Hiroyuki Sugiyama, Tokyo (JP); Satoshi Yamamura, Tokyo (JP); Johji Nomura, Tokyo (JP); Kei Segawa, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 33 days.

(21) Appl. No.: 13/266,651

(22) PCT Filed: Apr. 27, 2010

(86) PCT No.: PCT/JP2010/057422
§ 371 (c)(1),
(2), (4) Date: Oct. 27, 2011

(87) PCT Pub. No.: WO2010/126025
PCT Pub. Date: Nov. 4, 2010

(65) Prior Publication Data
US 2012/0046467 A1     Feb. 23, 2012

(30) Foreign Application Priority Data

Apr. 30, 2009 (JP) ................................. 2009-110760

(51) Int. Cl.
| | |
|---|---|
| *A61K 31/445* | (2006.01) |
| *C07D 215/16* | (2006.01) |
| *A61K 31/4709* | (2006.01) |
| *C07D 401/12* | (2006.01) |
| *C07D 413/12* | (2006.01) |
| *C07D 417/12* | (2006.01) |
| *C07D 491/18* | (2006.01) |

(52) U.S. Cl.
CPC .......... *A61K 31/4709* (2013.01); *C07D 215/16* (2013.01); *C07D 401/12* (2013.01); *C07D 413/12* (2013.01); *C07D 417/12* (2013.01); *C07D 491/18* (2013.01)

(58) Field of Classification Search
CPC .. C07D 215/16; C07D 401/12; C07D 413/12; C07D 417/12; C07D 491/18
USPC ........... 514/312, 317; 546/224, 204, 213, 153
See application file for complete search history.

(56) References Cited

U.S. PATENT DOCUMENTS

| | | | | |
|---|---|---|---|---|
| 3,240,784 | A | * 3/1966 | Flick et al. | .............. 546/239 |
| 7,141,671 | B2 | * 11/2006 | Mammen et al. | ............ 546/224 |
| 7,705,026 | B2 | * 4/2010 | Zhou et al. | .................. 514/376 |
| 7,947,730 | B2 | * 5/2011 | Collingwood et al. | ....... 514/422 |
| 2004/0209915 | A1 | 10/2004 | Mammen et al. | |
| 2006/0178410 | A1 | 8/2006 | Moran et al. | |
| 2007/0276003 | A1 | 11/2007 | Mammen et al. | |
| 2008/0249127 | A1 | 10/2008 | Laine et al. | |

FOREIGN PATENT DOCUMENTS

| | | |
|---|---|---|
| CN | 1929844 A | 3/2007 |
| JP | 2005-509024 A | 4/2005 |
| JP | 2006-517971 A | 8/2006 |
| JP | 2007-518740 A | 7/2007 |
| TW | 200424173 | 11/2004 |
| TW | I249515 | 2/2006 |
| WO | WO 2004/007426 A1 | 1/2004 |
| WO | WO 2004/089892 A2 | 10/2004 |
| WO | WO 2004/096127 A2 | 11/2004 |
| WO | WO 2004/106333 A1 | 12/2004 |
| WO | WO 2007/107828 A2 | 9/2007 |
| WO | WO 2009/098448 A1 | 8/2009 |

OTHER PUBLICATIONS

Barlow et al. "The contribution . . . " Br. J. Pharmacol. 106, 819-822 (1992).*
Cocaine, Wikipedia p. 1-34 (2013).*
Improper Markush, Fed. Reg. 76(27) 7162-7175, training slices p. 1, 64-67 (2011).*
Mamme et al. "Preparation of biphenyl . . ." CA141:703125 (2004).*
Ray et al. "Muscarinic antagonist . . . " Exp. Opin. Ther. Patents 19(1)1-12(2009).*
Scopolamine Wikepedia p. 1-2 (2013).*
Small Molecules "Thervavance . . . " p. 1-3 (2008).*
Mammen et al. "Preparation of biphenyll . . . " CA141:225161 (2004).*

(Continued)

*Primary Examiner* — Celia Chang
(74) *Attorney, Agent, or Firm* — Sughrue Mion, PLLC

(57) ABSTRACT

[Problem]
The object of the present invention is to provide a novel compound having β2 adrenergic receptor agonist activity and muscarinic receptor antagonist activity.
[Means for Solving the Problem]
The present invention is a quaternary ammonium salt compounds represented by formula (I), or a pharmaceutically acceptable salt thereof, with superior β2 adrenergic receptor agonist activity and muscarinic receptor antagonist activity.

[Chemical Formula 1]

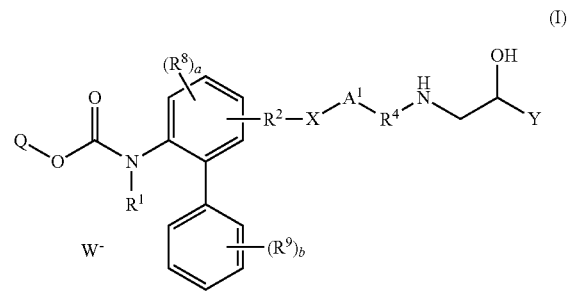

11 Claims, No Drawings

(56) References Cited

OTHER PUBLICATIONS

Mitsuyama et al. "Preparation of quaternary . . . " CA153:600759 (2010).*

International Search Report for PCT/JP2010/057422 dated May 25, 2010.

Japanese Office Action issued on Jun. 11, 2013 in Japanese Application No. 2011-511402.

Office Action dated Jan. 20, 2014 from the Taiwanese Patent Office in Taiwanese Application No. 099113895.

* cited by examiner

QUATERNARY AMMONIUM SALT COMPOUNDS

CROSS REFERENCE TO RELATED APPLICATIONS

This application is a National Stage of International Application No. PCT/JP2010/057422, filed on Apr. 27, 2010, which claims priority from Japanese Patent Application No. 2009-110760, filed Apr. 30, 2009, the contents of all of which are incorporated herein by reference in their entirety.

TECHNICAL FIELD

The present invention relates to novel compounds having β2 adrenergic receptor agonist activity and muscarinic receptor antagonist activity. The present invention also relates to pharmaceutical compositions comprising such compounds, processes and intermediates for preparing such compounds, and methods of using such compounds to treat pulmonary diseases.

BACKGROUND ART

Medical treatment for chronic pulmonary diseases, such as asthma and chronic obstructive pulmonary disease (COPD), commonly involves the use of bronchodilators. Bronchodilators in widespread use are β2 adrenergic receptor (adrenoceptor) agonists, such as albuterol, formoterol and salmeterol, and muscarinic receptor antagonists (anticholinergic compounds), such as ipratropium and tiotropium. These compounds are typically administered by inhalation.

It has been known in the art that, for the purpose of treating chronic pulmonary diseases, particularly COPD, administering a β2 adrenergic receptor agonist and a muscarinic receptor antagonist in combination is more effective as compared to administering each drug alone. However, since bronchodilators are used as inhalants in many cases, dosing becomes complicated or difficult when two drugs are desired to be administered and they are respectively dispensed in two inhalation devices to be administered. In addition, when two drugs are dispensed in one inhalation device, the desired formulation may differ and the chemical or physical action between the drugs may make it difficult to maintain a stable combination of the drugs.

On the other hand, compounds having both β2 adrenergic receptor agonist activity and muscarinic receptor antagonist activity produce bronchodilator effects through two distinct modes of action, although they are single molecules. Such disadvantages can be overcome by providing a drug of a single molecule having two actions. Furthermore, since such a single molecule is easier to co-formulate with another therapeutic agent to create a triple therapy combination, it would be beneficial to a patient being treated. Pharmacologically, in pulmonary tissue to which the drug is administered, the two actions are based on single molecule pharmacokinetics, so that these two actions can be synchronically exhibited. Moreover, side effects can be reduced by selecting a structural design which confers pharmacokinetic properties that cannot be achieved by combined use of two drugs or by a mixture of them. Such compounds, which are single molecules having two actions, have been reported, for example, in Patent Documents 1 to 6 and the like. However, these compounds clearly differ in structure from the compounds disclosed in the present invention.

PRIOR ART DOCUMENT

Patent Document

[Patent Document 1] International Publication No. WO/2004/007426
[Patent Document 2] International Publication No. WO/2004/089892
[Patent Document 3] International Publication No. WO/2004/106333
[Patent Document 4] International Publication No. WO/2008/096127
[Patent Document 5] International Publication No. WO/2007/107828
[Patent Document 6] International Publication No. WO/2009/098448

SUMMARY OF INVENTION

Problem to be Solved by the Invention

An object of the present invention is to provide quaternary ammonium salt compounds having both β2 adrenergic receptor agonist activity and muscarinic receptor antagonist activity.

Means for Solving the Problem

As a result of diligent studies for achieving the above object, the present inventors have found novel quaternary ammonium salt compounds having both β2 adrenergic receptor agonist activity and muscarinic receptor antagonist activity and arrived at the present invention.

That is, the present invention is as follows.

(1) A quaternary ammonium salt compound represented by general formula (I):

[Chemical Formula 1]

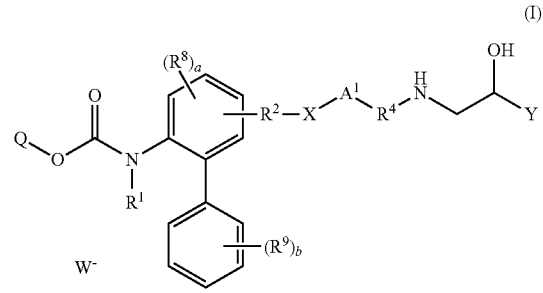

wherein
$R^1$ represents a hydrogen atom or an unsubstituted $C_{1-8}$ alkyl group;
$R^2$ represents a single bond, unsubstituted $C_{1-8}$ alkylene or $C_{1-8}$ alkylene substituted on carbon atoms by 1 to 2 oxygen atoms, unsubstituted $C_{2-4}$ alkenylene, or unsubstituted —O—$C_{1-4}$ alkylene;
X represents a single bond, —O—, —CONR$^3$—, —NR$^3$CO—, or —NR$^3$CO—CH$_2$—O—;
where $R^3$ represents a hydrogen atom or an unsubstituted $C_{1-8}$ alkyl group;
$A^1$ represents a single bond, unsubstituted $C_{6-10}$ arylene or $C_{6-10}$ arylene substituted with 1 to 4 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cyclo alkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, unsubstituted 5- to 10-membered heteroarylene or 5- to 10-membered heteroarylene substituted with 1 to 4 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cyclo alkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, unsubstituted $C_{1-4}$ alkylene-substituted or unsubstituted $C_{6-10}$ arylene where the substituents of the $C_{6-10}$ arylene are 1 to 3 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cyclo alkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, unsubstituted $C_{1-4}$ alkylene-substituted or unsubstituted 5- to 10-membered heteroarylene where the substituents of the 5- to 10-membered heteroarylene are 1 to 3 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cyclo alkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, or unsubstituted $C_{3-8}$ cycloalkylene or $C_{3-8}$ cycloalkylene substituted with 1 to 3 substituents selected from the group consisting of halogen and unsubstituted $C_{1-6}$ alkyl group;

$R^4$ represents unsubstituted $C_{1-10}$ alkylene;

$R^8$ and $R^9$ each independently represent a halogen atom, a cyano group, an unsubstituted $C_{1-6}$ alkyl group, a nitro group, —$NR^{10}R^{11}$ where $R^{10}$ and $R^{11}$ each independently represent a hydrogen atom or an unsubstituted $C_{1-6}$ alkyl group, an unsubstituted $C_{1-6}$ alkoxy group, a carboxyl group, an unsubstituted $C_{1-6}$ alkoxycarbonyl group, a hydroxyl group, a trifluoromethyl group, a mercapto group, or an unsubstituted $C_{1-6}$ alkylthio group;

a and b each independently represent an integer of 0 to 3;

Y represents a group represented by formula (II):

[Chemical Formula 2]

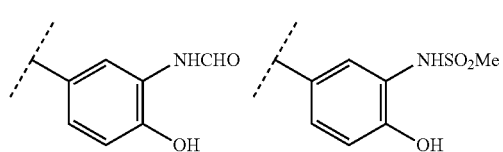

(II)

-continued

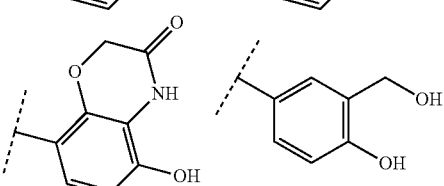

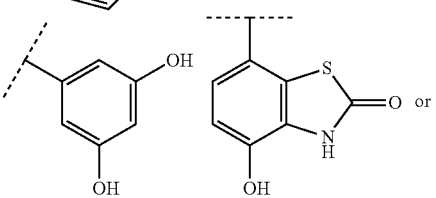

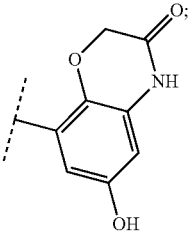

Q represents formula (III):

[Chemical Formula 3]

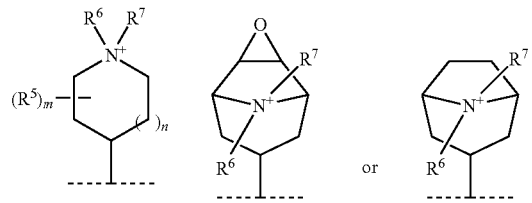

(III)

wherein $R^6$ and $R^7$ each independently represent an unsubstituted $C_{1-6}$ alkyl group or a $C_{1-6}$ alkyl group substituted with 1 to 4 substituents selected from the group consisting of halogen atom, hydroxyl group and unsubstituted $C_{1-6}$ alkoxy group, or an unsubstituted $C_{8-10}$ phenoxyalkyl group or a $C_{8-10}$ phenoxyalkyl group substituted with 1 to 4 substituents selected from the group consisting of halogen atom, hydroxyl group, unsubstituted $C_{1-6}$ alkyl group and unsubstituted $C_{1-6}$ alkoxy group;

$R^5$ represents an unsubstituted $C_{1-6}$ alkyl group or a $C_{1-6}$ alkyl group substituted with 1 to 4 substituents selected from the group consisting of halogen atom, hydroxyl group and unsubstituted $C_{1-6}$ alkoxy group; or any two of $R^5$, $R^6$ and $R^7$ may be bound to form a ring;

n represents an integer of 0 to 2; and m represents an integer of 0 to 3;

$W^-$ represents a negative ion;

or a pharmaceutically acceptable salt thereof.

(2) The quaternary ammonium salt compound or pharmaceutically acceptable salt thereof according to (1), wherein $R^2$, X, and $A^1$ are any of the following (i) to (iv):

(i) $R^2$ represents a single bond, $C_{1-4}$ alkylene substituted on a carbon atom by an oxygen atom, unsubstituted $C_{1-8}$ alkylene, or unsubstituted —O—$C_{1-4}$ alkylene; X represents —O—; $A^1$ represents a single bond or unsubstituted phenylene.

(ii) $R^2$ represents unsubstituted $C_{1-4}$ alkylene, unsubstituted $C_{2-4}$ alkenylene, or unsubstituted —O—$C_{1-4}$ alkylene; X represents —CONR$^3$—; $A^1$ represents a single bond, unsubstituted phenylene, unsubstituted $C_{1-4}$ alkylene-unsubstituted phenylene, or unsubstituted $C_{6-8}$ cycloalkylene.

(iii) $R^2$ represents unsubstituted $C_{1-4}$ alkylene; X represents —NR$^3$CO— or —NR$^3$CO—CH$_2$—O—; $A^1$ represents unsubstituted phenylene.

(iv) $R^2$, X, and $A^1$ represent a single bond.

(3) The quaternary ammonium salt compound or pharmaceutically acceptable salt thereof according to (1), wherein $R^2$, X, $A^1$, and $R^4$ are any of the following (v) to (xviii):

(v) $R^2$ represents a single bond; X represents —O—; $A^1$ represents a single bond; $R^4$ represents unsubstituted $C_{1-10}$ alkylene.

(vi) $R^2$ represents unsubstituted $C_{1-8}$ alkylene or $C_{1-8}$ alkylene substituted on a carbon atom by an oxygen atom; X represents —O—; $A^1$ represents a single bond; $R^4$ represents unsubstituted $C_{1-10}$ alkylene.

(vii) $R^2$ represents unsubstituted $C_{1-8}$ alkylene; X represents —O—; $A^1$ represents unsubstituted phenylene-; $R^4$ represents unsubstituted $C_{1-4}$ alkylene.

(viii) $R^2$ represents —O-unsubstituted $C_{1-4}$ alkylene; X represents —O—; $A^1$ represents unsubstituted phenylene; $R^4$ represents unsubstituted $C_{1-4}$ alkylene.

(ix) $R^2$ represents unsubstituted $C_{1-4}$ alkylene; X represents —CONR$^3$—; $A^1$ represents a single bond; $R^4$ represents unsubstituted $C_{1-8}$ alkylene.

(x) $R^2$ represents unsubstituted $C_{1-4}$ alkylene; X represents —CONR$^3$—; $A^1$ represents unsubstituted $C_{1-4}$ alkylene-unsubstituted phenylene; $R^4$ represents unsubstituted $C_{1-4}$ alkylene.

(xi) $R^2$ represents unsubstituted $C_{1-4}$ alkylene; X represents —CONR$^3$—; $A^1$ represents unsubstituted $C_{6-8}$ cycloalkylene; $R^4$ represents unsubstituted $C_{1-4}$ alkylene.

(xii) $R^2$ represents unsubstituted $C_{1-4}$ alkylene; X represents —CONR$^3$—; $A^1$ represents unsubstituted phenylene; $R^4$ represents unsubstituted $C_{1-4}$ alkylene.

(xiii) $R^2$ represents unsubstituted —O—$C_{1-4}$ alkylene; X represents —CONR$^3$—; $A^1$ represents unsubstituted phenylene; $R^4$ represents unsubstituted $C_{1-4}$ alkylene.

(xiv) $R^2$ represents unsubstituted $C_{2-4}$ alkenylene; X represents —CONR$^3$—; $A^1$ represents unsubstituted phenylene; $R^4$ represents unsubstituted $C_{1-4}$ alkylene.

(xv) $R^2$ represents unsubstituted $C_{2-4}$ alkenylene; X represents —CONR$^3$—; $A^1$ represents unsubstituted $C_{1-4}$ alkylene-unsubstituted phenylene; $R^4$ represents unsubstituted $C_{1-4}$ alkylene.

(xvi) $R^2$ represents unsubstituted $C_{1-4}$ alkylene; X represents —NR$^3$CO—; $A^1$ represents unsubstituted phenylene; $R^4$ represents unsubstituted $C_{1-4}$ alkylene.

(xvii) $R^2$ represents unsubstituted $C_{1-4}$ alkylene; X represents —NR$^3$CO—CH$_2$—O—; $A^1$ represents unsubstituted phenylene; $R^4$ represents unsubstituted $C_{1-4}$ alkylene.

(xviii) $R^2$ represents a single bond; X represents a single bond; $A^1$ represents a single bond; $R^4$ represents unsubstituted $C_{1-8}$ alkylene.

(4) The quaternary ammonium salt compound or pharmaceutically acceptable salt thereof according to (1), wherein $R^2$ is unsubstituted $C_{1-6}$ alkylene or $C_{1-6}$ alkylene substituted on a carbon atom by an oxygen atom, or unsubstituted —O—$C_{1-4}$ alkylene;

X is —CONR$^3$— or —NR$^3$CO—CH$_2$—O—;

$A^1$ is unsubstituted $C_{6-10}$ arylene or 5- to 10-membered heteroarylene, or $C_{6-10}$ arylene or 5- to 10-membered heteroarylene substituted with 1 to 3 substituents selected from the group consisting of halogen atom, hydroxyl group, unsubstituted $C_{1-4}$ alkyl group, unsubstituted $C_{1-4}$ alkoxy group and trifluoromethyl group; and $R^4$ is unsubstituted $C_{1-6}$ alkylene.

(5) The quaternary ammonium salt compound or pharmaceutically acceptable salt thereof according to (1), wherein $R^2$ is unsubstituted $C_{1-6}$ alkylene;

X is —CONR$^3$—;

$A^1$ is unsubstituted phenylene or naphthylene, or phenylene or naphthylene substituted with 1 to 4 substituents selected from the group consisting of halogen atom, hydroxyl group, unsubstituted $C_{1-4}$ alkyl group, unsubstituted $C_{1-4}$ alkoxy group and trihalomethyl group; and $R^4$ is unsubstituted $C_{1-6}$ alkylene.

(6) The quaternary ammonium salt compound or pharmaceutically acceptable salt thereof according to (1), wherein $R^2$ is unsubstituted $C_{1-6}$ alkylene;

X is —CONH—;

$A^1$ is unsubstituted phenylene or phenylene substituted with 1 to 2 substituents selected from the group consisting of halogen and methoxy group; and $R^4$ is substituted or unsubstituted $C_{1-6}$ alkylene.

(7) The quaternary ammonium salt compound or pharmaceutically acceptable salt thereof according to any one of (1) to (6), wherein $R^1$ represents a hydrogen atom and a represents an integer of 0.

(8) The quaternary ammonium salt compound or pharmaceutically acceptable salt thereof according to (7), wherein Q is a group represented by

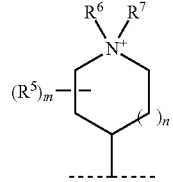

[Chemical Formula 4]

wherein
$R^6$ and $R^7$ each independently represent a methyl group or a phenoxyethyl group,
n represents an integer of 1, and
m represents an integer of 0.

(9) The quaternary ammonium salt compound or pharmaceutically acceptable salt thereof according to (7), wherein Q is a group represented by

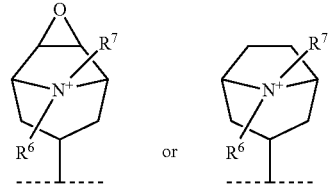

[Chemical Formula 5]

wherein $R^6$ and $R^7$ represent a methyl group.

(10) The quaternary ammonium salt compound or pharmaceutically acceptable salt thereof according to any one of (1) to (9), wherein Y is

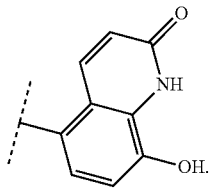

[Chemical Formula 6]

(11) A medicinal composition comprising a compound or a pharmaceutically acceptable salt thereof according to any one of (1) to (10) and a pharmaceutically acceptable carrier.

(12) A medicinal composition having β2 adrenergic receptor agonist activity and muscarinic receptor antagonist activity, comprising a compound or a pharmaceutically acceptable salt thereof according to any one of (1) to (10) as an active ingredient.

(13) A preventive or therapeutic agent for a pulmonary disease comprising a compound or a pharmaceutically acceptable salt thereof according to any one of (1) to (10) as an active ingredient.

(14) The preventive or therapeutic agent comprising a compound or a pharmaceutically acceptable salt thereof as an active ingredient according to (13), wherein the pulmonary disease is chronic obstructive pulmonary disease or asthma.

Effect of the Invention

The compound represented by formula (1) of the present invention or a pharmaceutically acceptable salt thereof has superior β2 adrenergic receptor agonist activity and muscarinic receptor antagonist activity, and thus is useful as a preventive or therapeutic agent for inflammatory diseases such as chronic obstructive pulmonary disease (COPD) or asthma. The compound of the present invention has a quaternary ammonium structure located at the terminal portion of the molecule and thereby has large bronchodilator effects. Furthermore, it is superior in duration of action, produces a reduced level of side effects such as saliva suppression, and is possible to also have stability and ease of manufacture.

DESCRIPTION OF EMBODIMENTS

Hereinafter, the present invention will be described in detail.

Each group consisting of the compound represented by general formula (I) of the present invention is defined as follows. The writing order in each group indicates the order of the bonds in formula (I). For example, the "$C_{1-4}$ alkylene-substituted or unsubstituted arylene" of $A^1$ represents a group whose "$C_{1-4}$ alkylene" on the left end is linked to X, whose "substituted or unsubstituted arylene" on the right end is linked to $R^4$, wherein the "$C_{1-4}$ alkylene" and the "substituted or unsubstituted arylene" are linked. The number situated to the right of carbon atom indicates the number of carbon atoms. For example, "$C_{1-6}$" represents having "1 to 6 carbon atoms."

The "$C_{1-8}$ alkyl group" in $R^1$ means a linear or branched carbon chain having 1 to 8 carbon atoms. It represents, for example, a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-ethylbutyl group, a 2-ethylbutyl group, an isoheptyl group, an octyl group, an isooctyl group, and the like, among which preferred is one having 1 to 4 carbon atoms, particularly a methyl group or an ethyl group.

Preferably, $R^1$ is hydrogen.

The "$C_{1-8}$ alkylene" in $R^2$ means a linear or branched carbon chain having 1 to 8 carbon atoms. Specifically, it represents methylene, ethylene, propylene, isopropylene, butylene, isobutylene, tert-butylene, pentylene, neopentylene, isopentylene, 1,2-dimethylpropylene, hexylene, isohexylene, 1,1-dimethylbutylene, 2,2-dimethylbutylene, octylene, nonylene, and the like, among which preferred is one having 1 to 6 carbon atoms; more preferred is one having 2 to 5 carbon atoms, particularly ethylene, propylene, or butylene. The $C_{1-8}$ g alkylene in $R^2$ may be substituted on carbon atoms with 1 to 2 oxygen atoms at any chemically feasible position. Being substituted on a carbon atom with an oxygen atom means that an oxo group is bound to the carbon atom (—C(=O)—).

The "$C_{2-4}$ alkenylene" in $R^2$ means a carbon chain with an unsaturated double bond. Specifically, it refers to vinylene, propenylene, butenylene, 2-methyl-1-propenylene, and the like. Vinylene or propenylene is preferred.

The "$C_{1-4}$ alkylene" in "—O—$C_{1-4}$ alkylene" of $R^2$ means a linear or branched carbon chain having 1 to 4 carbon atoms. Specifically, it represents methylene, ethylene, propylene, isopropylene, butylene, and the like. Preferred "—O—$C_{1-4}$ alkylene" is —O-ethylene, —O-propylene, or —O-butylene.

Preferably, $R^2$ is unsubstituted $C_{1-6}$ alkylene, particularly ethylene, propylene, or butylene.

The "CO" in the groups of X represents a carbonyl group. The "$C_{1-8}$ alkyl group" in $R^3$ of X means a linear or branched carbon chain having 1 to 8 carbon atoms. Specifically, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-ethylbutyl group, a 2-ethylbutyl group, an isoheptyl group, an octyl group, an isooctyl group, and the like, among which preferred is one having 1 to 4 carbon atoms, particularly a methyl group or an ethyl group.

Preferably, X is —O— or —$CONR^3$—, particularly —O— or —CONH—.

The "$C_{6-10}$ arylene" in $A^1$ means a $C_{6-10}$ aromatic hydrocarbon ring. Specifically, it represents hydrocarbon ring arylene such as phenylene and naphtylene. Phenylene or naphtylene is preferred.

The "5- to 10-membered heteroarylene" in $A^1$ means a 5- to 10-membered aromatic heterocyclic ring having 1 to 4 heteroatoms selected from sulfur atoms, nitrogen atoms, and oxygen atoms. Specifically, it represents pyridylene, thienylene, thiazolylene, benzothiazolylene, benzothiophenylene, and the like. Thienylene or pyridylene is preferred.

The "$C_{1-4}$ alkylene" in "$C_{1-4}$ alkylene-substituted or unsubstituted $C_{6-10}$ arylene" of $A^1$ means a linear or branched carbon chain having 1 to 4 carbon atoms. Specifically, it represents methylene, ethylene, propylene, isopropylene, butylene, and the like, among which methylene or ethylene is preferred. The "$C_{6-10}$ arylene" means a $C_{6-10}$ aromatic hydrocarbon ring. Specific examples include phenylene, naphtylene, and the like. Phenylene is preferred.

The "$C_{1-4}$ alkylene" in "$C_{1-4}$ alkylene-substituted or unsubstituted 5- to 10-membered heteroarylene" of $A^1$ means a linear or branched carbon chain having 1 to 4 carbon atoms. Specifically, it represents methylene, ethylene, propylene, isopropylene, butylene, and the like, among which methylene or ethylene is preferred. The "5- to 10-membered heteroarylene" means a 5- to 10-membered aromatic heterocyclic ring having 1 to 3 heteroatoms selected from sulfur atoms, nitrogen atoms, and oxygen atoms. Specifically, it represents pyridylene, thienylene, thiazolylene, benzothiazolylene, benzothiophenylene, and the like. Thienylene is preferred.

The substituents of the "arylene" or "heteroarylene" in $A^1$ include halogen atom, hydroxyl group, cyano group, nitro group, carboxyl group, trifluoromethyl group, $C_{1-6}$ alkyl group, $C_{3-8}$ cycloalkyl group, $C_{1-6}$ alkoxy group, $C_{3-8}$ cycloalkyloxy group, mercapto group, $C_{1-6}$ alkylthio group, $C_{3-8}$ cycloalkylthio group, amino group, mono($C_{1-6}$ alkyl) amino group, di($C_{1-6}$ alkyl)amino group, and the like. Halogen atom, $C_{1-6}$ alkyl group, $C_{1-6}$ alkoxy group, or trifluoromethyl group are preferred.

The "$C_{3-8}$ cycloalkylene" of $A^1$ includes cyclopropylene, cyclobutylene, cyclopentylene, cyclohexylene, and the like. Specifically, cyclohexylene is preferred.

The substituents of the "$C_{3-8}$ cycloalkylene" in $A^1$ include halogen, $C_{1-6}$ alkyl group. Methyl group is preferred.

The "halogen atom" mentioned as a substituent of the "arylene," "heteroarylene" or "$C_{3-8}$ cycloalkylene" in $A^1$ means a fluorine atom, a chlorine atom, a bromine atom, and an iodine atom. A fluorine atom, a chlorine atom, or a bromine atom is preferred.

The "$C_{1-6}$ alkyl group" mentioned as a substituent of the "arylene," "heteroarylene" or "$C_{3-8}$ cycloalkylene" in $A^1$ means a linear or branched carbon chain having 1 to 6 carbon atoms. Specifically, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-ethylbutyl group, a 2-ethylbutyl group, a hexyl group, and the like. A methyl group or an ethyl group is preferred.

The "$C_{3-8}$ cycloalkyl group" mentioned as a substituent of the "arylene" or "heteroarylene" in $A^1$ specifically means a cyclic alkyl group such as cyclopropyl, cyclobutyl, cyclopentyl, cyclohexyl, cycloheptyl, and cyclooctyl. A cyclopropyl group, a cyclopentyl group, or a cyclohexyl group is preferred.

The "$C_{1-6}$ alkoxy group" mentioned as a substituent of the "arylene" or "heteroarylene" in $A^1$ means a linear or branched $C_{1-6}$ alkoxy group such as a methoxy group, an ethoxy group, an n-propoxy group, an n-butoxy group, an isopropoxy group, an isobutoxy group, a sec-butoxy group, a tert-butoxy group, a 1-ethylpropoxy group, and a 2-propylbutoxy group. A methoxy group, an ethoxy group, or an isopropoxy group is preferred.

The "$C_{3-8}$ cycloalkyloxy group" mentioned as a substituent of the "arylene" or "heteroarylene" in $A^1$ means a group consisting of a $C_{3-8}$ cycloalkyl group as described above and an oxy group. Its preferred specific examples include a cyclopropyloxy group, a cyclopentyloxy group, a cyclohexyloxy group, and the like.

The "$C_{1-6}$ alkylthio group" mentioned as a substituent of the "arylene" or "heteroarylene" in $A^1$ means a group consisting of a $C_{1-6}$ alkyl group as described above and a thio group. Its preferred specific examples include a methylthio group, an ethylthio group, and the like.

The "$C_{3-8}$ cycloalkylthio group" mentioned as a substituent of the "arylene" or "heteroarylene" in $A^1$ means a group consisting of a $C_{3-8}$ cycloalkyl group as described above and a thio group. Its preferred specific examples include a cyclopropylthio group and the like.

The "mono($C_{1-6}$ alkyl)amino group" mentioned as a substituent of the "arylene" or "heteroarylene" in $A^1$ means a $C_{1-6}$ alkyl group-substituted amino group. Its preferred specific examples include a methylamino group and the like.

The "di($C_{1-6}$ alkyl)amino group" mentioned as a substituent of the "arylene" or "heteroarylene" in $A^1$ means an amino group disubstituted with the same or different $C_{1-6}$ alkyl groups. Its preferred specific examples include a dimethylamino group and the like.

Preferably, $A^1$ is unsubstituted phenylene or phenylene substituted with 1 to 3 substituents selected from the group consisting of halogen, hydroxyl group, $C_{1-4}$ alkyl group, $C_{1-4}$ alkoxy group, and trifluoromethyl group. More preferably, $A^1$ is unsubstituted phenylene or phenylene substituted with 1 to 2 substituents selected from the group consisting of halogen atom and methoxy group.

The "$C_{1-10}$ alkylene" in $R^4$ means a linear or branched carbon chain having 1 to 10 carbon atoms. Specifically, it represents methylene, ethylene, propylene, butylene, isopropylene, pentylene, isobutylene, hexylene, tert-butylene, 1,1-dimethylethylene, hexylene, isohexylene, 1,1-dimethylpropylene, 2,2-dimethylbutylene, 1-ethylbutylene, 2-ethylbutylene, isoheptylene, octylene, isooctylene, nonylene, and the like, among which preferred is one having 1 to 5 carbon atoms, particularly methylene, ethylene, propylene, or 1,1-dimethylethylene.

The "halogen atom" in $R^8$ and $R^9$ means a fluorine atom, a chlorine atom, a bromine atom, an iodine atom, and the like. Its preferred specific examples include a fluorine atom, a chlorine atom, a bromine atom, and an iodine atom.

The "$C_{1-6}$ alkyl group" in $R^8$ and $R^9$ means a linear or branched carbon chain having 1 to 6 carbon atoms. Specifically, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-exylbutyl group, a 2-ethylbutyl group, and the like, among which preferred is one having 1 to 4 carbon atoms, particularly a methyl group or an ethyl group.

The "$C_{1-6}$ alkyl group" in "$R^{10}$, $R^{11}$" of $R^8$ and $R^9$ means a linear or branched carbon chain having 1 to 6 carbon atoms. For example, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-exylbutyl group, a 2-ethylbutyl group, and the like, among which preferred is one having 1 to 4 carbon atoms, particularly a methyl group.

The "$C_{1-6}$ alkoxy group" in $R^8$ and $R^9$ means an alkoxy group having 1 to 6 carbon atoms. Specifically, it represents a methoxy group, an ethoxy group, a propoxy group, an isopropoxy group, a butoxy group, an isobutoxy group, a sec-butoxy group, a tert-butoxy group, a pentyloxy group, a neopentyloxy group, a tert-pentyloxy group, a 2-methylbutoxy group, a hexyloxy group, an isohexyloxy group, and the like, among which preferred is one having 1 to 4 carbon atoms; most preferred is a methoxy group or an ethoxy group.

The "$C_{1-6}$ alkoxycarbonyl group" in $R^8$ and $R^9$ specifically represents a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a hexyloxycarbonyl group, and the like. A methoxycarbonyl group, an ethoxycarbonyl group, or an isopropoxycarbonyl group is preferred. A methoxycarbonyl group is more preferred.

The "$C_{1-6}$ alkylthio group" in $R^8$ and $R^9$ means an alkylthio group having 1 to 6 carbon atoms. Specifically, it represents a methylthio group, an ethylthio group, a propylthio group, an isopropylthio group, a butylthio group, an isobutylthio group, a sec-butylthio group, a tert-butylthio group, a pentylthio group, a neopentylthio group, tert-pentylthio group, a 2-methylbutylthio group, a hexylthio group, an isohexylthio group, and the like, among which preferred is one having 1 to 4 carbon atoms; most preferred is a methylthio group or an ethylthio group.

Preferably, $R^8$ and $R^9$ are each independently a halogen atom or a hydroxyl group.

a and b each independently represent an integer of 0 to 3. Preferably, a and b are each 0 or 1. When a or b is 0, it represents the absence of the substituent corresponding to $R^8$ or $R^9$.

Preferably, Y is

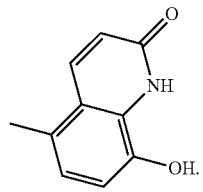

[Chemical Formula 7]

The "$C_{1-6}$ alkyl group" in $R^6$ and $R^7$ of Q means a linear or branched carbon chain having 1 to 6 carbon atoms. Specifically, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, a 1,1-dimethylbutyl group, a 2,2-dimethylbutyl group, or the like, among which preferred is one having 1 to 4 carbon atoms, particularly a methyl group or an ethyl group.

The "$C_{8-10}$ phenoxyalkyl group" in $R^6$ and $R^7$ means a group consisting of a phenoxy group and a $C_{2-4}$ alkyl group. Specifically, it represents a phenoxyethyl group, a phenoxypropyl group, a phenoxybutyl group, or the like, among which a phenoxyethyl group or a phenoxypropyl group is particularly preferred.

The "halogen atom" mentioned as a substituent of the "$C_{1-6}$ alkyl group" or "$C_{8-10}$ phenoxyalkyl group" in $R^6$ and $R^7$ means a fluorine atom, a chlorine atom, a bromine atom, an iodine atom, and the like. A fluorine atom, a chlorine atom, or a bromine atom is preferred.

The "$C_{1-6}$ alkyl group" mentioned as a substituent of the "$C_{8-10}$ phenoxyalkyl group" in $R^6$ and $R^7$ means a linear or branched carbon chain having 1 to 6 carbon atoms. Specifically, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, an isohexyl group, a 1,1-dimethylbutyl group, a 2,2-dimethylbutyl group, a 1-exylbutyl group, a 2-ethylbutyl group, a hexyl group, or the like. A methyl group or an ethyl group is preferred.

The "$C_{1-6}$ alkoxy group" mentioned as a substituent of the "$C_{1-6}$ alkyl group" or "$C_{8-10}$ phenoxyalkyl group" in $R^6$ and $R^7$ means a linear or branched $C_{1-6}$ alkoxy group such as a methoxy group, an ethoxy group, an n-propoxy group, an n-butoxy group, an isopropoxy group, an isobutoxy group, a sec-butoxy group, a tert-butoxy group, a 1-ethylpropoxy group, and a 2-propylbutoxy group. A methoxy group is preferred.

The substituents of the "$C_{1-6}$ alkyl group" in $R^6$ and $R^7$ include a halogen atom or hydroxyl group. A halogen atom is preferred.

The "$C_{1-6}$ alkyl group" in $R^5$ means a linear or branched carbon chain having 1 to 6 carbon atoms. For example, it represents a methyl group, an ethyl group, a propyl group, an isopropyl group, a butyl group, an isobutyl group, a tert-butyl group, a pentyl group, a neopentyl group, an isopentyl group, a 1,2-dimethylpropyl group, a hexyl group, a 1,1-dimethylbutyl group, a 2,2-dimethylbutyl group, or the like, among which preferred is one having 1 to 4 carbon atoms, particularly a methyl group or an ethyl group.

"Any two of $R^5$, $R^6$ and $R^7$ may be bound to form a ring" means, for example, that $R^6$ and $R^7$ are bound to form butylene, pentylene, or hexylene. Pentylene or hexylene is preferred. Or, it means, for example, that $R^5$ is bound to $R^6$ or $R^7$ to form, together with the original hetero ring, an azabicyclo ring or an azatricyclo ring. An example of such an azabicyclo ring is a quinuclidine ring.

Preferably, $R^6$ and $R^7$ are each independently a methyl group or a $C_2$ phenoxyalkyl group.

n represents an integer of 0 to 2, and 1 is preferred.

m represents an integer of 0 to 3, and 0 is preferred. When m is 0, it represents the absence of the substituent corresponding to $R^5$.

When Q is

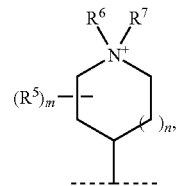

[Chemical Formula 8]

it is particularly preferred that $R^6$ and $R^7$ each independently represent a methyl group, n represents an integer of 1, and m represents an integer of 0.

Furthermore, when Q is

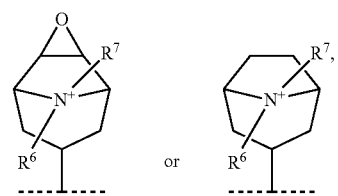

[Chemical Formula 9]

it is particularly preferred that $R^6$ and $R^7$ each independently represent a methyl group.

Specific examples of the negative ion represented as "$W^-$" include a fluorine ion, a chlorine ion, a bromine ion, an iodine ion, a sulfate ion, a phosphate ion, a nitrate ion, a carbonate ion, an acetate ion, a lactate ion, a tartrate ion, a benzoate ion, a citrate ion, a trifluoroacetate ion, a methanesulfonate ion, an ethanesulfonate ion, a methylsulfate ion, a benzenesulfonate ion, a p-toluenesulfonate ion, an isethionate ion, an adipate ion, an ethane-1,2-disulfonate ion, a 1,5-naphthalenedisulfonate ion, a naphthalene-2-sulfonate ion, a malate ion, a maleate ion, a malonate ion, a fumarate ion, a succinate ion, a 1-hydroxy-2-naphthoate ion, a phthalate ion, a sorbate ion, an oleate ion, a glucuronate ion, and the like, among which preferred is a fluorine ion, a chlorine ion, a bromine ion, an iodine ion, a sulfate ion, a lactate ion, a tartrate ion, a benzoate ion, a citrate ion, a methanesulfonate ion, a benzenesulfonate ion, a p-toluenesulfonate ion, an adipate ion, an ethane-1,2-disulfonate ion, a 1,5-naphthalenedisulfonate ion, a naphthalene-2-sulfonate ion, a malate ion, a maleate ion, a malonate ion, a fumarate ion, a succinate ion, a 1-hydroxy-2-naphthoate ion, or a glucuronate ion.

In the quaternary ammonium salt compounds represented by formula (I), those composed of combinations of groups defined to have the above-mentioned options and the preferred groups and those composed of combinations of preferred groups are also preferred compounds.

Further, the following compounds are also more preferred quaternary ammonium salt compounds:

4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[3-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[2-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[3-bromo-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[2-bromo-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)-3-methylphenyl]carbamoyl}ethyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)-2-methylphenyl]carbamoyl}ethyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)-3-methoxyphenyl]carbamoyl}ethyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-1,1-dimethylpiperidin-1-ium, 4-({[5-(2-{[3-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[2-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[2-fluoro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-1,1-dimethylpiperidin-1-ium, 4-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-1,1-dimethylpiperidin-1-ium, 4-({[5-(2-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-1,1-dimethylpiperidin-1-ium, 4-({[5-(2-{[2,5-difluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, 4-({[5-(2-{[6-({[(2R)-2-hydroxy-2-(8-hydroxy-2-oxo-1,2-dihydroquinolin-5-yl)ethyl]amino}methyl)naphthalen-2-yl]carbamoyl}ethyl)-2-phenylphenyl]carbamoyl}oxy)-1,1-dimethylpiperidin-1-ium, 4-({[5-(2-{[2-({[(2R)-2-hydroxy-2-(8-hydroxy-2-oxo-1,2-dihydroquinolin-5-yl)ethyl]amino}methyl)-1-benzothiophen-5-yl]carbamoyl}ethyl)-2-phenylphenyl]carbamoyl}oxy)-1,1-dimethylpiperidin-1-ium, 4-({[5-(2-{[5-({[(2R)-2-hydroxy-2-(8-hydroxy-2-oxo-1,2-dihydroquinolin-5yl)ethyl]amino}methyl)-2-methoxyphenyl]carbamoyl}ethyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)phenyl](methyl)carbamoyl}ethyl)-2-phenylphenyl]carbamoyl}oxy)-1,1-dimethylpiperidin-1-ium, 4-({[5-(2-{[5-({[(2R)-2-hydroxy-2-(8-hydroxy-2-oxo-1,2-dihydroquinolin-5-yl)ethyl]amino}methyl)thiophen-2-yl]carbamoyl}ethyl)-2-phenylphenyl]carbamoyl}oxy)-1,1-dimethylpiperidin-1-ium, 4-({[5-(2-{[5-({[(2R)-2-hydroxy-2-(8-hydroxy-2-oxo-1,2-dihydroquinolin-5yl)ethyl]amino}methyl)pyridin-2-yl]carbamoyl}ethyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[3-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[3-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[2-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)-3-methylphenyl]carbamoyl}propyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)-2-methoxyphenyl]carbamoyl}propyl)-2-phenylphenyl]carbamoyl}oxy)-1,1-dimethylpiperidin-1-ium, 4-({[5-(3-{[3-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[2-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[2-fluoro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium, 4-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium, 4-({[5-(3-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium, 4-({[5-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-1,1-dimethylpiperidin-1-ium, 4-({[5-(3-{[5-({[(2R)-2-hydroxy-2-(8-hydroxy-2-oxo-1,2-dihydroquinolin-5-yl)ethyl]amino}methyl)pyridin-2-yl]carbamoyl}propyl)-2-phenylphenyl]carbamoyl}oxy)-1,1-dimethylpiperidin-1-ium, 4-({[5-(3-{[2-chloro-5-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[3-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(3-{[4-({[(2R)-2-hydroxy-2-(8-hydroxy-2-oxo-1,2-dihydroquinolin-5-yl)ethyl]amino}methyl)-3-(trifluoromethyl)phenyl]carbamoyl}propyl)-2-phenylphenyl]carbamoyl}oxy)-1,1-dimethylpiperidin-1-ium, (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[3-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[2-chloro-4-({[(2R)-2-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[3-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[2-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-3-methylphenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxo)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-([{5-(3-{[4-({[(2R)-2-hydroxy-2-(8-hydroxy-2-oxo-1,2-dihydroquinolin-5-yl)ethyl]amino}methyl)-2-methoxyphenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[3-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(3-{[2-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-2-phenylphenyl]carbamoyl}oxy)-9,9-dimethyl-3-oxa-9-azatricyclo[3.3.1.0$^{2,4}$]nonan-9-ium, (1R,2R,4S,5S,7S)-7-({[5-(2-{[2-fluoro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-2-phenylphenyl]carbamoyl}oxy-9,9-dimethyl-3-oxa-9-azatricyclo[3.3.1.0$^{2,3}$]nonan-9-ium, (1R,2R,4S,5S,7S)-7-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-2-phenylphenyl]carbamoyl}oxy-9,9-dimethyl-3-oxa-9-azatricyclo[3.3.1.0$^{2,4}$]nonan-9-ium, (1R,2R,4S,5S,7S)-7-({[5-(2-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-2-phenylphenyl]}oxy-9,9-dimethyl-3-oxa-9-azatricyclo[3.3.1.0$^{2,4}$]nonan-9-ium, (1R,2R,4S,5S,7S)-7-({[5-(3-{[6-{[(2R)-2-hydroxy-2-(8-hydroxy-2-oxo-1,2-dihydroquinolin-5-yl)ethyl]amino}methyl)naphthalen-2-yl]carbamoyl}propyl)-2- phenylphenyl]carbamoyl}oxy)-2-phenylphenyl]
carbamoyl}oxy)-9,9-dimethyl-3-oxa-9-azatricyclo
[3.3.1.0$^{2,4}$]nonan-9-ium, (1R,2R,4S,5S,7S)-7-({[5-(2-{[4-({[(2R)-2-hydroxy-2-(8-hydroxy-2-oxo-1,2-dihydroquinolin-5-yl)ethyl]
amino}methyl)phenyl]carbamoyl}ethyl)-2-phenylphenyl]carbamoyl}oxy)-9,9-dimethyl-3-oxa-9-azatricyclo
[3.3.1.0$^{2,4}$]nonan-9-ium, (1R,2R,4S,5S,7S)-7-({[5-(2-{[3-chloro-4-({[(2R)-2-hydroxy-2-(8-hydroxy-2-oxo-1,2-dihydroquinolin-5-yl)
ethyl]amino}methyl)phenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[2-chloro-4-({[(2R-2-hydroxy-2-(8-hydroxy-2-oxo-1,2-dihydroquinolin-5-yl)
ethyl]amino}methyl)phenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[3-bromo-4-({[(2R)-2-hydroxy-2-(8-hydroxy-2-oxo-1,2-dihydroquinolin-5-yl)
ethyl]amino}methyl)phenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[2-bromo-4-({[(2R)-2-hydroxy-2-(8-hydroxy-2-oxo-1,2-dihydroquinolin-5-yl)
ethyl]amino}methyl)phenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[4-({[(2R)-2-hydroxy-2-(8-hydroxy-2-oxo-1,2-dihydroquinolin-5-yl)ethyl]
amino}methyl)-3-methylphenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[4-({[(2R)-2-hydroxy-2-(8-hydroxy-2-oxo-1,2-dihydroquinolin-5-yl)ethyl]
amino}methyl)-2-methylphenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[4-({[(2R)-2-hydroxy-2-(8-hydroxy-2-oxo-1,2-dihydroquinolin-5-yl)ethyl]
amino}methyl)-2-methoxyphenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[4-({[(2R)-2-hydroxy-2-(8-hydroxy-2-oxo-1,2-dihydroquinolin-5-yl)ethyl]
amino}methyl)-3-methoxyphenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[3-fluoro-4-({[2R)-2-hydroxy-2-(8-hydroxy-2-oxo-1,2-dihydroquinolin-5-yl)
ethyl]amino}methyl)phenyl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[5-(2-{[2-fluoro-4-({[(2R)-2-hydroxy-2-(8-hydroxy-2-oxo-1,2-dihydroquinolin-5-yl)ethyl]
amino}methyl)phenyl]carbamoyl}ethyl)-2-phenylphenyl]carbamoyl}oxy)-9,9-dimethyl-3-oxa-9-azatricyclo
[3.3.1.0$^{2,4}$]nonan-9-ium, (1R,2R,4S,5S,7S)-7-({[5-(2-{[2-fluoro-4-({[(2R)-2-hydroxy-2-(8-hydroxy-2-oxo-1,2-dihydroquinolin-5-yl)
ethyl]amino}methyl)-5-methoxyphenyl]
carbamoyl}ethyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[5-(2-{[2-chloro-4-({[(2R)-2-hydroxy-2-(8-hydroxy-2-oxo-1,2-dihydroquinolin-5-yl)
ethyl]amino}methyl)-5-methoxyphenyl]
carbamoyl}ethyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[5-(2-{[2-bromo-4-({[(2R)-2-hydroxy-2-(8-hydroxy-2-oxo-1,2-dihydroquinolin-5-yl)
ethyl]amino}methyl)-5-methoxyphenyl]
carbamoyl}ethyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[5-(2-{[3-ethoxy-4-({[(2R)-2-hydroxy-2(8-hydroxy-2-oxo-1,2-dihydroquinolin-5-yl)
ethyl]amino}methyl)-5-methoxyphenyl]
carbamoyl}ethyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[5-(2-{[6-({[(2R)-2-hydroxy-2-(8-hydroxy-2-oxo-1,2-dihydroquinolin-5-yl)ethyl]
amino}methyl)naphthalen-2-yl]carbamoyl}ethyl)-2-phenylphenyl]carbamoyl}oxy)-9,9-dimethyl-3-oxa-9-
azatricyclo[3.3.1.0$^{2,4}$]nonan-9-ium, (1R,2R,4S,5S,7S)-7-({[4-(3-{[4-({[(2R)-2-hydroxy-2-(8-hydroxy-2-oxo-1,2-dihydroquinolin-5-yl)ethyl]
amino}methyl)phenyl]carbamoyl}propyl)-2-phenylphenyl]carbamoyl}oxy)-9,9-dimethyl-3-oxa-9-azatricyclo
[3.3.1.0$^{2,4}$]nonan-9-ium, (1R,2R,4S,5S,7S)-7-({[4-(3-{[3-chloro-4-({[(2R)-2-hydroxy-2-(8-hydroxy-2-oxo-1,2-dihydroquinolin-5-yl)
ethyl]amino}methyl)phenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[2-chloro-4-({[(2R)-2-hydroxy-2-(8-hydroxy-2-oxo-1,2-dihydroquinolin-5-yl)
ethyl]amino}methyl)phenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[3-bromo-4-({[(2R)-2-hydroxy-2-(8-hydroxy-2-oxo-1,2-dihydroquinolin-5-yl)
ethyl]amino}methyl)phenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[2-bromo-4-({[(2R)-2-hydroxy-2-(8-hydroxy-2-oxo-1,2-dihydroquinolin-5-yl)
ethyl]amino}methyl)phenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[4-({[(2R)-2-hydroxy-2-(8-hydroxy-2-oxo-1,2-dihydroquinolin-5-yl)ethyl]
amino}methyl)-3-methylphenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[4-({[(2R)-2-hydroxy-2-(8-hydroxy-2-oxo-1,2-dihydroquinolin-5-yl)ethyl]
amino}methyl)-2-methylphenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[4-({[(2R)-2-hydroxy-2-(8-hydroxy-2-oxo-1,2-dihydroquinolin-5-yl)ethyl]
amino}methyl)-3-methoxyphenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[4-({[(2R)-2-hydroxy-2-(8-hydroxy-2-oxo-1,2-dihydroquinolin-5-yl)ethyl]
amino}methyl)-2-methoxyphenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[3-fluoro-4-({[(2R)-2-hydroxy-2-(8-hydroxy-2-oxo-1,2-dihydroquinolin-5-yl)
ethyl]amino}methyl)phenyl]amino}methyl)phenyl]
carbamoyl}propyl)-2-phenylphenyl]carbamoyl}oxy)-9,9-
dimethyl-3-oxa-9-azatricyclo[3.3.1.0$^{2,4}$]nonan-9-ium, (1R,2R,4S,5S,7S)-7-({[4-(3-{[2-fluoro-4-({[(2R)-2-hydroxy-2-(8-hydroxy-2-oxo-1,2-dihydroquinolin-5-yl)ethyl]amino}methyl)-5-methoxyphenyl]amino}methyl)phenyl]carbamoyl}propyl)-2-phenylphenyl]carbamoyl}oxy)-9,9-dimethyl-3-oxa-9-azatricyclo[3.3.1.0²,⁴]nonan-9-ium, (1R,2R,4S,5S,7S)-7-({[4-(3-{[2-fluoro-4-({[(2R)-2-hydroxy-2-(8-hydroxy-2-oxo-1,2-dihydroquinolin-5-yl)ethyl]amino}methyl)-5-methoxyphenyl]amino}methyl)phenyl]carbamoyl}propyl)-2-phenylphenyl]carbamoyl}oxy)-9,9-dimethyl-3-oxa-9-azatricyclo[3.3.1.0²,⁴]nonan-9-ium, (1R,2R,4S,5S,7S)-7-({[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}methyl)phenyl]carbamoyl}propyl)-2-phenylphenyl]carbamoyl}oxy)-9,9-dimethyl-3-oxa-9-azatricyclo[3.3.1.0²,⁴]nonan-9-ium, (1R,2R,4S,5S,7S)-7-({[4-(3-{[2-bromo-4-({[(2R)-2-hydroxy-2-(8-hydroxy-2-oxo-1,2-dihydroquinolin-5-yl)ethyl]amino}methyl)-5-methoxyphenyl]amino}methyl)phenyl]carbamoyl}propyl)-2-phenylphenyl]carbamoyl}oxy)-9,9-dimethyl-3-oxa-9-azatricyclo[3.3.1.0²,⁴]nonan-9-ium, (1R,2R,4S,5S,7S)-7-({[4-(3-{[6-({[(2R)-2-hydroxy-2-(8-hydroxy-2-oxo-1,2-dihydroquinolin-5-yl)ethyl]amino}methyl)naphthalen-2-yl]amino}methyl)phenyl]carbamoyl}propyl)-2-phenylphenyl]carbamoyl}oxy)-9,9-dimethyl-3-oxa-9-azatricyclo[3.3.1.0²,⁴]nonan-9-ium, (1R,3R)-3-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-8,8-dimethyl-8-azabicyclo[3.2.1]octan-8-ium, 4-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-1,1-dimethylpiperidin-1-ium, (1R,2R,4S,5S,7S)-7-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-9,9-dimethyl-3-oxa-9-azatricyclo[3.3.1.0²,⁴]nonan-9-ium, 4-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-1,1-dimethylpiperidin-1-ium, (1R,2R,4S,5S,7S)-7-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-9,9-dimethyl-3-oxa-9-azatricyclo[3.3.1.0²,⁴]nonan-9-ium, 4-({[4-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1-methyl-1-(2-phenoxyethyl)piperidin-1-ium, 4-[({5-[(8-{[(2R)-2-hydroxy-2-(8-hydroxy-2-oxo-1,2-dihydroquinolin-5-yl)ethyl]amino}octyl)oxy]-2-phenylphenyl}carbamoyl)oxy]-1,1-dimethylpiperidin-1-ium, 4-[({5-[(6-{[(2R)-2-hydroxy-2-(8-hydroxy-2-oxo-1,2-dihydroquinolin-5-yl)ethyl]amino}hexyl)oxy]-2-phenylphenyl}carbamoyl)oxy]-1,1-dimethylpiperidin-1-ium, 4-[({5-[(9-{[(2R)-2-hydroxy-2-(8-hydroxy-2-oxo-1,2-dihydroquinolin-5-yl)ethyl]amino}nonyl)oxy]-2-phenylphenyl}carbamoyl)oxy]-1,1-dimethylpiperidin-1-ium, 4-{[(5-{4-[4-({[(2R)-2-hydroxy-2-(8-hydroxy-2-oxo-1,2-dihydroquinolin-5-yl)ethyl]amino}methyl)phenoxy]butyl}-2-phenylphenyl)carbamoyl]oxy}-1,1-dimethylpiperidin-1-ium, 4-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-1,1-dimethylpiperidin-1-ium, 4-({[5-(2-{[4-(2-{[(2R)-2-hydroxy-2-(8-hydroxy-2-oxo-1,2-dihydroquinolin-5-yl)ethyl]amino}ethyl)phenyl]carbamoyl}ethyl)-2-phenylphenyl]carbamoyl}oxy)-1,1-dimethylpiperidin-1-ium, 4-({[5-({[4-({[(2R)-2-hydroxy-2-(8-hydroxy-2-oxo-1,2-dihydroquinolin-5-yl)ethyl]amino}methyl)phenyl]carbamoyl}methoxy)-2-phenylphenyl]carbamoyl}oxy)-1,1-dimethylpiperidin-1-ium, 4-[({5-[2-({[4-({[(2R)-2-hydroxy-2-(8-hydroxy-2-oxo-1,2-dihydroquinolin-5-yl)ethyl]amino}methyl)phenyl]methyl}carbamoyl)ethyl]-2-phenylphenyl}carbamoyl)oxy]-1,1-dimethylpiperidin-1-ium, 4-[({5-[3-({[4-({[(2R)-2-hydroxy-2-(8-hydroxy-2-oxo-1,2-dihydroquinolin-5-yl)ethyl]amino}methyl)phenyl]methyl}carbamoyl)propyl]-2-phenylphenyl}carbamoyl)oxy]-1,1-dimethylpiperidin-1-ium, 4-[({5-[(1E)-2-{[4-({[(2R)-2-hydroxy-2-(8-hydroxy-2-oxo-1,2-dihydroquinolin-5-yl)ethyl]amino}methyl)phenyl]carbamoyl}ethyl-1-en-1-yl]-2-phenylphenyl}carbamoyl)oxy]-1,1-dimethylpiperidin-1-ium, 4-({[5-(2-{[4-(2-{[(2R)-2-hydroxy-2-(8-hydroxy-2-oxo-1,2-dihydroquinolin-5-yl)ethyl]amino}-2-methylpropyl)phenyl]carbamoyl}ethyl)-2-phenylphenyl]carbamoyl}oxy)-1,1-dimethylpiperidin-1-ium, 4-({[4-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium, (1R,2R,4S,5S,7S)-7-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-9,9-dimethyl-3-oxa-9-azatricyclo[3.3.1.0²,⁴]nonan-9-ium, 4-{[(5-{2-[(5-{[(2R)-2-hydroxy-2-(8-hydroxy-2-oxo-1,2-dihydroquinolin-5-yl)ethyl]amino}pentyl)carbamoyl]ethyl}-2-phenylphenyl)carbamoyl]oxy}-1,1-dimethylpiperidin-1-ium, 4-{[(5-{[(7-{[(2R)-2-hydroxy-2-(8-hydroxy-2-oxo-1,2-dihydroquinolin-5-yl)ethyl]amino}heptyl)oxy]carbonyl}-2-phenylphenyl)carbamoyl]oxy}-1,1-dimethylpiperidin-1-ium, 4-({[5-(9-{[(2R)-2-hydroxy-2-(8-hydroxy-2-oxo-1,2-dihydroquinolin-5-yl)ethyl]amino}nonyl)-2-phenylphenyl]carbamoyl}oxy)-1,1-dimethylpiperidin-1-ium, 4-{[(5-{3-[4-(2-{[(2R)-2-hydroxy-2-(8-hydroxy-2-oxo-1,2-dihydroquinolin-5-yl)ethyl]amino}ethyl)phenoxy]propyl}-2-phenylphenyl)carbamoyl]oxy}-1,1-dimethylpiperidin-1-ium, 4-{[(5-{3-[(5-{[(2R)-2-hydroxy-2-(8-hydroxy-2-oxo-1,2-dihydroquinolin-5-yl)ethyl]amino}pentyl)oxy]propyl}-2-phenylphenyl)carbamoyl]oxy}-1,1-dimethylpiperidin-1-ium, 4-{[(5-{2-[4-(2-{[(2R)-2-hydroxy-2-(8-hydroxy-2-oxo-1,2-dihydroquinolin-5-yl)ethyl]amino}ethyl)phenoxy]ethoxy}-2-phenylphenyl)carbamoyl]oxy}-1,1-dimethylpiperidin-1-ium, 4-({[5-(2-{[4-({[(2R)-2-hydroxy-2-(8-hydroxy-2-oxo-1,2-dihydroquinolin-5-yl)ethyl]amino}methyl)phenyl]

formamido}ethyl)-2-phenylphenyl]carbamoyl}oxy)-1,1-dimethylpiperidin-1-ium, and 4-({[5-({2-[4-({[(2R)-2-hydroxy-2-(8-hydroxy-2-oxo-1,2-dihydroquinolin-5-yl)ethyl]amino}methyl)phenoxy]acetamido}methyl)-2-phenylphenyl]carbamoyl}oxy)-1,1-dimethylpiperidin-1-ium.

The compound (I) of the present invention may form an acid addition salt. In addition, it may form a salt with a base depending on the kind of the substituent. Such salts are not particularly limited as long as they are pharmaceutically acceptable salts. Specific examples of the acid addition salt include mineral acid salts such as hydrofluoride, hydrochloride, hydrobromide, hydroiodide, phosphorate, nitrate, sulfate; organic sulfonate such as methanesulfonate, ethanesulfonate, 2-hydroxyethanesulfonate, p-toluenesulfonate, benzenesulfonate, ethane-1,2-disulfonate ion, 1,5-naphthalenedisulfonate ion, and naphthalene-2-sulfonate ion; and organic carboxylate such as acetate, trifluoroacetate, propionate, oxalate, fumarate, phthalate, malonate, succinate, glutarate, adipate, tartrate, maleate, malate, 1-hydroxy-2-naphthoate and mandelate. Specific examples of the salt with a base include salts with inorganic bases such as sodium salt, potassium salt, magnesium salt, calcium salt, and aluminum salt and salts with organic bases such as methylamine salt, ethylamine salt, lysine salt, and ornithine salt.

The compound represented by formula (I) of the present invention may have isomers. Examples include isomers related to the ring or fused ring (E-, Z-, cis-, trans-form), isomers due to the presence of asymmetric carbon and the like (R-, S-form, α-, β-configuration, enantiomer, diastereomer), optically active substances having optical rotatory power (D-, L-, d-, l-form), tautomers, polar substances generated by chromatographic separation (high polar substance and low polar substance), equilibrium compounds, rotational isomers, mixtures thereof in any ratio, racemic mixtures, and the like.

Representative syntheses of the compounds of the present invention represented by general formula (I) are described below.

In the present invention, when raw material compounds or reaction intermediates have substituents that may affect reactions such as hydroxyl group, amino group and carboxyl group, it is desirable to carry out the reactions by suitably protecting the functional groups and eliminate the protecting groups after the reactions. The protecting groups are not particularly limited as long as they are commonly used for the respective substituents, and do not have adverse effects on other parts in protection or deprotection steps. Examples of the protecting groups for hydroxyl group include trialkylsilyl group, $C_{1-4}$ alkoxymethyl group, tetrahydropyranyl group, acyl group, $C_{1-4}$ alkoxycarbonyl group, and the like. Examples of the protecting groups for amino group include $C_{1-4}$ alkoxycarbonyl group, benzyloxycarbonyl group, acyl group, and the like. Examples of protecting groups of carboxyl group include $C_{1-4}$ alkyl group and the like. The deprotection reaction can be carried out according to a method usually used for each protecting group.

By way of example, the compounds of the present invention represented by general formula (I) can be produced by any of the general methods of production described below.

<Production Method 1>

[Chemical Formula 10]

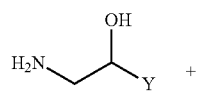

(a1)

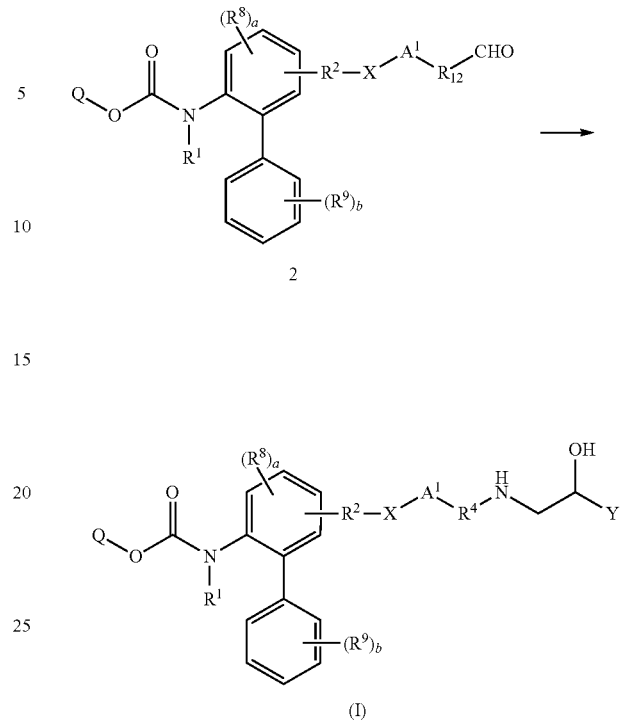

(In the formula, $A^1$, $R^4$, $R^8$, $R^9$, Y, Q, and $W^-$ are defined in the same way as those in general formula (I), and $R^{12}$ indicates alkylene having a number of carbon atoms less than that of $R^4$ by one (in the case where $R^4$ is methylene, a single bond).)

The reaction indicated by the reaction formula (a-1) above can be carried out by using well-known reductive amination reaction conditions. The reductive amination is carried out by reacting the compound 1 and compound 2 in the formula in an inert solvent (e.g., dimethyl sulfoxide, N,N-dimethylformamide, etc.) in the presence of a reducing agent (including borohydride reducing agents, e.g., sodium triacetoxyborohydride). $W^{1-}$, which is a counter ion of compound 2, is the same as $W^-$ or is replaced with $W^-$ by a known method after the reaction.

Compound 2 in the reaction formula (a-1) above can be prepared by oxidizing the compound of the following formula 3 using an appropriate oxidizing agent (e.g., manganese dioxide, or sulfur trioxide pyridine complex and dimethyl sulfoxide).

[Chemical Formula 11]

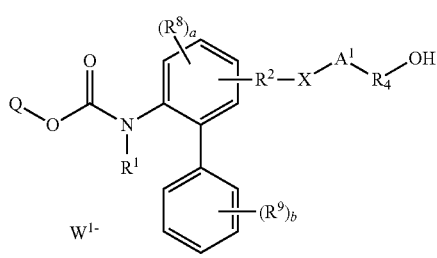

Compound 3 of the above formula can be prepared in two ways illustrated in the following reaction formula (a-2).

[Chemical Formula 12]

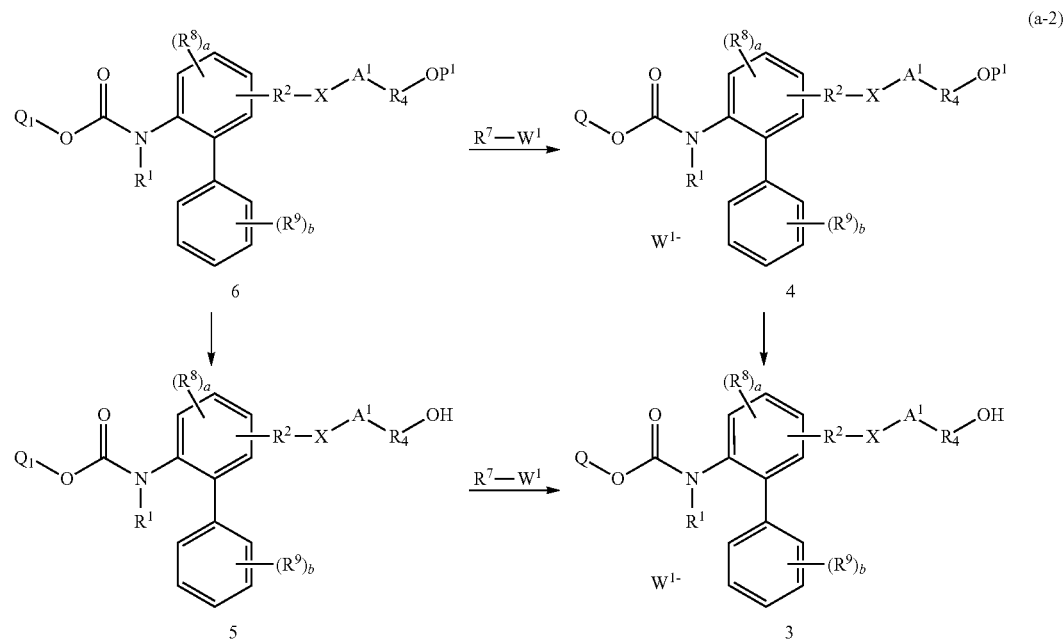

(In the above formula, $P^1$ indicates a general protecting group for hydroxyl group, and $Q^1$ indicates any of the following formulae.)

[Chemical Formula 13]

[Chemical Formula 14]

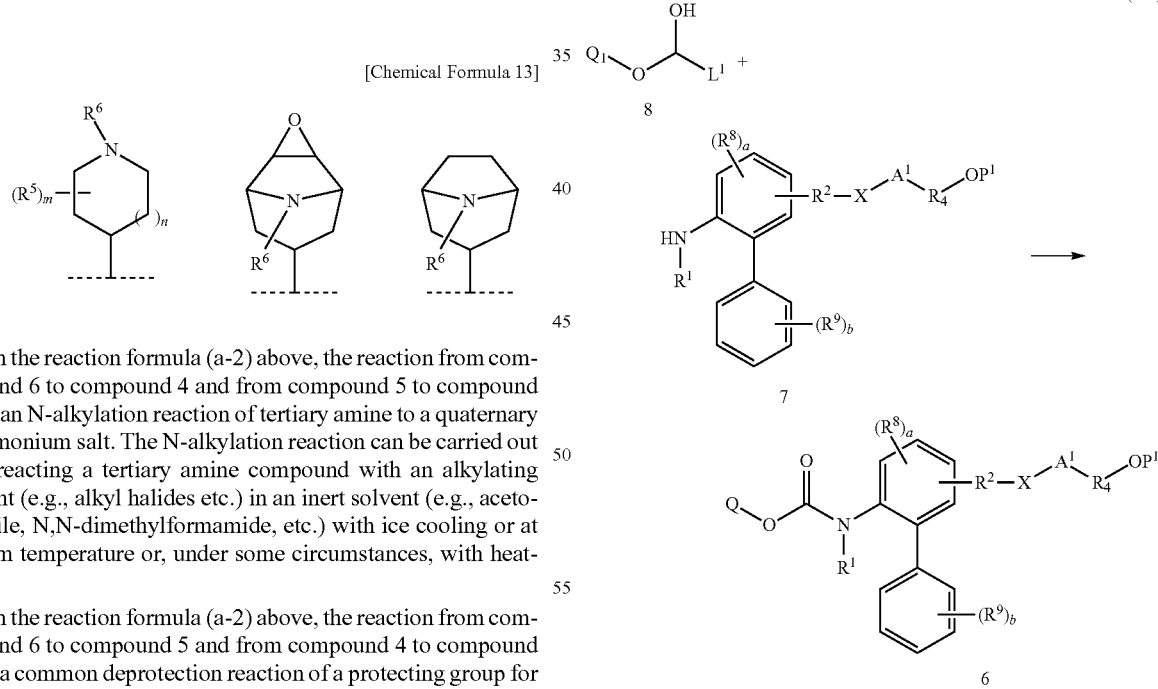

In the reaction formula (a-2) above, the reaction from compound 6 to compound 4 and from compound 5 to compound 3 is an N-alkylation reaction of tertiary amine to a quaternary ammonium salt. The N-alkylation reaction can be carried out by reacting a tertiary amine compound with an alkylating agent (e.g., alkyl halides etc.) in an inert solvent (e.g., acetonitrile, N,N-dimethylformamide, etc.) with ice cooling or at room temperature or, under some circumstances, with heating.

In the reaction formula (a-2) above, the reaction from compound 6 to compound 5 and from compound 4 to compound 3 is a common deprotection reaction of a protecting group for hydroxyl group. For example, when $P^1$ is a trialkylsilyl group, the reaction can be carried out by the treatment with trifluoroacetic acid, hydrogen fluoride-triethylamine complex, and the like; when $P^1$ is an acyl group, it can be carried out by the treatment under common alkaline hydrolysis conditions.

Compound 6 in the reaction formula (a-2) above can be prepared by the step illustrated in the following reaction formula (a-3).

(In the above reaction formula, $L^1$ indicates a leaving group.)

The reaction can be carried out in the presence of a base (e.g., pyridine, triethylamine, etc.) in an inert solvent (e.g., acetonitrile, N,N-dimethylformamide, etc.) or without a solvent, with ice cooling or at room temperature or, under some circumstances, with heating. Examples of the leaving group include halogen, methanesulfonyloxy, benzenesulfonyloxy, and the like.

In addition, when X indicates —CONR³—, compound 6 can also be prepared by the step illustrated in the following reaction formula (a-4).

[Chemical Formula 15]

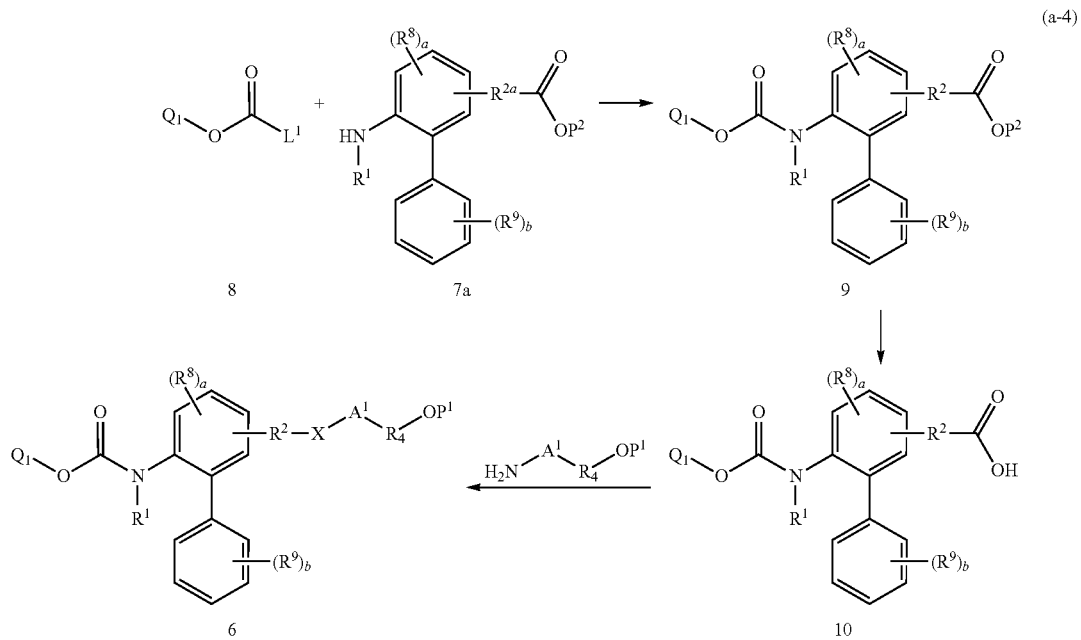

(a-4)

(In the above reaction formula, R¹² indicates alkylene having a number of carbon atoms less than that of R² by one (in the case where R⁴ is methylene, a single bond) and P² indicates a common protecting group for carboxyl group.)

In the reaction formula (a-4) above, the reaction from compound 8 and compound 7a to compound 9 can be carried out under the same conditions as the reaction in reaction formula (a-3). The reaction from compound 9 to compound 10 is a deprotection reaction of a protecting group for carboxyl group. The deprotection reaction can be carried out under common acid hydrolysis conditions, alkaline hydrolysis conditions, catalytic reduction conditions, or the like. The reaction from compound 10 to compound 6 can be carried out by using well-known amidation reaction conditions. Such amidation reaction can usually be carried out by subjecting amines to a condensation reaction with carboxylic acid in the presence of condensing agents such as carbodiimide. In this case, halogenated hydrocarbons such as N,N-dimethylformamide and chloroform are suitable as solvents, and N,N-dicyclohexylcarbodiimide, 1-ethyl-(3-(N,N-dimethylamino)propyl)carbodiimide, carbonyldiimidazol, diphenylphosphoryl azide, diethylphosphoryl cyanide and the like are used as the condensing agents. The reaction is usually carried out with cooling or at room temperature, or under some circumstances, with heating.

Compound 7 in the reaction formula (a-3) above can be prepared by the steps illustrated in the following reaction formula (a-5), when R² indicates a single bond; X indicates —O—; A¹ indicates a single bond; and R⁴ indicates $C_{1-10}$ alkylene, or when R² indicates —O—$C_{1-4}$ alkylene; X indicates —O—; A¹ indicates phenylene; and R⁴ indicates $C_{1-4}$ alkylene.

[Chemical Formula 16]

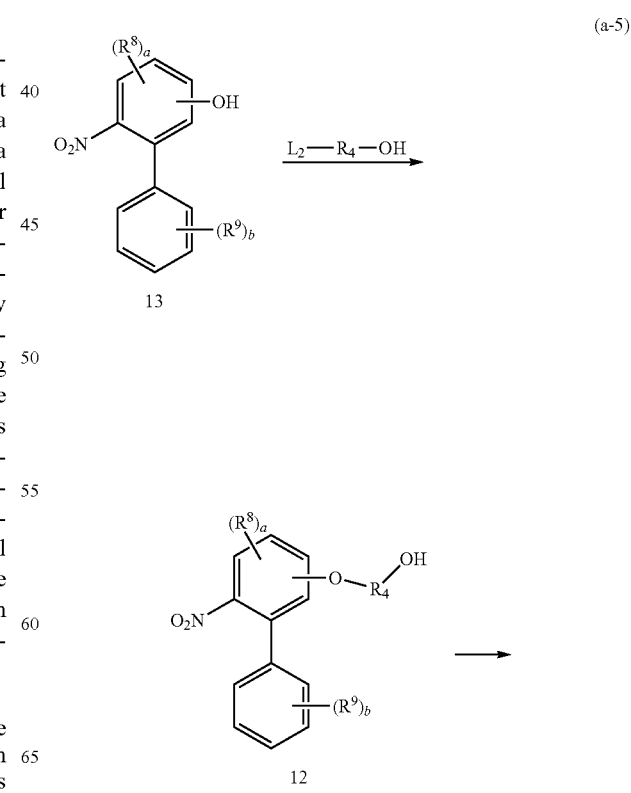

(a-5)

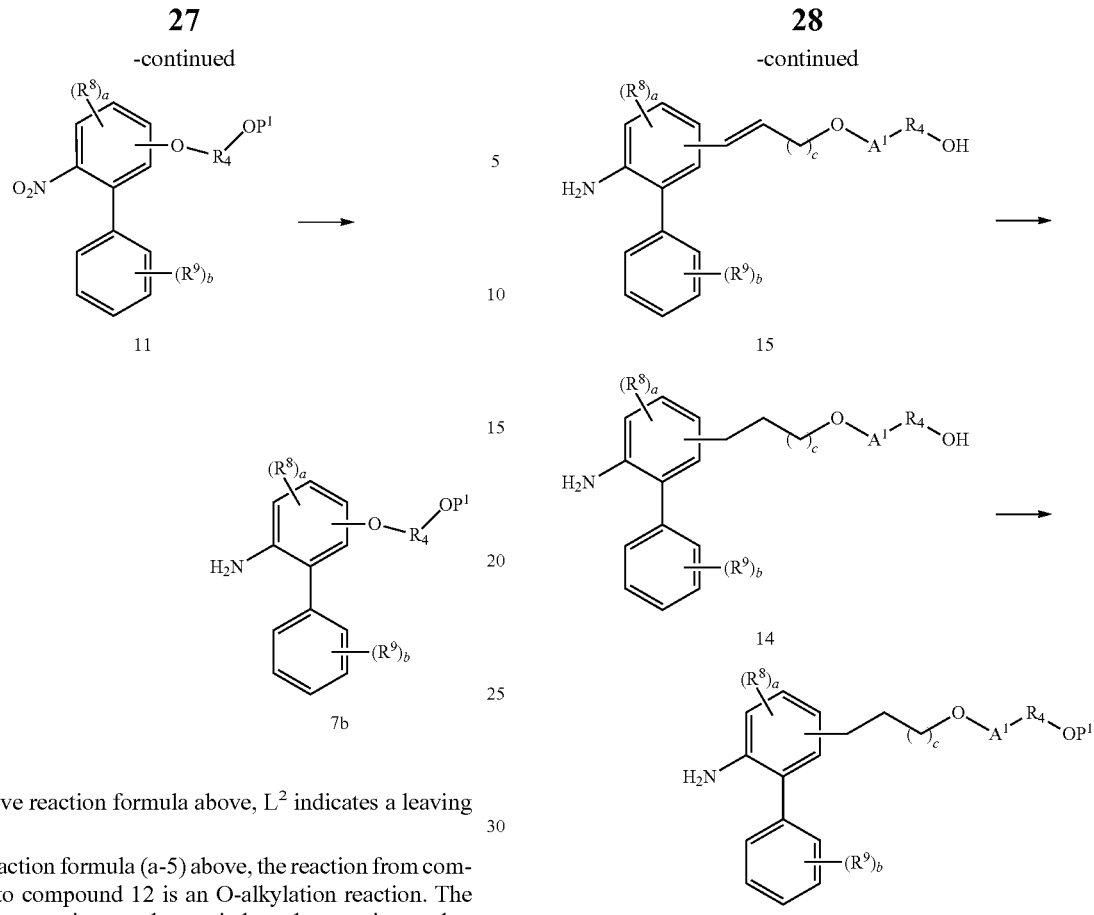

(In the above reaction formula above, $L^2$ indicates a leaving group.)

In the reaction formula (a-5) above, the reaction from compound 13 to compound 12 is an O-alkylation reaction. The O-alkylation reaction can be carried out by reacting a phenolic hydroxyl group-containing compound with an alkylating agent (e.g., alkyl halides etc.) in an inert solvent (e.g., acetonitrile, N,N-dimethylformamide, etc.) in the presence of a base (e.g., potassium carbonate etc.) at room temperature or, under some circumstances, with heating. The reaction from compound 12 to compound 11 is a protection reaction of a hydroxyl group, which can be carried out by a well-known method. The reaction from compound 11 to compound 7b is a reduction reaction of a nitro group, which can be carried out under common conditions of catalytic reduction, tin chloride treatment, and the like.

Compound 7 in the reaction formula (a-3) above can be prepared by the steps illustrated in the following reaction formula (a-6), when $R^2$ indicates $C_{1-8}$ alkylene; X indicates —O—; $A^1$ indicates phenylene; and $R^4$— indicates phenylene-$C_{3-4}$ alkylene.

[Chemical Formula 17]

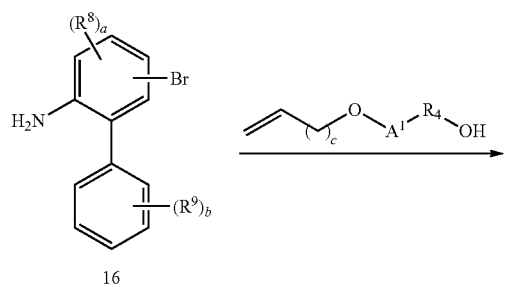

(a-6)

(In the above reaction formula, c indicates an integer of 1 or 2.)

In the reaction formula (a-6) above, the reaction from compound 16 to compound 15 is a so-called Heck reaction in which aryl halides react with alkene. The reaction can be carried out in the presence of palladium, a phosphine ligand and a base in an inert solvent, with heating and stirring. The reaction from compound 15 to compound 14 is a reduction reaction of a double bond, which can be carried out by a well-known method such as catalytic reduction. The reaction from compound 14 to compound 7c is a protection reaction of a hydroxyl group, which can be carried out by a well-known method.

Compound 7, compound 7a, compound 8, compound 13, and compound 16 can be prepared according to well-known procedures using starting materials and reagents which are well known in the art or which are commercially available.

<Production Method 2>

[Chemical Formula 18]

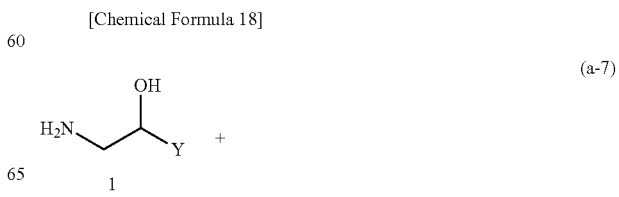

(a-7)

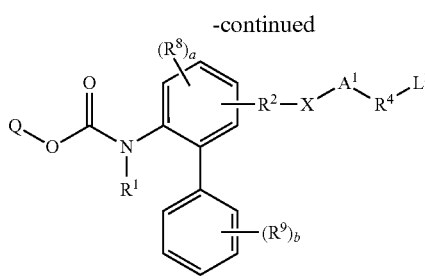

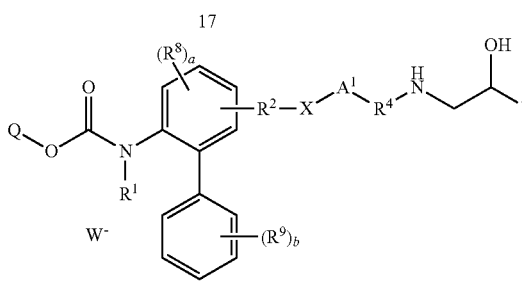

(In the formula, $A^1$, $R^4$, $R^8$, $R^9$, Y, Q, and $W^-$ are defined in the same way as those in general formula (I), and $L^3$ indicates a leaving group.)

The reaction indicated by the reaction formula (a-7) above is an N-alkylation reaction. Preferred examples of $L^3$ include a halogen atom (e.g., a chlorine atom, a bromine atom, an iodine atom), a sulfonyloxy group, and a benzenesulfonyloxy group. The reaction can be carried out in an inert solvent (e.g., acetonitrile, N,N-dimethylformamide, etc.) at room temperature or, under some circumstances, with heating. $W^{1-}$, which is a counter ion of compound 3, is the same as $W^-$ or is replaced with $W^-$ by a known method after the reaction. Compound 17 can be prepared from the above-mentioned compound 3 by a known method.

Compound 1 in the reaction formulae (a-1) and (a-7) above can be prepared by the steps illustrated in the following reaction formula (b-1).

[Chemical Formula 19]

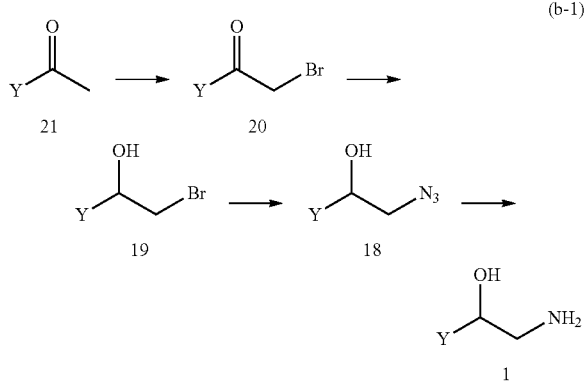

(b-1)

In the reaction formula (a-6) above, the reaction from compound 21 to compound 20 is a halogenation reaction, which can be carried by reacting a compound of compound 21 with bromine in the presence of Lewis acids (e.g., boron trifluoride diethyl etherate). The reaction from compound 20 to compound 19 is a reduction reaction, which can be carried out by reacting compound 20 with a reducing agent (e.g., borane). If desired, such a reduction can be performed in the presence of a chiral catalyst to provide an optically active compound 1. For example, the reduction can be carried out in the presence of a chiral catalyst (which is formed from (R)-(+)-α,α-diphenyl-2-pyrrolidinemethanol and trimethylboroxine; or from (S)-(−)-α,α-diphenyl-2-pyrrolidinemethanol and trimethylboroxine). The reaction from compound 19 to compound 18 is an azidation reaction, which can be carried out by reacting compound 19 with sodium azide. The reaction from compound 19 to compound 18 is a reducing reaction, which can be carried out by treating compound 18 under common catalytic reduction conditions. Compound 21 can be prepared according to well-known procedures using starting materials and reagents which are well known in the art or are commercially available.

<Production Method 3>

[Chemical Formula 20]

(In the formula, $A^1$, $R^4$, $R^8$, $R^9$, Y, Q, and $W^-$ are defined in the same way as those in general formula (I), and $P^3$ indicates a common protecting group for hydroxyl group.)

The reaction illustrated in the reaction formula (a-8) above is a deprotection reaction of a protection group for hydroxyl group. The deprotection can be carried out by a known method. For example, when $P^3$ is a tert-butyldimethylsilyl group, the reaction can be carried out by treating with tetrabutylammonium fluoride, trifluoroacetic acid, and the like.

Compound 22 in the reaction formula (a-8) above can be prepared by using the compound of the following formula 1a, instead of compound 1, in <Production Method 1> or <Production Method 2>.

[Chemical Formula 21]

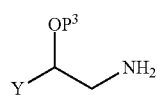

1a

Compound 1a in the above formula can be produced by carrying out a general introduction reaction of a protecting group to a hydroxyl group between any of the steps of the reaction formula (b-1) above.

<Production Method 4>

[Chemical Formula 22]

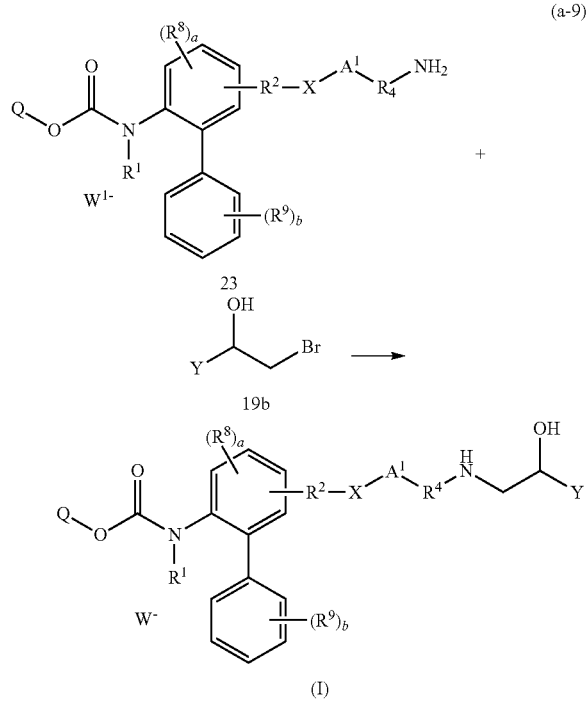

In the reaction formula (a-9) above, the reaction of compound 23 with compound 19b is an N-alkylation reaction. The N-alkylation reaction can be carried out in the presence of a base (e.g., potassium carbonate etc.) in an inert solvent (e.g., acetonitrile, N,N-dimethylformamide, etc.) at room temperature or, under some circumstances, with heating. It is desirable that the phenolic hydroxyl group contained in compound 19b is protected during the reaction. Examples of the protecting group include, for example, a benzyl group, a p-methoxybenzyl group, and the like. The protecting group can be deprotected under common conditions of deprotection reaction (e.g., catalytic reduction etc.), following the N-alkylation reaction. $W^{1-}$, which is a counter ion of compound 23, is the same as $W^-$ or is replaced with $W^-$ by a known method after the reaction.

The compound of formula (I) is isolated and purified as a substance such as a free compound, or a salt, hydrate or solvate thereof. Conventional salt-formation or salt-exchange reactions can also be employed to produce the salt of the compound of formula (I).

The isolation or purification can be carried out by applying common chemical operations such as extraction and/or various types of fractional chromatography.

The compounds of the present invention possess β2 adrenergic receptor agonist activity and muscarinic receptor antagonist activity and have persistent bronchodilator effects through topical administration. Therefore, they are useful for treating medical conditions mediated by the β2 adrenergic receptor or muscarinic receptor, i.e., medical conditions that are ameliorated by treatment with a β2 adrenergic receptor agonist or a muscarinic receptor antagonist). Such medical conditions include, for example, pulmonary disorders or diseases associated with reversible airway obstruction, such as chronic obstructive pulmonary disease (e.g., bronchitis which is chronic and involves wheezing (wheezes), and pulmonary emphysema), asthma, pulmonary fibrosis, and the like.

Other conditions that can be treated include premature labor, depression, congestive heart failure, and skin diseases (e.g., inflammatory, allergic, psoriatic and proliferative skin diseases, conditions where lowering peptic acidity is desirable (e.g., peptic and gastric ulceration), and muscle wasting disease).

In addition, the present invention provides a pharmaceutical composition comprising a pharmaceutically available carrier and a compound of formula (I) or a pharmaceutically acceptable salt, solvate, hydrate or stereoisomer thereof. Such a pharmaceutical composition may be administered in combination with other therapeutic agents as a concomitant drug if necessary, for the purposes of enhancement of preventive and/or therapeutic effects etc.

The concomitant drug of the pharmaceutical composition of the present invention and other agents may be administered in the form of a combined drug containing both components in a single preparation, or may take a form to be administered in separate preparations. The administration in separate preparations includes simultaneous administration and administration at different times. In the case of administration at different times, the pharmaceutical composition of the present invention may be administered prior to or after administration of other agents and the same or different administration methods may be employed in the administrations.

Other agents mentioned above may be low-molecular weight compounds, or may be high-molecular weight proteins, polypeptides, polynucleotides (DNA, RNA, genes), antisense, decoys, antibodies, vaccines, or the like. Doses of other agents can be appropriately selected based on the doses which are clinically used. For example, with respect to 1 part by mass of the compound of the present invention, from 0.01 to 100 parts by mass of other agents may be used. In addition, any two or more of other agents may be combined in appropriate proportions to be administered. Other agents capable of the enhancement of the preventive and/or therapeutic effects etc. of the therapeutic agents of the present invention include not only those which have been found so far but also those which will be found in the future, based on the mechanism described above. The diseases on which the above concomitant drugs exhibit preventive and/or therapeutic effects are not particularly limited and may include any diseases as long as the therapeutic agents of the present invention exhibit enhanced preventive and/or therapeutic effects etc. on them.

For example, other agents for enhancement of the preventive and/or therapeutic effects etc. of the therapeutic agents of the present invention include, for example, β2 adrenergic receptor agonists, muscarinic receptor antagonists, leukotriene receptor antagonists, antihistamines, antiallergic agents, steroidal anti-inflammatory agents, agents for vaccine therapy, herbal medicines, non-steroidal anti-inflammatory agents, 5-lipoxygenase inhibitors, 5-lipoxygenase activating protein antagonists, leukotriene synthesis inhibitors, prostaglandins, cannabinoid-2 receptor stimulants, antitussives, expectorants, phosphodiesterase inhibitors, extracts of inflamed rabbit skin induced by inoculation of vaccinia virus, and the like.

Representative β2 adrenergic receptor agonists that can be used in combination with the compounds of the present invention include, but are not limited to, salmeterol, salbutamol, formoterol, indacaterol, salmefamole, fenoterol, terbutaline, albuterol, isoetharine, metaproterenol, bitolterol, pirbuterol, levalbuterol and the like, or a pharmaceutically acceptable salt thereof Representative muscarinic antagonists that can be used in combination with the compounds of the present invention include, but are not limited to, atropine, atropine sulfate, atropine oxide, methylatropine sulfate, homatropine hydrobromide, hyoscyamine hydrobromide (d, l), scopolamine hydrobromide, ipratropium hydrobromide, oxitropium hydrobromide, tiotropium bromide, methantheline, propantheline hydrobromide, anisotropine methyl bromide, clidinium bromide, copyrrolate, isopropamide iodide, mepenzolate bromide, tridihexethyl chloride, hexocyclium methylsulfate, cyclopentolate hydrochloride, tropicamide, trihexyphenidyl hydrochloride, pirenzepine, telenzepine, methoctramine and the like, or a pharmaceutically acceptable salt thereof; or, for those compounds listed as a salt, alternate pharmaceutically acceptable salt thereof.

Representative leukotriene receptor antagonists that can be used in combination with the compounds of the present invention include, but are not limited to, pranlukast hydrate, montelukast sodium, zafirlukast and the like, or a pharmaceutically acceptable salt thereof; or, for those compounds listed as a salt, alternate pharmaceutically acceptable salt thereof.

Representative antihistamines that can be used in combination with the compounds of the present invention include, but are not limited to, carbinoxamine maleate, clemastine fumarate, diphenylhydramine hydrochloride, dimenhydrinate, pyrilamine maleate, tripelennamine hydrochloride, tripelennamine citrate, chlorpheniramine and acrivastine, hydroxyzine hydrochloride, hydroxyzine pamoate, cyclizine hydrochloride, cyclizine lactate, meclizine hydrochloride and cetirizine hydrochloride, astemizole, levocabastine hydrochloride, loratadine or its descarboethoxy analogue, terfenadine, fexofenadine hydrochloride, azelastine hydrochloride and the like, or a pharmaceutically acceptable salt thereof or, for those compounds listed as a salt, alternate pharmaceutically acceptable salt thereof.

Representative antiallergic agents that can be used in combination with the compounds of the present inventions include, but are not limited to, sodium cromoglicate, tranilast, amlexanox, repirinast, ibudilast, pemiro last potassium, tazanolast, ozagrel hydrochloride, imitrodast sodium, seratrodast, ramatroban, domitroban calcium and the like, or a pharmaceutically acceptable salt thereof; or, for those compounds listed as a salt, alternate pharmaceutically acceptable salt thereof.

Representative steroidal anti-inflammatory agents that can be used in combination with this compounds of the invention include, but are not limited to, methylprednisolone, prednisolone, dexamethasone, fluticasone, beclomethasone propionate, budesonide, flunisolide, ciclesonide and the like, or a pharmaceutically acceptable salt thereof or, for those compounds listed as a salt, alternate pharmaceutically acceptable salt thereof Representative agents for vaccine therapy that can be used in combination with the compounds of the present invention include paspat, asthremedin, Broncasma Berna, and the like.

Representative non-steroidal anti-inflammatory agents that can be used in combination with the compounds of the present invention include, but are not limited to, aspirin, loxonin, diclofenac, celecoxib, alminoprofen, pranoprofen, ibuprofen, droxicam, aceclofenac, ketoprofen, piroxicam, emorfazone, auranofin, piroxicam, lornoxicam, emorfazone and the like, or a pharmaceutically acceptable salt thereof.

Representative leukotriene synthesis inhibitors that can be used in combination with the compounds of the present invention include, but are not limited to, auranofin, proglumetacin maleate and the like, or a pharmaceutically acceptable salt thereof.

Representative antitussives that can be used in combination with the compounds of the present invention include, but are not limited to, codeine phosphate, dihydrocodeine phosphate, oxymetebanol, noscapine and the like, or a pharmaceutically acceptable salt thereof.

Representative expectorants that can be used in combination with the compounds of the present invention include, but are not limited to, foeniculated ammonia spirit, bromhexine hydrochloride, cherry bark extract, carbocisteine, ambroxol hydrochloride, methylcysteine hydrochloride, acetylcysteine, L-ethylcysteine hydrochloride and the like, or a pharmaceutically acceptable salt thereof; or, for those compounds listed as a salt, alternate pharmaceutically acceptable salt thereof.

Representative phosphodiesterase inhibitors that can be used in combination with the compounds of the present invention include, but are not limited to, doxofylline, roflumilast, cilomilast and the like, or a pharmaceutically acceptable salt thereof.

When used to treat or prevent a pulmonary disease, the compounds of the present invention are optionally administered in combination with other therapeutic agents. In particular, by combining the compounds of the present invention with a steroidal anti-inflammatory agent (e.g. a corticosteroid), the pharmaceutical compositions of the present invention can provide triple therapy, i.e., β2 adrenergic receptor agonist, muscarinic receptor antagonist and anti-inflammatory activity, using only two active components. Since pharmaceutical compositions containing two active components are typically easier to formulate compared to compositions containing three active components, such two-active-component compositions provide a significant advantage over single, three-active-component compositions consisting of three drugs. Accordingly, in a particular embodiment, the pharmaceutical compositions and methods of the present invention further include a therapeutically effective amount of a steroidal anti-inflammatory agent.

Technologies widely used as single or combined preparations can be used to formulate the compounds of the present invention, optionally adding pharmaceutically acceptable additives.

To use the compounds of the invention or concomitant drugs of the compounds of the invention and other agents for the purpose described above, they are usually administered topically in parenteral forms.

The doses of the compounds of the invention are generally about 0.1 μg to 10 mg per dose for adults, depending on age, body weight, symptom, therapeutic effect, administration method, and the like, and the dose frequency is preferably once to twice per day.

Parenterals include, for example, inhalants and the like. These preparations may be controlled-release preparations such as rapid-release preparations and sustained-release preparations. These preparations can be produced by known methods, such as those described in the Japanese Pharmacopoeia and the like.

Inhalants for parenteral administration include aerosols, powders for inhalation, liquids for inhalation (e.g., solutions for inhalation, suspensions for inhalation, etc.), or capsule-form inhalants. The liquid inhalants may be in the form that is dissolved or suspended in water or in any other suitable medium at the time of use. These inhalants can be applied using a suitable inhaler container. For example, sprayers (atomiser, nebulizer) and the like can be used to administer liquids for inhalation, and inhalation dosing devices for powder and the like can be used to administer powders for inhalation.

These inhalants are produced according to known methods. For example, the compounds of the present invention are mixed with a powdered or liquefied inhalation propellant and/or carrier and are then powdered according to a conventional method. For example, powders are prepared by making the compound fine powder together with lactose, starch, magnesium stearate and the like to make it a homogeneous mixture or to granulate it. When the compounds of the present invention are liquefied, the compounds may be dissolved, for example, in a liquid-form carrier such as water, physiologic saline or organic solvent. As the propellants, conventionally-known propellants, such as chlorofluorocarbon substitutes, liquefied gas propellants (e.g., fluorohydrocarbon, liquefied petroleum gas, diethyl ether, dimethyl ether, etc.), compressed gas (carbon dioxide gas, nitrous oxide gas, nitrogen gas, etc.) and the like are used.

The inhalants may further contain additives appropriately if necessary. Anything may be used as the additive as long as it is an additive commonly used. For example, the following additives are employed: a solid excipient (e.g., lactose, sucrose, glucose, cellulose, etc.); a liquid excipient (e.g., propylene glycol etc.); a binder (e.g., starch, dextrin, methylcellulose, hydroxypropylcellulose, polyethylene glycol, etc.); a lubricant (e.g., magnesium stearate, light silicic acid anhydride, talc, sodium laurate, etc.); a flavoring agent (e.g., citric acid, menthol, ammonium glycyrrhizate, glycine, orange powder, etc.); a preservative (e.g, sodium benzoate, sodium bisulfite, methylparaben, propylparaben, etc.); a stabilizer (e.g., citric acid, sodium citrate, etc.); a suspending agent or an emulsifier (e.g., methylcellulose, polyvinyl pyrrolidone, lecithin, sorbitan trioleate, etc.); a dispersing agent (e.g., surfactant etc.); a solvent (e.g., water etc.); an isotonic agent (e.g., sodium chloride, concentrated glycerin, etc.); a pH adjusting agent (e.g., hydrochloric acid, sulfuric acid, acetic acid, etc.); a solubilizing agent (e.g., ethanol etc.); an antiseptic (e.g., benzalkonium chloride, paraben, etc.); a colorant; a buffering agent (e.g., sodium phosphate, sodium acetate, etc.); a thickening agent (e.g., carboxyvinyl polymer etc.); an absorption promoter; and the like. For example, in the case of liquids for inhalation, an antiseptic, a suspending agent or a emulsifier, a solvent, a solubilizing agent, a preservative, a stabilizer, a colorant, a buffering agent, a pH adjusting agent, an isotonic agent, a thickener, and the like are appropriately selected, if necessary, to be used in the preparation. Also for example, in the case of powders for inhalation, a solid excipient, a binder, a lubricant, a preservative, a stabilizer, an antiseptic, and the like are appropriately selected, if necessary, to be used in the preparation.

Furthermore, in order to make the compound of the present invention sustained-release, the inhalant may contain an in vivo degrading polymer. Examples of the in vivo degrading polymer include fatty acid ester polymers or copolymers thereof, polyacrylic acid esters, polyhydroxy butyric acids, polyalkylene oxalates, polyorthoesters, polycarbonates, and polyamines. One kind of these or a mixture of more than one of these can be used. Phospholipids such as egg yolk lecithin, chitosan, and the like may also be employed. The fatty acid ester polymers or copolymers thereof include polylactic acid, polyglycolic acid, polycitric acid, polymalic acid, and lactic acid-glycolic acid copolymers. One kind of these or a mixture of more than one of these can be used. In addition, microspheres and nanospheres encapsulating drugs may also be prepared using an in vivo degrading polymer such as lactic acid-glycolic acid copolymer.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

EXAMPLES

Hereinafter, the present invention will be described in detail by way of Examples. However, the scope of the present invention is not limited in any way by these Examples. The Example number and the product number of a compound produced in the Example are the same.

Unless noted otherwise, reagents, starting materials, and solvents were purchased from vendors (for example, Aldrich, Wako Junyaku, Tokyo Kasei, Fluka, Sigma, and the like) and used without further purification.

Reference Example 1

Synthesis of 8-hydroxyquinoline-N-oxide

8-Quinolinol (351 g, 2.42 mol) was dissolved in dichloromethane (3.5 L) and, under ice-water cooling, meta-chloroperbenzoic acid (675.3 g, 2.74 mol) was added thereto in portions, and the mixture was stirred at room temperature for 2 hours. Insoluble matter was removed by filtration and was washed with dichloromethane. The filtrate and the washing were mixed and concentrated under reduced pressure. To the residue, 2% aqueous ammonia (2.1 L) was added and the mixture was stirred at room temperature overnight. The precipitate was collected by filtration, washed with purified water, and dried under reduced pressure to obtain 8-hydroxyquinoline-N-oxide (318.4 g).

$^1$H-NMR (400 MHz, DMSO-$d_6$) δ8.51 (d, J=8.0 Hz, 1H), 8.06 (d, J=8.0 Hz, 1H), 7.43-7.56 (m, 2H), 7.39 (d, J=8.0 Hz, 1H), 6.98 (d, J=8.0 Hz, 1H)

Reference Example 2

Synthesis of 8-acetoxy-1H-quinolin-2-one

8-Hydroxyquinoline-N-oxide (640 g, 3.97 mol) was suspended in acetic anhydride (2.0 L) and the mixture was stirred at 70° C. for 2.5 hours. Under ice-water cooling, the reaction mixture was stirred at 10° C. or lower for 1 hour and, thereafter, the precipitate was collected by filtration, washed with purified water, and dried under vacuum to obtain 8-acetoxy-1H-quinolin-2-one (570.6 g).

$^1$H-NMR (400 MHz, DMSO-$d_6$) δ11.6 (s, 1H), 7.94 (d, J=9.6 Hz, 1H), 7.56 (d, J=8.0 Hz, 1H), 7.28 (d, J=8.0 Hz, 1H), 7.17 (t, J=8.0 Hz, 1H), 6.53 (d, J=9.6 Hz, 1H), 7.56 (d, 2.36 (s, 3H)

Reference Example 3

Synthesis of 5-acetyl-8-hydroxy-1H-quinolin-2-one

8-Acetoxy-1H-quinolin-2-one (570.6 g, 2.81 mol) was suspended in dichloroethane (5.8 L), aluminum chloride (925 g, 6.94 mol) was added thereto in portions at 20° C. or lower under ice-water cooling, and the mixture was stirred at 70° C. to 80° C. for 3 hours. The reaction mixture was concentrated under reduced pressure. To the residue was added 1 M hydrochloric acid (10 L) and the mixture was stirred at room temperature overnight. The precipitate was collected by filtration, washed with purified water, and dried under reduced pressure to obtain 5-acetyl-8-hydroxy-1H-quinolin-2-one (584 g).

$^1$H-NMR (400 MHz, DMSO-$d_6$) δ 11.3 (s, 1H), 10.6 (s, 1H), 8.66 (d, J=10.0 Hz, 1H), 7.67 (d, J=8.4 Hz, 1H), 6.91 (d, J=8.4 Hz, 1H), 6.52 (d, J=10.0 Hz, 1H), 2.41 (s, 3H)

Reference Example 4

Synthesis of
5-acetyl-8-benzyloxy-1H-quinolin-2-one

5-Acetyl-8-hydroxy-1H-quinolin-2-one (430 g, 2.12 mol) was suspended in N,N-dimethylformamide (3.3 L), potassium carbonate (298 g, 2.16 mol) and subsequently benzyl bromide (298 g, 2.11 mol) were added thereto, and the mixture was stirred at room temperature for 2 hours. The insoluble matter was removed by filtration and washed with N,N-dimethylformamide. The filtrate and the washing were mixed and concentrated under reduced pressure. To the residue was added purified water (3.3 L) and the mixture was stirred at room temperature overnight. The precipitate was collected by filtration, washed with purified water, and dried under vacuum to obtain 5-acetyl-8-benzyloxy-1H-quinolin-2-one (541 g).

$^1$H-NMR (400 MHz, CDCl$_3$) δ 9.23 (s, 1H), 8.93 (d, J=10.0 Hz, 1H), 7.69 (d, J=8.0 Hz, 1H), 7.43 (s, 5H), 7.04 (d, J=8.0 Hz, 1H), 6.77 (d, J=10.0 Hz, 1H), 5.26 (s, 2H), 2.65 (s, 3H)

Reference Example 5

Synthesis of
8-benzyloxy-5-(2-bromoacetyl)-1H-quinolin-2-one

5-Acetyl-8-benzyloxy-1H-quinolin-2-one (372 g, 1.27 mol) was dissolved in tetrahydrofuran (3.6 L) and the solution was cooled to 0° C. Pyridinium tribromide (453 g, 1.27 mol) was added thereto in portions, and the mixture was heated under reflux for 3 hours. Thereafter, tetrahydrofuran (3.1 L) was added and the mixture was heated under reflux overnight. The precipitate was collected by filtration and washed with tetrahydrofuran. The solid was suspension-washed with tetrahydrofuran (2.3 L) and, thereafter, washed with purified water (3 L). Separately, the tetrahydrofuran filtrate and the washings were mixed, concentrated under reduced pressure, and the residue was suspension-washed with tetrahydrofuran (1 L). The solids were combined and dried under reduced pressure to obtain 8-benzyloxy-5-(2-bromoacetyl)-1H-quinolin-2-one (387 g).

$^1$H-NMR (400 MHz, DMSO-$d_6$) δ 11.1 (s, 1H), 8.49 (d, J=9.0 Hz, 1H), 7.86 (d, J=9.0 Hz, 1H), 7.58 (d, J=8.0 Hz, 2H), 7.25-7.45 (m, 5H), 6.67 (d, J=9.0 Hz, 1H), 7.86 (d, 5.42 (s, 2H), 4.91 (s, 2H)

Reference Example 6

Synthesis of 8-benzyloxy-5-((R)-2-bromo-1-hyroxyethyl)-1H-quinolin-2-one

Under an argon flow, 8-benzyloxy-5-(2-bromoacetyl)-1H-quinolin-2-one (374 g, 1.00 mol) was suspended in dehydrated tetrahydrofuran (3.8 L), CBS catalyst (27.8 g) was added thereto, and the mixture was stirred at −55 to −45° C. for 40 minutes. After adding dropwise a 0.9 M tetrahydrofuran solution of borane-tetrahydrofuran complex (1.27 L) at the same temperature, the reaction mixture was gradually warmed to 0° C. After adding methanol (1.3 L) dropwise, insoluble matter was removed by filtration and washed with tetrahydrofuran. The filtrate and the washing were mixed and concentrated under reduced pressure. To the residue was added purified water (6.3 L), and the mixture was stirred at room temperature overnight. The precipitate was collected by filtration and washed with purified water. Further, the precipitate was suspension-washed with ethyl acetate (4.8 L), collected by filtration, and dried under reduced pressure to obtain 8-benzyloxy-5-((R)-2-bromo-1-hyroxyethyl)-1H-quinolin-2-one (278 g). $^1$H-NMR (400 MHz, CDCl$_3$) δ 9.26 (s, 1H), 8.08 (d, J=10.0 Hz, 1H), 7.37-7.45 (m, 5H), 7.28 (d, J=8.0 Hz, 1H), 7.05 (d, J=8.0 Hz, 1H), 6.72 (d, J=10.0 Hz, 1H), 5.33 (dd, J=9.0 Hz, 4.0 Hz, 1H), 5.19 (s, 2H), 3.71-3.74 (m, 2H)

Reference Example 7

Synthesis of 5-((R)-2-azido-1-hyroxyethyl)-8-benzyloxy-1H-quinolin-2-one

8-Benzyloxy-5-((R)-2-bromo-1-hyroxyethyl)-1H-quinolin-2-one (20.8 g, 55.6 mmol) and sodium azide (3.61 g, 55.5 mmol) were suspended in N,N-dimethylformamide (100 mL) and the mixture was stirred at 65° C. for 3 hours. Sodium azide (1.81 g, 27.8 mmol) was added thereto and the mixture was stirred at the same temperature overnight. To the reaction solution was added purified water and stirred at room temperature for 1 hour. The precipitate was collected by filtration and washed with purified water. By drying under reduced pressure, 5-((R)-2-azido-1-hyroxyethyl)-8-benzyloxy-1H-quinolin-2-one (16.8 g) was obtained.

$^1$H-NMR (400 MHz, DMSO-$d_6$) δ 10.7 (s, 1H), 8.19 (d, J=12.0 Hz, 1H), 7.56 (d, J=8.0 Hz, 2H), 7.34-7.41 (m, 1H), 7.26-7.33 (m, 1H), 7.20 (s, 2H), 6.54 (d, J=8.0 Hz, 1H), 5.90 (d, J=8.0 Hz, 1H), 5.30 (s, 2H), 5.18-5.26 (m, 1H), 3.44 (dd, J=12.0 Hz, 8.0 Hz, 1H), 3.30 (dd, J=16.0 Hz, 4.0 Hz, 1H)

Reference Example 8

Synthesis of 5-((R)-2-amino-1-hyroxyethyl)-8-hydroxy-1H-quinolin-2-one acetate 5-((R)-2-Azido-1-hyroxyethyl)-8-benzyloxy-1H-quinolin-2-one (16.8 g, 49.9 mol) was suspended in acetic acid (50 mL), a catalytic amount of palladium hydroxide-carbon was added thereto, and the solution was stirred under a hydrogen atmosphere overnight. The catalyst was removed by filtration and the filtrate was concentrated under reduced pressure. To the residue were added methanol (100 mL) and ethyl acetate (100 mL), and the mixture was stirred. The precipitate was collected by filtration and dried to obtain 5-((R)-2-amino-1-hyroxyethyl)-8-hydroxy-1H-quinolin-2-one acetate (12.5 g).

$^1$H-NMR (400 MHz, DMSO-$d_6$) δ 8.16 (d, J=8.0 Hz, 1H), 7.05 (d, J=8.0 Hz, 1H), 6.91 (d, J=8.0 Hz, 1H), 6.49 (d, J=8.0 Hz, 1H), 5.06 (dd, J=8.0 Hz, 4.0 Hz, 1H), 2.85 (dd, J=12.0 Hz, 4.0 Hz, 1H), 2.73 (dd, J=12.0 Hz, 8.0 Hz, 1H), 1.84 (s, 3H)

Reference Example 9

Synthesis of tert-butyl
trans-3-(4-bromo-3-nitrophenyl)acrylate

Under a nitrogen flow, sodium hydride (40% of mineral oil added; 1.70 g, 42.6 mmol) was suspended in tetrahydrofuran (80 mL) and, under ice-water cooling, tert-butyl diethyl phosphonoacetate (8.59 g, 34.1 mmol) was added thereto. After stirring the mixture for 1 hour under ice-water cooling, a N,N-dimethylformamide (50 mL) solution of 4-bromo-3-nitro-benzaldehyde (6.53 g, 28.4 mmol) was added and the mixture was stirred for 16 hours while bringing the temperature gradually to room temperature. Under ice-water cooling, a saturated aqueous solution of ammonium chloride was added to stop the reaction and the reaction mixture was extracted with ethyl acetate. The organic layer was washed with a saturated solution of sodium chloride, dried over anhydrous magnesium sulfate, and concentrated under reduced pressure. The residue was purified by flash column chromatography to obtain tert-butyl trans-3-(4-bromo-3-nitrophenyl)acrylate (7.07 g).

$^1$H-NMR (400 MHz, CDCl$_3$) δ 7.95 (d, J=2.0 Hz, 1H), 7.75 (d, J=8.3 Hz, 1H), 7.52 (dd, J=8.3 Hz, 2.0 Hz, 1H), 7.51 (d, J=16.1 Hz, 1H), 6.45 (d, J=16.1 Hz, 1H), 1.54 (s, 9H)

Reference Example 10

Synthesis of tert-butyl trans-3-(3-nitro-4-phenylphenyl)acrylate tert-Butyl trans-3-(4-bromo-3-nitrophenyl)acrylate (7.07 g, 21.5 mmol) was dissolved in 1,4-dioxane (200 mL) and thereto were added phenyl boric acid (5.25 g, 42.1 mmol), cesium carbonate (56.1 g, 172.2 mmol), 1,1-[bis(diphenylphosphino)ferrocene]dichloropalladium(II) dichloromethane complex (0.88 g, 1.1 mmol), and purified water (50 mL). The mixture was stirred under a nitrogen flow at 80° C. for 4 hours. The reaction solution was filtered through celite, alumina, and Florisil, and, thereafter, extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl trans-3-(3-nitro-4-phenylphenyl)acrylate (6.52 g).

$^1$H-NMR (400 MHz, CDCl$_3$) δ 7.96 (d, J=1.7 Hz, 1H), 7.71 (dd, J=7.8 Hz, 1.7 Hz, 1H), 7.60 (d, J=16.1 Hz, 1H), 7.40-7.49 (m, 4H), 7.29-7.36 (m, 2H), 6.48 (d, J=16.1 Hz, 1H), 1.55 (s, 9H)

Reference Example 11

Synthesis of tert-butyl 3-(3-amino-4-phenylphenyl)propionate tert-Butyl trans-3-(3-nitro-4-phenylphenyl)acrylate (6.52 g, 20.0 mmol) was dissolved in methanol (100 mL) and ethyl acetate (100 mL), 10% palladium-carbon (500 mg) was added thereto, and the mixture was stirred under a hydrogen atmosphere at room temperature for 16 hours. The reaction solution was filtered through celite and the filtrate was concentrated under reduced pressure to obtain tert-butyl 3-(3-amino-4-phenylphenyl)propionate (5.94 g).

LC/MS: M+1=338.2

Reference Example 12

Synthesis of tert-butyl 3-[3-({[(1-methylpiperidin-4-yl)oxy]carbonyl}amino)-4-phenylphenyl]propionate Under a nitrogen flow, 4-hydroxy-1-methylpiperidine (2.88 g, 25.0 mmol) was dissolved in acetonitrile (80 mL) and, under ice-water cooling, a solution of diphosgene (9.89 g, 50 mmol) in acetonirile (20 mL) was added thereto. After stirring at room temperature for 1 hour, the reaction mixture was concentrated under reduced pressure to obtain a solid. The solid obtained was added to a solution of tert-butyl 3-(3-amino-4-phenylphenyl)propionate (2.97 g, 10.0 mmol) in pyridine (50 mL) and the mixture was stirred at room temperature for 16 hours. Under ice-water cooling, the reaction was stopped by addition of a dilute aqueous solution of sodium hydroxide and the mixture was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl 3-[3-({[(1-methylpiperidin-4-yl)oxy]carbonyl}amino)-4-phenylphenyl]propionate (5.08 g)

$^1$H-NMR (400 MHz, CDCl$_3$) δ 7.99 (s, 1H), 7.45-7.50 (m, 2H), 7.39-7.43 (m, 1H), 7.33-7.37 (m, 2H), 7.13 (d, J=7.8 Hz, 1H), 6.97 (dd, J=7.8 Hz, 1.7 Hz, 1H), 6.59 (s, 1H), 4.69-4.74 (m, 1H), 2.95 (t, J=7.9 Hz, 2H), 2.60-2.74 (m, 2H), 2.60 (t, J=7.5 Hz, 2H), 2.26 (s, 3H), 2.16-2.25 (m, 2H), 1.89-1.99 (m, 2H), 1.66-1.82 (m, 2H), 1.44 (s, 9H)

Reference Example 12-2

Synthesis of tert-butyl 3-(3-{[({[1R,2R,4S,5S,7S]-9-methyl-3-oxa-9-azatricyclo[3.3.1.0$^{2,4}$]nonan-9-yl}oxy)carbonyl]amino}-4-phenylphenyl)propionate In accordance with Reference Example 12, from tropenol (310 mg, 2.0 mmol) and tert-butyl 3-(3-amino-4-phenylphenyl)propionate (297 mg, 1.0 mmol), there was obtained tert-butyl 3-(3-{[({[1R,2R,4S,5S,7S]-9-methyl-3-oxa-9-azatricyclo[3.3.1.0$^{2,4}$]nonan-9-yl}oxy)carbonyl]amino}-4-phenylphenyl)propionate (121 mg).

LC/MS: M+1=479.3

Reference Example 13

Synthesis of 3-[3-({[(1-methylpiperidin-4-yl)oxy]carbonyl}amino)-4-phenylphenyl]propionate hydrochloride To tert-butyl 3-[3-({[(1-methylpiperidin-4-yl)oxy]carbonyl}amino)-4-phenylphenyl]propionate (5.08 g, 11.6 mmol) was added a 4M solution of hydrochloric acid in dioxane (70 mL) and the mixture was stirred at 70° C. for 2 hours. The reaction solution was concentrated under reduced pressure to obtain 3-[3-({[(1-methylpiperidin-4-yl)oxy]carbonyl}amino)-4-phenylphenyl]propionate hydrochloride (5.49 g).

Reference Example 13-2

Synthesis of 3-(3-{[({[1R,2R,4S,5S,7S]-9-methyl-3-oxa-9-azatricyclo[3.3.1.0$^{2,4}$]nonan-9-yl}oxy)carbonyl]amino}-4-phenylphenyl)propionate hydrochloride In accordance with Reference Example 13, from benzyl 3-(3-{[({[1R,2R,4S,5S,7S]-9-methyl-3-oxa-9-azatricyclo[3.3.1.0$^{2,4}$]nonan-9-yl}oxy)carbonyl]amino}-4-phenylphenyl)propionate (121 mg, 0.25 mmol) obtained in Reference Example 12-2, there was obtained 3-(3-{[({[1R,2R,4S,5S, 7S]-9-methyl-3-oxa-9-azatricyclo[3.3.1.0$^{2,4}$]nonan-9-yl}oxy)carbonyl]-4-phenylphenyl)propionate hydrochloride (105 mg).

LC/MS: M+1=423.3

Reference Example 14

Synthesis of 4-[(tert-butyldimethylsilanoyloxy)methyl]aniline

4-Aminobenzyl alcohol (5.00 g, 40.6 mmol) and imidazole (5.52 g, 81.2 mmol) were dissolved in tetrahydrofuran (30 mL) and a solution of tert-butyldimethylchlorosilane (9.14 g, 60.9 mmol) in tetrahydrofuran (10 mL) was added thereto. After stirring the reaction mixture at room temperature for 1 hour, the reaction was stopped by addition of purified water and the mixture was extracted with ethyl acetate. The organic layer was washed with a saturated aqueous solution of sodium chloride, dried over anhydrous magnesium sulfate, and concentrated under reduced pressure. The residue was purified by flash column chromatography to obtain 4-[(tert-butyldimethylsilanoyloxy)methyl]aniline (9.94 g).

Reference Example 15

Synthesis of 1-methylpiperidin-4-yl N-{5-[2-({4-[(tert-butyldimethylsilanoyloxy)methyl]phenyl}carbamoyl)ethyl]-2-phenylphenyl}carbamate 3-[3-({[(1-Methylpiperidin-4-yl)oxy]carbonyl}amino)-4-phenylphenyl]propionate hydrochloride (191 mg, 0.5 mmol) was dissolved in N,N-dimethylformamide (10 mL) and thereto was added N-ethyl-N'-(3-dimethylaminopropyl)carbodiimide hydrochloride (1.0 mmol), N-hydroxybenzotriazole (1.0 mmol), triethylamine (5.0 mmol), 4-[(tert-butyldimethylsilanoyloxy)methyl]aniline (1.0 mmol), and the mixture was stirred at room temperature for 16 hours. The reaction mixture was extracted with ethyl acetate and the organic layer was washed with a saturated aqueous solution of sodium chloride, dried over sodium sulfate, and concentrated under reduced pressure. The residue was purified by flash column chromatography to obtain 1-methylpiperidin-4-yl N-{5-[2-({4-[(tert-butyldimethylsilanoyloxy)methyl]phenyl}carbamoyl)ethyl]-2-phenylphenyl}carbamate (121.7 mg)

$^1$H-NMR (400 MHz, CDCl$_3$) δ 8.03 (s, 1H), 7.39-8.05 (m, 5H), 7.32-7.36 (m, 2H), 7.22-7.29 (m, 3H), 7.13 (d, J=7.8 Hz, 1H), 7.02 (d, J=7.8 Hz, 1H), 6.62 (s, 1H), 4.68-4.75 (m, 1H), 4.69 (s, 2H), 3.09 (t, J=7.6 Hz, 2H), 2.71 (t, J=7.6 Hz, 2H), 2.62-2.71 (m, 2H), 2.29 (s, 3H), 2.19-2.31 (m, 2H), 1.92-2.00 (m, 2H), 1.68-1.78 (m, 2H), 0.93 (s, 9H), 0.08 (s, 6H)

Reference Example 16

Synthesis of 3-(4-bromo-3-nitrobenzoyl)propionic acid

Under salt-ice cooling, 3-(4-bromobenzoyl)propionic acid (75.0 g, 291.7 mmol) was added to fuming nitric acid (200 mL) in portions at such a rate that the temperature of the reaction solution could be maintained at −5° C. or lower. After stirring at −12° C. to −10° C. for 1 hour, the reaction solution was poured onto ice. The solid which precipitated was collected by filtration, washed with purified water, and thereafter dried under reduced pressure to obtain 3-(4-bromo-3-nitrobenzoyl)propionic acid (91.0 g).

$^1$H-NMR (400 MHz, DMSO-d$_6$) δ 8.43 (d, J=2.0 Hz, 1H), 7.96-8.06 (m, 2H), 3.20 (t, J=6.2 Hz, 2H), 2.51 (t, J=6.2 Hz, 2H)

Reference Example 17

Synthesis of 3-(3-nitro-4-phenylbenzoyl)propionic acid 3-(4-Bromo-3-nitrobenzoyl)propionic acid (45.3 g, 150.0 mmol) was dissolved in 1,4-dioxane (400 mL), thereto were added phenyl boric acid (27.4 g, 225.0 mmol), cesium carbonate (146.6 g, 450.0 mmol), 1,1-[bis(diphenylphosphino)ferrocene]dichloropalladium(II) dichloromethane complex (3.7 g, 4.5 mmol), and purified water (150 mL), and the reaction mixture was stirred under a nitrogen flow at 80° C. for 18 hours. The reaction solution was filtered through celite, alumina, and Florisil, and, thereafter, the aqueous layer was separated. The organic layer was extracted with a dilute aqueous solution of sodium hydroxide. After the aqueous layers were combined and washed with ethyl acetate, the layer was acidified, under ice-water cooling, with 6 M hydrochloric acid and extracted with ethyl acetate. The organic layer was washed with a saturated aqueous solution of sodium chloride, dried over anhydrous magnesium sulfate, and concentrated under reduced pressure to obtain 3-(3-nitro-4-phenylbenzoyl)propionic acid (39.4 g).

$^1$H-NMR (400 MHz, DMSO-d$_6$) δ 12.22 (s, 1H), 8.48 (d, J=0.9 Hz, 1H), 8.30 (dd, J=8.2 Hz, 0.9 Hz, 1H), 7.73 (d, J=8.2 Hz, 1H), 7.45-7.50 (m, 3H), 7.37-7.41 (m, 2H), 3.34 (t, J=6.2 Hz, 2H), 2.63 (t, J=6.2 Hz, 2H)

Reference Example 18

Synthesis of 4-(3-amino-4-phenylphenyl)butyric acid 3-(3-Nitro-4-phenylbenzoyl)-propionic acid (18.6 g, 69.0 mmol) was dissolved in acetic acid (200 mL) and trifluoroacetic acid (20 mL), 10% palladium hydroxide-carbon (5 g) was added thereto, and the mixture was stirred under a hydrogen atmosphere at 70° C. for 16 hours. After filtering the reaction solution through celite, the filtrate was concentrated under reduced pressure.

To the residue was added methanol (100 mL) and a 5 M aqueous solution of sodium hydroxide (300 mL) and the mixture was heated under reflux for 6 hours. After cooling the reaction solution to room temperature, ethyl acetate and purified water were added and the aqueous layer was separated. The organic layer was extracted with a dilute aqueous solution of sodium hydroxide. The aqueous layers were combined and, under ice-water cooling, acidified with acetic acid and extracted with ethyl acetate. The organic layer was washed with a saturated aqueous solution of sodium chloride, dried over anhydrous magnesium sulfate, and concentrated under reduced pressure. The residue was purified by flash column chromatography to obtain 4-(3-amino-4-phenylphenyl)butyric acid (12.6 g).

$^1$H-NMR (400 MHz, DMSO-d$_6$) δ 7.35-7.44 (m, 4H), 7.27-7.33 (m, 1H), 6.90 (d, J=7.8 Hz, 1H), 6.60 (d, J=1.0 Hz, 1H), 6.48 (dd, J=7.8 Hz, 1.0 Hz, 1H), 2.47 (d, J=7.8 Hz, 2H), 2.24 (d, J=7.4 Hz, 2H), 1.74-1.82 (m, 2H)

Reference Example 19

Synthesis of benzyl 4-(3-amino-4-phenylphenyl)butyrate tosylate

To a suspension of 4-(3-Amino-4-phenylphenyl)butyric acid (21.6 g, 84.6 mmol) in toluene (300 mL), benzyl alcohol (50 mL) and tosylic acid hydrate (17.7 g, 93.0 mmol) were added, and the mixture was heated under reflux for 5 hours with water removed by a Dean-Stark trap. The reaction solution was concentrated under reduced pressure and a solid obtained was washed with a mixed solvent of hexane-ethyl acetate (4:1). The solid was collected by filtration and dried under reduced pressure to obtain benzyl 4-(3-amino-4-phenylphenyl)butyrate tosylate (41.2 g).

$^1$H-NMR (400 MHz, DMSO-$d_6$) δ 7.44-7.53 (m, 5H), 7.30-7.39 (m, 7H), 7.28 (d, J=7.8 Hz, 2H), 7.19-7.27 (m, 1H), 7.11 (d, J=7.8 Hz, 2H), 5.10 (s, 2H), 4.49 (s, 3H), 2.65 (t, J=7.7 Hz, 2H), 2.42 (d, J=7.4 Hz, 2H), 1.83-1.90 (m, 2H)

Reference Example 20

Synthesis of benzyl 4-[3-({[(1-methylpiperidin-4-yl)oxy]carbonyl}amino)-4-phenylphenyl]butyrate Under a nitrogen flow, 4-hydroxy-1-methylpiperidine (10.4 g, 90.0 mmol) was dissolved in acetonitrile (100 mL) and to the solution was added, under ice-water cooling, a solution of diphosgene (35.6 g, 180 mmol) in acetonirile (50 mL) After stirring at room temperature for 5 hours, the reaction mixture was concentrated under reduced pressure to obtain a solid. The solid obtained was added to a solution of benzyl 4-(3-amino-4-phenylphenyl)butyrate tosylate (31.1 g, 60.0 mmol) in a mixed solvent of pyridine (50 mL) and N,N-dimethylformamide (150 mL), and the mixture was stirred at room temperature for 2 hours. Under ice-water cooling, the reaction was stopped by addition of purified water and the reaction mixture was extracted with ethyl acetate. The organic layer was washed with a dilute aqueous solution of sodium hydroxide and a saturated aqueous solution of sodium chloride, dried over anhydrous magnesium sulfate, and concentrated under reduced pressure. The residue was purified by flash column chromatography to obtain benzyl 4-[3-({[(1-methylpiperidin-4-yl)oxy]carbonyl}amino)-4-phenylphenyl]butyrate (25.8 g).

$^1$H-NMR (400 MHz, CDCl$_3$) δ 7.96 (s, 1H), 7.43-7.50 (m, 2H), 7.39-7.42 (m, 1H), 7.30-7.38 (m, 7H), 7.12 (d, J=7.8 Hz, 1H), 6.93 (dd, J=7.7 Hz, 1.6 Hz, 1H), 6.58 (s, 1H), 5.13 (s, 2H), 4.65-4.75 (m, 1H), 2.69 (t, J=7.6 Hz, 2H), 2.60-2.68 (m, 2H), 2.42 (t, J=7.4 Hz, 2H), 2.26 (s, 3H), 2.16-2.21 (m, 2H), 2.98-1.08 (m, 2H), 1.68-1.88 (m, 2H), 1.64-1.75 (m, 2H)

Reference Example 20-2

Synthesis of benzyl 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyrate In accordance with Reference Example 20, from scopine (purchased from Shanghai FWD Chemicals Co, Ltd.; 9.31 g, 60.0 mmol) and benzyl 4-(3-amino-4-phenylphenyl)butyrate tosylate (31.1 g, 60.0 mmol), there was obtained benzyl 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyrate (9.14 g).

LC/MS: M+1=527.3

Reference Example 20-3

Synthesis of benzyl 4-(3-{[({(1R,3R)-8-methyl-8-azabicyclo[3.2.1]octan-3-yl}oxy)carbonyl]amino}-4-phenylphenyl)butyrate In accordance with Reference Example 20, from tropine (2.82 g, 20.0 ml) and benzyl 4-(3-amino-4-phenylphenyl) butyrate tosylate (5.17 g, 10.0 mmol), there was obtained benzyl 4-(3-{[({(1R,3R)-8-methyl-8-azabicyclo[3.2.1]octan-3-yl}oxy)carbonyl]amino}-4-phenylphenyl)butyrate (4.37 g).

LC/MS: M+1=513.3

Reference Example 21

Synthesis of 4-[3-({[(1-methylpiperidin-4-yl)oxy]carbonyl}amino)-4-phenylphenyl]butyric acid Benzyl 4-[3-({[(1-methylpiperidin-4-yl)oxy]carbonyl}amino)-4-phenylphenyl]butyrate (25.8 g, 5.30 mmol) was dissolved in ethyl acetate (250 mL), 10% palladium hydroxide-carbon (5 g) was added thereto, and the mixture was stirred under a hydrogen atmosphere at room temperature for 3 days and, thereafter, at 50° C. for 6 hours. After filtering the reaction solution through celite, the filtrate was concentrated under reduced pressure to obtain 4-[3-({[(1-methylpiperidin-4-yl)oxy]carbonyl}amino)-4-phenylphenyl]butyric acid (21.3 g).

$^1$H-NMR (400 MHz, DMSO-$d_6$) δ 7.94 (s, 1H), 7.43-7.48 (m, 5H), 7.27 (d, J=7.8 Hz, 1H), 7.26 (s, 1H), 7.16 (dd, J=7.8 Hz, 1.2 Hz, 1H), 4.46-4.54 (m, 1H), 2.66 (t, J=7.7 Hz, 2H), 2.55-2.62 (m, 2H), 2.30 (t, J=7.3 Hz, 2H), 2.20 (s, 3H), 2.12-2.23 (m, 2H), 1.82-1.92 (m, 2H), 1.72-1.79 (m, 2H), 1.48-1.58 (m, 2H)

Reference Example 21-2

Synthesis of 4-(3-{[({(1R,3R)-8-methyl-8-azabicyclo[3.2.1]octan-3-yl}oxy)carbonyl]amino}-4-phenylphenyl)butyric acid In accordance with Reference Example 21, from benzyl 4-(3-{[({(1R,3R)-8-methyl-8-azabicyclo[3.2.1]octan-3-yl}oxy)carbonyl]amino}-4-phenylphenyl)butyrate (2.09 g, 3.98 mmol) obtained in Reference Example 20-3, there was obtained 4-(3-{[({(1R,3R)-8-methyl-8-azabicyclo[3.2.1]octan-3-yl}oxy)carbonyl]amino}-4-phenylphenyl)butyric acid (706 mg).

LC/MS: M+1=423.3

Reference Example 21-3

Synthesis of 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid In accordance with Reference Example 21, from benzyl 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyrate (2.09 g, 3.98 mmol) obtained in Reference Example 20-2, there was 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (1.55 g).

LC/MS: M+1=437.3

Reference Example 21-6

Synthesis of 4-(4-bromobenzoyl)butyric acid

To a mixture of aluminum chloride (8 g, 60 mmol) and bromobenzene (30 mL), ethylglutaryl chloride (5 g, 28.0 mmol) was added under ice-water cooling and the mixture was stirred at room temperature for 2 hours. After stopping the reaction by pouring the reaction solution onto ice, the mixture was extracted with ethyl acetate. The organic layer was washed successively with a saturated aqueous solution of sodium chloride, a saturated aqueous solution of sodium bicarbonate, and a saturated aqueous solution of sodium chloride, and after drying over anhydrous magnesium sulfate, the solution was concentrated under reduced pressure.

To the residue were added a 5 M aqueous solution of sodium hydroxide (15 mL), tetrahydrofuran (50 mL), and methanol (20 mL), and the mixture was stirred at room temperature for 18 hours. To the reaction solution was added ethyl acetate and purified water, the aqueous layer was separated. Under ice-water cooling, the aqueous layer was acidified with 6 M hydrochloric acid and extracted with ethyl acetate. The organic layer was washed with a saturated aqueous solution of sodium chloride, dried over anhydrous magnesium sulfate, and concentrated under reduced pressure to obtain 4-(4-bromobenzoyl)butyric acid (5.96 g).

$^1$H-NMR (400 MHz, DMSO-$d_6$) δ 12.08 (s, 1H), 7.87 (dt, J=8.8 Hz, 2.0 Hz, 2H), 7.71 (dt, J=8.8 Hz, 2.0 Hz, 2H), 3.03 (t, J=7.2 Hz, 2H), 2.28 (t, J=7.4 Hz, 2H), 1.75-1.86 (m, 2H)

Reference Example 16-2

Synthesis of 4-(4-bromo-3-nitrobenzoyl)butyric acid

In accordance with Reference Example 16, from 4-(4-bromobenzoyl)butyric acid (5.95 g, 21.9 mmol) obtained in Reference Example 21-6, there was obtained 4-(4-bromo-3-nitrobenzoyl)butyric acid (6.76 g).

$^1$H-NMR (400 MHz, DMSO-$d_6$) δ 8.48 (d, J=1.7 Hz, 1H), 8.03-8.10 (m, 2H), 3.10 (t, J=7.2 Hz, 2H), 2.29 (t, J=7.4 Hz, 2H), 1.76-1.86 (m, 2H)

Reference Example 17-2

Synthesis of 4-(3-nitro-4-phenylbenzoyl)butyric acid

In accordance with Reference Example 17, from 4-(4-bromo-3-nitrobenzoyl)butyric acid (6.76 g, 19.0 mmol) obtained in Reference Example 16-2, there was obtained 4-(3-nitro-4-phenylbenzoyl)butyric acid (5.94 g).

$^1$H-NMR (400 MHz, DMSO-$d_6$) δ 12.11 (s, 1H), 8.45 (d, J=2.0 Hz, 1H), 8.27 (dd, J=8.0 Hz, 2.0 Hz, 1H), 7.72 (d, J=8.0 Hz, 1H), 7.44-7.50 (m, 3H), 7.36-7.40 (m, 2H), 3.16 (t, J=7.1 Hz, 2H), 2.32 (t, J=7.3 Hz, 2H), 1.81-1.90 (m, 2H)

Reference Example 18-2

Synthesis of 5-(3-amino-4-phenylphenyl)valeric acid

In accordance with Reference Example 18, from 4-(3-nitro-4-phenylbenzoyl)butyric acid (2.93 g, 10.0 mmol) obtained in Reference Example 17-2, there was obtained 5-(3-amino-4-phenylphenyl)valeric acid (1.52 g).

Reference Example 19-2

Synthesis of benzyl 5-(3-amino-4-phenylphenyl)valerate tosylate

According to Reference Example 19, from 5-(3-amino-4-phenylphenyl)valeric acid (1.37 g, 5.10 mmol) obtained in Reference Example 18-2, there was obtained benzyl 5-(3-amino-4-phenylphenyl)valerate tosylate (3.53 g).

$^1$H-NMR (400 MHz, DMSO-$d_6$) δ 7.43-7.53 (m, 5H), 7.29-7.39 (m, 9H), 7.19-7.24 (m, 1H), 7.11 (d, J=7.8 Hz, 2H), 5.08 (s, 2H), 4.48 (s, 3H), 2.63 (t, J=6.8 Hz, 2H), 2.41 (d, J=8.8 Hz, 2H), 1.56-1.61 (m, 4H)

Reference Example 20-4

Synthesis of benzyl 5-[3-({[(1-methylpiperidin-4-yl)oxy]carbonyl}amino)-4-phenylphenyl)valerate In accordance with Reference Example 20, from benzyl 5-(3-amino-4-phenylphenyl)valerate tosylate (1.32 g, 2.5 mmol) obtained in Reference Example 19-2 and 4-hydroxy-1-methylpiperidine (0.58 g, 5.0 mmol), there was obtained benzyl 5-[3-({[(1-methylpiperidin-4-yl)oxy]carbonyl}amino)-4-phenylphenyl)valerate (985 mg).

$^1$H-NMR (400 MHz, CDCl$_3$) δ 7.95 (s, 1H), 7.46-7.50 (m, 2H), 7.26-7.42 (m, 8H), 7.11 (d, J=7.8 Hz, 1H), 6.92 (dd, J=7.8 Hz, 1.5 Hz, 1H), 6.60 (s, 1H), 5.12 (s, 2H), 4.67-4.74 (m, 1H), 2.66 (t, J=7.0 Hz, 2H), 2.62-2.70 (m, 2H), 2.40 (t, J=7.3 Hz, 2H), 2.26 (s, 3H), 2.18-2.21 (m, 2H), 1.90-2.00 (m, 2H), 1.66-1.83 (m, 6H)

Reference Example 20-5

Synthesis of benzyl 5-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)valerate In accordance with Reference Example 20, from benzyl 5-(3-amino-4-phenylphenyl)valerate tosylate (1.32 g, 2.5 mmol) obtained in Reference Example 19-2 and scopine (0.95 g, 5.0 mmol), there was obtained benzyl 5-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)valerate (985 mg).

LC/MS: M+1=541.3

Reference Example 21-4

Synthesis of 5-[3-({[(1-methylpiperidin-4-yl)oxy]carbonyl}amino)-4-phenylphenyl)valeric acid In accordance with Reference Example 21, from benzyl 5-[3-({[(1-methylpiperidin-4-yl)oxy]carbonyl}amino)-4-phenylphenyl)valerate (500 mg, 0.5 mmol) obtained in Reference Example 20-4, there was obtained 5-[3-({[(1-methylpiperidin-4-yl)oxy]carbonyl}amino)-4-phenylphenyl)valeric acid (410 mg).

LC/MS: M+1=411.3

Reference Example 21-5

Synthesis of 5-(3-{[({[1R,2R,4S,5S,7S]-9-methyl-3-oxa-9-azatricyclo[3.3.1.0$^{2,4}$]nonan-7-yl}oxycarbonyl]amino}-4-phenylphenyl)valeric acid In accordance with Reference Example 21, from benzyl 5-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)valerate (540 mg, 1.0 mmol) obtained in Reference Example 20-4, there was obtained 5-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)valeric acid (450 mg).

LC/MS: M+1=451.3

Reference Example 22

Synthesis of 1-(2-phenoxyethyl)piperidin-4-ol

4-Hydroxypiperidine (5.06 g, 50 mmol) was dissolved in N,N-dimethylformamide (200 mL), potassium carbonate (13.8 g, 100 mmol) and (2-bromoethoxy)benzene (12.9 g, 60 mmol) were added thereto, and the mixture was stirred at 70° C. for 18 hours. The reaction solution was extracted with ethyl acetate and the organic layer was washed with a saturated aqueous solution of sodium chloride, dried over anhydrous magnesium sulfate, and concentrated under reduced pressure. The residue was purified by flash column chromatography to obtain 1-(2-phenoxyethyl)piperidin-4-ol (8.48 g).
LC/MS: M+1=222.3

Reference Example 23

Synthesis of 4-amino-5-chloro-2-methoxybenzyl alcohol

To a suspension of lithium aluminum hydride (25.0 g, 116 mmol) in tetrahydrofuran (150 mL), 4-amino-5-chloro-2-methoxybenzoic acid (5 g, 28.0 mmol) was added in portions under ice-water cooling and the mixture was heated under reflux for 5 hours. Under ice-water cooling, a saturated aqueous solution of Rochelle salt was added to stop the reaction and the reaction mixture was extracted with ethyl acetate. The organic layer was washed with a saturated aqueous solution of Rochelle salt and a saturated aqueous solution of sodium chloride, dried over anhydrous magnesium sulfate, and concentrated under reduced pressure. The solid obtained was washed with a mixed solvent of hexane-ethyl acetate (4:1), collected by filtration, and dried under reduced pressure to obtain 4-amino-5-chloro-2-methoxybenzyl alcohol (11.8 g)
$^1$H-NMR (400 MHz, CDCl$_3$) δ 7.13 (s, 1H), 6.31 (s, 1H), 4.53 (d, J=2.4 Hz, 2H), 4.02-4.08 (broad, 2H), 3.80 (s, 3H)

Reference Example 14-2

Synthesis of 4-[(tert-butyldimethylsilanoyloxy)methyl]-2-chloro-5-methoxyaniline In accordance with Reference Example 14, from 4-amino-5-chloro-2-methoxybenzyl alcohol (11.8 g, 62.9 mmol) obtained in Reference Example 23, there was obtained 4-[(tert-butyldimethylsilanoyloxy)methyl]-2-chloro-5-methoxyaniline (18.1 g).
$^1$H-NMR (400 MHz, CDCl$_3$) δ 7.25 (s, 1H), 6.26 (s, 1H), 4.61 (s, 2H), 3.92-4.02 (broad, 2H), 3.74 (s, 3H), 0.94 (s, 9H), 0.08 (s, 6H)

Reference Example 14-3

Synthesis of 4-[(tert-butyldimethylsilanoyloxy)methyl]-3-chloroaniline

In accordance with Reference Example 23 and Reference Example 14, from 4-amino-2-chlorobenzoic acid (858 mg, 5 mmol) was obtained 4-[(tert-butyldimethylsilanoyloxy)methyl]-3-chloroaniline (1.3 g).
LC/MS: M+1=271.2

Reference Example 14-4

Synthesis of 4-[(tert-butyldimethylsilanoyloxy)methyl]-2-fluoroaniline

In accordance with Reference Example 23 and Reference Example 14, from 4-amino-3-fluorobenzoic acid (776 mg, 5 mmol), there was obtained 4-[(tert-butyldimethylsilanoyloxy)methyl]-2-fluoroaniline (0.66 g).
LC/MS: M+1=256.2

Reference Example 14-5

Synthesis of 4-[(tert-butyldimethylsilanoyloxy)methyl]-2,5-difluoroaniline

In accordance with Reference Example 23 and Reference Example 14, from 4-amino-2,5-difluorobenzoic acid (406 mg, 2.0 mmol), there was obtained 4-[(tert-butyldimethylsilanoyloxy)methyl]-2,5-difluoroaniline (94.2 mg).
LC/MS: M+1=274.2

Reference Example 14-6

Synthesis of 4-[(tert-butyldimethylsilanoyloxy)methyl]-3-methoxyaniline

In accordance with Reference Example 23 and Reference Example 14, from 4-amino-2-methoxybenzoic acid (836 mg, 5 mmol), there was obtained 4-[(tert-butyldimethylsilanoyloxy)methyl]-3-methoxyaniline (0.30 g).
LC/MS: M+1=268.2

Reference Example 14-7

Synthesis of 4-[(tert-butyldimethylsilanoyloxy)methyl]-3-fluoroaniline

In accordance with Reference Example 23 and Reference Example 14, from 4-amino-2-fluorobenzoic acid (776 mg, 5 mmol), there was obtained 4-[(tert-butyldimethylsilanoyloxy)methyl]-3-fluoroaniline (0.45 g).
LC/MS: M+1=256.2

Reference Example 14-8

Synthesis of 4-[(tert-butyldimethylsilanoyloxy)methyl]-3-methylaniline

2-Methyl-4-nitrobenzoic acid (741 g, 5 mmol) was dissolved in methanol (20 mL), 10% palladium-carbon (100 mg) was added, and the mixture was stirred under a hydrogen atmosphere at room temperature for 16 hours. The reaction solution was filtered through celite and, thereafter, the filtrate was concentrated under reduced pressure to obtain 4-amino-2-methylbenzoic acid as a crude material. In accordance with Reference Example 23 and Reference Example 14, from 4-amino-2-methylbenzoic acid obtained, there was obtained 4-[(tert-butyldimethylsilanoyloxy)methyl]-3-methylaniline (0.33 g).
LC/MS: M+1=252.2

Reference Example 14-9

Synthesis of 4-[(tert-butyldimethylsilanoyloxy)methyl]-2-chloroaniline

In accordance with Reference Example 23 and Reference Example 14, from 4-amino-3-chlorobenzoic acid (858 mg, 5 mmol), there was obtained 4-[(tert-butyldimethylsilanoyloxy)methyl]-2-chloroaniline (0.49 g).
LC/MS: M+1=272.2

Reference Example 14-10

Synthesis of 5-[(tert-butyldimethylsilanoyloxy)methyl]-2-methoxyaniline

In accordance with Reference Example 23 and Reference Example 14, from 4-amino-3-methoxybenzoic acid (836 mg, 5 mmol), there was obtained 5-[(tert-butyldimethylsilanoyloxy)methyl]-2-methoxyaniline (0.45 g).
LC/MS: M+1=268.2

Reference Example 14-11

Synthesis of 4-[(tert-butyldimethylsilanoyloxy)methyl]-2-methylaniline

In accordance with Reference Example 23 and Reference Example 14, from 4-amino-3-methylbenzoic acid (756 mg, 5 mmol), there was obtained 4-[(tert-butyldimethylsilanoyloxy)methyl]-2-methylaniline (0.17 g).
LC/MS: M+1=252.2

Reference Example 14-12

Synthesis of 6-[(tert-butyldimethylsilanoyloxy)methyl]naphthalen-2-amine

In accordance with Reference Example 23 and Reference Example 14, from 2-amino-6-naphthoic acid (936 mg, 5 mmol), there was obtained 6-[(tert-butyldimethylsilanoyloxy)methyl]naphthalen-2-amine (0.97 g).
LC/MS: M+1=288.2

Reference Example 14-13

Synthesis of 2-[(tert-butyldimethylsilanoyloxy)methyl]-1-benzothiophen-5-amine

In accordance with Reference Example 23 and Reference Example 14, from methyl 5-amino-1-benzothiophene-2-carboxylate (1.04 mg, 5 mmol), there was obtained 2-[(tert-butyldimethylsilanoyloxy)methyl]-1-benzothiophen-5-amine (0.64 g).
LC/MS: M+1=294.1

Reference Example 14-14

Synthesis of 3-[(tert-butyldimethylsilanoyloxy)methyl]-4-methoxyaniline

In accordance with Reference Example 23 and Reference Example 14, from 5-amino-2-methoxybenzoic acid (836 mg, 5 mmol), there was obtained 3-[(tert-butyldimethylsilanoyloxy)methyl]-4-methoxyaniline (0.89 g).
LC/MS: M+1=268.2

Reference Example 14-15

Synthesis of 4-[(tert-butyldimethylsilanoyloxy)methyl]-N-methylaniline

In accordance with Reference Example 23 and Reference Example 14, from 4-methylaminobenzoic acid (756 mg, 5 mmol), there was obtained 4-[(tert-butyldimethylsilanoyloxy)methyl]-N-methylaniline (0.84 g)
LC/MS: M+1=252.2 .

Reference Example 14-16

Synthesis of 5-[(tert-butyldimethylsilanoyloxy)methyl]thiophen-2-amine

5-Nitro-2-thiophenecarbaldehyde (15.7 g, 10.0 mmol) was dissolved in tetrahydrofuran, thereto was added dropwise borane-tetrahydrofuran complex (a 1 M tetrahydrofuran solution, 25.0 mmol) under ice-water cooling, and the reaction mixture was stirred at room temperature for 2 hours. Under ice-water cooling, a saturated aqueous solution of Rochelle salt was added to stop the reaction and the reaction mixture was extracted with ethyl acetate. The organic layer was washed with a saturated aqueous solution of Rochelle salt and a saturated aqueous solution of sodium chloride, dried over anhydrous magnesium sulfate, and concentrated under reduced pressure. The solid obtained was dissolved in methanol (20 mL), a catalytic amount of Raney nickel was added thereto, and the mixture was stirred under a hydrogen atmosphere at room temperature for 2 hours. The reaction solution was filtered through celite and, thereafter, the filtrate was concentrated under reduced pressure to obtain (5-aminothiophen-2-yl)methanol as a crude material. In accordance with Reference Example 14, from (5-aminothiophen-2-yl)methanol obtained, there was obtained 5-[(tert-butyldimethylsilanoyloxy)methyl]thiophen-2-amine (170 mg).
LC/MS: M+1=244.3

Reference Example 14-17

Synthesis of 5-[(tert-butyldimethylsilanoyloxy)methyl]pyridin-2-amine

In accordance with Reference Example 23 and Reference Example 14, from 6-aminonicotinic acid (691 mg, 5 mmol), there was obtained 5-[(tert-butyldimethylsilanoyloxy)methyl]pyridin-2-amine (0.14 g).
LC/MS: M+1=239.2

Reference Example 14-18

Synthesis of 2-bromo-4-[(tert-butyldimethylsilanoyloxy)methyl]-5-methoxyaniline

In accordance with Reference Example 23 and Reference Example 14, from methyl 4-amino-5-bromo-2-metoxybenzoate (500 mg, 2 mmol), there was obtained 2-bromo-4-[(tert-butyldimethylsilanoyloxy)methyl]-5-methoxyaniline (0.35 g).
LC/MS: M+1=347.1

Reference Example 14-19

Synthesis of 4-[(tert-butyldimethylsilanoyloxy)methyl]-2-chloro-5-ethoxyaniline

In accordance with Reference Example 23 and Reference Example 14, from 4-amino-5-chloro-2-ethoxybenzoic acid (863 mg, 4 mmol), there was obtained 4-[(tert-butyldimethylsilanoyloxy)methyl]-2-chloro-5-ethoxyaniline (0.87 g).
LC/MS: M+1=316.1

Reference Example 14-20

Synthesis of 4-[(tert-butyldimethylsilanoyloxy)methyl]-3-ethoxyaniline

In accordance with Reference Example 14-8, from 2-ethoxy-4-nitrobenzoic acid (702 mg, 3.32 mmol), there was obtained 4-[(tert-butyldimethylsilanoyloxy)methyl]-3-ethoxyaniline (0.65 g).
LC/MS: M+1=282.3

Reference Example 14-21

Synthesis of 2-bromo-4-[(tert-butyldimethylsilanoyloxy)methyl]aniline

In accordance with Reference Example 23 and Reference Example 14, from 4-amino-2-bromobenzoic acid (460 mg, 2 mmol), there was obtained 2-bromo-4-[(tert-butyldimethylsilanoyloxy)methyl]aniline (0.59 g).
LC/MS: M+1=317.1

Reference Example 14-22

Synthesis of 4-[(tert-butyldimethylsilanoyloxy)methyl]-3-(trifluoromethyl)aniline In accordance with Reference Example 14-8, from 4-nitro-2-(trifluoromethyl)benzoic acid (1.18 g, 5 mmol), there was obtained 4-[(tert-butyldimethylsilanoyloxy)methyl]-3-(trifluoromethyl)aniline (0.94 g).
LC/MS: M+1=306.2

Reference Example 15-2

Synthesis of 1-methylpiperidin-4-yl N-{5-[2-({4-[(tert-butyldimethylsilanoyloxy)methyl]-2-chloro-5-methoxyphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (191 mg, 0.5 mmol) and 4-[(tert-butyldimethylsilanoyloxy)methyl]-2-chloro-5-methoxyaniline (188 mg, 1.0 mmol) obtained in Reference Example 14-2, there was obtained 1-methylpiperidin-4-yl N-{5-[2-({4-[(tert-butyldimethylsilanoyloxy)methyl]-2-chloro-5-methoxyphenyl}carbamoyl)ethyl]-2-phenylphenyl}carbamate (20 mg).
LC/MS: M+1=666.3

Reference Example 15-3

Synthesis of 1-methylpiperidin-4-yl N-{5-[2-({4-[(tert-butyldimethylsilanoyloxy)methyl]-3-chlorophenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 4-[(tert-butyldimethylsilanoyloxy)methyl]-3-chloroaniline (544 mg, 2.0 mmol) obtained in Reference Example 14-3, there was obtained 1-methylpiperidin-4-yl N-{5-[2-({4-[(tert-butyldimethylsilanoyloxy)methyl]-3-chlorophenyl}carbamoyl)ethyl]-2-phenylphenyl}carbamate (340 mg).
LC/MS: M+1=636.3

Reference Example 15-4

Synthesis of 1-methylpiperidin-4-yl N-{5-[2-({4-[(tert-butyldimethylsilanoyloxy)methyl]-2-fluorophenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 4-[(tert-butyldimethylsilanoyloxy)methyl]-2-fluoroaniline (383 mg, 1.5 mmol) obtained in Reference Example 14-4, there was obtained 1-methylpiperidin-4-yl N-{5-[2-({4-[(tert-butyldimethylsilanoyloxy)methyl]-2-fluorophenyl}carbamoyl)ethyl]-2-phenylphenyl}carbamate (266 mg).
LC/MS: M+1=620.3

Reference Example 15-5

Synthesis of 1-methylpiperidin-4-yl N-{5-[2-({4-[(tert-butyldimethylsilanoyloxy)methyl]-2,5-difluorophenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (126 mg, 0.3 mmol) and 4-[(tert-butyldimethylsilanoyloxy)methyl]-2,5-difluoroaniline (94.2 mg, 0.35 mmol) obtained in Reference Example 14-5, there was obtained 1-methylpiperidin-4-yl N-{5-[2-({4-[(tert-butyldimethylsilanoyloxy)methyl]-2,5-difluorophenyl}carbamoyl)ethyl]-2-phenylphenyl}carbamate (44 mg)
LC/MS: M+1=637.3

Reference Example 15-6

Synthesis of 1-methylpiperidin-4-yl N-{5-[2-({4-[(tert-butyldimethylsilanoyloxy)methyl]-3-methoxyphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (181 mg, 0.5 mmol) and 4-[(tert-butyldimethylsilanoyloxy)methyl]-3-methoxyaniline (201 mg, 0.75 mmol) obtained in Reference Example 14-6, there was obtained 1-methylpiperidin-4-yl N-{5-[2-({4-[(tert-butyldimethylsilanoyloxy)methyl]-3-methoxyphenyl}carbamoyl)ethyl]-2-phenylphenyl}carbamate (89 mg).
LC/MS: M+1=632.3

Reference Example 15-7

Synthesis of 1-methylpiperidin-4-yl N-{5-[2-({4-[(tert-butyldimethylsilanoyloxy)methyl]-3-fluorophenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (419 mg, 1.1 mmol) and 4-[(tert-butyldimethylsilanoyloxy)methyl]-3-fluoroaniline (383 mg, 1.5 mmol) obtained in Reference Example 14-7, there was obtained 1-methylpiperidin-4-yl N-{5-[2-({4-[(tert-butyldimethylsilanoyloxy)methyl]-3-fluorophenyl}carbamoyl)ethyl]-2-phenylphenyl}carbamate (308 mg).

LC/MS: M+1=620.3

Reference Example 15-8

Synthesis of 1-methylpiperidin-4-yl N-{5-[2-({4-[(tert-butyldimethylsilanoyloxy)methyl]-3-methylphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (419 mg, 1.1 mmol) and 4-[(tert-butyldimethylsilanoyloxy)methyl]-3-methylaniline (330 mg, 1.3 mmol) obtained in Reference Example 14-8, there was obtained 1-methylpiperidin-4-yl N-{5-[2-({4-[(tert-butyldimethylsilanoyloxy)methyl]-3-methylphenyl}carbamoyl)ethyl]-2-phenylphenyl}carbamate (250 mg)

LC/MS: M+1=616.3

Reference Example 15-9

Synthesis of 1-methylpiperidin-4-yl N-{5-[2-({4-[(tert-butyldimethylsilanoyloxy)methyl]-2-chlorophenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 4-[(tert-butyldimethylsilanoyloxy)methyl]-2-chloro aniline (360 mg, 1.3 mmol) obtained in Reference Example 14-9, there was obtained 1-methylpiperidin-4-yl N-{5-[2-({4-[tert-butyldimethylsilanoyloxy)methyl]-2-chlorophenyl}carbamoyl)ethyl]-2-phenylphenyl}carbamate (195 mg)

LC/MS: M+1=636.2

Reference Example 15-10

Synthesis of 1-methylpiperidin-4-yl N-{5-[4-{4-[(tert-butyldimethylsilanoyloxy)methyl]-2-methoxyphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 4-[(tert-butyldimethylsilanoyloxy)methyl]-2-methoxyaniline (401 mg, 1.5 mmol) obtained in Reference Example 14-10, there was obtained 1-methylpiperidin-4-yl N-{5-[2-({4-[(tert-butyldimethylsilanoyloxy)methyl]-2-methoxyphenyl}carbamoyl)ethyl]-2-phenylphenyl}carbamate (340 mg).

LC/MS: M+1=632.3

Reference Example 15-11

Synthesis of 1-methylpiperidin-4-yl N-{5-[2-({4-[(tert-butyldimethylsilanoyloxy)methyl]-2-methylphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (260 mg, 0.68 mmol) and 4-[(tert-butyldimethylsilanoyloxy)methyl]-2-methylaniline (170 mg, 0.68 mmol) obtained in Reference Example 14-11, there was obtained 1-methylpiperidin-4-yl N-{5-[2-{4-[(tert-butyldimethylsilanoyloxy)methyl]-2-methylphenyl}carbamoyl)ethyl]-2-phenylphenyl}carbamate (82 mg).

LC/MS: M+1=616.3

Reference Example 15-12

Synthesis of 1-methylpiperidin-4-yl N-(5-{2-[(6-{[(tert-butyldimethylsilyl)oxy]methyl}naphthalen-2-yl)carbamoyl]ethyl}-2-phenylphenyl)carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 6-[(tert-butyldimethylsilanoyloxy)methyl]naphthalen-2-amine (431 mg, 1.5 mmol) obtained in Reference Example 14-12, there was obtained 1-methylpiperidin-4-yl N-(5-{2-[(6-{[(tert-butyldimethylsilyl)oxy]methyl}naphthalen-2-yl)carbamoyl]ethyl}-2-phenylphenyl)carbamate (279 mg).

LC/MS: M+1=652.3

Reference Example 15-13

Synthesis of 1-methylpiperidin-4-yl N-(5-{2-[(5-{[(tert-butyldimethylsilyl)oxy]methyl}-1-benzothiophen-5-yl)carbamoyl]ethyl}-2-phenylphenyl)carbamate In accordance with Reference Example 15, from 3-[3-({[(1-methylpiperidin-4-yl)oxy]carbonyl}amino)-4-phenylphenyl]propionate hydrochloride (419 mg, 1.1 mmol) and 2-[(tert-butyldimethylsilanoyloxy)methyl]-1-benzothiophen-5-amine (440 mg, 1.5 mmol) obtained in Reference Example 14-13, there was obtained 1-methylpiperidin-4-yl N-(5-{2-[(5-{[(tert-butyldimethylsilyl)oxy]methyl}-1-benzothiophen-5-yl)carbamoyl]ethyl}-2-phenylphenyl)carbamate (204 mg).

LC/MS: M+1=685.3

Reference Example 15-14

Synthesis of 1-methylpiperidin-4-yl N-{5-[2-({5-[(tert-butyldimethylsilanoyloxy)methyl]-2-methoxyphenyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (382 mg, 1.0 mmol) and 5-[(tert-butyldimethylsilanoyloxy)methyl]-2-methoxyaniline (401 mg, 1.5 mmol) obtained in Reference Example 14-14, there was obtained 1-methylpiperidin-4-yl N-{5-[2-({5-[(tert-butyldimethylsilanoyloxy)methyl]-2- methoxyphenyl}carbamoyl)ethyl]-2-phenylphenyl}carbamate (322 mg).
LC/MS: M+1=632.3

Reference Example 15-15

Synthesis of 1-methylpiperidin-4-yl N-{5-[2-({4-[(tert-butyldimethylsilanoyloxy)methyl]phenyl}{methyl}carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (419 mg, 1.1 mmol) and 4-[(tert-butyldimethylsilanoyloxy)methyl]-N-methylaniline (377 mg, 1.5 mmol) obtained in Reference Example 14-15, there was obtained 1-methylpiperidin-4-yl N-{5-[2-({4-[(tert-butyldimethylsilanoyloxy)methyl]phenyl}{methyl}carbamoyl)ethyl]-2-phenylphenyl}carbamate (172 mg).
LC/MS: M+1=616.3

Reference Example 15-16

Synthesis of 1-methylpiperidin-4-yl N-(5-{2-[(5-{[(tert-butyldimethylsilyl)oxy]methyl}thiophen-2-yl)carbamoyl]ethyl}-2-phenylphenyl)carbamate In accordance with Reference Example 15, from 3-[3-({[(1-methylpiperidin-4-yl)oxy]carbonyl}amino)-4-phenylphenyl]propionate hydrochloride (293 mg, 0.7 mmol) and 5-[(tert-butyldimethylsilanoyloxy)methyl]thiophen-2-amine (170 mg, 0.7 mmol) obtained in Reference Example 14-16, there was obtained 1-methylpiperidin-4-yl N-(5-{2-[(5-{[(tert-butyldimethylsilyl)oxy]methyl}thiophen-2-yl)carbamoyl]ethyl}-2-phenylphenyl)carbamate (105.7 mg)
LC/MS: M+1=608.3

Reference Example 15-17

Synthesis of 1-methylpiperidin-4-yl N-(5-{2-[(5-{[(tert-butyldimethylsilyl)oxy]methyl}pyridin-2-yl)carbamoyl]ethyl}-2-phenylphenyl)carbamate In accordance with Reference Example 15, from 3-[3-({[(1-methylpiperidin-4-yl)oxy]carbonyl}amino)-4-phenylphenyl]propionate hydrochloride (209 mg, 0.5 mmol) and 5-[(tert-butyldimethylsilanoyloxy)methyl]pyridin-2-amine (179 mg, 0.75 mmol) obtained in Reference Example 14-17, there was obtained 1-methylpiperidin-4-yl N-(5-{2-[(5-{[(tert-butyldimethylsilyl)oxy]methyl}pyridin-2-yl)carbamoyl]ethyl}-2-phenylphenyl)carbamate (120 mg)
LC/MS: M+1=603.3

Reference Example 15-18

Synthesis of 1-methylpiperidin-4-yl N-{5-[3-({4-[(tert-butyldimethylsilanoyloxy)methyl]-2-chloro-5-methoxyphenyl}carbamoyl)propyl]-2-phenylphenyl)carbamate In accordance with Reference Example 15, from 3-[3-({[(1-methylpiperidin-4-yl)oxy]carbonyl}amino)-4-phenylphenyl]butyric acid (173.2 mg, 0.4 mmol) and 4-[(tert-butyldimethylsilanoyloxy)methyl]-2-chloro-5-methoxyaniline (181.1 mg, 0.6 mmol) obtained in Reference Example 14-2, there was obtained 1-methylpiperidin-4-yl N-{5-[3-({4-[(tert-butyldimethylsilanoyloxy)methyl]-2-chloro-5-methoxyphenyl}carbamoyl)propyl]-2-phenylphenyl)carbamate (108.5 mg)
LC/MS: M+1=680.3

Reference Example 15-19

Synthesis of 1-methylpiperidin-4-yl N-{5-[3-({4-[(tert-butyldimethylsilanoyloxy)methyl]-2-chlorophenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-2-chloroaniline (203.9 mg, 0.75 mmol) obtained in Reference Example 14-9, there was obtained 1-methylpiperidin-4-yl N-{5-[3-({4-[(tert-butyldimethylsilanoyloxy)methyl]-2-chlorophenyl}carbamoyl)propyl]-2-phenylphenyl}carbamate (192 mg)
LC/MS: M+1=650.3

Reference Example 15-20

Synthesis of 1-methylpiperidin-4-yl N-{5-[3-({4-[(tert-butyldimethylsilanoyloxy)methyl]-3-methoxyphenyl}carbamoyl propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-3-methoxyaniline (200.6 mg, 0.75 mmol) obtained in Reference Example 14-6, there was obtained 1-methylpiperidin-4-yl N-{5-[3-({4-[(tert-butyldimethylsilanoyloxy)methyl]-3-methoxyphenyl}carbamoyl)propyl]-2-phenylphenyl}carbamate (172 mg).
LC/MS: M+1=646.3

Reference Example 15-21

Synthesis of 1-methylpiperidin-4-yl N-{5-[3-({4-[(tert-butyldimethylsilanoyloxy)methyl]-2-methoxyphenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 5-[(tert-butyldimethylsilanoyloxy)methyl]-2-methoxyaniline (200.6 mg, 0.75 mmol) obtained in Reference Example 14-10, there was obtained 1-methylpiperidin-4-yl N-{5-[3-({4-[(tert-butyldimethylsilanoyloxy)methyl]-2-methoxyphenyl}carbamoyl)propyl]-2-phenylphenyl}carbamate (212 mg)
LC/MS: M+1=646.3

Reference Example 15-22

Synthesis of 1-methylpiperidin-4-yl N-{5-[3-({4-[(tert-butyldimethylsilanoyloxy)methyl]-2-methylphenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 5-[(tert-butyldimethylsilanoyloxy)methyl]-2-methylaniline (188.6 mg, 0.75 mmol) obtained in Reference Example 14-11, there was obtained 1-methylpiperidin-4-yl N-{5-[3-({4-[(tert-butyldimethylsilanoyloxy)methyl]-2-methylphenyl}carbamoyl)propyl]-2-phenylphenyl}carbamate (212 mg).

LC/MS: M+1=630.3

Reference Example 15-23

Synthesis of 1-methylpiperidin-4-yl N-(5-{3-[(6-{[(tert-butyldimethylsilyl)oxy]methyl}naphthalen-2-yl)carbamoyl]propyl}-2-phenylphenyl) carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 6-[(tert-butyldimethylsilanoyloxy)methyl]naphthalen-2-amine (215.6 mg, 0.75 mmol) obtained in Reference Example 14-12, there was obtained 1-methylpiperidin-4-yl N-(5-{3-[(6-{[(tert-butyldimethylsilyl)oxy]methyl}naphthalen-2-yl)carbamoyl]propyl}-2-phenylphenyl)carbamate (214 mg)

LC/MS: M+1=666.3

Reference Example 15-24

Synthesis of 1-methylpiperidin-4-yl N-(5-{3-[(5-{[(tert-butyldimethylsilyl)oxy]methyl}pyridin-2-yl)carbamoyl]propyl}-2-phenylphenyl)carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 5-[(tert-butyldimethylsilanoyloxy)methyl]pyridin-2-amine (179 mg, 0.75 mmol) obtained in Reference Example 14-17, there was obtained 1-methylpiperidin-4-yl N-(5-{3-[(5-{[(tert-butyldimethylsilyl)oxy]methyl}pyridin-2-yl)carbamoyl]propyl}-2-phenylphenyl)carbamate (175 mg)

LC/MS: M+1=617.3

Reference Example 15-25

Synthesis of 1-methylpiperidin-4-yl N-{5-[3-({2-bromo-4-[(tert-butyldimethylsilanoyloxy)methyl]-5-methoxyphenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (303 mg, 0.7 mmol) and 2-bromo-4-[(tert-butyldimethylsilanoyloxy)methyl]-5-methoxyaniline (363 mg, 1.0 mmol) obtained in Reference Example 14-18, there was obtained 1-methylpiperidin-4-yl N-{5-[3-({2-bromo-4-[(tert-butyldimethylsilanoyloxy)methyl]-5-methoxyphenyl}carbamoyl)propyl]-2-phenylphenyl}carbamate (124 mg)

LC/MS: M+1=726.2

Reference Example 15-26

Synthesis of 1-methylpiperidin-4-yl N-{5-[3-({4-[(tert-butyldimethylsilanoyloxy)methyl]-2-chloro-5-ethoxyphenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-2-chloro-5-ethoxyaniline (316 mg, 1.0 mmol) obtained in Reference Example 14-19, there was obtained 1-methylpiperidin-4-yl N-{5-[3-({4-[(tert-butyldimethylsilanoyloxy)methyl]-2-chloro-5-ethoxyphenyl}carbamoyl)propyl]-2-phenylphenyl}carbamate (53 mg)

LC/MS: M+1=694.4

Reference Example 15-27

Synthesis of 1-methylpiperidin-4-yl N-{5-[3-({4-[(tert-butyldimethylsilanoyloxy)methyl]-3-ethoxyphenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (217 mg, 0.50 mmol) and 4-[(tert-butyldimethylsilanoyloxy)methyl]-3-ethoxyaniline (106 mg, 0.38 mmol) obtained in Reference Example 14-20, there was obtained 1-methylpiperidin-4-yl N-{5-[3-{4-[(tert-butyldimethylsilanoyloxy)methyl]-3-ethoxyphenyl}carbamoyl)propyl]-2-phenylphenyl}carbamate (145 mg).

LC/MS: M+1=660.4

Reference Example 15-28

Synthesis of 1-methylpiperidin-4-yl N-{5-[3-({4-[(tert-butyldimethylsilanoyloxy)methyl]-2-fluorophenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-2-fluoroaniline (255 mg, 1.0 mmol) obtained in Reference Example 14-4, there was obtained 1-methylpiperidin-4-yl N-{5-[3-({4-[(tert-butyldimethylsilanoyloxy)methyl]-2-fluorophenyl}carbamoyl)propyl]-2-phenylphenyl}carbamate (173 mg)

LC/MS: M+1=634.3

Reference Example 15-29

Synthesis of 1-methylpiperidin-4-yl N-{5-[3-({4-[(tert-butyldimethylsilanoyloxy)methyl]-3-chlorophenyl}carbamoyl)propyl]-2-phenylphenyl carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-3-chloroaniline (272 mg, 1.0 mmol) obtained in Reference Example 14-3, there was obtained 1-methylpiperidin-4-yl N-{5-[3-({4-[(tert-butyldimethylsilanoyloxy)methyl]-3-chlorophenyl}carbamoyl)propyl]-2-phenylphenyl carbamate (157 mg)

LC/MS: M+1=650.3

Reference Example 15-30

Synthesis of 1-methylpiperidin-4-yl N-{5-[3-({2-bromo-4-[(tert-butyldimethylsilanoyloxy)methyl]phenyl}carbamoyl)propyl]-2-phenylphenyl carbamate In accordance with Reference Example 15, from 4-[3-({[(1-methylpiperidin-4-yl)oxy]carbonyl}amino)-4-phenylphenyl]butyric acid (216 mg, 0.5 mmol) and 2-bromo-4-[(tert-butyldimethylsilanoyloxy)methyl]aniline (316 mg, 1.0 mmol) obtained in Reference Example 14-21, there was obtained 1-methylpiperidin-4-yl N-{5-[3-({2-bromo-4-[(tert-butyldimethylsilanoyloxy)methyl]phenyl}carbamoyl)propyl]-2-phenylphenyl carbamate (110 mg).
LC/MS: M+1=696.3

Reference Example 15-31

Synthesis of 1-methylpiperidin-4-yl N-{5-[3-({4-[(tert-butyldimethylsilanoyloxy)methyl]-3-(trifluoromethyl)phenyl}carbamoylpropyl]-2-phenylphenyl}carbamate In accordance with Reference Example 15, from 4-[3-({[(1-methylpiperidin-4-yl)oxy]carbonyl}amino)-4-phenylphenyl]butyric acid (216.5 mg, 0.5 mmol) and 4-[(tert-butyldimethylsilanoyloxy)methyl]-3-(trifluoromethyl)aniline (305 mg, 1.0 mmol) obtained in Reference Example 14-22, there was obtained 1-methylpiperidin-4-yl N-{5-[3-({4-[(tert-butyldimethylsilanoyloxy)methyl]-3-(trifluoromethyl)phenyl}carbamoyl)propyl]-2-phenylphenyl}carbamate (172 mg).
LC/MS: M+1=684.3

Reference Example 15-32

Synthesis of 1-methylpiperidin-4-yl N-{5-[3-({4-[(tert-butyldimethylsilanoyloxy)methyl]phenyl}carbamoyl)propyl]-2-phenylphenyl}carbamate In accordance with Reference Example 15, from 4-[3-({[(1-methylpiperidin-4-yl)oxy]carbonyl}amino)-4-phenylphenyl]butyric acid (161 mg, 0.4 mmol) and 4-[(tert-butyldimethylsilanoyloxy)methyl]aniline (142 mg, 0.6 mmol) obtained in Reference Example 14, there was obtained 1-methylpiperidin-4-yl N-{5-[3-({4-[(tert-butyldimethylsilanoyloxy)methyl]phenyl}carbamoyl)propyl]-2-phenylphenyl}carbamate (122 mg).
LC/MS: M+1=616.3

Reference Example 15-33

Synthesis of (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]phenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (161 mg, 0.4 mmol) and 4-[(tert-butyldimethylsilanoyloxy)methyl]aniline (142 mg, 0.6 mmol) obtained in Reference Example 14, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]phenyl}carbamoyl)propyl]-2-phenylphenyl}carbamate (122 mg).
LC/MS: M+1=656.3

Reference Example 15-34

Synthesis of (1R,2R,4S,5 S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chloro-5-methoxyphenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (173 mg, 0.40 mmol) and 4-[(tert-butyldimethylsilanoyloxy)methyl]-2-chloro-5-methoxyaniline (181.1 mg, 0.6 mmol) obtained in Reference Example 14-2, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chloro-5-methoxyphenyl}carbamoyl)propyl]-2-phenylphenyl}carbamate (108.5 mg).
LC/MS: M+1=720.3

Reference Example 15-35

Synthesis of (1R,2R,4S,5S,7S)-9-methyl-3-oxa-9-azatricyclo[3.3.1.0$^{2,4}$]nonan-7-yl N-(5-{3-[(6-{[(tert-butyldimethylsilyl)oxy]methyl}naphthalen-2-yl)carbamoyl]propyl}-2-phenylphenyl)carbamate In accordance with Reference Example 15, from 4-[3-{[({[1R,2R,4S,5 S,7S]-9-methyl-3-oxa-9-azatricyclo[3.3.1.0$^{2,4}$]nonan-7-yl}oxy)carbonyl]amino}-4-phenylphenyl)butyric acid (218 mg, 0.5 mmol) and 6-[(tert-butyldimethylsilanoyloxy)methyl]naphthalen-2-amine (287 mg, 1.0 mmol) obtained in Reference Example 14-12, there was obtained (1R,2R,4S,5S,7S)-9-methyl-3-oxa-9-azatricyclo[3.3.1.0$^{2,4}$]nonan-7-yl N-(5-{3-[(6-{[(tert-butyldimethylsilyl)oxy]methyl}naphthalen-2-yl)carbamoyl]propyl}-2-phenylphenyl)carbamate (181 mg).
LC/MS: M+1=706.3

Reference Example 15-36

Synthesis of (1R,2R,4 S,5 S,7S)-9-methyl-3-oxa-9-azatricyclo[3.3.1.0$^{2,4}$]nonan-7-yl N-{5-[3-({4-[(tert-butyldimethylsilanoyloxy)methyl]-3-methoxyphenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (218 mg, 0.5 mmol) and 4-[(tert-butyldimethylsilanoyloxy)methyl]-3-methoxyaniline (266.6 mg, 1.0 mmol) obtained in Reference Example 14-6, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-3-methoxyphenyl}carbamoyl)propyl]-2-phenylphenyl}carbamate (251 mg).
LC/MS: M+1=686.3

Reference Example 15-37

Synthesis of (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chlorophenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (218 mg, 0.5 mmol) and 4-[(tert-butyldimethylsilanoyloxy)methyl]-2-chloroaniline (270 mg, 1.0 mmol) obtained in Reference Example 14-9, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chlorophenyl}carbamoyl)propyl]-2-phenylphenyl}carbamate (161 mg).
LC/MS: M+1=690.3

Reference Example 15-38

Synthesis of (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methoxyphenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (218 mg, 0.5 mmol) and 5-[(tert-butyldimethylsilanoyloxy)methyl]-2-methoxyaniline (267 mg, 1.0 mmol) obtained in Reference Example 14-10, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methoxyphenyl}carbamoyl)propyl]-2-phenyl}carbamate (311 mg).
LC/MS: M+1=686.3

Reference Example 15-39

Synthesis of (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methylphenyl}carbamoyl)propyl]-2-phenylphenyl}carbamate In accordance with Reference Example 15, from 4-[3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (218 mg, 0.5 mmol) and 5-[(tert-butyldimethylsilanoyloxy)methyl]-2-methylaniline (250 mg, 1.0 mmol) obtained in Reference Example 14-10, there was obtained (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methylphenyl}carbamoyl)propyl]-2-phenylphenyl}carbamate (149 mg).
LC/MS: M+1=670.3

Reference Example 15-40

Synthesis of (1R,2R,4S,5S,7S)-9-methyl-3-oxa-9-azatricyclo[3.3.1.0$^{2,4}$]nonan-7-yl N-(5-{2-[(6-{[(tert-butyldimethylsilyl)oxy]methyl}naphthalen-2-yl)carbamoyl]ethyl}-2-phenylphenyl)carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (382 mg, 1.0 mmol) and 6-[(tert-butyldimethylsilanoyloxy)methyl]naphthalen-2-amine (250 mg, 0.87 mmol) obtained in Reference Example 14-12, there was obtained (1R,2R,4S,5S,7S)-9-methyl-3-oxa-9-azatricyclo[3.3.1.0$^{2,4}$]nonan-7-yl N-(5-{2-[(6-{[(tert-butyldimethylsilyl)oxy]methyl}naphthalen-2-yl)carbamoyl]ethyl}-2-phenylphenyl)carbamate (311 mg).
LC/MS: M+1=692.3

Reference Example 15-41

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methoxyphenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (230 mg, 0.5 mmol) and 4-[(tert-butyldimethylsilanoyloxy)methyl]-2-methoxyaniline (200 mg, 0.75 mmol) obtained in Reference Example 14-10 was obtained (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methoxyphenyl}carbamoyl)ethyl]-2-phenylphenyl}carbamate (281 mg).
LC/MS: M+1=672

Reference Example 15-42

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-methoxyphenyl}carbamoyl)ethyl-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (230 mg, 0.5 mmol) and 4-[(tert-butyldimethylsilanoyloxy)methyl]-3-methoxyaniline (200 mg, 0.75 mmol) obtained in Reference Example 14-6, there was obtained (1R,2R,4S,5S,7S)-9-methyl-3-oxa-9-azatricyclo[3.3.1.0$^{2,4}$]nonan-7N-{5-[2-({4-[(tert-butyldimethylsilanoyloxy)methyl]-3-methoxyphenyl}carbamoyl)ethyl]-2-phenylphenyl}carbamate (239 mg).
LC/MS: M+1=672.3

Reference Example 15-43

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methylphenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (206 mg, 0.45 mmol) and 4-[(tert-butyldimethylsilanoyloxy)methyl]-2-methylaniline (170 mg, 0.68 mmol) obtained in Reference Example 14-11, there was obtained (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methylphenyl}carbamoyl)ethyl]-2-phenylphenyl}carbamate (296 mg).
LC/MS: M+1=656.3

Reference Example 15-44

Synthesis of (1R,2R,4S,5S,7S)-9-methyl-3-oxa-9-azatricyclo[3.3.1.0$^{2,4}$]nonan-7-yl N-{5-[2-{4-[(tert-butyldimethylsilanoyloxy)methyl]-2-chlorophenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (165 mg, 0.36 mmol) and 4-[(tert-butyldimethylsilanoyloxy)methyl]-2-chloro aniline (294 mg, 1.08 mmol) obtained in Reference Example 14-9, there was obtained (1R,2R,4S,5 S,7S)-9-methyl-3-oxa-9-azatricyclo[3.3.1.0$^{2,4}$]nonan-7-yl N-{5-[2-({4-[(tert-butyldimethylsilanoyloxy)methyl]-2-chlorophenyl}carbamoyl)ethyl]-2-phenylphenyl}carbamate (96 mg).
LC/MS: M+1=676.2

Reference Example 15-45

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-chlorophenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (156 mg, 0.34 mmol) and 4-[(tert-butyldimethylsilanoyloxy)methyl]-3-chloroaniline (137 mg, 0.51 mmol) obtained in Reference Example 14-3, there was obtained (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-chlorolphenyl}carbamoyl)ethyl]-2-phenylphenyl}carbamate (156 mg).
LC/MS: M+1=676.2

Reference Example 15-46

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-chlorol-5-methoxyphenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (138 mg, 0.3 mmol) and 4-[(tert-butyldimethylsilanoyloxy)methyl]-2-chloro-5-methoxyaniline (151 mg, 0.5 mmol) obtained in Reference Example 14-2, there was obtained (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-chlorol-5-methoxyphenyl}carbamoyl)ethyl]-2-phenylphenyl}carbamate (52 mg).
LC/MS: M+1=706.3

Reference Example 15-47

Synthesis of (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-ethoxyphenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)propionate hydrochloride (174 mg, 0.38 mmol) and 4-[(tert-butyldimethylsilanoyloxy)methyl]-3-ethoxyaniline (160 mg, 0.57 mmol) obtained in Reference Example 14-20, there was obtained (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-ethoxyphenyl}carbamoyl)propyl]-2-phenylphenyl}carbamate (216 mg).
LC/MS: M+1=687.3

Reference Example 15-48

Synthesis of (1R,3R)-8-methyl-8-azabicyclo[3.2.1]octan-3-yl N-{5-[3-({4-[(tert-butyldimethylsilanoyloxy)methyl]-2-chloro-5-methoxyphenyl}carbamoyl)propyl]-2-phenylphenyl}carbamate In accordance with Reference Example 15, from 4-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)butyric acid (173 mg, 0.40 mmol) obtained in Reference Example 21-3 and 4-[(tert-butyldimethylsilanoyloxy)methyl]-2-chloro-5-methoxyaniline (181.1 mg, 0.60 mmol) obtained in Reference Example 14-2, there was obtained (1R,3R)-8-methyl-8-azabicyclo[3.2.1]octan-3-yl N-{5-[3-({4-[(tert-butyldimethylsilanoyloxy)methyl]-2-chloro-5-methoxyphenyl}carbamoyl)propyl]-2-phenylphenyl}carbamate (108.5 mg).
LC/MS: M+1=720.3

Reference Example 15-49

Synthesis of 1-methylpiperidin-4-yl N-{5-[4-({4-[(tert-butyldimethylsilanoyloxy)methyl]-3-methoxyphenyl}carbamoyl)butyl]-2-phenylphenyl}carbamate In accordance with Reference Example 15, from 5-[3-({[(1-methylpiperidin-4-yl)oxy]carbonyl}amino)-4-phenylphenyl]valeric acid (205 mg, 0.50 mmol) obtained in Reference Example 21-4 and 4-[(tert-butyldimethylsilanoyloxy)methyl]aniline (237 mg, 1.00 mmol) obtained in Reference Example 14, there was obtained 1-methylpiperidin-4-yl N-{5-[4-({4-[(tert-butyldimethylsilanoyloxy)methyl]-3-methoxyphenyl}carbamoyl)butyl]-2-phenylphenyl}carbamate (137 mg).
LC/MS: M+1=630.3

Reference Example 15-50

Synthesis of (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]phenyl}carbamoyl)butyl]-2-phenylphenyl}carbamate In accordance with Reference Example 15, from 5-(3-{[({[1R,2R,4S,5S,7S]-9-methyl-3-oxa-9-azatricyclo[3.3.1.0$^{2,4}$]

nonan-7-yl}oxy)carbonyl]amino}-4-phenylphenyl)valeric acid (225 mg, 0.50 mmol) obtained in Reference Example 21-5 and 4-[(tert-butyldimethylsilanoyloxy)methyl]aniline (237 mg, 1.00 mmol) obtained in Reference Example 14, there was obtained (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]phenyl}carbamoyl)butyl]-2-phenylphenyl}carbamate (64 mg).

LC/MS: M+1=670.3

Reference Example 15-51

Synthesis of 1-methylpiperidin-4-yl N-{5-[4-({4-[(tert-butyldimethylsilanoyloxy)methyl]-2-chloro-5-methoxyphenyl}carbamoyl)butyl]-2-phenylphenyl}carbamate In accordance with Reference Example 15, from 5-[3-({[(1-methylpiperidin-4-yl)oxy]carbonyl}amino)-4-phenylphenyl]valeric acid (205 mg, 0.50 mmol) obtained in Reference Example 21-4 and 4-[(tert-butyldimethylsilanoyloxy)methyl]-2-chloro-5-methoxyaniline (181.1 mg, 0.60 mmol) obtained in Reference Example 14-2, there was obtained 1-methylpiperidin-4-yl N-{5-[4-({4-[(tert-butyldimethylsilanoyloxy)methyl]-2-chloro-5-methoxyphenyl}carbamoyl)butyl]-2-phenylphenyl}carbamate (60.5 mg).

LC/MS: M+1=694.3

Reference Example 15-52

Synthesis of (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]-2-chloro-5-methoxyphenyl}carbamoyl)butyl]-2-phenylphenyl}carbamate In accordance with Reference Example 15, from 5-(3-{[({[1R,2R,4S,5S,7S]-9-methyl-3-oxa-9-azatricyclo[3.3.1.0$^{2,4}$]nonan-7-yl}oxy)carbonyl]amino}-4-phenylphenyl)valeric acid (225 mg, 0.50 mmol) obtained in Reference Example 21-5 and 4-[(tert-butyldimethylsilanoyloxy)methyl]-2-chloro-5-methoxylaniline (181.1 mg, 0.60 mmol) obtained in Reference Example 14-2, there was obtained (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]-2-chloro-5-methoxyphenyl}carbamoyl)butyl]-2-phenylphenyl}carbamate (76.5 mg).

LC/MS: M+1=734.3

Reference Example 24

Synthesis of 2-phenyl-N-acetylaniline

2-Phenylaniline (5 g, 29.55 mmol) was dissolved in acetic acid (30 mL), acetic anhydride (3.62 g, 35.45 mmol) was added thereto under ice bath, and the mixture was stirred under ice bath for 2 hours. The solution was concentrated under reduced pressure. to the residue was added water (15 mL), and the mixture was stirred at room temperature for 3 hours. The precipitate was collected by filtration, washed with purified water, and dried under reduced pressure to obtain 2-phenyl-N-acetylaniline (6.21 g).

$^1$H-NMR (400 MHz, CDCl$_3$) δ 8.27 (d, J=8.0 Hz, 1H), 7.12-7.51 (m, 8H), 2.02 (s, 3H)

Reference Example 25

Synthesis of 2-phenyl-4-bromo-N-acetylaniline

2-Phenyl-N-acetylaniline (6.21 g, 29.40 mmol) was dissolved in acetic acid (70 mL). Thereto was dropwise added under ice bath a separately prepared solution of hydrogen bromide (6.14 g, 38.42 mmol) dissolved in carbon tetrachloride (19.21 mL) and the mixture was stirred at room temperature overnight. The solution was concentrated under reduced pressure, to the residue was added water (20 mL) and subsequently ethanol (30 mL), and the mixture was stirred under ice bath for 1 hour. The precipitate was collected by filtration, washed with ethanol/water (=1:1), dried under reduced pressure to obtain 2-phenyl-4-bromo-N-acetylaniline (7.79 g).

$^1$H-NMR (400 MHz, CDCl$_3$) δ 8.22 (d, J=8.8 Hz, 1H), 7.44-7.52 (m, 4H), 7.34-7.38 (m, 3H), 2.01 (s, 3H)

Reference Example 26

Synthesis of 2-phenyl-4-bromo aniline

2-Phenyl-4-bromo-N-acetylaniline (7.79 g, 26.85 mmol) was dissolved in ethanol (100 mL), 2 N hydrochloric acid (33.56 mmol, 67.12 mL) was added dropwise under ice bath, and the mixture was heated under reflux overnight. The solution was concentrated under reduced pressure and to the residue were added ethyl acetate (50 mL) and water (40 mL) for extraction. The organic layer was dried over sodium sulfate and, after filtration, concentrated under reduced pressure. The residue was purified by a silica gel column to obtain 2-phenyl-4-bromoaniline (6.58 g).

$^1$H-NMR (400 MHz, CDCl$_3$) δ 7.40-7.47 (m, 4H), 7.36-7.39 (m, 1H), 7.22-7.24 (m, 2H), 6.65 (dd, J=6.6 Hz, 2.4 Hz, 1H), 3.76 (bs, 1H)

Reference Example 27

Synthesis of tert-butyl(3E)-4-(3-amino-4-phenylphenyl)-3-butenoate

2-Phenyl-4-bromoaniline (564.7 mg, 2.28 mmol) was dissolved in N,N-dimethylformamide (25 mL) and, at room temperature, thereto were added tert-butyl-3-butenoate (582.5 mg, 4.10 mmol), tri-(o-tolyl)phosphine (1.87 g, 6.16 mmol), and diisopropylethylamine (0.78 mL, 4.56 mmol). The reaction mixture was deaerated, palladium acetate (67.4 mg, 0.30 mmol) was added, and the mixture was deaerated again. After stirring at 90° C. overnight, the reaction mixture was filtered through celite and washed with ethyl acetate (120 mL). The organic layer was washed with a saturated aqueous solution of sodium chloride (50 mL), thereafter dried over sodium sulfate, filtered, and concentrated under reduced pressure. The residue was purified by a silica gel column to obtain tert-butyl (3E)-4-(3-amino-4-phenylphenyl)-3-butenoate (555.8 mg).

$^1$H-NMR (400 MHz, CDCl$_3$) δ 7.45 (d, J=4.4 Hz, 1H), 7.33-7.38 (m, 1H), 7.18 (dt, J=12.5 Hz, 4.5 Hz, 2H), 6.71 (d, J=8.3 Hz, 1H), 6.38 (d, J=15.9 Hz, 1H), 6.05-6.14 (m, 1H), 3.79 (bs, 1H), 3.12 (dd, J=7.2 Hz, 1.3 Hz, 1H), 1.46 (s, 9H)

Reference Example 11-2

Synthesis of tert-butyl 4-(3-amino-4-phenylphenyl)butanoate

In accordance with Reference Example 11, from tert-butyl (3E)-4-(3-amino-4-phenylphenyl)but-3-enoate (555.8 mg, 1.80 mmol), there was obtained tert-butyl 4-(3-amino-4-phenylphenyl)butanoate (450.1 mg).
$^1$H-NMR (400 MHz, CDCl$_3$) δ 7.44-7.47 (m, 4H), 7.30-7.38 (m, 1H), 6.94-7.00 (m, 2H), 6.71 (d, J=8.0 Hz, 1H), 2.56 (t, J=7.6 Hz, 2H), 2.24 (t, J=7.6 Hz, 2H), 1.84-1.92 (m, 2H), 1.44 (s, 9H)

Reference Example 12-3

Synthesis of tert-butyl 4-[4-({[(1-methylpiperidin-4-yl)oxy]carbonyl}amino)-3-phenylphenyl]butyrate In accordance with Reference Example 12, from tert-butyl 4-(4-amino-3-phenylphenyl)butyrate (158.2 mg, 0.51 mmol), there was obtained tert-butyl 4-[4-({[(1-methylpiperidin-4-yl)oxy]carbonyl}amino)-3-phenylphenyl)butyrate (224.7 mg).
LC/MS: M+1=453.2

Reference Example 12-4

Synthesis of tert-butyl 4-(4-{[({[1R,2R,4S,5S,7S)-9-methyl-3-oxa-9-azatricyclo[3.3.1.0$^{2,4}$]nonan-7-yl}oxy)carbonyl]amino}-3-phenylphenyl)butyrate In accordance with Reference Example 12, from scopine (118.3 mg, 0.76 mmol) and tert-butyl 4-(4-amino-3-phenylphenyl)butyrate (158.2 mg, 0.51 mmol), there was obtained tert-butyl 4-(4-{[({[1R,2R,4S,5S,7S)-9-methyl-3-oxa-9-azatricyclo[3.3.1.0$^{2,4}$]nonan-7-yl}oxy)carbonyl]amino}-3-phenylphenyl)butyrate (181.2 mg, 0.37 mmol).
LC/MS: M+1=493.2

Reference Example 13-3

Synthesis of 4-[4-({[(1-methylpiperidin-4-yl)oxy]carbonyl}amino)-3-phenylphenyl]butyrate hydrochloride In accordance with Reference Example 13, from tert-butyl 4-[4-({[(1-methylpiperidin-4-yl)oxy]carbonyl}amino)-3-phenylphenyl]butyrate (224.7 mg, 0.50 mmol), there was obtained 4-[4-({[(1-methylpiperidin-4-yl)oxy]carbonyl}amino)-3-phenylphenyl]butyrate hydrochloride.
LC/MS: M+1=397.1

Reference Example 13-4

Synthesis of 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate hydrochloride In accordance with Reference Example 13, from tert-butyl 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate (181.2 mg, 0.37 mmol), there was obtained 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate hydrochloride.
LC/MS: M+1=437.1 .

Reference Example 15-53

Synthesis of (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]phenyl}carbamoyl)propyl]-2-phenylphenyl}carbamate In accordance with Reference Example 15, from 4-(4-{[({[1R,2R,4S,5S,7S)-9-methyl-3-oxa-9-azatricyclo[3.3.1.0$^{2,4}$]nonan-7-yl}oxy)carbonyl]amino}-3-phenylphenyl)butyrate hydrochloride (0.37 mmol) obtained in Reference Example 13-4 and 4-[(tert-butyldimethylsilanoyloxy)methyl]aniline (66.5 mg, 0.28 mmol) obtained in Reference Example 14, there was obtained (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]phenyl}carbamoyl)propyl]-2-phenylphenyl}carbamate (70.1 mg).
LC/MS: M+1=656.3

Reference Example 15-54

Synthesis of 1-methylpiperidin-4-yl N-{4-[3-({4-[(tert-butyldimethylsilanoyloxy)methyl]phenyl}carbamoyl)propyl]-2-phenylphenyl}carbamate In accordance with Reference Example 15, from 4-[3-({[(1-methylpiperidin-4-yl)oxy]carbonyl}amino)-3-phenylphenyl)butyric acid (161 mg, 0.4 mmol) obtained in Reference Example 13-3 and 4-[(tert-butyldimethylsilanoyloxy)methyl]aniline (90.2 mg, 0.38 mmol) obtained in Reference Example 14, there was obtained 1-methylpiperidin-4-yl N-{4-[3-({4-[(tert-butyldimethylsilanoyloxy)methyl]phenyl}carbamoyl)propyl]-2-phenylphenyl}carbamate (88.2 mg).
LC/MS: M+1=616.3

Reference Example 15-55

Synthesis of (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-chloro-5-methoxyphenyl}carbamoyl)propyl]-2-phenylphenyl}carbamate In accordance with Reference Example 15, from 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyate hydrochloride (0.75 mmol) obtained in Reference Example 13-4 and 4-[(tert-butyldimethylsilanoyloxy)methyl]-2-chloro-5-methoxyaniline (339.6 mg, 1.13 mmol) obtained in Reference Example 14-2, there was obtained (1R,2R,4S,5S,7S)-9-methyl-3-oxa-9-azatricyclo[3.3.1.0$^{2,4}$]nonan-7-yl N-{4-[3({4-[(tert-butyldimethylsilanoyloxy)methyl]-2-chloro-5-methoxyphenyl}carbamoyl)propyl]-2-phenylphenyl}carbamate (201.2 mg).
LC/MS: M+1=720.2

Reference Example 15-56

Synthesis of (1R,2R,4S,5S,7S)-9-methyl-3-oxa-9-azatricyclo[3.3.1.0$^{2,4}$]nonan-7-yl N-(4-{3-[(6-{[(tert-butyldimethylsilyl)oxy]methyl}naphthalen-2-yl)carbamoyl]propyl}-2-phenylphenyl)carbamate In accordance with Reference Example 15, from 4-(4-{[({[1R,2R,4S,5S,7S]-9-methyl-3-oxa-9-azatricyclo[3.3.1.0$^{2,4}$]

nonan-7-yl}oxy)carbonyl]amino}-3-phenylphenyl)butyate hydrochloride (0.23 mmol) obtained in Reference Example 13-4 and 6-[(tert-butyldimethylsilanoyloxy)methyl]naphthalen-2-amine (99.2 mg, 0.35 mmol) obtained in Reference Example 14-12, there was obtained (1R,2R,4S,5S,7S)-9-methyl-3-oxa-9-azatricyclo[3.3.1.0$^{2,4}$]nonan-7-yl N-(4-{3-[(6-{[(tert-butyldimethylsilyl)oxy]methyl}naphthalen-2-yl)carbamoyl]propyl}-2-phenylphenyl)carbamate.
LC/MS: M+1=706.2

Reference Example 12-5

Synthesis of tert-butyl 3-{3-[({[1-(2-phenoxyethyl)piperidin-4-yl]oxy}carbonyl)amino]-4-phenylphenyl}propionate In accordance with Reference Example 12, from 1-(2-phenoxyethyl)piperidin-4-ol (712 mg, 3.22 mmol) obtained in Reference Example 22 and tert-butyl 3-(3-amino-4-phenylphenyl)propionate (239 mg, 0.80 mmol), there was obtained tert-butyl 3-{3-[({[1-(2-phenoxyethyl)piperidin-4-yl]oxy}carbonyl)amino]-4-phenylphenyl}propionate (471 mg).
LC/MS: M+1=545.3

Reference Example 13-5

Synthesis of 3-{3-[({[1-(2-phenoxyethyl)piperidin-4-yl]oxy}carbonyl)amino]-4-phenylphenyl}propionate hydrochloride In accordance with Reference Example 13, from tert-butyl 3-{3-[({[1-(2-phenoxyethyl)piperidin-4-yl]oxy}carbonyl)amino]-4-phenylphenyl}propionate (471 mg, 0.86 mmol) obtained in Reference Example 12-5, there was obtained 3-{3-[({[1-(2-phenoxyethyl)piperidin-4-yl]oxy}carbonyl)amino]-4-phenylphenyl}propionate hydrochloride (422 mg).
LC/MS: M+1=489.3

Reference Example 15-57

Synthesis of 1-(2-phenoxyethyl)piperidin-4-yl N-{5-[2-({4-[(tert-butyldimethylsilanoyloxy)methyl]phenyl}carbamoyl)ethyl]-2-phenylphenyl}carbamate In accordance with Reference Example 15, from 3-{3-[({[1-(2-phenoxyethyl)piperidin-4-yl]oxy}carbonyl)amino]-4-phenylphenyl}propionate hydrochloride (227.1 mg, 0.43 mmol) obtained in Reference Example 13-5, there was obtained 1-(2-phenoxyethyl)piperidin-4-yl N-{5-[2-({4-[(tert-butyldimethylsilanoyloxy)methyl]phenyl}carbamoyl)ethyl]-2-phenylphenyl}carbamate (237 mg).
LC/MS: M+1=708.3

Reference Example 28

Synthesis of 4-methoxy-2-nitro-1-phenylbenzene

1-Bromo-4-methoxy-2-nitrobenzene (2.32 g, 10 mmol) was dissolved in 1,4-dioxane (30 mL) and, thereto, were added phenyl boric acid (2.44 g, 20 mmol), cesium carbonate (26 g, 80 mmol), 1,1-[bis(diphenylphosphino)ferrocene]dichloropalladium(II) dichloromethane complex (0.82 g, 1 mmol), and purified water (12 mL). The reaction mixture was stirred under a nitrogen flow at 80° C. for 18 hours. The reaction solution was filtered through celite, alumina, and Florisil, and, thereafter, extracted with ethyl acetate. The organic layer was washed with a saturated aqueous solution of sodium chloride, dried over anhydrous magnesium sulfate, and concentrated under reduced pressure. The residue was purified by flash column chromatography to obtain 4-methoxy-2-nitro-1-phenylbenzene (1.86 g).

Reference Example 29

Synthesis of 3-nitro-4-phenylphenol

4-Methoxy-2-nitro-1-phenylbenzene (1.86 g, 8.31 mmol) was dissolved in dichloromethane (40 mL) and thereto was added, under ice-water cooling, a solution of boron tribromide (2 mL) in dichloromethane (10 mL) After stirring at room temperature for 18 hours, the reaction mixture was poured onto ice to stop the reaction and extracted with ethyl acetate. The organic layer was washed with a saturated aqueous solution of sodium chloride, dried over anhydrous magnesium sulfate, and concentrated under reduced pressure to obtain 3-nitro-4-phenylphenol as a crude material.

Reference Example 30

Synthesis of 8-(3-nitro-4-phenylphenoxy)octan-1-ol

3-Nitro-4-phenylphenol (860 mg, 4.0 mmol) was dissolved in N,N-dimethylformamide (40 mL), followed by addition of 8-bromo-1-octanol (1.86 g, 6.0 mmol). After stirring at 50° C. for 5 hours, the reaction solution was extracted with ethyl acetate. The organic layer was washed with a saturated aqueous solution of sodium chloride, dried over anhydrous magnesium sulfate, and concentrated under reduced pressure. The residue was purified by flash column chromatography to obtain 8-(3-nitro-4-phenylphenoxy)octan-1-ol (1.23 g).
$^1$H-NMR (400 MHz, CDCl$_3$) δ 7.34-7.44 (m, 5H), 7.26-7.33 (m, 2H), 7.13 (dd, J=8.5 Hz, 2.4 Hz, 1H), 4.03 (t, J=6.5 Hz, 2H), 3.65 (t, J=6.5 Hz, 2H), 1.78-1.87 (m, 2H), 1.44-1.65 (m, 4H), 1.31-1.42 (m, 6H)

Reference Example 31

Synthesis of tert-butyldimethyl{[8-(3-nitro-4-phenylphenoxy)octyl]oxy}silane 8-(3-Nitro-4-phenylphenoxy)octan-1-ol (1.23 g, 3.5 mmol) and imidazole (408 mg, 6.0 mmol) were dissolved in tetrahydrofuran (15 mL) and a solution of tert-butyldimethylchlorosilane (750 mg, 5.0 mmol) in tetrahydrofuran (5 mL) was added thereto. After stirring the reaction mixture at room temperature for 18 hours, purified water was added to stop the reaction and the mixture was extracted with ethyl acetate. The organic layer was washed with a saturated aqueous solution of sodium bicarbonate, a saturated aqueous solution of ammonium chloride, and a saturated aqueous solution of sodium chloride, dried over anhydrous magnesium sulfate, and concentrated under reduced pressure. The residue was purified by flash column chromatography to obtain tert-butyldimethyl{[8-(3-nitro-4-phenylphenoxy)octyl]oxy}silane (1.38 g).
$^1$H-NMR (400 MHz, CDCl$_3$) δ 7.32-7.44 (m, 5H), 7.26-7.30 (m, 2H), 7.13 (dd, J=8.5 Hz, 2.7 Hz, 1H), 4.03 (t, J=6.5 Hz, 2H), 3.61 (t, J=6.5 Hz, 2H), 1.78-1.87 (m, 2H), 1.44-1.65 (m, 4H), 1.31-1.42 (m, 6H), 0.90 (s, 9H), 0.05 (s, 6H)

Reference Example 32

Synthesis of 5-{[8-(tert-butyldimethylsilanoyloxy)octyl]oxy}-2-phenylaniline

{[8-(3-Nitro-4-phenylphenoxy)octyl]oxy}silane (1.38 g, 3.02 mmol) was dissolved in methanol (20 mL), 10% palladium-carbon (50 mg) was added thereto, and the reaction mixture was stirred under a hydrogen atmosphere at room temperature for 2 hours. The reaction solution was filtered through celite and the filtrate was concentrated under reduced pressure to obtain 5-{[8-(tert-butyldimethylsilanoyloxy)octyl]oxy}-2-phenylaniline as a crude material.
LC/MS: M+1=428.3

Reference Example 32-2

Synthesis of 5-{[6-(tert-butyldimethylsilanoyloxy)hexyl]oxy}-2-phenylaniline

In accordance with Reference Examples 30, 31, and 32, from 6-bromo-1-hexanol (543 mg, 3.0 mmol) and 3-nitro-4-phenylphenol (430 mg, 2.0 mmol), there was obtained 5-{[6-(tert-butyldimethylsilanoyloxy)hexyl]oxy}-2-phenylaniline.
LC/MS: M+1=316.3

Reference Example 32-3

Synthesis of 5-{[9-(tert-butyldimethylsilanoyloxy)nonyl]oxy}-2-phenylaniline

In accordance with Reference Examples 30, 31, and 32, from 9-bromo-1-nonanol (669 mg, 3.0 mmol) and 3-nitro-4-phenylphenol (430 mg, 2.0 mmol), there was obtained 5-{[9-(tert-butyldimethylsilanoyloxy)nonyl]oxy}-2-phenylaniline.
LC/MS: M+1=358.3

Reference Example 12-6

Synthesis of 1-methylpiperidin-4-yl N-(5-{[8-(tert-butyldimethylsilanoyloxy)octyl]oxy}-2-phenylphenyl)carbamate In accordance with Reference Example 12, from 1-methylpiperidinol (1.15 g, 10 mmol) and 5-{[8-(tert-butyldimethylsilanoyloxy)octyl]oxy}-2-phenylaniline (777 mg, 1.82 mmol) obtained in Reference Example 32, there was obtained 1-methylpiperidin-4-yl N-(5-{[8-(tert-butyldimethylsilanoyloxy)octyl]oxy}-2-phenylphenyl)carbamate (283 mg).
LC/MS: M+1=589.3

Reference Example 12-7

Synthesis of 1-methylpiperidin-4-yl N-(5-{[6-(tert-butyldimethylsilanoyloxy)hexyl]oxy}-2-phenylphenyl)carbamate In accordance with Reference Example 12, from 1-methylpiperidinol (865 mg, 7.5 mmol) and 5-{[6-(tert-butyldimethylsilanoyloxy)hexyl]oxy}-2-phenylaniline obtained in Reference Example 32-2, there was obtained 1-methylpiperidin-4-yl N-(5-{[6-(tert-butyldimethylsilanoyloxy)hexyl]oxy}-2-phenylphenyl)carbamate (626 mg)
LC/MS: M+1=540.3 .

Reference Example 12-8

Synthesis of 1-methylpiperidin-4-yl N-(5-{[9-(tert-butyldimethylsilanoyloxy)nonyl]oxy}-2-phenylphenyl)carbamate In accordance with Reference Example 12, from 1-methylpiperidinol (865 mg, 7.5 mmol) and 5-{[9-(tert-butyldimethylsilanoyloxy)nonyl]oxy}-2-phenylaniline obtained in Reference Example 32-3, there was obtained 1-methylpiperidin-4-yl N-(5-{[9-(tert-butyldimethylsilanoyloxy)nonyl]oxy}-2-phenylphenyl)carbamate (408 mg).
LC/MS: M+1=583.3

Reference Example 33

Synthesis of 3-bromo-5-phenylaniline

4-Bromo-2-nitro-1-phenylbenzene (1.15 g, 4.1 mmol) was dissolved in ethyl acetate (10 mL) and ethanol (10 mL), tin chloride (2.85 g, 15 mmol) was added thereto, and the mixture was stirred at 80° C. for 18 hours. The reaction solution was returned to room temperature, neutralized with a saturated aqueous solution of sodium bicarbonate, filtered through celite, alumina, and Florisil, and extracted with ethyl acetate. The organic layer was washed with a saturated aqueous solution of sodium chloride, dried over anhydrous magnesium sulfate, and concentrated under reduced pressure. The residue was purified by flash column chromatography to obtain 3-bromo-5-phenylaniline (533 mg).
$^1$H-NMR (400 MHz, CDCl$_3$) δ 7.32-7.46 (m, 5H), 6.90-6.97 (m, 3H), 3.65-3.85 (broad, 2H)

Reference Example 34

Synthesis of [4-(2-propenoyloxy)phenyl]methanol 4-(Hydroxymethyl)phenol (620 mg, 5.0 mmol) was dissolved in N,N-dimethylformamide (25 ml) and potassium carbonate (1.38 g, 10.0 mmol) and 4-bromo-1-butene (1.08 g, 8.0 mmol) were added thereto. After stirring at 70° C. for 4 hours, the reaction solution was extracted with ethyl acetate. The organic layer was washed with a saturated aqueous solution of sodium chloride, dried over anhydrous magnesium sulfate, and concentrated under reduced pressure. The residue was purified by flash column chromatography to obtain [4-(2-propenoyloxy)phenyl]methanol (267 mg).
$^1$H-NMR (400 MHz, CDCl$_3$) δ 7.26-7.30 (m, 2H), 6.86-6.92 (m, 2H), 5.85-5.95 (m, 1H), 5.09-5.20 (m, 2H), 4.61 (s, 2H), 4.02 (t, J=6.8 Hz, 2H), 2.50-2.58 (m, 2H)

Reference Example 35

Synthesis of (4-[{(3E)-4-(3-amino-4-phenylphenyl)-3-buten-1-yl}oxy]phenyl)methanol 3-Bromo-5-phenylaniline (248 mg, 1.0 mmol) obtained in Reference Example 33 was dissolved in N,N-dimethylformamide (10 mL) and thereto were added [4-(2-propenoyloxy)phenyl]methanol (267 mg, 1.5 mmol) obtained in Reference Example 34, tri-(o-tolyl)phosphine (913 mg, 3.0 mmol), diisopropylethylamine (258 mg, 2.0 mmol), and palladium acetate (45 mg, 0.2 mmol). After stirring at 120° C. for 18 hours, the reaction solution was diluted with ethyl acetate, filtered through celite, and the organic layer was washed with a saturated aqueous solution of sodium chloride, dried over anhydrous magnesium sulfate, and concentrated under reduced pressure. The residue was purified by flash column chromatography to obtain (4-[{(3E)-4-(3-amino-4-phenylphenyl)-3-buten-1-yl}oxy]phenyl)methanol (268 mg).

Reference Example 36

Synthesis of [4-{4-(3-amino-4-phenylphenyl)butoxy}phenyl]methanol (4-[{(3E)-4-(3-Amino-4-phenylphenyl)-3-buten-1-yl}oxy]phenyl)methanol (268 mg, 0.78 mmol) obtained in Reference Example 35 was dissolved in methanol (5 mL), 10% palladium-carbon (10 mg) was added thereto, and the mixture was stirred under a hydrogen atmosphere at room temperature for 3 hours. The reaction solution was filtered through celite and the filtrate was concentrated under reduced pressure to obtain [4-{4-(3-amino-4-phenylphenyl)butoxy}phenyl]methanol as a crude material.

Reference Example 37

Synthesis of 5-(4-{4-[(tert-butyldimethylsilanoyloxy)methyl]phenoxy}butyl)-2-phenylaniline

[4-{4-(3-Amino-4-phenylphenyl)butoxy}phenyl]methanol obtained in Reference Example 35 and imidazole (170 mg, 2.5 mmol) were dissolved in tetrahydrofuran (15 mL), and a solution of tert-butyldimethylchlorosilane (300 mg, 2.0 mmol) in tetrahydrofuran (5 mL) was added thereto. After stirring the reaction mixture at room temperature for 1 hour, purified water was added to stop the reaction, and the mixture was extracted with ethyl acetate. The organic layer was washed with a saturated aqueous solution of sodium chloride, dried over anhydrous sodium sulfate, and concentrated under reduced pressure. The residue was purified by flash column chromatography to obtain 5-(4-{4-[(tert-butyldimethylsilanoyloxy)methyl]phenoxy}butyl)-2-phenylaniline (260 mg).
$^1$H-NMR (400 MHz, CDCl$_3$) δ 7.40-7.46 (m, 4H), 7.30-7.34 (m, 1H), 7.19-7.23 (m, 2H), 7.85 (d, J=7.8 Hz, 1H), 6.83-6.88 (m, 2H), 6.66-6.69 (m, 1H), 6.61 (s, 1H), 4.67 (s, 2H), 3.94-4.01 (m, 2H), 2.63 (t, J=7.2 Hz, 2H), 1.75-1.89 (m, 4H), 0.92 (s, 9H), 0.08 (s, 6H)

Reference Example 12-9

Synthesis of 1-methylpiperidin-4-yl N-[5-(4-{4-[(tert-butyldimethylsilanoyloxy)methyl]phenoxy}butyl)-2-phenylphenyl]carbamate In accordance with Reference Example 12, from 1-methylpiperidinol (144 mg, 1.25 mmol) and 5-(4-{4-[(tert-butyldimethylsilanoyloxy)methyl]phenoxy}butyl)-2-phenylaniline (115 mg, 0.25 mmol) obtained in Reference Example 37, there was obtained 1-methylpiperidin-4-yl N-[5-(4-{4-[(tert-butyldimethylsilanoyloxy)methyl]phenoxy}butyl)-2-phenylphenyl]carbamate (129 mg).
LC/MS: M+1=603.3

Reference Example 14-23

Synthesis of 4-[3-(tert-butyldimethylsilanoyloxy)propyl]aniline

In accordance with Reference Example 23 and Reference Example 14, from 3-(4-aminophenyl)propionic acid (991 mg, 6 mmol), there was obtained 4-[3-(tert-butyldimethylsilanoyloxy)propyl]aniline (1.31 g).
LC/MS: M+1=266.3

Reference Example 15-58

Synthesis of 1-methylpiperidin-4-yl N-{5-[2-({4-[3-(tert-butyldimethylsilanoyloxy)propyl]phenyl}carbamoyl)ethyl]-2-phenylphenyl]carbamate In accordance with Reference Example 15, from 3-[3-({[(1-methylpiperidin-4-yl)oxy]carbonyl}amino)-4-phenylphenyl]propionate hydrochloride (191 mg, 0.5 mmol) and 4-[3-(tert-butyldimethylsilanoyloxy)propyl]aniline obtained in Reference Example 14-23, there was obtained 1-methylpiperidin-4-yl N-{5-[2-({4-[3-(tert-butyldimethylsilanoyloxy)propyl]phenyl}carbamoyl)ethyl]-2-phenylphenyl]carbamate (155 mg).
LC/MS: M+1=630.3

Reference Example 14-24

Synthesis of 4-[2-(tert-butyldimethylsilanoyloxy)ethyl]aniline

In accordance with Reference Example 23 and Reference Example 14, from 2-(4-aminophenyl)ethyl alcohol (1.37 g, 10 mmol), there was obtained 4-[2-(tert-butyldimethylsilanoyloxy)ethyl]aniline (2.25 g).
LC/MS: M+1=252.3

Reference Example 15-59

Synthesis of 1-methylpiperidin-4-yl N-{5-[2-({4-[2-(tert-butyldimethylsilanoyloxy)ethyl]phenyl}carbamoyl)ethyl]-2-phenylphenyl]carbamate In accordance with Reference Example 15, from 3-[3-({[(1-methylpiperidin-4-yl)oxy]carbonyl}amino)-4-phenylphenyl]propionate hydrochloride (76 mg, 0.2 mmol) and 4-[2-(tert-butyldimethylsilanoyloxy)ethyl]aniline obtained in Reference Example 14-24, there was obtained 1-methylpiperidin-4-yl N-{5-[2-({4-[2-(tert-butyldimethylsilanoyloxy)ethyl]phenyl}carbamoyl)ethyl]-2-phenylphenyl]carbamate (188 mg).
LC/MS: M+1=616.3

Reference Example 38

Synthesis of tert-butyl 2-(3-nitro-4-phenylphenoxy)acetate

3-Nitro-4-phenylphenol (215 mg, 1.0 mmol) was dissolved in N,N-dimethylformamide (5 mL) and tert-butyl 2-bromoacetate (292 mg, 1.5 mmol) was added thereto. After stirring at 80° C. for 18 hours, the reaction solution was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl 2-(3-nitro-4-phenylphenoxy)acetate (370 mg).

Reference Example 39

Synthesis of tert-butyl 2-[3-({[(1-methylpiperidin-4-yl)oxy]carbonyl}amino)-4-phenylphenoxy]acetate In accordance with Reference Examples 11 and 12, from tert-butyl 2-(3-nitro-4-phenylphenoxy)acetate (329 mg, 1.0 mmol) obtained in Reference Example 38, there was obtained tert-butyl 2-[3-({[(1-methylpiperidin-4-yl)oxy]carbonyl}amino)-4-phenylphenoxy]acetate (531 mg).

Reference Example 13-6

Synthesis of 2-[3-({[(1-methylpiperidin-4-yl)oxy]carbonyl}amino)-4-phenylphenoxy]acetate hydrochloride In accordance with Reference Example 13, from tert-butyl 2-[3-({[(1-methylpiperidin-4-yl)oxy]carbonyl}amino)-4-phenylphenoxy]acetate (531 mg, 1.2 mmol) obtained in Reference Example 39, there was obtained 2-[3-({[(1-methylpiperidin-4-yl)oxy]carbonyl}amino)-4-phenylphenoxy]acetate hydrochloride (509 mg).
LC/MS: M+1=384.3

Reference Example 15-60

Synthesis of 4-[(tert-butyldimethylsilanoyloxy)methyl]phenyl 2-[3-({[(1-methylpiperidin-4-yl)oxy]carbonyl}amino)-4-phenylphenyl]acetate In accordance with Reference Example 15, from 2-[3-({[(1-methylpiperidin-4-yl)oxy]carbonyl}amino)-4-phenylphenoxy]acetate hydrochloride (210 mg, 0.5 mmol) obtained in Reference Example 13-6 and 4-(tert-butyldimethylsilanoyloxy)methyl]aniline (237 mg, 1.0 mmol) obtained in Reference Example 14, there was obtained 4-[(tert-butyldimethylsilanoyloxy)methyl]phenyl 2-[3-({[(1-methylpiperidin-4-yl)oxy]carbonyl}amino)-4-phenylphenyl]acetate (28 mg).
LC/MS: M+1=603.3

Reference Example 15-61

Synthesis of 1-methylpiperidin-4-yl N-(5-{2-[({4-[(tert-butoxycarbonyl)amino]phenyl}methyl)carbamoyl]ethyl}-2-phenylphenyl)carbamate In accordance with Reference Example 15, from salt of 3-[3-({[(1-methylpiperidin-4-yl)oxy]carbonyl}amino)-4-phenylphenyl]propionate hydrochloride (50 mg, 0.12 mmol) and 1-(N-Boc-aminomethyl)-4-(aminomethyl)benzene (94 mg, 0.4 mmol), there was obtained 1-methylpiperidin-4-yl N-(5-{2-[({4-[(tert-butoxycarbonyl)amino]phenyl}methyl)carbamoyl]ethyl}-2-phenylphenyl)carbamate (94 mg).
LC/MS: M+1=601.3

Reference Example 4-2]

Synthesis of 5-acetyl-8-[(4-methoxyphenyl)methoxy]-1,2-dihydroquinolin-2-one

5-Acetyl-8-hydroxy-1H-quinolin-2-one (29.5 g, 0.15 mol) was suspended in N,N-dimethylformamide (145 mL), potassium carbonate (22.2 g, 0.16 mol) and successively 4-methoxybenzyl chloride (22.7 g, 0.15 mol) were added thereto, and the mixture was stirred at 90° C. overnight. To the reaction mixture was added purified water (0.5 L) and the mixture was stirred at room temperature overnight. The precipitate was collected by filtration, washed with purified water, dried under reduced pressure to obtain 5-acetyl-8-[(4-methoxyphenyl)methoxy]-1,2-dihydroquinolin-2-one (26.1 g).
$^1$H-NMR (400 MHz, DMSO-d$_6$) δ 10.90 (s, 1H), 8.67 (d, J=8.0 Hz, 1H), 7.78 (d, J=8.0 Hz, 1H), 7.51 (d, J=8.0 Hz, 2H), 7.27 (d, J=8.0 Hz, 1H), 6.92 (d, J=8.0 Hz, 2H), 6.62 (d, J=8.0 Hz, 1H), 5.32 (s, 2H), 3.73 (s, 3H)

Reference Example 5-2

Synthesis of 5-(2-bromoacetyl)-8-[(4-methoxyphenyl)methoxy]-1,2-dihydroquinolin-2-one 5-Acetyl-8-[(4-methoxyphenyl)methoxy]-1,2-dihydroquinolin-2-one (1.25 g, 3.87 mmol) was dissolved in tetrahydrofuran (10 mL) and the solution was cooled to 0° C. Pyridinium tribromide (1.51 g, 4.25 mmol) was added in portions thereto and the reaction mixture was heated under reflux overnight. The precipitate was collected by filtration and washed with tetrahydrofuran. The filtrate was concentrated under reduced pressure and, thereafter, the residue was suspension-washed with purified water (20 mL). The precipitate was collected by filtration and washed with purified water. The solid was suspension-washed with ethyl acetate (20 mL), collected by filtration, and dried under reduced pressure to obtain 5-(2-bromoacetyl)-8-[(4-methoxyphenyl)methoxy]-1,2-dihydroquinolin-2-one (515 mg).
$^1$H-NMR (400 MHz, DMSO-d$_6$) δ 11.00 (s, 1H), 8.49 (d, J=8.0 Hz, 1H), 7.85 (d, J=8.0 Hz, 1H), 7.52 (d, J=8.0 Hz, 2H), 7.30 (d, J=8.0 Hz, 1H), 6.93 (d, J=8.0 Hz, 2H), 6.56 (d, J=8.0 Hz, 1H), 5.34 (s, 2H), 4.91 (s, 2H), 3.73 (s, 2H)

Reference Example 6-2

Synthesis of 5-[(1R)-2-bromo-1-hydroxyethyl]-8-[(4-methoxyphenyl)methoxy]-1,2-dihydroquinolin-2-one Under an argon flow, 5-(2-bromoacetyl)-8-[(4-methoxyphenyl)methoxy]-1,2-dihydroquinolin-2-one (7.15 g, 17.8 mmol) was suspended in dehydrated tetrahydrofuran (40 mL), the CBS catalyst (493 mg) was added thereto, and the reaction mixture was stirred at −20° C. for 40 minutes. After adding dropwise a 1.0 M solution of borane-tetrahydrofuran complex in tetrahydrofuran (21.4 mL) at the same temperature, the mixture was warmed gradually to 0° C. After adding methanol (20 mL) dropwise, insoluble matter was filtered off and washed with tetrahydrofuran. The filtrate and the washing were mixed and concentrated under reduced pressure. To the residue was added purified water (100 mL) and the mixture was stirred at room temperature overnight. The precipitate was collected by filtration and washed with purified water. The precipitate was further suspension-washed with ethyl acetate (200 mL), collected by filtration, and dried under reduced pressure to obtain 5-[(1R)-2-bromo-1-hydroxyethyl]-8-[(4-methoxyphenyl)methoxy]-1,2-dihydroquinolin-2-one (3.06 g).
$^1$H-NMR (400 MHz, DMSO-d$_6$) δ 10.60 (s, 1H), 8.17 (d, J=8.0 Hz, 1H), 7.49 (d, J=8.0 Hz, 2H), 7.20 (d, J=8.0 Hz, 1H), 6.92 (d, J=8.0 Hz, 2H), 6.54 (d, J=8.0 Hz, 1H), 5.93 (d, J=8.0

Hz, 1H), 5.18-5.24 (m, 3H), 3.67 (dd, J=12.0 Hz, 8.0 Hz, 1H), 3.60 (dd, J=12.0 Hz, 8.0 Hz, 1H)

Reference Example 15-62

Synthesis of 1-methylpiperidin-4-yl N-(5-{3-[({4-[(tert-butoxycarbonyl)amino]phenyl}methyl)carbamoyl]propyl}-2-phenylphenyl)carbamate In accordance with Reference Example 15, from 4-[3-({[(1-methylpiperidin-4-yl)oxy]carbonyl}amino)-4-phenylphenyl]butyrate hydrochloride (86 mg, 0.2 mmol) and 1-(N-Boc-aminomethyl)-4-(aminomethyl)benzene (118 mg, 0.5 mmol), there was obtained 1-methylpiperidin-4-yl N-(5-{3-[({4-[(tert-butoxycarbonyl)amino]phenyl}methyl)carbamoyl]propyl}-2-phenylphenyl)carbamate (86 mg).
LC/MS: M+1=615.3

Reference Example 40

Synthesis of tert-butyl trans-3-(3-amino-4-phenylphenyl)acrylate tert-Butyl trans-3-(3-nitro-4-phenylphenyl)acrylate (325 mg, 1.0 mmol) obtained in Reference Example 10 was dissolved in tetrahydrofuran (15 mL), zinc powder (196 mg, 3.0 mmol) and acetic acid (0.2 mL) were added thereto under water cooling, and the mixture was stirred at room temperature for 3 hours. The reaction solution was diluted with ethyl acetate, neutralized with a saturated aqueous solution of sodium bicarbonate, and filtered through celite. The organic layer was washed with a saturated aqueous solution of sodium chloride, dried over anhydrous magnesium sulfate, and concentrated under reduced pressure to obtain tert-butyl trans-3-(3-amino-4-phenylphenyl)acrylate as a crude material.
LC/MS: M+1=296.3

Reference Example 12-10

Synthesis of tert-butyl (2E)-3-[3-({[(1-methylpiperidin-4-yl)oxy]carbonyl}amino)-4-phenylphenyl]-2-propenate In accordance with Reference Example 12, from 4-hydroxy-1-methylpiperidine (172 mg, 1.5 mmol) and tert-butyl trans-3-(3-amino-4-phenylphenyl)acrylate (150 mg, 0.5 mmol) obtained in Reference Example 40, there was obtained tert-butyl (2E)-3-[3-({[(1-methylpiperidin-4-yl)oxy]carbonyl}amino)-4-phenylphenyl]-2-propenate (117 mg).
LC/MS: M+1=437.3

Reference Example 13-7

Synthesis of (2E)-3-[3-({[(1-methylpiperidin-4-yl)oxy]carbonyl}amino)-4-phenylphenyl]-2-propenate hydrochloride In accordance with Reference Example 13, from tert-butyl (2E)-3-[3-({[(1-methylpiperidin-4-yl)oxy]carbonyl}amino)-4-phenylphenyl]-2-propenate (117 mg, 0.27 mmol) obtained from Reference Example 39, there was obtained (2E)-3-[3-({[(1-methylpiperidin-4-yl)oxy]carbonyl}amino)-4-phenylphenyl]-2-propenate hydrochloride (112 mg).
LC/MS: M+1=381.3

Reference Example 15-63

Synthesis of 1-methylpiperidin-4-yl N-{5-[(1E)-2-({4-[(tert-butyldimethylsilanoyloxy)methyl]phenyl}carbamoyl)-1-ethen-1-yl]-2-phenylphenyl}carbamate In accordance with Reference Example 15, from (2E)-3-[3-({[(1-methylpiperidin-4-yl)oxy]carbonyl}amino)-4-phenylphenyl]-2-propenoate hydrochloride (112 mg, 0.27 mmol) obtained in Reference Example 13-7 and 4-[(tert-butyldimethylsilanoyloxy)methyl]aniline (1.0 mmol), there was obtained 1-methylpiperidin-4-yl N-{5-[(1E)-2-({4-[(tert-butyldimethylsilanoyloxy)methyl]phenyl}carbamoyl)-1-ethen-1-yl]-2-phenylphenyl}carbamate (57 mg).
LC/MS: M+1=600.3

Reference Example 41

Synthesis of 1-(2-methyl-2-nitropropyl)-4-nitrobenzene

To a solution of sodium ethoxide (3.5 g, 50 mmol) in ethanol (100 mL), 1-(chloromethyl)-4-nitrobenzene (8.6 g, 50 mmol) and 2-nitropropane (2.2 g, 250 mmol) were added at room temperature, and the mixture was heated under reflux for 18 hours. The reaction solution was filtered, concentrated under reduced pressure, and diluted with ethyl acetate. The organic layer was washed with a saturated aqueous solution of sodium chloride, dried over anhydrous magnesium sulfate, and concentrated under reduced pressure. The residue was purified by flash column chromatography to obtain 1-(2-methyl-2-nitropropyl)-4-nitrobenzene (8.52 g).
$^1$H-NMR (400 MHz, CDCl$_3$) δ 8.17 (d, J=8.5 Hz, 2H), 7.29 (d, J=8.5 Hz, 2H), 3.32 (s, 2H), 1.59 (s, 6H)

Reference Example 42

Synthesis of 4-(2-methyl-2-nitropropyl)aniline 1-(2-Methyl-2-nitropropyl)-4-nitrobenzene (673 mg, 3.0 mmol) obtained in Reference Example 41 was dissolved in methanol (20 mL) A catalytic amount of palladium-carbon was added thereto, and the solution was stirred under a hydrogen atmosphere for 6 hours. The reaction solution was filtered through celite and the filtrate was concentrated to obtain 4-(2-methyl-2-nitropropyl)aniline as a crude material.
LC/MS: M+1=195.3

Reference Example 15-64

Synthesis of 1-methylpiperidin-4-yl N-[5-(2-{[4-(2-methyl-2-nitropropyl)phenyl]carbamoyl}ethyl)-2-phenylphenyl]carbamate In accordance with Reference Example 15, from 3-[3-({[(1-methylpiperidin-4-yl)oxy]carbonyl}amino)-4-phenylphenyl]propionate hydrochloride (418 mg, 1.0 mmol) and 4-(2-methyl-2-nitropropyl)aniline (582 mg, 3.0 mmol), there was obtained 1-methylpiperidin-4-yl N-[5-(2-{4-(2-methyl-2-nitropropyl)phenyl]carbamoyl}ethyl)-2-phenylphenyl]carbamate (193.5 mg).
LC/MS: M+1=559.3

Reference Example 9-2

Synthesis of tert-butyl trans-3-(3-bromo-4-nitrophenyl)acrylate

In accordance with Reference Example 9, from tert-butyl diethyl phosphonoacetate (920 mg, 4.0 mmol) and 3-bromo-4-nitrobenzaldehyde (1.0 g, 3.9 mmol), there was obtained tert-butyl trans-3-(3-bromo-4-nitrophenyl)acrylate (777 mg).

$^1$H-NMR (400 MHz, CDCl$_3$) δ 8.17 (d, J=8.5 Hz, 1H), 7.86 (d, J=1.7 Hz, 1H), 7.55 (dd, J=8.5 Hz, 1.7 Hz, 1H), 7.50 (d, J=15.9 Hz, 1H), 6.46 (d, J=15.9 Hz, 1H), 1.54 (s, 9H)

Reference Example 10-2

Synthesis of tert-butyl trans-3-(4-nitro-3-phenylphenyl)acrylate

In accordance with Reference Example 10, from tert-butyl trans-3-(3-bromo-4-nitrophenyl)acrylate (777 mg, 2.37 mmol) obtained in Reference Example 9-2, there was obtained tert-butyl trans-3-(4-nitro-3-phenylphenyl)acrylate (802 mg).

$^1$H-NMR (400 MHz, CDCl$_3$) δ 7.88 (d, J=8.3 Hz, 1H), 7.55-7.66 (m, 3H), 7.42-7.46 (m, 3H), 7.30-7.36 (m, 2H), 6.48 (d, J=15.9 Hz, 1H), 1.54 (s, 9H)

Reference Example 11-3

Synthesis of tert-butyl 3-(4-amino-3-phenylphenyl)propionate

In accordance with Reference Example 11, from tert-butyl trans-3-(4-nitro-3-phenylphenyl)acrylate (802 g, 2.5 mmol), there was obtained tert-butyl 3-(4-amino-3-phenylphenyl)propionate (742 mg).

LC/MS: M+1=298.3

Reference Example 12-11

Synthesis of tert-butyl 3-[4-({[(1-methylpiperidin-4-yl)oxy]carbonyl}amino)-3-phenylphenyl]propionate In accordance with Reference Example 12, from 4-hydroxy-1-methylpiperidine (450 mg, 15.0 mmol) and tert-butyl 3-(4-amino-3-phenylphenyl)propionate (742 mg, 2.5 mmol) obtained in Reference Example 11-3, there was obtained tert-butyl 3-[4-({[(1-methylpiperidin-4-yl)oxy]carbonyl}amino)-3-phenylphenyl]propionate (878 mg).

$^1$H-NMR (400 MHz, CDCl$_3$) δ 7.97 (s, 1H), 7.38-7.49 (m, 3H), 7.34-7.38 (m, 2H), 7.19 (dd, J=8.5 Hz, 2.0 Hz, 1H), 7.06 (d, J=2.0 Hz, 1H), 6.54 (s, 1H), 4.70-4.74 (m, 1H), 2.90 (t, J=7.8 Hz, 1H), 2.62-2.70 (m, 2H), 2.54 (t, J=7.8 Hz, 1H), 2.29 (s, 3H), 2.23-2.30 (m, 2H), 1.92-2.00 (m, 2H), 1.66-1.75 (m, 2H), 1.41 (s, 9H)

LC/MS: M+1=439.3

Reference Example 15-65

Synthesis of 1-methylpiperidin-4-yl N-{4-[2-({4-[(tert-butyldimethylsilanoyloxy)methyl]phenyl}carbamoyl)ethyl]-2-phenylphenyl}carbamate In accordance with Reference Examples 13 and 15, from tert-butyl 3-[4-({[(1-methylpiperidin-4-yl)oxy]carbonyl}amino)-3-phenylphenyl]propionate (219 mg, 0.5 mmol) obtained in Reference Example 12-11, there was obtained 1-methylpiperidin-4-yl N-{4-[2-({4-[(tert-butyldimethylsilanoyloxy)methyl]phenyl}carbamoyl)ethyl]-2-phenylphenyl}carbamate (235 mg).

$^1$H-NMR (400 MHz, CDCl$_3$) δ 8.01 (s, 1H), 7.37-7.48 (m, 5H), 7.29-7.32 (m, 2H), 7.21-7.25 (m, 3H), 7.15 (s, 1H), 7.09 (d, J=2.0 Hz, 1H), 6.54 (s, 1H), 4.68 (s, 2H), 4.70-4.73 (m, 1H), 3.04 (t, J=7.4 Hz, 1H), 2.62-2.66 (m, 2H), 2.64 (t, J=7.6 Hz, 1H), 2.26 (s, 3H), 2.16-2.22 (m, 2H), 1.91-1.96 (m, 2H), 1.64-1.74 (m, 2H), 0.93 (s, 9H), 0.09 (s, 6H)

LC/MS: M+1=602.3

Example 1

Synthesis of 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate 1-Methylpiperidin-4-yl N-{5-[2-({4-[(tert-butyldimethylsilanoyloxy)methyl]phenyl}carbamoyl)ethyl]-2-phenylphenyl}carbamate (178.1 mg, 0.296 mmol) obtained in Reference Example 15 was dissolved in tetrahydrofuran (10 mL), hydrogen trifluoride-triethylamine complex (0.3 mL) was added thereto, and the mixture was stirred at 70° C. for 1.5 hours. The reaction mixture was extracted with ethyl acetate and the organic layer was washed with a dilute aqueous solution of sodium hydroxide and a saturated aqueous solution of sodium chloride, dried over sodium sulfate, and concentrated under reduced pressure.

A half amount of the residue was dissolved in acetonitrile (10 mL), methyl iodide (2 mL) was added thereto, the mixture was stirred at room temperature for 1 hour, and, thereafter, the reaction solution was concentrated under reduced pressure.

The residue was dissolved in dichloromethane (10 mL) and methanol (1 mL), manganese dioxide (300 mg) was added thereto, and the mixture was stirred at room temperature for 16 hours. The reaction solution was filtered through celite and, thereafter, the filtrate was concentrated under reduced pressure.

The residue was suspended in dimethyl sulfoxide (5 mL), 5-((R)-2-amino-1-hydroxyethyl)-8-hydroxy-1H-quinolin-2-one acetate (280.3 mg, 1 mmol) was added thereto, and the mixture was stirred at 70° C. for 1 hour. To the reaction solution was added sodium triacetoxyborohydride (424.0 mg, 2 mmol) and the mixture was stirred at 70° C. for 1 hour. After addition of purified water (0.5 mL) to the reaction solution, the mixture was purified by HPLC fractionation to obtain 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (34.5 mg).

$^1$H-NMR (400 MHz, DMSO-d$_6$) δ 10.47 (s, 1H), 10.14 (s, 1H), 9.07 (d, J=50.5 Hz, 1H), 8.75 (s, 1H), 8.05 (d, J=10.0 Hz, 1H), 7.63 (d, J=8.5 Hz, 2H), 7.44 (d, J=8.5 Hz, 2H), 7.27-7.40 (m, 6H), 7.24 (d, J=8.0 Hz, 1H), 7.19 (d, J=8.0 Hz, 1H), 7.10 (d, J=8.0 Hz, 1H), 6.96 (d, J=8.0 Hz, 1H), 6.53 (d, J=10.0 Hz, 1H), 5.28-5.33 (m, 1H), 4.58-4.66 (m, 1H), 4.12-4.18 (m, 2H), 3.35-3.43 (m, 2H), 3.25-3.35 (m, 2H), 3.07 (s, 3H), 3.06 (s, 3H), 3.05-3.09 (m, 2H), 2.94 (t, J=7.5 Hz, 2H), 2.68 (t, J=7.5 Hz, 2H), 1.94-2.04 (m, 2H), 1.70-1.82 (m, 2H)

LC/MS: [M]+=704.3

Example 2

Synthesis of 4-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-1,1-dimethylpiperidin-1-ium trifluoroacetate In accordance with Example 1, from 1-Methylpiperidin-4-yl N-{5-[2-({4-[(tert-butyldimethylsilanoyloxy)methyl]-2-chloro-5-methoxyphenyl}carbamoyl)ethyl]-2-phenylphenyl}carbamate (17 mg, 0.03 mmol) obtained in Reference Example 15-2, there was obtained 4-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-1,1-dimethylpiperidin-1-ium trifluoroacetate (11.6 mg).

$^1$H-NMR (400 MHz, DMSO-$d_6$) δ 10.46 (s, 1H), 9.61 (s, 1H), 8.87 (d, J=25.0 Hz, 1H), 8.74 (s, 1H), 8.09 (d, J=10.0 Hz, 1H), 7.58 (s, 1H), 7.57 (s, 1H), 7.29-7.44 (m, 6H), 7.16-7.29 (m, 2H), 7.13 (d, J=8.3 Hz, 1H), 6.97 (d, J=8.3 Hz, 1H), 6.56 (d, J=10.0 Hz, 1H), 5.32-5.37 (m, 1H), 4.57-4.66 (m, 1H), 4.12-4.18 (m, 2H), 3.80 (s, 3H), 3.35-3.43 (m, 2H), 3.25-3.35 (m, 2H), 3.04-3.09 (m, 2H), 3.07 (s, 3H), 3.06 (s, 3H), 2.95 (t, J=7.7 Hz, 2H), 2.79 (t, J=7.7 Hz, 2H), 1.95-2.04 (m, 2H), 1.69-1.81 (m, 2H)

LC/MS: [M]+=768.3

Example 3

Synthesis of 4-({[5-(2-{[3-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-3-chlorophenyl}carbamoyl)ethyl]-2-phenylphenyl}carbamate (64.2 mg, 0.12 mmol) obtained in Reference Example 15-3, there was obtained 4-({[5-(2-{[3-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (10.6 mg).

$^1$H-NMR (400 MHz, DMSO-$d_6$) δ 10.48 (s, 1H), 10.32 (s, 1H), 9.12-9.02 (broad, 1H), 8.72 (s, 1H), 8.10 (d, J=10.0 Hz, 1H), 7.91 (d, J=2.0 Hz, 1H), 7.58 (d, J=8.5 Hz, 1H), 7.51 (dd, J=8.5 Hz, 2.0 Hz, 1H), 7.28-7.44 (m, 5H), 7.25 (d, J=7.8 Hz, 1H), 7.19 (d, J=7.8 Hz, 1H), 7.13 (d, J=8.3 Hz, 1H), 6.97 (d, J=8.3 Hz, 1H), 6.55 (d, J=10.0 Hz, 1H), 5.32-5.38 (m, 1H), 4.57-4.66 (m, 1H), 4.22-4.40 (m, 2H), 3.34-3.42 (m, 2H), 3.26-3.34 (m, 2H), 3.06-3.14 (m, 2H), 3.07 (s, 3H), 3.06 (s, 3H), 2.94 (t, J=7.7 Hz, 2H), 2.70 (t, J=7.7 Hz, 2H), 1.95-2.05 (m, 2H), 1.68-1.81 (m, 2H)

LC/MS: [M]+=738.2

Example 4

Synthesis of 4-({[5-(2-{[2-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-5-chlorophenyl}carbamoyl)ethyl]-2-phenylphenyl}carbamate (104 mg, 0.20 mmol) obtained in Reference Example 15-4, there was obtained 4-({[5-(2-{[2-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (29.4 mg).

$^1$H-NMR (400 MHz, DMSO-$d_6$) δ 10.47 (s, 1H), 9.89 (s, 1H), 9.11 (d, J=33.4 Hz, 1H), 8.73 (s, 1H), 8.07 (d, J=10.0 Hz, 1H), 7.94-8.00 (m, 1H), 7.28-7.46 (m, 6H), 7.31 (d, J=8.0 Hz, 1H), 7.20 (d, J=8.0 Hz, 1H), 7.11 (d, J=8.0 Hz, 1H), 6.96 (d, J=8.0 Hz, 1H), 6.55 (d, J=10.0 Hz, 1H), 5.30-5.35 (m, 1H), 4.58-4.66 (m, 1H), 4.18-4.25 (m, 2H), 3.34-3.42 (m, 2H), 3.26-3.34 (m, 2H), 3.03-3.08 (m, 2H), 3.07 (s, 3H), 3.06 (s, 3H), 2.93 (t, J=7.7 Hz, 2H), 2.75 (t, J=7.7 Hz, 2H), 1.95-2.05 (m, 2H), 1.68-1.81 (m, 2H)

LC/MS: [M]+=722.3

Example 5

Synthesis of 4-({[5-(2-{[2,5-difluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-2,5-difluorophenyl}carbamoyl)ethyl]-2-phenylphenyl}carbamate (44.7 mg, 0.07 mmol) obtained in Reference Example 15-5, there was obtained 4-({[5-(2-{[2,5-difluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (16.8 mg).

$^1$H-NMR (400 MHz, DMSO-$d_6$) δ 10.48 (s, 1H), 10.10 (s, 1H), 9.02-9.18 (broad, 1H), 8.72 (s, 1H), 8.12 (d, J=10.0 Hz, 1H), 8.01 (dd, J=11.6 Hz, 6.7 Hz, 1H), 7.54 (dd, J=11.6 Hz, 6.7 Hz, 1H), 7.27-7.44 (m, 6H), 7.18-7.27 (m, 2H), 7.13 (d, J=8.0 Hz, 1H), 6.97 (d, J=8.0 Hz, 1H), 6.56 (d, J=10.0 Hz, 1H), 5.31-5.36 (m, 1H), 4.58-4.65 (m, 1H), 4.18-4.26 (m, 2H), 3.35-3.43 (m, 2H), 3.26-3.35 (m, 2H), 3.07-3.15 (m, 2H), 3.07 (s, 3H), 3.06 (s, 3H), 2.93 (t, J=7.4 Hz, 2H), 2.79 (t, J=7.4 Hz, 2H), 1.93-2.04 (m, 2H), 1.70-1.82 (m, 2H)

LC/MS: [M]+=740.3

Example 6

Synthesis of 4-({[5-(2-{[4-({[(2R)-2-hydroxy-2-(8-hydroxy-2-oxo-1,2-dihydroquinolin-5-yl)ethyl]amino}methyl)-3-methoxyphenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-3-methoxyphenyl}carbamoyl)ethyl]-2-phenylphenyl}carbamate (74.3 mg, 0.14 mmol) obtained in Reference Example 15-6, there was obtained 4-({[5-(2-{[4-({[(2R)-2-hydroxy-2-(8-hydroxy-2-oxo-1,2-dihydroquinolin-5-yl)ethyl]amino}methyl)-3-methoxyphenyl]carbamoyl}ethyl)-2-phenylphenyl]carbamoyl}oxy)-1,1-dimethylpiperidin-1-ium trifluoroacetate (19.1 mg).

$^1$H-NMR (400 MHz, DMSO-$d_6$) δ 10.48 (s, 1H), 10.14 (s, 1H), 8.72 (s, 1H), 8.60-8.80 (broad, 1H), 8.04 (d, J=10.0 Hz, 1H), 7.14-7.48 (m, 11H), 7.11 (d, J=8.3 Hz, 1H), 6.96 (d, J=8.3 Hz, 1H), 6.55 (d, J=10.0 Hz, 11H), 5.28-5.34 (m, 1H), 4.58-4.64 (m, 1H), 4.12-4.22 (m, 2H), 3.34-3.43 (m, 2H), 3.26-3.34 (m, 2H), 3.79 (s, 3H), 3.07 (s, 3H), 3.06 (s, 3H), 2.97-3.02 (m, 2H), 2.94 (t, J=7.6 Hz, 2H), 2.68 (t, J=7.6 Hz, 2H), 1.92-2.04 (m, 2H), 1.68-1.80 (m, 2H)

LC/MS: [M]+=734.3

Example 7

Synthesis of 4-({[5-(2-{[3-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoro acetate In accordance with Example 1, from 1-methylpiperidin-4-yl N-{5-[2-({4-[(tert-butyldimethylsilanoyloxy)methyl]-3-fluorophenyl}carbamoyl)ethyl]-2-phenylphenyl}carbamate (155.6 mg, 0.30 mmol) obtained in Reference Example 15-7, there was obtained 4-({[5-(2-{[3-fluoro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (27.2 mg).

$^1$H-NMR (400 MHz, DMSO-$d_6$) δ 10.47 (s, 1H), 10.38 (s, 1H), 9.13 (d, J=48.8 Hz, 1H), 8.75 (s, 1H), 8.11 (d, J=9.8 Hz, 1H), 7.64-7.71 (m, 1H), 7.52 (t, J=8.5 Hz, 1H), 7.28-7.44 (m, 5H), 7.24 (d, J=8.0 Hz, 1H), 7.19 (dd, J=8.0 Hz, 1.5 Hz, 1H), 7.12 (d, J=8.3 Hz, 1H), 6.98 (d, J=8.3 Hz, 1H), 6.54 (d, J=9.8 Hz, 1H), 5.30-5.37 (m, 1H), 4.58-4.64 (m, 1H), 4.18-4.29 (m, 2H), 3.34-3.43 (m, 2H), 3.26-3.34 (m, 2H), 3.03-3.08 (m, 2H), 3.07 (s, 3H), 3.06 (s, 3H), 2.94 (t, J=7.6 Hz, 2H), 2.70 (t, J=7.6 Hz, 2H), 1.95-2.04 (m, 2H), 1.68-1.80 (m, 2H)

LC/MS: [M]+=722.3

Example 8

Synthesis of 4-({[5-(2-{[4-({[(2R)-2-hydroxy-2-(8-hydroxy-2-oxo-1,2-dihydroquinolin-5-yl)ethyl]amino}methyl)-3-methylphenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-3-methylphenyl}carbamoyl)ethyl]-2-phenylphenyl}carbamate (102.9 mg, 0.20 mmol) obtained in Reference Example 15-8, there was obtained 4-({[5-(2-{[4-({[(2R)-2-hydroxy-2-(8-hydroxy-2-oxo-1,2-dihydroquinolin-5-yl)ethyl]amino}methyl)-3-methylphenyl]carbamoyl}ethyl)-2-phenylphenyl]carbamoyl}oxy)-1,1-dimethylpiperidin-1-ium trifluoroacetate (7.3 mg).

LC/MS: [M]+=718.3

Example 9

Synthesis of 4-({[5-(2-{[2-chloro-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-2-chlorophenyl}carbamoyl)ethyl]-2-phenylphenyl}carbamate (107 mg, 0.20 mmol) obtained in Reference Example 15-9, there was obtained 4-({[5-(2-{[2-chloro-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (27.2 mg).

$^1$H-NMR (400 MHz, DMSO-$d_6$) δ 10.50 (s, 1H), 9.65 (s, 1H), 8.80-9.18 (broad, 1H), 8.74 (s, 1H), 8.07 (d, J=10.0 Hz, 1H), 7.78 (d, J=8.5 Hz, 1H), 7.69 (d, J=2.0 Hz, 1H), 7.45 (dd, J=8.5 Hz, 2.0 Hz, 1H), 7.28-7.45 (m, 6H), 7.18-7.27 (m, 2H), 7.12 (d, J=8.3 Hz, 1H), 6.96 (d, J=8.3 Hz, 1H), 6.56 (d, J=9.8 Hz, 1H), 5.28-5.34 (m, 1H), 4.58-4.66 (m, 1H), 4.16-4.23 (m, 2H), 3.33-3.42 (m, 2H), 3.26-3.33 (m, 2H), 3.07 (s, 3H), 3.06 (s, 3H), 2.90-2.98 (m, 2H), 2.94 (t, J=8.0 Hz, 2H), 2.76 (t, J=8.0 Hz, 2H), 1.92-2.04 (m, 2H), 1.68-1.80 (m, 2H)

LC/MS: [M]+=738.2

Example 10

Synthesis of 4-({[5-(2-{[4-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-2-methoxyphenyl}carbamoyl)ethyl]-2-phenylphenyl}carbamate (106.1 mg, 0.20 mmol) obtained in Reference Example 15-10, there was obtained 4-({[5-(2-{[4-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-1,1-dimethylpiperidin-1-ium trifluoroacetate (18.5 mg).

$^1$H-NMR (400 MHz, DMSO-$d_6$) δ 10.47 (s, 1H), 9.27 (s, 1H), 9.00-9.22 (broad, 1H), 8.74 (s, 1H), 8.06 (d, J=9.8 Hz, 1H), 8.01 (d, J=7.8 Hz, 1H), 7.28-7.44 (m, 6H), 7.18-7.27 (m, 3H), 7.11 (d, J=8.3 Hz, 1H), 7.01-7.06 (m, 1H), 6.97 (d, J=8.3 Hz, 1H), 6.56 (d, J=9.8 Hz, 1H), 5.32-5.36 (m, 1H), 4.58-4.66 (m, 1H), 4.16-4.23 (m, 2H), 3.83 (s, 3H), 3.34-3.43 (m, 2H), 3.27-3.34 (m, 2H), 3.07 (s, 3H), 3.06 (s, 3H), 2.90-2.98 (m, 2H), 2.92 (t, J=7.6 Hz, 2H), 2.76 (t, J=7.6 Hz, 2H), 1.94-2.06 (m, 2H), 1.67-1.80 (m, 2H)

LC/MS: [M]+=734.3

Example 11

Synthesis of 4-({[5-(2-{[4-({[(2R)-2-hydroxy-2-(8-hydroxy-2-oxo-1,2-dihydroquinolin-5-yl)ethyl]amino}methyl)-2-methylphenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]-2-methylphenyl}carbamoyl)ethyl]-2-phenylphenyl}carbamate (66.9 mg, 0.13 mmol) obtained in Reference Example 15-11, there was obtained 4-({[4-(2-{[4-({[(2R)-2-hydroxy-2-(8-hydroxy-2-oxo-1,2-dihydroquinolin-5-yl)ethyl]amino}methyl)-2-methylphenyl]carbamoyl}ethyl)-2-phenylphenyl]carbamoyl}oxy)-1,1-dimethylpiperidin-1-ium trifluoroacetate (8.1 mg).

$^1$H-NMR (400 MHz, DMSO-$d_6$) δ 10.48 (s, 1H), 9.38 (s, 1H), 8.80-9.20 (broad, 1H), 8.73 (s, 1H), 8.05 (d, J=10.0 Hz, 1H), 8.47 (d, J=8.0 Hz, 1H), 7.20-7.44 (m, 10H), 7.11 (d, J=8.3 Hz, 1H), 6.97 (d, J=8.0 Hz, 1H), 6.56 (d, J=10.0 Hz, 1H), 5.30-5.33 (m, 1H), 4.58-4.64 (m, 1H), 4.13-4.18 (m, 2H), 3.34-3.42 (m, 2H), 3.26-3.34 (m, 2H), 3.07 (s, 3H), 3.06

(s, 3H), 3.00-3.08 (m, 2H), 2.95 (t, J=7.7 Hz, 2H), 2.71 (t, J=7.7 Hz, 2H), 2.16 (s, 3H), 1.94-2.06 (m, 2H), 1.68-1.82 (m, 2H)

LC/MS: [M]+=718.3

Example 12

Synthesis of 4-({[5-(2-{[6-({[(2R)-2-hydroxy-2-(8-hydroxy-2-oxo-1,2-dihydroquinolin-5-yl)ethyl]amino}methyl)naphthalen-2-yl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-(5-{2-[(6-{[(tert-butyldimethylsilyl)oxy]methyl}naphthalen-2-yl)carbamoyl]ethyl}-2-phenylphenyl)carbamate (110.1 mg, 0.20 mmol) obtained in Reference Example 15-12, there was obtained 4-({[5-(2-{[6-({[(2R)-2-hydroxy-2-(8-hydroxy-2-oxo-1,2-dihydroquinolin-5-yl)ethyl]amino}methyl)naphthalen-2-yl]carbamoyl}ethyl)-2-phenylphenyl]carbamoyl}oxy)-1,1-dimethylpiperidin-1-ium trifluoroacetate (8.1 mg).

$^1$H-NMR (400 MHz, DMSO-d$_6$) δ 10.44 (s, 1H), 10.26 (s, 1H), 9.16 (d, J=23.7 Hz, 1H), 8.72 (s, 1H), 8.36 (s, 1H), 8.04 (d, J=10.0 Hz, 1H), 7.96 (s, 1H), 7.88 (d, J=6.0 Hz, 1H), 7.85 (d, J=6.0 Hz, 1H), 7.58-7.65 (m, 2H), 7.28-7.44 (m, 6H), 7.19-7.27 (m, 2H), 7.10 (d, J=8.3 Hz, 1H), 6.95 (d, J=8.0 Hz, 1H), 6.56 (d, J=10.0 Hz, 1H), 5.32-5.36 (m, 1H), 4.57-4.66 (m, 1H), 4.33-4.38 (m, 2H), 3.34-3.43 (m, 2H), 3.27-3.34 (m, 2H), 3.07 (s, 3H), 3.06 (s, 3H), 3.00-3.07 (m, 2H), 2.98 (t, J=7.7 Hz, 2H), 2.75 (t, J=7.7 Hz, 2H), 1.94-2.05 (m, 2H), 1.68-1.80 (m, 2H)

LC/MS: [M]+=754.3

Example 13

Synthesis of 4-({[5-(2-{[2-({[(2R)-2-hydroxy-2-(8-hydroxy-2-oxo-1,2-dihydroquinolin-5-yl)ethyl]amino}methyl)-1-benzothiophen-5-yl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-(5-{2-[(5-{[(tert-butyldimethylsilyl)oxy]methyl}-1-benzothiophen-5-yl)carbamoyl]ethyl}-2-phenylphenyl)carbamate (105.8 mg, 0.19 mmol) obtained in Reference Example 15-13, there was obtained 4-({[5-(2-{[2-({[(2R)-2-hydroxy-2-(8-hydroxy-2-oxo-1,2-dihydroquinolin-5-yl)ethyl]amino}methyl)-1-benzothiophen-5-yl]carbamoyl}ethyl)-2-phenylphenyl]carbamoyl}oxy)-1,1-dimethylpiperidin-1-ium trifluoroacetate (13.3 mg).

$^1$H-NMR (400 MHz, DMSO-d$_6$) δ 10.46 (s, 1H), 10.12 (s, 1H), 9.22-9.30 (broad, 1H), 8.71 (s, 1H), 8.27 (d, J=1.7 Hz, 1H), 8.07 (d, J=9.8 Hz, 1H), 7.91 (d, J=8.5 Hz, 1H), 7.56 (s, 1H), 7.28-7.44 (m, 6H), 7.19-7.27 (m, 2H), 7.11 (d, J=8.3 Hz, 1H), 6.96 (d, J=8.0 Hz, 1H), 6.51 (d, J=9.8 Hz, 1H), 5.32-5.36 (m, 1H), 4.57-4.62 (m, 1H), 4.51-4.56 (m, 2H), 3.34-3.43 (m, 2H), 3.27-3.34 (m, 2H), 3.07 (s, 3H), 3.06 (s, 3H), 3.00-3.07 (m, 2H), 2.96 (t, J=8.2 Hz, 2H), 2.70 (t, J=8.2 Hz, 2H), 1.92-2.04 (m, 2H), 1.68-1.81 (m, 2H)

LC/MS: [M]+=760.3

Example 14

Synthesis of 4-({[5-(2-{[5-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({5-[(tert-butyldimethylsilanoyloxy)methyl]-2-methoxyphenyl}carbamoyl)ethyl]-2-phenylphenyl}carbamate (138.0 mg, 0.26 mmol) obtained in Reference Example 15-14, there was obtained 4-({[5-(2-{[5-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-1,1-dimethylpiperidin-1-ium trifluoroacetate (28.2 mg).

$^1$H-NMR (400 MHz, DMSO-d$_6$) δ 10.45 (s, 1H), 9.26 (s, 1H), 8.98 (d, J=24.4 Hz, 1H), 8.74 (s, 1H), 8.19 (s, 1H), 8.06 (d, J=10.0 Hz, 1H), 7.20-7.44 (m, 6H), 7.18-7.25 (m, 3H), 7.06-7.13 (m, 2H), 6.96 (d, J=8.0 Hz, 1H), 6.56 (d, J=10.0 Hz, 1H), 4.98-5.36 (m, 1H), 4.58-4.66 (m, 1H), 4.13-4.18 (m, 2H), 3.84 (s, 3H), 3.34-3.42 (m, 2H), 3.26-3.34 (m, 2H), 3.07 (s, 3H), 3.06 (s, 3H), 3.00-3.08 (m, 2H), 2.92 (t, J=7.6 Hz, 2H), 2.78 (t, J=7.6 Hz, 2H), 1.94-2.05 (m, 2H), 1.67-1.81 (m, 2H)

LC/MS: [M]+=734.3

Example 15

Synthesis of 4-({[5-(2-{[4-({[(2R)-2-hydroxy-2-(8-hydroxy-2-oxo-1,2-dihydroquinolin-5-yl)ethyl]amino}methyl)phenyl](methyl)carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{5-[2-({4-[(tert-butyldimethylsilanoyloxy)methyl]phenyl}{methyl}carbamoyl)ethyl]-2-phenylphenyl}carbamate (139.0 mg, 0.27 mmol) obtained in Reference Example 15-15, there was obtained 4-({[5-(2-{[4-({[(2R)-2-hydroxy-2-(8-hydroxy-2-oxo-1,2-dihydroquinolin-5-yl)ethyl]amino}methyl)phenyl](methyl)carbamoyl}ethyl)-2-phenylphenyl]carbamoyl}oxy)-1,1-dimethylpiperidin-1-ium trifluoroacetate (45.7 mg).

$^1$H-NMR (400 MHz, DMSO-d$_6$) δ 10.47 (s, 1H), 9.12 (d, J=40.7 Hz, 1H), 8.72 (s, 1H), 8.04 (d, J=10.0 Hz, 1H), 7.51 (d, J=8.0 Hz, 2H), 7.24-7.38 (m, 6H), 7.07-7.12 (m, 1H), 7.70 (d, J=8.0 Hz, 2H), 7.06-7.13 (m, 2H), 6.92 (d, J=8.0 Hz, 1H), 6.49 (d, J=10.0 Hz, 1H), 5.27-5.32 (m, 1H), 4.55-4.60 (m, 1H), 4.16-4.22 (m, 2H), 3.33-3.38 (m, 2H), 3.24-3.33 (m, 2H), 3.12 (s, 3H), 3.12-3.15 (m, 2H), 3.03 (s, 3H), 3.02 (s, 3H), 3.00-3.04 (m, 2H), 2.73-2.80 (m, 2H), 1.90-2.00 (m, 2H), 1.65-1.75 (m, 2H)

LC/MS: [M]+=718.3

Example 16

Synthesis of 4-({[5-(2-{[5-({[(2R)-2-hydroxy-2-(8-hydroxy-2-oxo-1,2-dihydroquinolin-5-yl)ethyl]amino}methyl)thiophen-2-yl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-(5-{2-[(5-{[(tert-butyldimethylsilyl)oxy]methyl}thiophen-2-yl)carbamoyl]ethyl}-2-phenylphenyl)carbamate (40.5 mg, 0.08 mmol) obtained in Reference Example 15-16, there was obtained 4-({[5-(2-{[5-({[(2R)-2-hydroxy-2-(8-hydroxy-2-oxo-1,2-dihydroquinolin-5-yl)ethyl]amino}methyl)thiophen-2-yl]carbamoyl}ethyl)-2-phenylphenyl]carbamoyl}oxy)-1,1-dimethylpiperidin-1-ium trifluoroacetate (15.1 mg).

$^1$H-NMR (400 MHz, DMSO-d$_6$) δ 11.35 (s, 1H), 10.46 (s, 1H), 9.07 (broad, 1H), 8.71 (s, 1H), 8.02 (d, J=10.0 Hz, 1H), 7.25-7.39 (m, 5H), 7.17-7.25 (m, 2H), 7.12-7.16 (m, 1H), 7.06 (d, J=8.0 Hz, 1H), 6.97 (d, J=3.9 Hz, 1H), 6.92 (d, J=8.0

Hz, 1H), 6.52 (d, J=3.9 Hz, 1H), 6.51 (d, J=10.0 Hz, 1H), 5.23-5.28 (m, 1H), 4.55-4.62 (m, 1H), 4.25-4.33 (m, 2H), 3.33-3.40 (m, 2H), 3.20-3.33 (m, 2H), 3.03 (s, 3H), 3.02 (s, 3H), 2.95-3.02 (m, 2H), 2.90 (t, J=7.6 Hz, 2H), 2.65 (t, J=7.6 Hz, 2H), 1.90-2.00 (m, 2H), 1.65-1.75 (m, 2H)

LC/MS: [M]+=710.2

Example 17

Synthesis of 4-({[5-(2-{[5-({[(2R)-2-hydroxy-2-(8-hydroxy-2-oxo-1,2-dihydroquinolin-5-yl)ethyl]amino}methyl)pyridin-2-yl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-(5-{2-[(5-{[(tert-butyldimethylsilyl)oxy]methyl}pyridine-2-yl)carbamoyl]ethyl}-2-phenylphenyl)carbamate (90.3 mg, 0.18 mmol) obtained in Reference Example 15-17, there was obtained 4-({[5-(2-{[5-({[(2R)-2-hydroxy-2-(8-hydroxy-2-oxo-1,2-dihydroquinolin-5-yl)ethyl]amino}methyl)pyridin-2-yl]carbamoyl}ethyl)-2-phenylphenyl]carbamoyl}oxy)-1,1-dimethylpiperidin-1-ium trifluoroacetate (37.0 mg).

LC/MS: [M]+=705.3

Example 18

Synthesis of 4-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-chloro-5-methoxyphenyl}carbamoyl)propyl]-2-phenylphenyl}carbamate (10.9 mg, 0.16 mmol) obtained in Reference Example 15-18, there was obtained 4-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium trifluoroacetate (45 mg).

$^1$H-NMR (400 MHz, DMSO-$d_6$) δ 10.49 (s, 1H), 8.94 (d, J=58.8 Hz, 1H), 8.76 (s, 1H), 8.09 (d, J=10.0 Hz, 1H), 7.56 (d, J=15.6 Hz, 2H), 7.25-7.48 (m, 4H), 7.28-7.35 (m, 1H), 7.26 (s, 1H), 7.24 (d, J=8.0 Hz, 1H), 7.17 (dd, J=8.0 Hz, 1.5 Hz, 1H), 7.13 (d, J=8.0 Hz, 1H), 6.98 (d, J=8.0 Hz, 1H), 6.55 (d, J=10.0 Hz, 1H), 5.28-5.33 (m, 1H), 4.60-4.65 (m, 1H), 4.24-4.15 (m, 2H), 3.79 (s, 3H), 3.34-3.42 (m, 2H), 3.28-3.38 (m, 2H), 3.07-3.09 (m, 2H), 3.07 (s, 3H), 3.06 (s, 3H), 2.67 (t, J=7.6 Hz, 2H), 2.49-2.50 (m, 2H), 1.97-2.06 (m, 2H), 1.90-1.97 (m, 2H), 1.73-1.79 (m, 2H)

LC/MS: [M]+=782.3

Example 19

Synthesis of 4-({[5-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-chlorophenyl}carbamoyl)propyl]-2-phenylphenyl}carbamate (164.7 mg, 0.3 mmol) obtained in Reference Example 15-19, there was obtained 4-({[5-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (79.1 mg).

$^1$H-NMR (400 MHz, DMSO-$d_6$) δ 10.46 (s, 1H), 9.62 (s, 1H), 9.20 (d, J=62.4 Hz, 1H), 8.73 (s, 1H), 8.09 (d, J=10.0 Hz, 1H), 7.75 (d, J=8.3 Hz, 1H), 7.70 (d, J=1.7 Hz, 1H), 7.45 (dd, J=8.3 Hz, 1.7 Hz, 1H), 7.35-7.42 (m, 4H), 7.29-7.34 (m, 1H), 7.26 (s, 1H), 7.25 (d, J=8.0 Hz, 1H), 7.17 (dd, J=8.0 Hz, 1.5 Hz, 1H), 7.12 (d, J=8.3 Hz, 1H), 6.98 (d, J=8.3 Hz, 1H), 6.55 (d, J=10.0 Hz, 1H), 5.32-5.37 (m, 1H), 4.59-4.65 (m, 1H), 4.13-4.18 (m, 2H), 3.35-3.42 (m, 2H), 3.28-3.35 (m, 2H), 3.08 (s, 3H), 3.07 (s, 3H), 2.96-3.02 (m, 2H), 2.67 (t, J=7.6 Hz, 2H), 2.46 (t, J=7.4 Hz, 2H), 1.97-2.06 (m, 2H), 1.88-1.97 (m, 2H), 1.72-1.81 (m, 2H)

LC/MS: [M]+=752.3

Example 20

Synthesis of 4-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-3-methoxyphenyl}carbamoyl)propyl]-2-phenylphenyl}carbamate (147.1 mg, 0.27 mmol) obtained in Reference Example 15-20, there was obtained 4-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxy)-1,1-dimethylpiperidin-1-ium trifluoroacetate (103.2 mg).

$^1$H-NMR (400 MHz, DMSO-$d_6$) δ 10.46 (s, 1H), 10.12 (s, 1H), 8.80 (d, J=51.2 Hz, 1H), 8.73 (s, 1H), 8.05 (d, J=10.0 Hz, 1H), 7.47 (d, J=1.5 Hz, 1H), 7.35-7.44 (m, 4H), 7.29-7.34 (m, 2H), 7.26 (s, 1H), 7.25 (d, J=8.0 Hz, 1H), 7.17 (dd, J=8.0 Hz, 1.5 Hz, 2H), 7.11 (d, J=8.0 Hz, 1H), 6.97 (d, J=8.0 Hz, 1H), 6.53 (d, J=10.0 Hz, 1H), 5.30-5.35 (m, 1H), 4.59-4.65 (m, 1H), 4.09-4.23 (m, 2H), 3.77 (s, 3H), 3.35-3.42 (m, 2H), 3.26-3.35 (m, 2H), 3.08 (s, 3H), 3.07 (s, 3H), 2.96-3.02 (m, 2H), 2.65 (t, J=7.6 Hz, 2H), 2.39 (t, J=7.4 Hz, 2H), 1.97-2.06 (m, 2H), 1.88-1.96 (m, 2H), 1.70-1.82 (m, 2H)

LC/MS: [M]+=748.2

Example 21

Synthesis of 4-({[5-(3-{[4-({[(2R)-2-hydroxy-2-(8-hydroxy-2-oxo-1,2-dihydroquinolin-5-yl)ethyl]amino}methyl)-2-methoxyphenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-methoxyphenyl}carbamoyl)propyl]-2-phenylphenyl}carbamate (179.7 mg, 0.33 mmol) obtained in Reference Example 15-21, there was obtained 4-({[5-(3-{[4-({[(2R)-2-hydroxy-2-(8-hydroxy-2-oxo-1,2-dihydroquinolin-5-yl)ethyl]amino}methyl)-2-methoxyphenyl]

carbamoyl}propyl)-2-phenylphenyl]carbamoyl}oxy)-1,1-dimethylpiperidin-1-ium trifluoroacetate (218 mg).

$^1$H-NMR (400 MHz, DMSO-$d_6$) δ 10.47 (s, 1H), 9.20 (s, 1H), 9.24 (d, J=95.2 Hz, 1H), 8.75 (s, 1H), 8.09 (d, J=10.0 Hz, 1H), 7.99 (d, J=8.0 Hz, 1H), 7.36-7.44 (m, 4H), 7.22-7.34 (m, 4H), 7.16 (dd, J=7.8 Hz, 1.3 Hz, 1H), 7.13 (d, J=8.0 Hz, 1H), 7.02 (dd, J=8.0 Hz, 1.3 Hz, 1H), 6.99 (d, J=8.0 Hz, 1H), 6.52 (d, J=10.0 Hz, 1H), 5.32-5.38 (m, 1H), 4.60-4.68 (m, 1H), 4.16-4.22 (m, 2H), 3.84 (s, 3H), 3.37-3.44 (m, 2H), 3.28-3.37 (m, 2H), 3.08 (s, 3H), 3.07 (s, 3H), 2.96-3.04 (m, 2H), 2.65 (t, J=7.8 Hz, 2H), 2.47 (t, J=7.6 Hz, 2H), 1.96-2.04 (m, 2H), 1.86-1.95 (m, 2H), 1.70-1.82 (m, 2H)

LC/MS: [M]+=748.3

Example 22

Synthesis of 4-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-methylphenyl}carbamoyl)propyl]-2-phenylphenyl}carbamate (111 mg, 0.21 mmol) obtained in Reference Example 15-22, there was obtained 4-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-1,1-dimethylpiperidin-1-ium trifluoro acetate (72.9 mg).

$^1$H-NMR (400 MHz, DMSO-$d_6$) δ 10.48 (s, 1H), 9.39 (s, 1H), 9.10 (d, J=51.5 Hz, 1H), 8.74 (s, 1H), 8.06 (d, J=10.0 Hz, 1H), 7.29-7.48 (m, 8H), 7.26 (s, 1H), 7.25 (d, J=8.0 Hz, 1H), 7.17 (d, J=8.0 Hz, 1H), 7.11 (d, J=8.3 Hz, 1H), 6.97 (d, J=8.3 Hz, 1H), 6.54 (d, J=10.0 Hz, 1H), 5.31-5.36 (m, 1H), 4.59-4.66 (m, 1H), 4.13-4.18 (m, 2H), 3.36-3.42 (m, 2H), 3.28-3.36 (m, 2H), 3.08 (s, 3H), 3.07 (s, 3H), 2.92-3.02 (m, 2H), 2.67 (t, J=7.6 Hz, 2H), 2.34 (t, J=7.4 Hz, 2H), 2.21 (s, 3H), 1.97-2.04 (m, 2H), 1.90-1.97 (m, 2H), 1.70-1.82 (m, 2H)

LC/MS: [M]+=732.2

Example 23

Synthesis of 4-({[5-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-(5-{3-[6-{[(tert-butyldimethylsilyl)oxy]methyl}naphthalen-2-yl)carbamoyl]propyl}-2-phenylphenyl)carbamate (180.7 mg, 0.32 mmol) obtained in Reference Example 15-23, there was obtained 4-({[5-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-1,1-dimethylpiperidin-1-ium trifluoroacetate (109 mg).

$^1$H-NMR (400 MHz, DMSO-$d_6$) δ 10.47 (s, 1H), 10.26 (s, 1H), 9.27 (d, J=66.8 Hz, 1H), 8.75 (s, 1H), 8.38 (s, 1H), 8.06 (d, J=9.8 Hz, 1H), 7.96 (s, 1H), 7.85 (d, J=8.0 Hz, 2H), 7.59-7.66 (m, 2H), 7.36-7.44 (m, 4H), 7.27-7.36 (m, 2H), 7.25 (d, J=8.0 Hz, 1H), 7.18 (dd, J=7.8 Hz, 1.3 Hz, 1H), 7.11 (d, J=8.3 Hz, 1H), 6.97 (d, J=8.3 Hz, 1H), 6.54 (d, J=9.8 Hz, 1H), 5.35-5.39 (m, 1H), 4.58-4.68 (m, 1H), 4.34-4.38 (m, 2H), 3.35-3.43 (m, 2H), 3.27-3.35 (m, 2H), 3.08 (s, 3H), 3.07 (s, 3H), 2.96-3.06 (m, 2H), 2.68 (t, J=7.6 Hz, 2H), 2.45 (t, J=7.4 Hz, 2H), 2.21 (s, 3H), 1.92-2.05 (m, 4H), 1.70-1.82 (m, 2H)

LC/MS: [M]+=768.3

Example 24

Synthesis of 4-({[5-(3-{[5-({[(2R)-2-hydroxy-2-(8-hydroxy-2-oxo-1,2-dihydroquinolin-5-yl)ethyl]amino}methyl)pyridin-2-yl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-(5-{3-[(5-{[(tert-butyldimethylsilyl)oxy]methyl}pyridin-2-yl)carbamoyl]propyl}-2-phenylphenyl)carbamate (139.2 mg, 0.27 mmol) obtained in Reference Example 15-24, there was obtained 4-({[5-(3-{[5-({[(2R)-2-hydroxy-2-(8-hydroxy-2-oxo-1,2-dihydroquinolin-5-yl)ethyl]amino}methyl)pyridin-2-yl]carbamoyl}propyl)-2-phenylphenyl]carbamoyl}oxy)-1,1-dimethylpiperidin-1-ium trifluoroacetate (101 mg).

$^1$H-NMR (400 MHz, DMSO-$d_6$) δ 10.60 (s, 1H), 10.49 (s, 1H), 9.23 (d, J=77.8 Hz, 1H), 8.75 (s, 1H), 8.40 (d, J=2.2 Hz, 1H), 8.13 (d, J=8.3 Hz, 1H), 8.12 (d, J=10.0 Hz, 1H), 7.92 (dd, J=8.7 Hz, 2.2 Hz, 1H), 7.29-7.48 (m, 5H), 7.25 (s, 1H), 7.24 (d, J=8.0 Hz, 1H), 7.14-7.16 (m, 1H), 7.12 (d, J=8.3 Hz, 1H), 6.98 (d, J=8.3 Hz, 1H), 6.54 (d, J=10.0 Hz, 1H), 5.33-5.38 (m, 1H), 4.59-4.66 (m, 1H), 4.18-4.24 (m, 2H), 3.36-3.42 (m, 2H), 3.28-3.36 (m, 2H), 3.08 (s, 3H), 3.07 (s, 3H), 2.92-3.02 (m, 2H), 2.64 (t, J=7.7 Hz, 2H), 2.47 (t, J=7.3 Hz, 2H), 1.96-2.04 (m, 2H), 1.89-1.96 (m, 2H), 1.70-1.82 (m, 2H)

LC/MS: [M]+=719.3

Example 25

Synthesis of 4-({[5-(3-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({2-bromo-4-[(tert-butyldimethylsilanoyloxy)methyl]-5-methoxyphenyl}carbamoyl)propyl]-2-phenylphenyl}carbamate (106.2 mg, 0.17 mmol) obtained in Reference Example 15-25, there was obtained 4-({[5-(3-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-1,1-dimethylpiperidin-1-ium trifluoroacetate (56.2 mg).

$^1$H-NMR (400 MHz, DMSO-$d_6$) δ 10.49 (s, 1H), 9.53 (s, 1H), 8.90 (d, J=38.3 Hz, 1H), 8.75 (s, 1H), 8.08 (d, J=10.0 Hz, 1H), 7.73 (s, 1H), 7.29-7.44 (m, 6H), 7.26 (s, 1H), 7.25 (d, J=8.0 Hz, 1H), 7.15-7.19 (m, 1H), 7.13 (d, J=8.0 Hz, 1H), 6.97 (d, J=8.0, Hz, 1H), 6.56 (d, J=10.0 Hz, 1H), 5.32-5.37 (m, 1H), 4.58-4.64 (m, 1H), 4.14-4.24 (m, 2H), 3.79 (s, 3H), 3.28-3.43 (m, 4H), 3.07 (s, 3H), 3.06 (s, 3H), 2.98-3.06 (m, 2H), 2.67 (t, J=7.7 Hz, 2H), 2.46 (t, J=7.4 Hz, 2H), 1.96-2.04 (m, 2H), 1.89-1.96 (m, 2H), 1.70-1.82 (m, 2H)

LC/MS: [M]+=826.3

Example 26

Synthesis of 4-({[5-(3-{[2-chloro-5-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-chloro-5-ethoxyphenyl}carbamoyl)propyl]-2-phenylphenyl}carbamate (45 mg, 0.076 mmol) obtained in Reference Example 15-26, there was obtained 4-({[5-(3-{[2-chloro-5-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (18 mg).
LC/MS: [M]+=796.4

Example 27

Synthesis of 4-({[5-(3-{[5-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-3-ethoxyphenyl}carbamoyl)propyl]-2-phenylphenyl}carbamate (123 mg, 0.22 mmol) obtained in Reference Example 15-27, there was obtained 4-({[5-(3-{[5-ethoxy-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (48 mg).
LC/MS: [M]+=762.4

Example 28

Synthesis of 4-({[5-(3-{[2-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-2-fluorophenyl}carbamoyl)propyl]-2-phenylphenyl}carbamate (144 mg, 0.27 mmol) obtained in Reference Example 15-28, there was obtained 4-({[5-(3-{[2-fluoro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (102 mg).
$^1$H-NMR (400 MHz, DMSO-$d_6$) δ 10.48 (s, 1H), 9.88 (s, 1H), 9.21 (d, J=82.7 Hz, 1H), 8.74 (s, 1H), 8.09 (d, J=9.8 Hz, 1H), 7.92 (t, J=8.3 Hz, 1H), 7.28-7.47 (m, 7H), 7.25 (s, 1H), 7.23 (d, J=8.0 Hz, 1H), 7.15-7.18 (m, 1H), 7.11 (d, J=8.0 Hz, 1H), 6.97 (d, J=8.0 Hz, 1H), 6.54 (d, J=9.8 Hz, 1H), 5.32-5.37 (m, 1H), 4.58-4.64 (m, 1H), 4.16-4.23 (m, 2H), 3.26-3.43 (m, 4H), 3.08 (s, 3H), 3.07 (s, 3H), 2.94-3.02 (m, 2H), 2.65 (t, J=7.7 Hz, 2H), 2.46 (t, J=7.4 Hz, 2H), 1.96-2.04 (m, 2H), 1.87-1.95 (m, 2H), 1.70-1.82 (m, 2H)
LC/MS: [M]+=736.3

Example 29

Synthesis of 4-({[5-(3-{[3-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-3-chlorophenyl}carbamoyl)propyl]-2-phenylphenyl}carbamate (131.8 mg, 0.24 mmol) obtained in Reference Example 15-29, there was obtained 4-({[5-(3-{[3-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (108 mg).
$^1$H-NMR (400 MHz, DMSO-$d_6$) δ 10.48 (s, 1H), 10.31 (s, 1H), 9.18 (d, J=54.1 Hz, 1H), 8.75 (s, 1H), 8.12 (d, J=10.0 Hz, 1H), 7.92 (d, J=2.0 Hz, 1H), 7.59 (d, J=8.5 Hz, 1H), 7.52 (dd, J=8.5 Hz, 2.0 Hz, 1H), 7.29-7.44 (m, 5H), 7.25 (s, 1H), 7.24 (d, J=8.0 Hz, 1H), 7.14-7.18 (m, 1H), 7.13 (d, J=8.5 Hz, 1H), 6.98 (d, J=8.5, Hz, 1H), 6.54 (d, J=10.0 Hz, 1H), 5.34-5.40 (m, 1H), 4.58-4.68 (m, 1H), 4.24-4.40 (m, 2H), 3.28-3.44 (m, 4H), 3.08 (s, 3H), 3.07 (s, 3H), 3.04-3.15 (m, 2H), 2.65 (t, J=7.6 Hz, 2H), 2.40 (t, J=7.3 Hz, 2H), 1.96-2.04 (m, 2H), 1.87-1.95 (m, 2H), 1.70-1.82 (m, 2H)
LC/MS: [M]+=752.3

Example 30

Synthesis of 4-({[5-(3-{[2-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({2-bromo-4-[(tert-butyldimethylsilanoyloxy)methyl]phenyl}carbamoyl)propyl]-2-phenylphenyl}carbamate (95 mg, 0.16 mmol) obtained in Reference Example 15-25, there was obtained 4-({[5-(3-{[2-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (34 mg).
$^1$H-NMR (400 MHz, DMSO-$d_6$) δ 10.49 (s, 1H), 9.58 (s, 1H), 9.16 (d, J=42.4 Hz, 1H), 8.74 (s, 1H), 8.09 (d, J=10.0 Hz, 1H), 7.86 (d, J=1.7 Hz, 1H), 7.63 (d, J=8.3 Hz, 1H), 7.50 (dd, J=8.3 Hz, 1.7 Hz, 1H), 7.29-7.44 (m, 5H), 7.26 (s, 1H), 7.25 (d, J=8.0 Hz, 1H), 7.14-7.18 (m, 1H), 7.12 (d, J=8.0 Hz, 1H), 6.97 (d, J=8.0 Hz, 1H), 6.56 (d, J=10.0 Hz, 1H), 5.30-5.38 (m, 1H), 4.58-4.68 (m, 1H), 4.18-4.25 (m, 2H), 3.28-3.42 (m, 4H), 3.07 (s, 3H), 3.06 (s, 3H), 2.98-3.05 (m, 2H), 2.67 (t, J=7.6 Hz, 2H), 2.44 (t, J=7.3 Hz, 2H), 1.96-2.04 (m, 2H), 1.87-1.95 (m, 2H), 1.70-1.82 (m, 2H)
LC/MS: [M]+=796.3

Example 31

Synthesis of 4-({[5-(3-{[4-({[(2R)-2-hydroxy-2-(8-hydroxy-2-oxo-1,2-dihydroquinolin-5-yl)ethyl]amino}methyl)-3-(trifluoromethyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]-3-

(trifluoromethyl)phenyl}carbamoyl)propyl]-2-phenylphenyl}carbamate (145.2 mg, 0.25 mmol) obtained in Reference Example 15-31, there was obtained 4-({[5-(3-{[4-({[(2R)-2-hydroxy-2-(8-hydroxy-2-oxo-1,2-dihydroquinolin-5-yl)ethyl]amino}methyl)-3-(trifluoromethyl)phenyl]carbamoyl}propyl)-2-phenylphenyl]carbamoyl}oxy)-1,1-dimethylpiperidin-1-ium trifluoroacetate (98 mg).

$^1$H-NMR (400 MHz, DMSO-d$_6$) δ 10.48 (s, 1H), 9.34 (d, J=78.3 Hz, 1H), 8.76 (s, 1H), 8.13 (s, 1H), 8.13 (d, J=10.0 Hz, 1H), 7.88-7.93 (m, 1H), 7.77 (d, J=8.5 Hz, 1H), 7.29-7.44 (m, 5H), 7.26 (s, 1H), 7.25 (d, J=8.0 Hz, 1H), 7.14-7.18 (m, 1H), 7.14 (d, J=8.0 Hz, 1H), 6.99 (d, J=8.0 Hz, 1H), 6.54 (d, J=10.0 Hz, 1H), 5.36-5.43 (m, 1H), 4.58-4.68 (m, 1H), 4.30-4.44 (m, 2H), 3.26-3.44 (m, 4H), 3.08 (s, 3H), 3.07 (s, 3H), 2.98-3.05 (m, 2H), 2.66 (t, J=7.6 Hz, 2H), 2.43 (t, J=7.3 Hz, 2H), 1.96-2.04 (m, 2H), 1.90-1.96 (m, 2H), 1.70-1.82 (m, 2H)
LC/MS: [M]+=786.3

Example 32

Synthesis of 4-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{5-[3-({4-[(tert-butyldimethylsilanoyloxy)methyl]phenyl}carbamoyl)propyl]-2-phenylphenyl}carbamate (122 mg, 0.2 mmol) obtained in Reference Example 15-32, there was obtained 4-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (40 mg).

$^1$H-NMR (400 MHz, DMSO-d$_6$) δ 10.45 (s, 1H), 10.06 (s, 1H), 9.02 (d, J=38.8 Hz, 1H), 8.70 (s, 1H), 8.09 (d, J=10.0 Hz, 1H), 7.63 (d, J=8.5 Hz, 2H), 7.35-7.45 (m, 6H), 7.28-7.35 (m, 1H), 7.25 (s, 1H), 7.24 (d, J=7.8 Hz, 1H), 7.14-7.18 (m, 1H), 7.10 (d, J=8.0 Hz, 1H), 6.96 (d, J=8.0 Hz, 1H), 6.54 (d, J=10.0 Hz, 1H), 5.28-5.33 (m, 1H), 4.59-4.66 (m, 1H), 4.13-4.18 (m, 2H), 3.34-3.42 (m, 2H), 3.28-3.34 (m, 2H), 3.07 (s, 3H), 3.06 (s, 3H), 2.90-3.09 (m, 2H), 2.65 (t, J=7.6 Hz, 2H), 2.38 (t, J=7.3 Hz, 2H), 1.97-2.06 (m, 2H), 1.88-1.97 (m, 2H), 1.73-1.81 (m, 2H)
LC/MS: [M]+=718.3

Example 33

Synthesis of (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]phenyl}carbamoyl)propyl]-2-phenylphenyl}carbamate (57.6 mg, 0.088 mmol) obtained in Reference Example 15-33, there was obtained (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (25 mg).

$^1$H-NMR (400 MHz, DMSO-d$_6$) δ 10.47 (s, 1H), 10.06 (s, 1H), 8.99 (d, J=18.5 Hz, 1H), 8.75 (s, 1H), 8.03 (d, J=10.0 Hz, 1H), 7.63 (d, J=8.5 Hz, 2H), 7.31-7.46 (m, 7H), 7.27 (s, 1H), 7.25 (d, J=7.8 Hz, 1H), 7.13-7.18 (m, 1H), 7.10 (d, J=8.3 Hz, 1H), 6.95 (d, J=8.3 Hz, 1H), 6.54 (d, J=10.0 Hz, 1H), 5.28-5.34 (m, 1H), J=5.6 Hz, 1H), 4.13-4.19 (m, 2H), 4.08-4.12 (m, 2H), 3.76-3.95 (broad, 2H), 3.25 (s, 3H), 3.01 (s, 3H), 2.92-3.02 (m, 2H), 2.94 (t, J=7.8 Hz, 2H), 2.53 (dt, J=16.9 Hz, 5.2 Hz, 2H), 2.38 (t, J=7.3 Hz, 2H), 1.88-1.96 (m, 2H), 1.79 (d, J=17.1 Hz, 2H)
LC/MS: [M]+=758.3

Example 34

Synthesis of (1R,2R,4S,5S,7S)-7-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chloro-5-methoxyphenyl}carbamoyl)propyl]-2-phenylphenyl}carbamate (136.8 mg, 0.2 mmol) obtained in Reference Example 15-18, there was obtained (1R,2R,4S,5S,7S)-7-({[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (87 mg).

$^1$H-NMR (400 MHz, DMSO-d$_6$) δ 10.54 (s, 1H), 9.60 (s, 1H), 8.92 (d, J=48.0 Hz, 1H), 8.78 (s, 1H), 8.08 (d, J=10.0 Hz, 1H), 7.58 (s, 1H), 7.54 (s, 1H), 7.31-7.46 (m, 5H), 7.28 (s, 1H), 7.25 (d, J=7.8 Hz, 1H), 7.13-7.18 (m, 1H), 7.12 (d, J=8.3 Hz, 1H), 6.97 (d, J=8.3 Hz, 1H), 6.55 (d, J=10.0 Hz, 1H), 5.32-5.37 (m, 1H), 4.78 (t, J=5.2 Hz, 1H), 4.14-4.24 (m, 2H), 4.08-4.12 (m, 2H), 3.82-3.98 (broad, 2H), 3.79 (s, 3H), 3.25 (s, 3H), 3.01 (s, 3H), 2.94-3.07 (m, 2H), 2.65 (t, J=7.6 Hz, 2H), 2.53-2.58 (m, 2H), 2.43-2.50 (m, 2H), 1.88-1.96 (m, 2H), 1.79 (d, J=12.9 Hz, 2H)
LC/MS: [M]+=822.3

Example 35

Synthesis of (1R,2R,4S,5S,7S)-7-({[5-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-(5-{3-[(6-{[(tert-butyldimethylsilyl)oxy]methyl}naphthalen-2-yl)carbamoyl]propyl}-2-phenylphenyl)carbamate (181 mg, 0.26 mmol) obtained in Reference Example 15-35, there was obtained (1R,2R,4S,5S,7S)-7-({[5-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (26 mg).

$^1$H-NMR (400 MHz, DMSO-d$_6$) δ 10.50 (s, 1H), 10.23 (s, 1H), 9.17 (d, J=22.2 Hz, 1H), 8.78 (s, 1H), 8.38 (s, 1H), 8.03 (d, J=10.0 Hz, 1H), 7.95 (s, 1H), 7.83-7.89 (m, 2H), 7.58-7.66 (m, 2H), 7.31-7.46 (m, 5H), 7.29 (s, 1H), 7.26 (d, J=7.8 Hz,

1H), 7.16-7.20 (m, 1H), 7.10 (d, J=8.0 Hz, 1H), 6.95 (d, J=8.0 Hz, 1H), 6.48 (d, J=10.0 Hz, 1H), 5.31-5.36 (m, 1H), 4.79 (t, J=6.0 Hz, 1H), 4.32-4.38 (m, 2H), 4.07-4.13 (m, 2H), 3.78-4.00 (broad, 2H), 3.25 (s, 3H), 3.05-3.13 (m, 2H), 3.01 (s, 3H), 2.67 (t, J=7.6 Hz, 2H), 2.49-2.58 (m, 2H), 2.44 (t, J=7.3 Hz, 2H), 1.92-2.00 (m, 2H), 1.79 (d, J=14.1 Hz, 2H)

LC/MS: [M]+=808.3

Example 36

Synthesis of (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-3-methoxyphenyl}carbamoyl)propyl]-2-phenylphenyl}carbamate (251 mg, 0.36 mmol) obtained in Reference Example 15-36, there was obtained (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-3-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (81 mg).

$^1$H-NMR (400 MHz, DMSO-d$_6$) δ 10.50 (s, 1H), 10.14 (s, 1H), 8.79 (d, J=52.9 Hz, 1H), 8.78 (s, 1H), 8.05 (d, J=10.0 Hz, 1H), 7.31-7.46 (m, 7H), 7.28 (s, 1H), 7.25 (d, J=7.8 Hz, 1H), 7.13-7.19 (m, 2H), 7.11 (d, J=8.0 Hz, 1H), 6.97 (d, J=8.0 Hz, 1H), 6.53 (d, J=10.0 Hz, 1H), 5.29-5.35 (m, 1H), 4.79 (t, J=5.4 Hz, 1H), 4.10-4.23 (m, 2H), 4.07-4.13 (m, 2H), 3.78-4.0 (broad, 2H), 3.78 (s, 3H), 3.26 (s, 3H), 3.02 (s, 3H), 2.94-3.04 (m, 2H), 2.64 (t, J=7.7 Hz, 2H), 2.49-2.57 (m, 2H), 2.38 (t, J=7.3 Hz, 2H), 1.88-1.96 (m, 2H), 1.78 (d, J=13.2 Hz, 2H)

LC/MS: [M]+=788.3

Example 37

Synthesis of (1R,2R,4S,5S,7S)-7-({[5-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-chlorophenyl}carbamoyl)propyl]-2-phenylphenyl}carbamate (116.1 mg, 0.23 mmol) obtained in Reference Example 15-37, there was obtained (1R,2R,4S,5S,7S)-7-({[5-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (19.7 mg).

$^1$H-NMR (400 MHz, DMSO-d$_6$) δ 10.52 (s, 1H), 9.63 (s, 1H), 9.02-9.15 (broad, 1H), 8.77 (s, 1H), 8.07 (d, J=10.0 Hz, 1H), 7.75 (d, J=8.3 Hz, 1H), 7.69 (d, J=2.0 Hz, 1H), 7.31-7.47 (m, 6H), 7.28 (s, 1H), 7.25 (d, J=7.8 Hz, 1H), 7.14-7.18 (m, 1H), 7.12 (d, J=8.3 Hz, 1H), 6.96 (d, J=8.3 Hz, 1H), 6.53 (d, J=10.0 Hz, 1H), 5.29-5.34 (m, 1H), 4.78 (t, J=5.7 Hz, 1H), 4.16-4.24 (m, 2H), 4.07-4.13 (m, 2H), 3.78-4.00 (broad, 2H), 3.25 (s, 3H), 3.02-3.12 (m, 2H), 3.01 (s, 3H), 2.65 (t, J=7.4 Hz, 2H), 2.49-2.57 (m, 2H), 2.46 (t, J=7.3 Hz, 2H), 1.88-1.96 (m, 2H), 1.78 (d, J=13.3 Hz, 2H)

LC/MS: [M]+=792.3

Example 38

Synthesis of (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-2-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methoxyphenyl}carbamoyl)propyl]-2-phenylphenyl}carbamate (311.2 mg, 0.45 mmol) obtained in Reference Example 15-38, there was obtained (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-2-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (61 mg).

$^1$H-NMR (400 MHz, DMSO-d$_6$) δ 10.50 (s, 1H), 9.21 (s, 1H), 9.15 (d, J=67.6 Hz, 1H), 8.77 (s, 1H), 8.07 (d, J=10.0 Hz, 1H), 7.98 (d, J=8.0 Hz, 1H), 7.31-7.47 (m, 5H), 7.22-7.28 (m, 3H), 7.15 (d, J=8.5 Hz, 1H), 7.11 (d, J=8.3 Hz, 1H), 7.01-7.06 (m, 1H), 6.97 (d, J=8.3 Hz, 1H), 6.53 (d, J=10.0 Hz, 1H), 5.30-5.38 (m, 1H), 4.78 (t, J=5.6 Hz, 1H), 4.14-4.22 (m, 2H), 4.07-4.13 (m, 2H), 3.82-4.02 (broad, 2H), 3.83 (s, 3H), 3.25 (s, 3H), 3.01 (s, 3H), 2.90-3.08 (m, 2H), 2.63 (t, J=7.6 Hz, 2H), 2.49-2.58 (m, 2H), 2.46 (t, J=7.3 Hz, 2H), 1.88-1.96 (m, 2H), 1.78 (d, J=13.2 Hz, 2H)

LC/MS: [M]+=788.3

Example 39

Synthesis of (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[3-({4-[(tert-butyldimethylsilanoyloxy)methyl]-2-methylphenyl}carbamoyl)propyl]-2-phenylphenyl}carbamate (149 mg, 0.22 mmol) obtained in Reference Example 15-39, there was obtained (1R,2R,4S,5S,7S)-7-({[5-(3-{[4-({[(2R)-2-hydroxy-2-(8-hydroxy-2-oxo-1,2-dihydroquinolin-5-yl)ethyl]amino}methyl)-2-methylphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (38 mg).

$^1$H-NMR (400 MHz, DMSO-d$_6$) δ 10.51 (s, 1H), 9.39 (s, 1H), 9.07 (d, J=41.2 Hz, 1H), 8.78 (s, 1H), 8.05 (d, J=10.0 Hz, 1H), 7.30-7.48 (m, 8H), 7.28 (s, 1H), 7.25 (d, J=7.8 Hz, 1H), 7.16 (d, J=7.8 Hz, 1H), 7.11 (d, J=8.3 Hz, 1H), 6.97 (d, J=8.3 Hz, 1H), 6.55 (d, J=10.0 Hz, 1H), 5.30-5.36 (m, 1H), 4.79 (t, J=5.5 Hz, 1H), 4.12-4.18 (m, 2H), 4.07-4.12 (m, 2H), 3.82-4.02 (broad, 2H), 3.83 (s, 3H), 3.25 (s, 3H), 3.01 (s, 3H), 2.90-3.06 (m, 2H), 2.65 (t, J=7.6 Hz, 2H), 2.49-2.58 (m, 2H), 2.41 (t, J=7.1 Hz, 2H), 1.87-1.97 (m, 2H), 1.78 (d, J=17.1 Hz, 2H)

LC/MS: [M]+=772.3

Example 40

Synthesis of (1R,2R,4S,5S,7S)-7-({[5-(2-{[6-({[(2R)-2-hydroxy-2-(8-hydroxy-2-oxo-1,2-dihydroquinolin-5-yl)ethyl]amino}methyl)naphthalen-2-yl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-(5-{2-[(6-{[(tert-butyldimethylsilyl)oxy]methyl}naphthalen-2-yl)carbamoyl]ethyl}-2-phenylphenyl)carbamate (77 mg, 0.13 mmol) obtained in Reference Example 15-40, there was obtained (1R,2R,4S,5S,7S)-7-({[5-(2-{[6-({[(2R)-2-hydroxy-2-(8-hydroxy-2-oxo-1,2-dihydroquinolin-5-yl)ethyl]amino}methyl)naphthalen-2-yl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (19.5 mg).

$^1$H-NMR (400 MHz, DMSO-d$_6$) δ 10.50 (s, 1H), 10.27 (s, 1H), 9.07-9.15 (broad, 1H), 8.77 (s, 1H), 8.37 (s, 1H), 8.02 (d, J=10.0 Hz, 1H), 7.95 (s, 1H), 7.84-7.90 (m, 2H), 7.57-7.65 (m, 2H), 7.31-7.46 (m, 6H), 7.20-7.28 (m, 2H), 7.10 (d, J=8.3 Hz, 1H), 6.94 (d, J=8.3 Hz, 1H), 6.49 (d, J=10.0 Hz, 1H), 5.30-5.36 (m, 1H), 4.79 (t, J=5.4 Hz, 1H), 4.33-4.38 (m, 2H), 4.07-4.12 (m, 2H), 3.78-3.98 (broad, 2H), 3.24 (s, 3H), 3.05-3.14 (m, 2H), 3.00 (s, 3H), 2.97 (t, J=8.0 Hz, 2H), 2.75 (t, J=8.0 Hz, 2H), 2.46-2.58 (m, 2H), 1.78 (d, J=16.8 Hz, 2H)
LC/MS: [M]+=794.3

Example 41

Synthesis of (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methoxyphenyl}carbamoyl)ethyl]-2-phenylphenyl}carbamate (50 mg, 0.08 mmol) obtained in Reference Example 15-41, there was obtained (1R,2R,4S,5S,7S)-7-({[5-(2-{[4-{[(2R)-2-hydroxy-2-(8-hydroxy-2-oxo-1,2-dihydroquinolin-5-yl)ethyl]amino}methyl)-2-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (10.5 mg).
LC/MS: [M]+=774.3

Example 42

Synthesis of (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-3-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-methoxyphenyl}carbamoyl)ethyl-2-phenylphenyl}carbamate (64.3 mg, 0.11 mmol) obtained in Reference Example 15-42, there was obtained (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-3-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (11.4 mg).
LC/MS: [M]+=774.3

Example 43

Synthesis of (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-2-methylphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-methylphenyl}carbamoyl)ethyl]-2-phenylphenyl}carbamate (196 mg, 0.3 mmol) obtained in Reference Example 15-43, there was obtained (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-2-methylphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (128 mg).
LC/MS: [M]+=758.3

Example 44

Synthesis of (1R,2R,4S,5S,7S)-7-({[5-(2-{[2-chloro-4-({[(2R)-2-hydroxy-2-(8-hydroxy-2-oxo-1,2-dihydroquinolin-5yl)ethyl]amino}methyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-chlorolphenyl}carbamoyl)ethyl]-2-phenylphenyl}carbamate (95 mg, 0.14 mmol) obtained in Reference Example 15-44, there was obtained (1R,2R,4S,5S,7S)-7-({[5-(2-{[2-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (25.5 mg).
LC/MS: [M]+=779.4

Example 45

Synthesis of (1R,2R,4S,5S,7S)-7-({[5-(2-{[3-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2({4-[(tert-butyldimethylsilanoyloxy)methyl]-3-chlorophenyl}carbamoyl)ethyl]-2-phenylphenyl}carbamate (256 mg, 0.23 mmol) obtained in Reference Example 15-45, there was obtained (1R,2R,4S,5S, 7S)-7-({[5-(2-{[3-chloro-4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (45 mg).
LC/MS: [M]+=778.3

Example 46

Synthesis of (1R,2R,4S,5S,7S)-7-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-2-chloro-5-methoxyphenyl}carbamoyl)ethyl]-2-phenylphenyl}carbamate (52 mg, 0.074 mmol) obtained in Reference Example 15-46, there was obtained (1R,2R,4S,5S,7S)-7-({[5-(2-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (25.6 mg).
$^{1}$H-NMR (400 MHz, DMSO-d$_6$) δ 10.47 (s, 1H), 9.60 (s, 1H), 8.86 (d, J=29.3 Hz, 1H), 8.77 (s, 1H), 8.08 (d, J=10.0 Hz, 1H), 7.58 (s, 1H), 7.57 (s, 1H), 7.30-7.46 (m, 5H), 7.18-7.28 (m, 2H), 7.13 (d, J=8.3 Hz, 2H), 6.97 (d, J=8.3 Hz, 1H), 6.56 (d, J=10.0 Hz, 1H), 5.34 (dd, J=9.1 Hz, 3.5 Hz, 1H), 4.79 (t, J=5.6 Hz, 1H), 4.14-4.24 (m, 2H), 4.07-4.13 (m, 2H), 3.80-3.98 (broad, 2H), 3.80 (s, 3H), 3.26 (s, 3H), 3.01 (s, 3H), 2.98-3.08 (m, 2H), 2.94 (t, J=7.7 Hz, 2H), 2.78 (t, J=7.7 Hz, 2H), 2.54 (dt, J=17.7 Hz, 5.2 Hz, 2H), 1.77 (d, J=11.0 Hz, 2H)
LC/MS: [M]+=808.3

Example 47

Synthesis of (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-3-ethoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[2-({4-[(tert-butyldimethylsilanoyloxy)methyl]-3-ethoxyphenyl}carbamoyl)ethyl]-2-phenylphenyl}carbamate (219 mg, 0.32 mmol) obtained in Reference Example 15-47, there was obtained (1R,2R,4S,5S,7S)-7-({[5-(2-{[4-({[(2R)-2-hydroxy-2-(8-hydroxy-2-oxo-1,2-dihydroquinolin-5-yl)ethyl]amino}methyl)-3-ethoxyphenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (109 mg).
LC/MS: [M]+=788.3

Example 48

Synthesis of (1R,3R)-3-{[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-8,8-dimethyl-8-azabicyclo[3.2.1]nonan-8-ium trifluoroacetate In accordance with Example 1, from (1R,3R)-8-methyl-8-azabicyclo[3.2.1]octan-3-yl N-{5-[3-({4-[(tert-butyldimethylsilanoyloxy)methyl]-2-chloro-5-methoxyphenyl}carbamoyl)propyl]-2-phenylphenyl}carbamate (488 mg, 0.69 mmol) obtained in Reference Example 15-48, there was obtained (1R,3R)-3-{[5-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-8,8-dimethyl-8-azabicyclo[3.2.1]nonan-8-ium trifluoroacetate (285 mg).
$^{1}$H-NMR (400 MHZ, DMSO-D$_6$) □10.49 (s, 1H), 9.59 (s, 1H), 8.99 (d, J=39.8 Hz, 1H), 8.90 (s, 1H), 8.08 (d, J=9.8 Hz, 1H), 7.58 (s, 1H), 7.54 (s, 1H), 7.31-7.46 (m, 8H), 7.13 (d, J=8.3 Hz, 1H), 6.97 (d, J=8.3 Hz, 1H), 6.56 (d, J=9.8 Hz, 1H), 5.30-5.36 (m, 1H), 4.72 (t, J=5.2 Hz, 1H), 4.12-4.26 (m, 2H), 3.80 (s, 3H), 3.77 (s, 3H), 3.00-3.12 (m, 4H), 2.99 (s, 3H), 2.67 (t, J=7.0 Hz, 2H), 2.36-2.56 (m, 4H), 2.12-2.28 (m, 2H), 1.86-1.96 (m, 2H), 1.67 (d, J=16.1 Hz, 2H)
LC/MS: [M]+=808.3

Example 49

Synthesis of 4-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-1,1-dimethylpiperidin-1-ium trifluoroacetate In accordance with Example 1, from 1-methylpiperidin-4-yl N-{5-[4-({4-[(tert-butyldimethylsilanoyloxy)methyl]-3-methoxyphenyl}carbamoyl)butyl]-2-phenylphenyl}carbamate (137 mg, 0.218 mmol) obtained in Reference Example 15-49, there was obtained 4-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-1,1-dimethylpiperidin-1-ium trifluoroacetate (64 mg).
$^{1}$H-NMR (400 MHz, DMSO-d$_6$) δ 10.48 (s, 1H), 10.08 (s, 1H), 9.10 (d, J=68.8 Hz, 1H), 8.73 (s, 1H), 8.06 (d, J=10.0 Hz, 1H), 7.62 (d, J=8.8 Hz, 2H), 7.28-7.45 (m, 7H), 7.23 (s, 1H), 7.23 (d, J=7.6 Hz, 1H), 7.14 (dd, J=7.9 Hz, 1.3 Hz, 1H), 7.10 (d, J=8.3 Hz, 1H), 6.97 (d, J=8.3 Hz, 1H), 6.53 (d, J=10.0 Hz, 1H), 5.30-5.35 (m, 1H), 4.57-4.62 (m, 1H), 4.12-4.18 (m, 2H), 3.36-3.42 (m, 2H), 3.26-3.36 (m, 2H), 3.07 (s, 3H), 3.06 (s, 3H), 2.88-3.09 (m, 2H), 2.63 (t, J=7.0 Hz, 2H), 2.36 (t, J=7.0 Hz, 2H), 1.94-2.06 (m, 2H), 1.69-1.82 (m, 2H), 1.60-1.68 (m, 4H)
LC/MS: [M]+=732.3

Example 50

Synthesis of (1R,2R,4S,5S,7S)-7-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]phenyl}carbamoyl)butyl]-2-phenylphenyl}carbamate (64 mg, 0.1 mmol) obtained in Reference Example 15-50, there was obtained (1R,2R,4S,5S,7S)-7-({[5-(4-{[4-({[(2R)-2-hydroxy-2-(8-hydroxy-2-oxo-1,2-dihydroquinolin-5-yl)ethyl]amino}methyl)phenyl]carbamoyl}butyl)-2-phenylphenyl]carbamoyl}oxy)-9,9-dimethyl-3-oxa-9-azatricyclo[3.3.1.0$^{2,4}$]nonan-9-ium trifluoroacetate (21.4 mg).
LC/MS: [M]+=772.3

Example 51

Synthesis of 4-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-1,1-dimethylpiperidin-1-ium trifluoroacetate In accordance with Example 1, from 1-methylpiperidin-4-yl N-{5-[4-({4-[(tert-butyldimethylsilanoyloxy)methyl]-2-chloro-5-methoxyphenyl}carbamoyl)butyl]-2-phenylphenyl}carbamate (60.5 mg, 0.087 mmol) obtained in Reference Example 15-51, there was obtained 4-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-1,1-dimethylpiperidin-1-ium trifluoroacetate (17 mg).

LC/MS: [M]+=796.3

Example 52

Synthesis of (1R,2R,4S,5S,7S)-7-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-9,9-dimethyl-3-oxa-9-azatricyclo[3.3.1.0$^{2,4}$]nonan-9-ium trifluoro acetate In accordance with Example 1, from (1R,2R,4S,5S,7S)-9-methyl-3-oxa-9-azatricyclo[3.3.1.0$^{2,4}$]nonan-7-yl N-{5-[4-({4-[(tert-butyldimethylsilanoyloxy)methyl]-2-chloro-5-methoxyphenyl}carbamoyl)butyl]-2-phenylphenyl}carbamate (76 mg, 0.1 mmol) obtained in Reference Example 15-52, there was obtained (1R,2R,4S,5S,7S)-7-({[5-(4-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}butyl)-2-phenylphenyl]carbamoyl}oxy)-9,9-dimethyl-3-oxa-9-azatricyclo[3.3.1.0$^{2,4}$]nonan-9-ium trifluoroacetate (11.9 mg).

LC/MS: [M]+=836.3

Example 53

Synthesis of (1R,2R,4S,5S,7S)-7-({[4-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]phenyl}carbamoyl)propyl]-2-phenylphenyl}carbamate (70.1 mg, 0.11 mmol) obtained in Reference Example 15-53, there was obtained (1R,2R,4S,5S,7S)-7-({[4-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (30.9 mg).

LC/MS: [M]+=758.3

Example 54

Synthesis of 4-({[4-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate In accordance with Example 1, from 1-methylpiperidin-4-yl N-{4-(3-{[4-[(tert-butyldimethylsilanoyloxy)methyl]phenyl}carbamoyl)propyl]-2-phenylphenyl}carbamate (88.2 mg, 0.14 mmol) obtained in Reference Example 15-54, there was obtained 4-({[4-(3-{[4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-1,1-dimethylpiperidin-1-ium trifluoroacetate (45 mg).

$^1$H-NMR (400 MHz, DMSO-d$_6$) δ 10.49 (s, 1H), 10.03 (s, 1H), 8.88-8.98 (broad, 1H), 8.70 (s, 1H), 8.02 (d, J=10.0 Hz, 1H), 7.61 (d, J=8.3 Hz, 2H), 7.26-7.44 (m, 8H), 7.20 (d, J=8.5 Hz, 1H), 7.15 (s, 1H), 7.09 (d, J=8.3 Hz, 1H), 6.94 (d, J=8.3 Hz, 1H), 6.54 (d, J=10.0 Hz, 1H), 5.26-5.34 (m, 1H), 4.58-4.66 (m, 1H), 4.12-4.17 (m, 2H), 3.34-3.42 (m, 2H), 3.26-3.34 (m, 2H), 3.07 (s, 3H), 3.06 (s, 3H), 2.90-3.06 (m, 2H), 2.65 (t, J=7.2 Hz, 2H), 2.38 (t, J=7.7 Hz, 2H), 1.94-2.04 (m, 2H), 1.87-1.94 (m, 2H), 1.70-1.82 (m, 2H)

LC/MS: [M]+=718.3

Example 55

Synthesis of (1R,2R,4S,5S,7S)-7-({[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-chloro-5-methoxyphenyl}carbamoyl)propyl]-2-phenylphenyl}carbamate (201 mg, 0.28 mmol) obtained in Reference Example 15-55, there was obtained (1R,2R,4S,5S,7S)-7-({[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (59 mg).

$^1$H-NMR (400 MHz, DMSO-d$_6$) δ 10.49 (s, 1H), 9.55 (s, 1H), 8.75-8.84 (broad, 1H), 8.73 (s, 1H), 8.07 (d, J=10.0 Hz, 1H), 7.57 (s, 1H), 7.53 (s, 1H), 7.31-7.46 (m, 6H), 7.21 (d, J=8.3 Hz, 1H), 7.17 (s, 1H), 7.12 (d, J=8.3 Hz, 1H), 6.96 (d, J=8.3 Hz, 1H), 6.57 (d, J=10.0 Hz, 1H), 5.28-5.34 (m, 1H), 4.78 (t, J=5.9 Hz, 1H), 4.14-4.22 (m, 2H), 4.07-4.12 (m, 2H), 3.79 (s, 3H), 3.82-3.98 (broad, 2H), 3.25 (s, 3H), 3.01-3.07 (m, 2H), 3.01 (s, 3H), 2.66 (t, J=7.3 Hz, 2H), 2.49-2.58 (m, 2H), 2.43-2.49 (m, 2H), 1.87-1.96 (m, 2H), 1.77 (d, J=17.1 Hz, 2H)

LC/MS: [M]+=822.3

Example 56

Synthesis of (1R,2R,4S,5S,7S)-7-({[4-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-(4-{3-

[(6-{[(tert-butyldimethylsilyl)oxy]methyl}naphthalen-2-yl)carbamoyl]propyl}-2-phenylphenyl)carbamate obtained in Reference Example 15-56, there was obtained (1R,2R,4S,5S,7S)-7-({[4-(3-{[6-({[(2R)-2-hydroxy-2-(8-hydroxy-2-oxo-1,2-dihydroquinolin-5-yl)ethyl]amino}methyl)naphthalen-2-yl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (59.9 mg).

$^1$H-NMR (400 MHz, DMSO-d$_6$) δ 10.48 (s, 1H), 10.19 (s, 1H), 9.02-9.14 (broad, 1H), 8.74 (s, 1H), 8.37 (s, 1H), 8.02 (d, J=10.0 Hz, 1H), 7.94 (s, 1H), 7.83-7.90 (m, 2H), 7.57-7.62 (m, 2H), 7.31-7.47 (m, 6H), 7.22 (d, J=8.8 Hz, 1H), 7.18 (s, 1H), 7.10 (d, J=8.3 Hz, 1H), 6.94 (d, J=8.3 Hz, 1H), 6.49 (d, J=10.0 Hz, 1H), 5.28-5.35 (m, 1H), 4.78 (t, J=5.5 Hz, 1H), 4.32-4.37 (m, 2H), 4.07-4.12 (m, 2H), 3.82-3.98 (broad, 2H), 3.25 (s, 3H), 3.06-3.14 (m, 2H), 3.00 (s, 3H), 2.68 (t, J=7.8 Hz, 2H), 2.49-2.58 (m, 2H), 2.42 (t, J=7.2 Hz, 2H), 1.92-1.99 (m, 2H), 1.77 (d, J=18.0 Hz, 2H)

LC/MS: [M]+=808.3

Example 57

Synthesis of 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1-methyl-1-(2-phenoxyethyl)piperidin-1-ium trifluoro acetate In accordance with Example 1, from 1-(2-phenoxyethyl)piperidin-4-yl N-{5-[2-({4-[(tert-butyldimethylsilanoyloxy)methyl]phenyl}carbamoyl)ethyl]-2-phenylphenyl}carbamate (227 mg, 0.43 mmol) obtained in Reference Example 15-57, there was obtained 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1-methyl-1-(2-phenoxyethyl)piperidin-1-ium trifluoroacetate (82.5 mg).

$^1$H-NMR (400 MHz, DMSO-d$_6$) δ 10.48 (s, 1H), 10.14 (s, 1H), 9.07 (d, J=51.7 Hz, 1H), 8.75 (d, J=6.1 Hz, 1H), 8.06 (d, J=10.0 Hz, 1H), 7.63 (d, J=8.5 Hz, 2H), 7.44 (d, J=8.5 Hz, 2H), 7.27-7.42 (m, 8H), 7.18-7.27 (m, 2H), 7.10 (d, J=8.3 Hz, 1H), 6.95-7.04 (m, 3H), 6.97 (d, J=8.3 Hz, 1H), 6.53 (d, J=10.0 Hz, 1H), 5.29-5.34 (m, 1H), 4.62-4.71 (m, 1H), 4.46-4.50 (m, 2H), 4.12-4.20 (m, 2H), 3.80-3.86 (m, 2H), 3.47-3.60 (m, 2H), 3.40-3.52 (m, 2H), 3.15 (s, 3H), 2.96-3.05 (m, 2H), 2.94 (t, J=7.5 Hz, 2H), 2.68 (t, J=7.5 Hz, 2H), 2.02-2.12 (m, 2H), 1.73-1.86 (m, 2H)

LC/MS: [M]+=810.3

Example 58

Synthesis of 4-[({5-[(8-{[(2R)-2-hydroxy-2-(8-hydroxy-2-oxo-1,2-dihydroquinolin-5-yl)ethyl]amino}octyl)oxy]-2-phenylphenyl}carbamoyl)oxy]-1,1-dimethylpiperidin-1-ium trifluoroacetate 1-Methylpiperidin-4-yl N-(5-{[8-(tert-butyldimethylsilanoyloxy)octyl]oxy}-2-phenylphenyl)carbamate (283 mg, 0.50 mmol) obtained in Reference Example 12-6 was dissolved in tetrahydrofuran (10 mL), hydrogen trifluoride-triethylamine complex (0.4 mL) was added thereto, and the mixture was stirred at room temperature for 18 hours. The reaction mixture was extracted with ethyl acetate and the organic layer was washed with a dilute aqueous solution of sodium hydroxide and a saturated aqueous solution of sodium chloride, dried over anhydrous magnesium sulfate, and concentrated under reduced pressure.

A half of the residue was dissolved in acetonitrile (5 mL), methyl iodide (1 mL) was added thereto, and after stirring at room temperature for 1 hour, the reaction solution was concentrated under reduced pressure.

Triphenylphosphin polymer bound (3.00 mmol/g) 200 mg and iodine (136 mg, 0.54 mmol) were stirred in dichloromethane for 1 hour, the aforementioned methylated residue dissolved in dichloromethane (10 mL) was added thereto, and the mixture was stirred for further 2 hours. Subsequently, the reaction solution was filtered through celite and the filtrate was concentrated under reduced pressure.

The residue was suspended in N,N-dimethylformamide (2 mL), thereto was added 5-((R)-2-amino-1-hydroxyethyl)-8-hydroxy-1H-quinolin-2-one acetate (84 mg, 0.3 mmol), and the mixture was stirred at 70° C. for 18 hours. The reaction solution was concentrated and, thereafter, the residue was purified by HPLC fractionation to obtain 4-[({5-[(8-{[(2R)-2-hydroxy-2-(8-hydroxy-2-oxo-1,2-dihydroquinolin-5-yl)ethyl]amino}octyl)oxy]-2-phenylphenyl}carbamoyl)oxy]-1,1-dimethylpiperidin-1-ium trifluoroacetate (17.5 mg).

$^1$H-NMR (400 MHz, DMSO-d$_6$) δ 10.54 (s, 1H), 8.67 (s, 1H), 8.54-8.72 (broad, 1H), 8.15 (d, J=10.0 Hz, 1H), 7.27-7.43 (m, 5H), 7.21 (d, J=8.5 Hz, 1H), 7.14 (d, J=8.0 Hz, 1H), 7.00 (s, 1H), 6.98 (d, J=8.0 Hz, 1H), 6.86 (dd, J=8.5 Hz, 2.4 Hz, 1H), 6.56 (d, J=10.0 Hz, 1H), 5.27-5.32 (m, 1H), 4.58-4.66 (m, 1H), 3.97 (t, J=7.1 Hz, 2H), 3.25-3.43 (m, 4H), 3.07 (s, 3H), 3.06 (s, 3H), 3.00-3.12 (m, 2H), 2.92-3.00 (m, 2H), 1.94-2.04 (m, 2H), 1.67-1.82 (m, 4H), 1.54-1.67 (m, 2H), 1.34-1.46 (m, 2H), 1.20-1.34 (m, 6H)

LC/MS: [M]+=671.3

Example 59

Synthesis of 4-[({5-[(6-{[(2R)-2-hydroxy-2-(8-hydroxy-2-oxo-1,2-dihydroquinolin-5-yl)ethyl]amino}hexyl)oxy]-2-phenylphenyl}carbamoyl)oxy]-1,1-dimethylpiperidin-1-ium trifluoroacetate In accordance with Example 58, from 1-methylpiperidin-4-yl N-(5-{[6-(tert-butyldimethylsilanoyloxy)hexyl]oxy}-2-phenylphenyl)carbamate (163 mg, 0.30 mmol), obtained in Reference Example 12-7, there was obtained 4-[({5-[(6-{[(2R)-2-hydroxy-2-(8-hydroxy-2-oxo-1,2-dihydroquinolin-5-yl)ethyl]amino}hexyl)oxy]-2-phenylphenyl}carbamoyl)oxy]-1,1-dimethylpiperidin-1-ium trifluoroacetate (30.1 mg).

$^1$H-NMR (400 MHz, DMSO-d$_6$) δ 10.50 (s, 1H), 8.68 (s, 1H), 8.65 (d, J=24.6 Hz, 1H), 8.16 (d, J=10.0 Hz, 1H), 7.27-7.43 (m, 5H), 7.21 (d, J=8.5 Hz, 1H), 7.14 (d, J=8.5 Hz, 1H), 7.00 (s, 1H), 6.98 (d, J=8.0 Hz, 1H), 6.86 (dd, J=8.5 Hz, 2.4 Hz, 1H), 6.56 (d, J=10.0 Hz, 1H), 5.28-5.33 (m, 1H), 4.58-4.66 (m, 1H), 3.98 (t, J=6.2 Hz, 2H), 3.26-3.44 (m, 4H), 3.07-3.14 (m, 2H), 3.07 (s, 3H), 3.06 (s, 3H), 2.94-3.02 (m, 2H), 1.94-2.04 (m, 2H), 1.60-1.82 (m, 6H), 1.30-1.48 (m, 4H)

LC/MS: [M]+=643.3

Example 60

Synthesis of 4-[({5-[(9-{[(2R)-2-hydroxy-2-(8-hydroxy-2-oxo-1,2-dihydroquinolin-5-yl)ethyl]amino}nonyl)oxy]-2-phenylphenyl}carbamoyl)oxy]-1,1-dimethylpiperidin-1-ium trifluoroacetate In accordance with Example 58, from 1-methylpiperidin-4-yl N-(5-{[9-(tert-butyldimethylsilanoyloxy)nonyl]oxy}-2-phenylphenyl)carbamate (175 mg, 0.30 mmol) obtained in Reference Example 12-8, there was obtained 4-[({5-[(9-{

105

[(2R)-2-hydroxy-2-(8-hydroxy-2-oxo-1,2-dihydroquinolin-5-yl)ethyl]amino}nonyl)oxy]-2-phenylphenyl}carbamoyl)oxy]-1,1-dimethylpiperidin-1-ium trifluoroacetate (31.8 mg).

$^1$H-NMR (400 MHz, DMSO-d$_6$) δ 10.47 (s, 1H), 8.65 (s, 1H), 8.54-8.72 (broad, 1H), 8.15 (d, J=10.0 Hz, 1H), 7.27-7.43 (m, 5H), 7.21 (d, J=8.5 Hz, 1H), 7.14 (d, J=8.5 Hz, 1H), 7.00 (s, 1H), 6.98 (d, J=8.0 Hz, 1H), 6.86 (dd, J=8.4 Hz, 2.6 Hz, 1H), 6.56 (d, J=10.0 Hz, 1H), 5.28-5.33 (m, 1H), 4.58-4.66 (m, 1H), 3.97 (t, J=6.7 Hz, 2H), 3.25-3.43 (m, 4H), 3.07 (s, 3H), 3.06 (s, 3H), 3.00-3.12 (m, 2H), 2.92-3.00 (m, 2H), 1.94-2.04 (m, 2H), 1.60-1.82 (m, 4H), 1.55-1.66 (m, 2H), 1.34-1.46 (m, 2H), 1.20-1.34 (m, 8H)

LC/MS: [M]+=685.3

Example 61

Synthesis of 4-{[(5-{4-[4-({[(2R)-2-hydroxy-2-(8-hydroxy-2-oxo-1,2-dihydroquinolin-5-yl)ethyl]amino}methyl)phenoxy]butyl}-2-phenylphenyl)carbamoyl]oxy}-1,1-dimethylpiperidin-1-ium trifluoroacetate In accordance with Example 1, from 1-methylpiperidin-4-yl N-[5-(4-{4-[(tert-butyldimethylsilanoyloxy)methyl]phenoxy}butyl)-2-phenylphenyl]carbamate (115 mg, 0.25 mmol) obtained in Reference Example 12-9, there was obtained 4-{[(5-{4-[4-({[(2R)-2-hydroxy-2-(8-hydroxy-2-oxo-1,2-dihydroquinolin-5-yl)ethyl]amino}methyl)phenoxy]butyl}-2-phenylphenyl)carbamoyl]oxy}-1,1-dimethylpiperidin-1-ium trifluoroacetate (102 mg).

$^1$H-NMR (400 MHz, DMSO-d$_6$) δ 10.45 (s, 1H), 9.02 (d, J=59.3 Hz, 1H), 8.95 (s, 1H), 8.06 (d, J=9.8 Hz, 1H), 7.27-7.44 (m, 6H), 7.25 (s, 1H), 7.24 (d, J=7.8 Hz, 2H), 7.14-7.20 (m, 1H), 7.10 (d, J=8.3 Hz, 2H), 6.95-6.99 (m, 2H), 6.53 (d, J=9.8 Hz, 1H), 5.29-5.34 (m, 1H), 4.58-4.66 (m, 1H), 4.12-4.17 (m, 2H), 4.01 (t, J=5.5 Hz, 2H), 3.25-3.43 (m, 4H), 3.07 (s, 3H), 3.06 (s, 3H), 2.88-3.05 (m, 2H), 2.67 (t, J=6.6 Hz, 2H), 1.96-2.08 (m, 2H), 1.70-1.82 (m, 6H)

LC/MS: [M]+=705.3

Example 62

Synthesis of 4-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-1,1-dimethylpiperidin-1-ium trifluoroacetate In accordance with Example 58, from 1-methylpiperidin-4-yl N-{5-[2-({4-[3-(tert-butyldimethylsilanoyloxy)propyl]phenyl}carbamoyl)]ethyl}-2-phenylphenyl]carbamate (63 mg, 0.1 mmol) obtained in Reference Example 15-58, there was obtained 4-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-1,1-dimethylpiperidin-1-ium trifluoroacetate (16 mg).

$^1$H-NMR (400 MHz, DMSO-d$_6$) δ 10.45 (s, 1H), 9.91 (s, 1H), 8.70 (s, 1H), 8.56-8.66 (broad, 1H), 8.05 (d, J=10.0 Hz, 1H), 7.49-7.55 (m, 2H), 7.27-7.43 (m, 6H), 7.11-7.26 (m, 5H), 6.97 (d, J=8.0 Hz, 1H), 6.56 (d, J=10.0 Hz, 1H), 5.25-5.31 (m, 1H), 4.58-4.66 (m, 1H), 3.35-3.43 (m, 2H), 3.25-3.35 (m, 2H), 3.07 (s, 3H), 3.06 (s, 3H), 3.00-3.06 (m, 2H), 2.93 (t, J=7.7 Hz, 2H), 2.64 (t, J=7.7 Hz, 2H), 2.57 (t, J=7.4 Hz, 2H), 1.94-2.04 (m, 2H), 1.84-1.94 (m, 2H), 1.68-1.80 (m, 2H)

LC/MS: [M]+=732.3

106

Example 63

Synthesis of 4-({[5-(2-{[4-(2-{[(2R)-2-hydroxy-2-(8-hydroxy-2-oxo-1,2-dihydroquinolin-5-yl)ethyl]amino}ethyl)phenyl]carbamoyl}ethyl)-2-phenylphenyl]carbamoyl}oxy)-1,1-dimethylpiperidin-1-ium trifluoroacetate In accordance with Example 58, from 1-methylpiperidin-4-yl N-{5-[2-({4-[2-(tert-butyldimethylsilanoyloxy)ethyl]phenyl}carbamoyl)]ethyl}-2-phenylphenyl]carbamate (61 mg, 0.1 mmol) obtained in Reference Example 15-59, there was obtained 4-({[5-(2-{[4-(2-{[(2R)-2-hydroxy-2-(8-hydroxy-2-oxo-1,2-dihydroquinolin-5-yl)ethyl]amino}ethyl)phenyl]carbamoyl}ethyl)-2-phenylphenyl]carbamoyl}oxy)-1,1-dimethylpiperidin-1-ium trifluoroacetate (4.4 mg).

LC/MS: [M]+=718.3

Example 64

Synthesis of 4-({[5-(2-{[4-({[(2R)-2-hydroxy-2-(8-hydroxy-2-oxo-1,2-dihydroquinolin-5-yl)ethyl]amino}methyl)phenyl]carbamoyl}methoxy)-2-phenylphenyl]carbamoyl}oxy)-1,1-dimethylpiperidin-1-ium trifluoroacetate In accordance with Example 58, from 1-methylpiperidin-4-yl N-{5-(2-({4-[3-(tert-butyldimethylsilanoyloxy)ethyl]phenyl}carbamoyl)]ethyl}-2-phenylphenyl]carbamate (61 mg, 0.1 mmol) obtained in Reference Example 15-60, there was obtained 4-({[5-(2-{[4-({[(2R)-2-hydroxy-2-(8-hydroxy-2-oxo-1,2-dihydroquinolin-5-yl)ethyl]amino}methyl)phenyl]carbamoyl}methoxy)-2-phenylphenyl]carbamoyl}oxy)-1,1-dimethylpiperidin-1-ium trifluoroacetate (15 mg).

LC/MS: [M]+=706.3

Example 65

Synthesis of 4-[({5-[2-({[4-({[(2R)-2-hydroxy-2-(8-hydroxy-2-oxo-1,2-dihydroquinolin-5-yl)ethyl]amino}methyl)phenyl]methyl}carbamoyl)ethyl]-2-phenylphenyl}carbamoyl)oxy]-1,1-dimethylpiperidin-1-ium trifluoroacetate 1-Methylpiperidin-4-yl N-(5-{2-[({4-[(tert-butoxycarbonyl)amino]phenyl}methyl)carbamoyl]ethyl}-2-phenylphenyl)carbamate (94 mg, 0.16 mmol) obtained in Reference Example 15-61 was dissolved in acetonitrile (5 mL), methyl iodide (1 mL) was added thereto, and after stirring at room temperature for 1 hour, the reaction solution was concentrated under reduced pressure.

To the residue was added a 5% methanol solution of hydrobromic acid (10 mL) and, after stirring at 80° C. for 2 hours, the reaction solution was concentrated under reduced pressure.

The residue was suspended in acetonitrile (5 mL) and propionitrile (5 mL), thereto were added sodium bicarbonate (84 mg, 1.00 mmol), potassium iodide (50 mg, 0.3 mmol), and 5-[(1R)-2-bromo-1-hydroxyethyl]-8-[(4-methoxyphenyl)methoxy]-1,2-dihydroquinolin-2-one (40 mg, 0.10 mmol) obtained in Reference Example 6-2, and the mixture was stirred at 120° C. for 18 hours. The reaction solution was filtered and concentrated under reduced pressure. To the residue was added trifluoroacetic acid (1 mL) and, after stirring at room temperature for 1 hour, the reaction solution was concentrated under reduced pressure. The residue was purified by HPLC fractionation to obtain 4-[({5-[2-({[4-({[(2R)-2-hydroxy-2-(8-hydroxy-2-oxo-1,2-dihydroquinolin-5-yl)ethyl]amino}methyl)phenyl]methyl}carbamoyl)ethyl]-2-phenylphenyl}carbamoyl)oxy]-1,1-dimethylpiperidin-1-ium trifluoroacetate (10.6 mg).

LC/MS: [M]+=718.3

Example 66

Synthesis of 4-[({5-[3-({[4-({[(2R)-2-hydroxy-2-(8-hydroxy-2-oxo-1,2-dihydroquinolin-5-yl)ethyl]amino}methyl)phenyl]methyl}carbamoyl)propyl]-2-phenylphenyl}carbamoyl)oxy]-1,1-dimethylpiperidin-1-ium trifluoroacetate In accordance with Example 65, from 1-methylpiperidin-4-yl N-(5-{3-[({4-[(tert-butoxycarbonyl)amino]phenyl}methyl)carbamoyl]propyl}-2-phenylphenyl)carbamate (86 mg, 0.14 mmol) obtained in Reference Example 15-62, there was obtained 4-[({5-[3({[4-({[2R)-2-hydroxy-2-(8-hydroxy-2-oxo-1,2-dihydroquinolin-5-yl)ethyl]amino}methyl)phenyl]methyl}carbamoyl)propyl]-2-phenylphenyl}carbamoyl)oxy]-1,1-dimethylpiperidin-1-ium trifluoroacetate (3.3 mg).

LC/MS: [M]+=732.3

Example 67

Synthesis of 4-[({5-[(1E)-2-{[4-({[(2R)-2-hydroxy-2-(8-hydroxy-2-oxo-1,2-dihydroquinolin-5-yl)ethyl]amino}methyl)phenyl]carbamoyl}-1-ethen-1-yl]-2-phenylphenyl}carbamoyl)oxy]-1,1-dimethylpiperidin-1-ium trifluoroacetate In accordance with Example 1, from 1-methylpiperidin-4-yl N-{5-[(1E)-2-({4-[(tert-butyldimethylsilanoyloxy)methyl]phenyl}carbamoyl)-1-ethen-1-yl]-2-phenylphenyl}carbamate (57 mg, 0.095 mmol) obtained in Reference Example 15-63, there was obtained 4-[({5-[(1E)-2-{[4-({[(2R)-2-hydroxy-2-(8-hydroxy-2-oxo-1,2-dihydroquinolin-5-yl)ethyl]amino}methyl)phenyl]carbamoyl}-1-ethen-1-yl]-2-phenylphenyl}carbamoyl)oxy]-1,1-dimethylpiperidin-1-ium trifluoroacetate (29.9 mg).

$^1$H-NMR (400 MHz, DMSO-$d_6$) δ 10.45 (s, 1H), 9.07 (d, J=43.7 Hz, 1H), 8.89 (s, 1H), 8.06 (d, J=10.0 Hz, 1H), 8.75 (d, J=8.8 Hz, 2H), 7.70 (s, 1H), 7.61 (d, J=15.6 Hz, 1H), 7.57 (d, J=8.3 Hz, 1H), 7.49 (d, J=8.8 Hz, 2H), 7.27-7.46 (m, 6H), 7.11 (d, J=8.3 Hz, 1H), 6.97 (d, J=8.3 Hz, 1H), 6.90 (d, J=15.6 Hz, 1H), 6.54 (d, J=10.0 Hz, 1H), 5.30-5.35 (m, 1H), 4.62-4.68 (m, 1H), 4.15-4.21 (m, 2H), 3.25-3.43 (m, 4H), 3.07 (s, 3H), 3.06 (s, 3H), 2.88-3.05 (m, 2H), 1.96-2.08 (m, 2H), 1.70-1.82 (m, 2H)

LC/MS: [M]+=702.3

Example 68

Synthesis of 4-({[5-(2-{[4-(2-{[(2R)-2-hydroxy-2-(8-hydroxy-2-oxo-1,2-dihydroquinolin-5-yl)ethyl]amino}-2-methylpropyl)phenyl]carbamoyl}ethyl)-2-phenylphenyl]carbamoyl}oxy)-1,1-dimethylpiperidin-1-ium trifluoroacetate 1-Methylpiperidin-4-yl N-[5-(2-{[4-(2-methyl-2-nitropropyl)phenyl]carbamoyl}ethyl)-2-phenylphenyl]carbamate (193 mg, 0.35 mmol) obtained in Reference Example 15-64 was dissolved in acetonitrile (10 mL), methyl iodide (2 mL) was added thereto, and, after stirring at room temperature for 1 hour, the reaction solution was concentrated under reduced pressure.

The residue was dissolved in methanol (10 mL), a catalytic amount of palladium hydroxide-carbon was added, and the solution was stirred under a hydrogen atmosphere for 4 days. The reaction solution was filtered through celite and concentrated under reduced pressure.

To the residue, a 5% methanol solution of hydrobromic acid (10 mL) was added and, after stirring at 80° C. for 2 hours, the reaction solution was concentrated under reduced pressure.

The residue was dissolved in acetonitrile (5 mL), propionitrile (5 mL), and N,N-dimethylformamide (10 mL), thereto were added sodium bicarbonate (84 mg, 1 mmol), potassium iodide (83 mg, 0.5 mmol), and 8-benzyloxy-5-((R)-2-bromo-1-hydroxyethyl)-1H-quinolin-2-one (74 mg, 0.2 mmol) obtained in Reference Example 6, and the mixture was stirred at 120° C. for 4 hours. The reaction solution was filtered and concentrated under reduced pressure. The residue was purified by HPLC fractionation to obtain 4-({[5-(2-{[4-(2-{[(2R)-2-hydroxy-2-(8-benzyloxy-2-oxo-1,2-dihydroquinolin-5-yl)ethyl]amino}-2-methylpropyl)phenyl]carbamoyl}ethyl)-2-phenylphenyl]carbamoyl}oxy)-1,1-dimethylpiperidin-1-ium trifluoro acetate.

The obtained 4-({[5-(2-{[4-(2-{[(2R)-2-hydroxy-2-(8-benzyloxy-2-oxo-1,2-dihydroquinolin-5-yl)ethyl]amino}-2-methylpropyl)phenyl]carbamoyl}ethyl)-2-phenylphenyl]carbamoyl}oxy)-1,1-dimethylpiperidin-1-ium trifluoro acetate was dissolved in methanol (10 mL), a catalytic amount of palladium hydroxide-carbon was added, and the mixture was stirred under a hydrogen atmosphere for 3 hours. The reaction solution was filtered through celite and concentrated under reduced pressure.

To the residue was added a 5% methanol solution of hydrobromic acid (10 mL) and, after stirring at 80° C. for 2 hours, the reaction solution was concentrated under reduced pressure. The residue was purified by HPLC fractionation to obtain 4-({[5-(2-{[4-(2-{[(2R)-2-hydroxy-2-(8-hydroxy-2-oxo-1,2-dihydroquinolin-5-yl)ethyl]amino}-2-methylpropyl)phenyl]carbamoyl}ethyl)-2-phenylphenyl]carbamoyl}oxy)-1,1-dimethylpiperidin-1-ium trifluoroacetate (3.3 mg).

LC/MS: [M]+=746.3

Example 69

Synthesis of 4-({[4-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate In accordance with Example 1, from 1-methylpiperidin-4-yl N-{4-[2-({4-[(tert-butyldimethylsilanoyloxy)methyl]phenyl}carbamoyl)ethyl]-2-phenylphenyl}carbamate (227 mg, 0.377 mmol) obtained in Reference Example 15-65, there was obtained 4-({[4-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-ium trifluoroacetate (87 mg).

$^1$H-NMR (400 MHz, DMSO-$d_6$) δ 10.46 (s, 1H), 10.10 (s, 1H), 9.06 (d, J=52.0 Hz, 1H), 8.70 (s, 1H), 8.06 (d, J=10.0 Hz, 1H), 7.61 (d, J=8.5 Hz, 2H), 7.43 (d, J=8.5 Hz, 2H), 7.27-7.40 (m, 6H), 7.20-7.25 (m, 2H), 7.10 (d, J=8.0 Hz, 1H), 6.97 (d,

J=8.0 Hz, 1H), 6.53 (d, J=10.0 Hz, 1H), 5.28-5.34 (m, 1H), 4.58-4.66 (m, 1H), 4.12-4.18 (m, 2H), 3.34-3.43 (m, 2H), 3.25-3.35 (m, 2H), 3.07 (s, 3H), 3.06 (s, 3H), 3.00-3.05 (m, 2H), 2.94 (t, J=7.4 Hz, 2H), 2.67 (t, J=7.4 Hz, 2H), 1.94-2.04 (m, 2H), 1.68-1.80 (m, 2H)

LC/MS: [M]+=704.3

Reference Example 15-66

Synthesis of (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromo-5-methoxyphenyl}carbamoyl)propyl]-2-phenylphenyl}carbamate In accordance with Reference Example 15, from 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate hydrochloride (0.50 mmol) obtained in Reference Example 13-4 and 4-[(tert-butyldimethylsilanoyloxy)methyl]-2-bromo-5-methoxyaniline (346.35 mg, 1.0 mmol) obtained in Reference Example 14-18, there was obtained (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromo-5-methoxyphenyl}carbamoyl)propyl]-2-phenylphenyl}carbamate (196.3 mg).

LC/MS: M+1=765.3

Reference Example 15-67

Synthesis of (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-chlorophenyl}carbamoyl) propyl]-2-phenylphenyl}carbamate In accordance with Reference Example 15, from 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate hydrochloride (0.50 mmol) obtained in Reference Example 13-4 and 4-[(tert-butyldimethylsilanoyloxy)methyl]-2-chloroaniline (163.1 mg, 1.0 mmol) obtained in Reference Example 14-9, there was obtained (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-chlorophenyl}carbamoyl)propyl]-2-phenylphenyl}carbamate (137.2 mg).

LC/MS: M+1=692.3

Reference Example 15-68

Synthesis of (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromophenyl}carbamoyl)propyl]-2-phenylphenyl}carbamate In accordance with Reference Example 15, from 4-(4-{[({[1R,2R,4S,5S,7S]-9-methyl-3-oxa-9-azatricyclo[3.3.1.0$^{2,4}$]nonan-7-yl}oxy)carbonyl]amino}-3-phenylphenyl)butyrate hydrochloride (0.50 mmol) obtained in Reference Example 13-4 and 4-[(tert-butyldimethylsilanoyloxy)methyl]-2-bromoaniline (237.2 mg, 1.0 mmol) obtained in Reference Example 14-21, there was obtained (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromophenyl}carbamoyl)propyl]-2-phenylphenyl}carbamate (168.8 mg).

LC/MS: M+1=736.3

Example 70

Synthesis of (1R,2R,4S,5S,7S)-7-({[4-(3-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromo-5-methoxyphenyl}carbamoyl)propyl]-2-phenylphenyl}carbamate (196.3 mg, 0.257 mmol) obtained in Reference Example 15-66, there was obtained (1R,2R,4S,5S,7S)-7-({[4-(3-{[2-bromo-4-({[(2R)-2-hydroxy-2-(8-hydroxy-2-oxo-1,2-dihydroquinolin-5-yl)ethyl]amino}methyl)-5-methoxyphenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (24.6 mg).

LC/MS: [M]+=866.3

Example 71

Synthesis of (1R,2R,4S,5S,7S)-7-({[4-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromo-5-methoxyphenyl}carbamoyl)propyl]-2-phenylphenyl}carbamate (137.2 mg, 0.199 mmol) obtained in Reference Example 15-67, there was obtained (1R,2R,4S,5S,7S)-7-({[4-(3-{[2-chloro-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (34.19 mg).

LC/MS: [M]+=792.3

Example 72

Synthesis of (1R,2R,4S,5S,7S)-7-({[4-(3-{[2-bromo-4-({[(2R)-2-hydroxy-2-(8-hydroxy-2-oxo-1,2-dihydroquinolin-5-yl)ethyl]amino}methyl)phenyl]carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 1, from (1R,2R,4S,5S,7S)-9-methyl-3-oxa-9-azatricyclo[3.3.1.0$^{2,4}$]nonan-7-yl N-{4-[3-({4-[(tert-butyldimethylsilanoyloxy)methyl]-2-bromophenyl}carbamoyl)propyl]-2-phenylphenyl carbamate (168.8 mg, 0.230 mmol) obtained in Reference Example 15-66, there was obtained (1R,2R,4S,5S,7S)-7-({[4-(3-{[2-bromo-4-({[(2R)-2-hydroxy-2-(8-hydroxy-2-oxo-1,2-dihydroquinolin-5-yl)ethyl]amino}methyl)phenyl]

carbamoyl}propyl)-2-phenylphenyl]carbamoyl}oxy)-9,9-dimethyl-3-oxa-9-azatricyclo[3.3.1.0$^{2,4}$]nonan-9-ium trifluoroacetate (9.16 mg).

LC/MS: [M]+=836.3

Reference Example 15-69

Synthesis of (1R,2R,4S,5S,7S)-9-methyl-3-oxa-9-azatricyclo[3.3.1.0$^{2,4}$]nonan-7-yl N-{5-[2-({4-[3-(tert-butyldimethylsilanoyloxy)propyl]phenyl}carbamoyl)ethyl]-2-phenylphenyl}carbamate In accordance with Reference Example 15, from 3-(3-{[({[1R,2R,4S,5S,7S]-9-methyl-3-oxa-9-azatricyclo[3.3.1.0$^{2,4}$]nonan-9-yl}oxy)carbonyl]amino}-4-phenylphenyl)propionate hydrochloride (137.3 mg, 0.3 mmol) obtained in Reference Example 13-2 and 4-[3-(tert-butyldimethylsilanoyloxy)propyl]aniline (132.7 mg, 0.5 mmol) obtained in Reference Example 14-23, there was obtained (1R,2R,4S,5S,7S)-9-methyl-3-oxa-9-azatricyclo[3.3.1.0$^{2,4}$]nonan-7-yl N-{5-[2-({4-[3-(tert-butyldimethylsilanoyloxy)propyl]phenyl}carbamoyl)ethyl]-2-phenylphenyl}carbamate (165.3 mg).

LC/MS: M+1=670.3

Example 73

Synthesis of (1R,2R,4S,5S,7S)-7-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate In accordance with Example 58, from (1R,2R,4S,5S,7S)-9-methyl-3-oxa-9-azatricyclo[3.3.1.0$^{2,4}$]nonan-7-yl N-{5-[2-({4-[3-(tert-butyldimethylsilanoyloxy)propyl]phenyl}carbamoyl)ethyl]-2-phenylphenyl}carbamate (100.5 mg, 0.15 mmol) obtained in Reference Example 15-69, there was obtained (1R,2R,4S,5S,7S)-7-({[5-(2-{[4-(3-{[(2R)-2-hydroxy-2-(8-hydroxy-2-oxo-1,2-dihydroquinolin-5-yl)ethyl]amino}propyl)phenyl]carbamoyl}ethyl)-2-phenylphenyl]carbamoyl}oxy)-9,9-dimethyl-3-oxa-9-azatricyclo[3.3.1.0$^{2,4}$]nonan-9-ium trifluoroacetate (7.9 mg).

LC/MS: [M]+=772.3

Reference Example 15-70

Synthesis of 1-methylpiperidin-4-yl N-{5-[2-(5-[(tert-butyldimethylsilanoyloxy)pentyl]carbamoyl)ethyl]-2-phenylphenyl}carbamate In accordance with Reference Example 15, from 3-[3-({[(1-methylpiperidin-4-yl)oxy]carbonyl}amino)-4-phenylphenyl]propionate hydrochloride (242 mg, 0.59 mmol) obtained in Reference Example 13 and [(5-aminopentyl)oxy](tert-butyl)dimethylsilane (217.4 mg, 1.0 mmol), there was obtained 1-methylpiperidin-4-yl N-{5-[2-(5-[(tert-butyldimethylsilanoyloxy)pentyl]carbamoyl)ethyl]-2-phenylphenyl}carbamate (163.1 mg).

LC/MS: M+1=582.3

Example 74

Synthesis of 4-({[5-(2-{[5-{[(2R)-2-hydroxy-2-(8-hydroxy-2-oxo-1,2-dihydroquinolin-5-yl)ethyl]amino}pentyl]carbamoyl}ethyl)-2-phenylphenyl]carbamoyl}oxy)-1,1-dimethylpiperidin-1-ium trifluoroacetate In accordance with Example 58, from 1-methylpiperidin-4-yl N-{5-[2-(5-[(tert-butyldimethylsilanoyloxy)pentyl]carbamoyl)ethyl]-2-phenylphenyl}carbamate (163.1 mg, 0.28 mmol) obtained in Reference Example 15-70, there was obtained 4-({[5-(2-{[5-{[(2R)-2-hydroxy-2-(8-hydroxy-2-oxo-1,2-dihydroquinolin-5-yl)ethyl]amino}pentyl]carbamoyl}ethyl)-2-phenylphenyl]carbamoyl}oxy)-1,1-dimethylpiperidin-1-ium trifluoroacetate (3.27 mg).

LC/MS: [M]+=684.3

Reference Example 41

Synthesis of 7-hydroxyheptyl 4-bromo-3-nitrobenzoate

4-Bromo-3-nitrobenzoic acid (1.0 g, 2.5 mmol) was dissolved in 1,4-dioxane (30 mL), and, thereto were added phenyl boric acid (610 mg, 5.0 mmol), cesium carbonate (6.5 g, 20.0 mmol), 1,1-[bis(diphenylphosphino)ferrocene]dichloropalladium(II) dichloromethane complex (204 mg, 0.10 mmol), and purified water (10 mL). The reaction mixture was stirred under a nitrogen flow at 80° C. overnight. The reaction solution was filtered through celite, alumina, and Florisil, and, thereafter, was extracted with ethyl acetate. The organic layer was washed with a saturated aqueous solution of sodium chloride, dried over anhydrous magnesium sulfate, and concentrated under reduced pressure to obtain 3-nitro-4-phenylbenzoic acid as a crude material.

The obtained 3-nitro-4-phenylbenzoic acid was dissolved in N,N-dimethylformamide (20 mL), thereto were added O-(7-azabenzotriazol-1-yl)-N,N,N',N'-tetramethyluronium hexafluorophosphate (3 mmol), triethylamine (10 mmol), and heptane-1,7-diol (10 mmol), and the mixture was stirred at room temperature for 4 hours. The reaction mixture was extracted with ethyl acetate and the organic layer was washed with a saturated aqueous solution of sodium chloride, dried over anhydrous magnesium sulfate, and concentrated under reduced pressure. The residue was purified by flash column chromatography to obtain 7-hydroxyheptyl 4-bromo-3-nitrobenzoate (824.9 mg).

Reference Example 42

Synthesis of 7-(tert-butyldimethylsilanoyloxy)heptyl 3-nitro-4-phenylbenzoate

4-Bromo-3-nitrobenzoate (824.9 mg, 2.3 mmol) obtained in Reference Example 41 and imidazole (1.3 g, 4.0 mmol) were dissolved in tetrahydrofuran (10 mL) and a solution of tert-butyldimethylchlorosilane (450 mg, 3.0 mmol) in tetrahydrofuran (5 mL) was added thereto. After stirring the mixture at room temperature overnight, the reaction was stopped by addition of purified water and the mixture was extracted with ethyl acetate. The organic layer was washed with a saturated aqueous solution of sodium bicarbonate, a saturated aqueous solution of ammonium chloride, and a saturated aqueous solution of sodium chloride. The organic layer was dried over anhydrous magnesium sulfate and concentrated under reduced pressure. The residue was dissolved in methanol (20 mL), 10% palladium-carbon (50 mg) was added, and the mixture was stirred under a hydrogen atmosphere at room temperature for 4 days. The reaction solution was filtered through celite and the filtrate was concentrated under reduced pressure to obtain 7-(tert-butyldimethylsilanoyloxy)heptyl 3-nitro-4-phenylbenzoate as a crude material.
LC/MS: M+1=442.3

Reference Example 12-12

Synthesis of 7-(tert-butyldimethylsilanoyloxy)heptyl 3-({[(1-methylpiperidin-4-yl)oxy]carbamoyl}amino)-4-phenylbenzoate In accordance with Reference Example 12, from 4-hydroxy-1-methylpiperidine (576 mg, 5.0 mmol) and 7-(tert-butyldimethylsilanoyloxy)heptyl 3-nitro-4-phenylbenzoate obtained in Reference Example 42, there was obtained 7-(tert-butyldimethylsilanoyloxy)heptyl 3-({[(1-methylpiperidin-4-yl)oxy]carbamoyl}amino)-4-phenylbenzoate (491.3 mg).
LC/MS: M+1=583.3

Example 75

Synthesis of 4-{[5-({[(7-{[(2R)-2-hydroxy-2-(8-hydroxy-2-oxo-1,2-dihydroquinolin-5-yl)ethyl]amino}heptyl)oxy]carbonyl}-2-phenylphenyl)carbamoyl]oxy}-1,1-dimethylpiperidin-1-ium trifluoro acetate In accordance with Example 58, from 7-(tert-butyldimethylsilanoyloxy)heptyl 3-({[(1-methylpiperidin-4-yl)oxy]carbamoyl}amino)-4-phenylbenzoate (491.3 mg, 0.84 mmol) obtained in Reference Example 12-12, there was obtained 4-{[5-({[(7-{[(2R)-2-hydroxy-2-(8-hydroxy-2-oxo-1,2-dihydroquinolin-5-yl)ethyl]amino}heptyl)oxy]carbonyl}-2-phenylphenyl)carbamoyl]oxy}-1,1-dimethylpiperidin-1-ium trifluoroacetate (27.6 mg).
LC/MS: [M]+=685.3

Reference Example 44

Synthesis of tert-butyl N-(8-bromooctyl)-N-[(tert-butoxy)carbonyl]carbamate

Under a nitrogen flow, sodium hydride (40% of mineral oil added; 935 mg, 17 mmol) was suspended in N,N-dimethylformamide (160 mL) and, under ice-water cooling, di-tert-butyl iminodicarboxylate (3.26 g, 15 mmol) was added. After stirring under ice-water cooling for 1 hour, a solution of 1,8-dibromooctane (8.16 g, 30 mmol) in N,N-dimethylformamide (10 mL) was added and the mixture was stirred for 16 hours while allowing the mixture to return to room temperature. Under ice-water cooling, a saturated aqueous solution of ammonium chloride was added to stop the reaction and the mixture was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl N-(8-bromooctyl)-N-[(tert-butoxy)carbonyl]carbamate (4.26 g).

Reference Example 45

Synthesis of tert-butyl N-[9-(4-bromo-3-nitrophenyl)-8-nonen-1-yl]-N-[(tert-butoxy)carbonyl]carbamate tert-Butyl N-(8-bromooctyl)-N-[(tert-butoxy)carbonyl]carbamate (1.02 g, 2.5 mmol) obtained in Reference Example 44 and triphenylphosphine (1.18 g, 4.5 mmol) were dissolved in acetonitrile (50 mL), the mixture was stirred overnight under heating at reflux, and, thereafter, the reaction solution was concentrated under reduced pressure. The residue was dissolved in tetrahydrofuran (50 mL), cooled to −78° C. under a nitrogen flow, and n-butyllithium (a 2.5 M hexane solution; 1.08 mL, 2.7 mmol) was added dropwise. After stirring under ice-water cooling for 1 hour, the mixture was cooled to −78° C. A solution of 4-bromo-3-nitrobenzaldehyde (575 mg, 2.5 mmol) in tetrahydrofuran was added thereto and the mixture was stirred for 16 hours while allowing the same to return slowly to room temperature. Water was added to stop the reaction and the mixture was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl N-[9-(4-bromo-3-nitrophenyl)-8-nonen-1-yl]-N-[(tert-butoxy)carbonyl]carbamate (375 mg).

Reference Example 46

Synthesis of tert-butyl N-[9-(3-nitro-4-phenylphenyl)-8-nonen-1-yl]carbamate tert-Butyl N-[9-(4-bromo-3-nitrophenyl)-8-nonen-1-yl]-N-[(tert-butoxy)carbonyl]carbamate (375 mg, 0.7 mmol) obtained in Reference Example 45 was dissolved in 1,4-dioxane (30 mL), thereto were added phenyl boric acid (244 mg, 2.0 mmol), cesium carbonate (2.6 g, 8.0 mmol), 1,1-[bis(diphenylphosphino)ferrocene]dichloropalladium(II) dichloromethane complex (82 mg, 0.10 mmol), and purified water (10 mL), and the reaction mixture was stirred under a nitrogen flow at 80° C. for 3 days. The reaction solution was filtered through celite, alumina, and Florisil, and, thereafter, was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyl N-[9-(3-nitro-4-phenylphenyl)-8-nonen-1-yl]carbamate (305 mg).

Reference Example 47

Synthesis of tert-butyl N-[9-(4-phenyl-3-amino-phenyl)-8-nonen-1-yl]carbamate tert-Butyl N-[9-(3-nitro-4-phenylphenyl)-8-nonen-1-yl]carbamate (305 mg, 0.7 mmol) obtained in Reference Example 46 was dissolved in ethyl acetate (15 mL) and methanol (5 mL), 10% palladium-carbon (50 mg) was added, and the mixture was stirred under a hydrogen atmosphere at room temperature overnight. The reaction solution was filtered through celite and, thereafter, the filtrate was concentrated under reduced pressure to obtain tert-butyl N-[9-(4-phenyl-3-amino-phenyl)-8-nonen-1-yl]carbamate as a crude material.
LC/MS: M+1=411.2

Reference Example 12-13

Synthesis of 1-methylpiperidin-4-yl N-[5-(9-{[(tert-butoxy)carbonyl]amino}nonyl)-2-phenylphenyl]carbamate In accordance with Reference Example 12, from 4-hydroxy-1-methylpiperidine (460 mg, 4.0 mmol) and tert-butyl N-[9-(4-phenyl-3-aminophenyl)-8-nonen-1-yl]carbamate obtained in Reference Example 47, there was obtained 1-methylpiperidin-4-yl N-[5-(9-{[(tert-butoxy)carbonyl]amino}nonyl)-2-phenylphenyl]carbamate (351.7 mg).
LC/MS: M+1=552.3

Example 76

Synthesis of 4-({[5-(9-{[(2R)-2-hydroxy-2-(8-hydroxy-2-oxo-1,2-dihydroquinolin-5-yl)ethyl]amino}nonyl)-2-phenylphenyl]carbamoyl}oxy)-1,1-dimethylpiperidin-1-ium trifluoroacetate 1-Methylpiperidin-4-yl N-[5-(9-{[(tert-butoxy)carbonyl]amino}nonyl)-2-phenylphenyl}carbamate (110.4 mg, 0.2 mmol) obtained in Reference Example 12-13 was dissolved in acetonitrile (5 mL), methyl iodide (1 mL) was added thereto, and, after stirring at room temperature for 1 hour, the reaction solution was concentrated under reduced pressure. To the residue was a 5% solution of hydrobromic acid in methanol (5 mL) and, after stirring at 80° C. for 3 hours, the reaction solution was concentrated under reduced pressure. The residue was dissolved in propionitrile (3 mL) and acetonitrile (5 mL), thereto were added 8-benzyloxy-5-((R)-2-bromo-1-hydroxyethyl)-1H-quinolin-2-one (56.1 mg, 0.15 mmol), potassium iodide (50 mg, 0.3 mmol), and sodium bicarbonate (168 mg, 2.0 mmol), and the mixture was stirred at 100° C. overnight. The reaction solution was filtered, concentrated under reduced pressure, and purified by HPLC fractionation to obtain 4-({[5-(9-[{(2R)-[8-(benzyloxy)-2-oxo-1,2-dihydroquinolin-5-yl]-2-hydroxyethyl}amino]nonyl)-2-phenylphenyl]carbamoyl}oxy)-1,1-dimethylpiperidin-1-ium trifluoroacetate.

The obtained 4-({[5-(9-[{(2R)-[8-(benzyloxy)-2-oxo-1,2-dihydroquinolin-5-yl]-2-hydroxyethyl}amino]nonyl)-2-phenylphenyl]carbamoyl}oxy)-1,1-dimethylpiperidin-1-ium trifluoroacetate was dissolved in methanol (5 mL), 10% palladium-carbon (50 mg) was added thereto, and the mixture was stirred under a hydrogen atmosphere at room temperature for 2 hours. The reaction solution was filtered through celite and the filtrate was concentrated under reduced pressure. The residue was purified by HPLC fractionation to obtain 4-({[5-(9-{[(2R)-2-hydroxy-2-(8-hydroxy-2-oxo-1,2-dihydroquinolin-5-yl)ethyl]amino}nonyl)-2-phenylphenyl]carbamoyl}oxy)-1,1-dimethylpiperidin-1-ium trifluoroacetate (12.79 mg).
LC/MS: [M]+=669.4

Reference Example 48

Synthesis of tert-butyl N-[2-(4-hydroxyphenyl)ethyl]carbamate 4-(2-Aminoethyl)phenol (2.74 g, 20.0 mmol) was dissolved in tetrahydrofuran (30 mL) and water (30 mL), di-tert-butyl dicarbonate (6.50 g, 30.0 mmol) and sodium bicarbonate (4.20 g, 50.0 mmol) were added thereto, and the mixture was stirred at room temperature for 3 hours. The reaction solution was extracted with ethyl acetate, and the organic layer was washed with a saturated aqueous solution of ammonium chloride and a saturated aqueous solution of sodium chloride, dried over anhydrous magnesium sulfate, and concentrated under reduced pressure. The residue was purified by flash column chromatography to obtain tert-butyl N-[2-(4-hydroxyphenyl)ethyl]carbamate (4.97 g).

Reference Example 34-2

Synthesis of tert-butyl N-{2-[4-(2-propen-1-yloxy)phenyl]ethyl}carbamate

In accordance with Reference Example 34, from tert-butyl N-[2-(4-hydroxyphenyl)ethyl]carbamate (2.37 g, 10.0 mmol) obtained in Reference Example 48 and 3-bromo-1-butene (1.81 g, 15.0 mmol), there was obtained tert-butyl N-{2-[4-(2-propen-1-yloxy)phenyl]ethyl}carbamate (2.49 g).

Reference Example 35-2

Synthesis of tert-butyl N-[2-(4-{[(2E)-3-(3-amino-4-phenylphenyl)-2-propen-1-yl]oxy}phenyl)ethyl]carbamate In accordance with Reference Example 35, from tert-butyl N-{2-[4-(2-propen-1-yloxy)phenyl]ethyl}carbamate (832.1 mg, 3.0 mmol) obtained in Reference Example 34-2, there was obtained tert-butyl N-[2-(4-{[(2E)-3-(3-amino-4-phenylphenyl)-2-propen-1-yl]oxy}phenyl)ethyl]carbamate (288.0 mg).

Reference Example 12-14

Synthesis of 1-methylpiperidin-4-yl N-{5-[(1E)-3-[4-(2-{[(tert-butoxy)carbonyl]amino}ethyl)phenoxy]-1-propen-1-yl]-2-phenylphenyl}carbamate In accordance with Reference Example 12, from 4-hydroxy-1-methylpiperidine (345.5 mg, 3.0 mmol) and tert-butyl N-[2-(4-{[(2E)-3-(3-amino-4-phenylphenyl)-2-propen-1-yl]oxy}phenyl)ethyl]carbamate (288.0 mg, 0.7 mmol) obtained in Reference Example 44, there was obtained 1-methylpiperidin-4-yl N-{5-[(1E)-3-[4-(2-{[(tert-butoxy)carbonyl]amino}ethyl)phenoxy]-1-propen-1-yl]-2-phenylphenyl}carbamate (321.9 mg).
LC/MS: M+1=586.2

Reference Example 49

Synthesis of 1-methylpiperidin-4-yl N-(5-{3-[4-(2-{[(tert-butoxy)carbonyl]amino}ethyl)phenoxy]propyl}-2-phenylphenyl)carbamate 1-Methylpiperidin-4-yl N-{5-[(1E)-3-[4-(2-{[(tert-butoxy)carbonyl]amino}ethyl)phenoxy]-1-propen-1-yl]-2-phenylphenyl}carbamate (321.9 mg, 0.49 mmol) obtained in Reference Example 12-14 was dissolved in methanol (10 mL), 10% palladium-carbon (20 mg) was added, and the mixture was stirred under a hydrogen atmosphere at room temperature overnight. The reaction solution was filtered through celite and, thereafter, the filtrate was concentrated under reduced pressure to obtain 1-methylpiperidin-4-yl N-(5-{3-[4-(2-{[(tert-butoxy)carbonyl]amino}ethyl)phenoxy]propyl}-2-phenylphenyl)carbamate (265.7 mg) as a crude material.

Example 77

Synthesis of 4-{[(5-{3-[4-(2-{[(2R)-2-hydroxy-2-(8-hydroxy-2-oxo-1,2-dihydroquinolin-5-yl)ethyl]amino}ethyl)phenoxy]propyl}-2-phenylphenyl)carbamoyl]oxy}-1,1-dimethylpiperidin-1-ium trifluoroacetate In accordance with Example 76, from 1-methylpiperidin-4-yl N-(5-{3-[4-(2-{[(tert-butoxy)carbonyl]amino}ethyl)phenoxy]propyl}-2-phenylphenyl)carbamate (117.6 mg, 0.20 mmol) obtained from Reference Example 49 and 8-benzyloxy-5-((R)-2-bromo-1-hydroxyethyl)-1H-quinolin-2-one (29.9 mg, 0.08 mmol), there was obtained 4-{[(5-{3-[4-(2-{[(2R)-2-hydroxy-2-(8-hydroxy-2-oxo-1,2-dihydroquinolin-5-yl)ethyl]amino}ethyl)phenoxy]propyl}-2-phenylphenyl)carbamoyl]oxy}-1,1-dimethylpiperidin-1-ium trifluoroacetate (11.1 mg).
LC/MS: [M]+=705.3

Reference Example 34-3

Synthesis of ({[5-(2-propen-1-yloxy)pentyl]oxy}methyl)benzene

In accordance with Reference Example 34, from 5-(benzyloxy)propen-1-ol (1.91 g, 10.0 mmol) and 3-bromo-1-butene (1.45 g, 12.0 mmol), there was obtained ({[5-(2-propen-1-yloxy)pentyl]oxy}methyl)benzene (1.67 g).

Reference Example 35-3

Synthesis of 5-[(1E)-3-{[5-(benzyloxy)pentyl]oxy}-1-propen-1-yl]-2-phenylaniline In accordance with Reference Example 35, from 3-bromo-5-phenylaniline (496.3 mg, 2.0 mmol) obtained in Reference Example 33 and ({[5-(2-propen-1-yloxy)pentyl]oxy}methyl)benzene (703.0 mg, 3.0 mmol) obtained in Reference Example 34-3, there was obtained 5-[(1E)-3-{[5-(benzyloxy)pentyl]oxy}-1-propen-1-yl]-2-phenylaniline (483.4 mg).

Reference Example 12-15

Synthesis of 1-methylpiperidin-4-yl N-{5-[(1E)-3-{[5-(benzyloxy)pentyl]oxy}-1-propen-1-yl]-2-phenylphenyl}carbamate In accordance with Reference Example 12, from 4-hydroxy-1-methylpiperidine (230.4 mg, 2.0 mmol) and 5-[(1E)-3-{[5-(benzyloxy)pentyl]oxy}-1-propen-1-yl]-2-phenylaniline (240.9 mg, 0.6 mmol) obtained in Reference Example 35-3, there was obtained 1-methylpiperidin-4-yl N-{5-[(1E)-3-{[5-(benzyloxy)pentyl]oxy}-1-propen-1-yl]-2-phenylphenyl}carbamate (403.4 mg).
LC/MS: M+1=543.3

Reference Example 50

Synthesis of 1-methylpiperidin-4-yl N-(5-{3-[(5-(hydroxypentyl)oxy))propyl)-2-phenylphenyl}carbamate 1-Methylpiperidin-4-yl N-{5-[(1E)-3-{[5-(benzyloxy)pentyl]oxy}-1-propen-1-yl]-2-phenylphenyl}carbamate (403.4 mg, 0.74 mmol) obtained in Reference Example 12-15 was dissolved in methanol (20 mL), 20% palladium hydroxide-carbon (50 mg) was added thereto, and the mixture was stirred under a hydrogen atmosphere at room temperature for 4 days. The reaction temperature was raised to 90° C. and the mixture was stirred further for one day. The reaction solution was filtered through celite and the filtrate was concentrated under reduced pressure to obtain 1-methylpiperidin-4-yl N-(5-{3-[(5-(hydroxypentyl)oxy]propyl}-2-phenylphenyl)carbamate as a crude material.

Example 78

Synthesis of 4-{[(5-{3-[(5-{[(2R)-2-hydroxy-2-(8-hydroxy-2-oxo-1,2-dihydroquinolin-5-yl)ethyl]amino}pentyl)oxy]propyl}-2-phenylphenyl)carbamoyl]oxy}-1,1-dimethylpiperidin-1-ium trifluoroacetate 1-Methylpiperidin-4-yl N-(5-{3-[(5-(hydroxypentyl)oxy]propyl}-2-phenylphenyl)carbamate (113.6 mg, 0.25 mmol) obtained in Reference Example 50 was dissolved in acetonitrile (10 mL), methyl iodide (2 mL) was added thereto, and, after stirring at room temperature for 1 hour, the reaction solution was concentrated under reduced pressure.

Triphenylphosphin polymer bound (3.00 mml/g) (300 mg) and iodine (208.0 mg, 0.81 mmol) was stirred in dichloromethane for 1 hour, thereto was added the foregoing residue dissolved in dichloromethane (10 mL), and the mixture was stirred for further 2 hours. Thereafter, the reaction solution was filtered through celite and the filtrate was concentrated under reduced pressure.

The residue was suspended in N,N-dimethylformamide (2 mL), 5-((2R)-2-amino-1-hydroxyethyl)-8-hydroxy-1H-quinolin-2-one acetate (84 mg, 0.3 mmol) was added thereto, and the mixture was stirred at 70° C. for 3 hours. The reaction solution was concentrated under reduced pressure and, thereafter, purified by HPLC fractionation to obtain 4-{[(5-{3-[(5-{[(2R)-2-hydroxy-2-(8-hydroxy-2-oxo-1,2-dihydroquinolin-5-yl)ethyl]amino}pentyl)oxy]propyl}-2-phenylphenyl)carbamoyl]oxy}-1,1-dimethylpiperidin-1-ium trifluoroacetate (17.1 mg).
LC/MS: [M]+=671.3

Reference Example 51

Synthesis of 2-[4-(2-bromoethoxy)phenyl]-1-ethanol 4-(Hydroxyethyl)phenol (2.7 g, 20.0 mmol) was dissolved in N,N-dimethylformamide (50 mL) and thereto were added potassium carbonate (6.90 g, 50.0 mmol) and 1,2-dibromoethane (15.03 g, 80.0 mmol). After stirring at 80° C. for 6 hours, the reaction solution was extracted with ethyl acetate. The organic layer was washed with a saturated aqueous solution of sodium chloride, dried over anhydrous magnesium sulfate, and concentrated under reduced pressure. The residue was purified by flash column chromatography to obtain 2-[4-(2-bromoethoxy)phenyl]-1-ethanol (750.0 mg).

Reference Example 52

Synthesis of 2-{4-[2-(3-nitro-4-phenylphenoxy)ethoxy]phenyl}-1-ethanol

In accordance with Reference Example 38, from 3-nitro-4-phenylphenol (215 mg, 1.0 mmol) and 2-[4-(2-bromoethoxy)pheny]-1-ethanol obtained in Reference Example 50, there was obtained 2-{4-[2-(3-nitro-4-phenylphenoxy)ethoxy]phenyl}-1-ethanol (263.1 mg).

Reference Example 53

Synthesis of tert-butyldimethyl(2-{4-[2-(3-nitro-4-phenylphenoxy)ethoxy]phenyl}ethoxy)silane 2-{4-[2-(3-Nitro-4-phenylphenoxy)ethoxy]phenyl}-1-ethanol (263.1 mg, 0.69 mmol) obtained in Reference Example 52 and imidazole (115.6 mg, 17.3 mmol) was dissolved in tetrahydrofuran (10 mL) and thereto was added a tetrahydrofuran (5 mL) solution of tert-butyldimethylchlorosilane (207.9 mg, 1.39 mmol). After stirring the reaction mixture at room temperature for 16 hours, purified water was added to stop the reaction, and the mixture was extracted with ethyl acetate. The organic layer was washed with a saturated aqueous solution of sodium chloride, dried over anhydrous magnesium sulfate, and concentrated under reduced pressure. The residue was purified by flash column chromatography to obtain tert-butyldimethyl(2-{4-[2-(3-nitro-4-phenylphenoxy)ethoxy]phenyl}ethoxy)silane (336.2 mg).

Reference Example 54

Synthesis of 1-methylpiperidin-4-yl N-{5-[2-(4-{2-[(tert-butyldimethylsilyl)oxy]ethyl}phenoxy)ethoxy]-2-phenylphenyl}carbamate In accordance with Reference Examples 11 and 12, from tert-butyldimethyl(2-{4-[2-(3-nitro-4-phenylphenoxy)ethoxy]phenyl}ethoxy)silane (336.2 mg, 0.68 mmol) obtained in Reference Example 53, there was obtained 1-methylpiperidin-4-yl N-{5-[2-(4-{2-[(tert-butyldimethylsilyl)oxy]ethyl]phenoxy}ethoxy]-2-phenylphenyl}carbamate (164.3 mg).

Example 79

Synthesis of 4-{[(5-{2-[4-(2-{[(2R)-2-hydroxy-2-(8-hydroxy-2-oxo-1,2-dihydroquinolin-5-yl)ethyl]amino}ethyl)phenoxy]ethoxy}-2-phenylphenyl)carbamoyl]oxy}-1,1-dimethylpiperidin-1-ium trifluoro acetate In accordance with Example 58, from 1-methylpiperidin-4-yl N-{5-[2-(4-{2-[(tert-butyldimethylsilyl)oxy]ethyl}phenoxy)ethoxy]-2-phenylphenyl}carbamate (81.7 mg, 0.135 mmol) obtained in Reference Example 54, there was obtained 4-{[(5-{2-[4-(2-{[(2R)-2-hydroxy-2-(8-hydroxy-2-oxo-1,2-dihydroquinolin-5-yl)ethyl]amino}ethy)phenoxy]ethoxy}-2-phenylphenyl)carbamoyl]oxy}-1,1-dimethylpiperidin-1-ium trifluoroacetate (11.7 mg).
LC/MS: [M]+=707.3

Reference Example 55

Synthesis of N-[2-(4-bromo-3-nitrophenyl)ethyl]-2,2,2-trifluoroacetamide

To a solution of 2-(4-bromophenyl)ethan-1-amine (5.0 g, 25.0 mmol) in dichloroethane (100 ml), triethylamine (7.0 mL) and trifluoroacetic acid anhydride (7.88 g, 37.5 mmol) were added under ice cooling, and the mixture was stirred for 1 hour. Thereafter, the mixture was stirred at room temperature for further 3 hours. Under ice cooling, water was added to the reaction solution and, after stirring for 20 minutes, the mixture was extracted with ethyl acetate. The organic layer was washed with a saturated aqueous solution of sodium bicarbonate, a saturated aqueous solution of ammonium chloride, and a saturated aqueous solution of sodium chloride, dried over anhydrous magnesium sulfate, and concentrated under reduced pressure. The residue was dissolved in acetic acid (15 mL), fuming nitric acid (30 mL) was slowly added dropwise under ice cooling, and, thereafter, the reaction mixture was stirred under ice cooling for 1 hour and at room temperature for 16 hours. The reaction solution was poured onto ice and extracted with ethyl acetate. The organic layer was washed with a saturated aqueous solution of sodium bicarbonate and a saturated aqueous solution of sodium chloride, dried over anhydrous magnesium sulfate, and concentrated under reduced pressure. The residue was purified by flash column chromatography to obtain N-[2-(4-bromo-3-nitrophenyl)ethyl]-2,2,2-trifluoroacetamide (5.17 g).

Reference Example 56

Synthesis of 2,2,2-trifluoro-N-[2-(3-nitro-4-phenylphenyl)ethyl]acetamide

In accordance with Reference Example 10, from N-[2-(4-bromo-3-nitrophenyl)ethyl]-2,2,2-trifluoroacetamide (5.17 g, 15.1 mmol) obtained in Reference Example 55, there was obtained 2,2,2-trifluoro-N-[2-(3-nitro-4-phenylphenyl)ethyl]acetamide (3.34 g).
LC/MS: M+1=339.2

Reference Example 57

Synthesis of (4-{[2-(3-nitro-4-phenylphenyl)ethyl]carbamoyl}phenyl)methyl acetate 2,2,2-Trifluoro-N-[2-(3-nitro-4-phenylphenyl)ethyl]-acetamide (338.3 mg, 1.0 mmol) obtained in Reference Example 56 was dissolved in methanol (1 mL) and tetrahydrofuran (10 mL), an aqueous solution of sodium hydroxide (5 M, 0.5 mL) was added, and the mixture was stirred at room temperature for 5 hours. The reaction solution was extracted with ethyl acetate and the organic layer was washed with a saturated aqueous solution of sodium chloride, dried over anhydrous sodium sulfate, and concentrated under reduced pressure.

The residue was dissolved in N,N-dimethylformamide (10 mL) and thereto were added N-ethyl-N'-(3-dimethylaminopropyl)carbodiimide hydrochloride (1.5 mmol), N-hydroxybenzotriazole (1.5 mmol), triethylamine (3.0 mmol), and 4-[(acetyloxy)methyl]benzoic acid (1.1 mmol). The mixture was stirred at room temperature for 16 hours. The reaction solution was extracted with ethyl acetate and the organic layer was washed with a saturated aqueous solution of sodium chloride, dried over anhydrous magnesium sulfate, and concentrated under reduced pressure. The residue was purified by flash column chromatography to obtain (4-{[2-(3-nitro-4-phenylphenyl)ethyl]carbamoyl}phenyl)methyl acetate (379.7 mg).

Reference Example 58

Synthesis of [4-({2-[3({[(1-methylpiperidin-4-yl)oxy]carbonyl}amino)-4-phenylphenyl]ethyl}carbamoyl)phenyl]methyl acetate In accordance with Reference Examples 11 and 12, from (4-{[2-(3-nitro-4-phenylphenyl)ethyl]carbamoyl}phenyl)

methyl acetate (379.7 mg, 0.91 mmol) obtained in Reference Example 57, there was obtained [4-({2-[3({[(1-methylpiperidin-4-yl)oxy]carbonyl}amino)-4-phenylphenyl]ethyl]carbamoyl)phenyl]methyl acetate (209.0 mg).

Example 80

Synthesis of 4-({[5-(2-{[4-({[(2R)-2-hydroxy-2-(8-hydroxy-2-oxo-1,2-dihydroquinolin-5-yl)ethyl]amino}methyl)phenyl]formamide}ethyl)-2-phenylphenyl]carbamoyl}oxy)-1,1-dimethylpiperidin-1-ium trifluoro acetate

[4-({2-[3({[(1-methylpiperidin-4-yl)oxy]carbonyl}amino)-4-phenylphenyl]ethyl}carbamoyl)phenyl] methyl acetate (53.0 mg, 0.10 mmol) obtained in Reference Example 58 was dissolved in methanol (1 mL) and tetrahydrofuran (10 mL), an aqueous solution of sodium hydroxide (5 M, 0.1 mL) was added, and the mixture was stirred at room temperature for 1 hour. The reaction solution was extracted with ethyl acetate and the organic layer was washed with a saturated aqueous solution of sodium chloride, dried over anhydrous sodium sulfate, and concentrated under reduced pressure.

The residue was dissolved in acetonitrile (10 mL), methyl iodide (1 mL) was added thereto, and, after stirring at room temperature for 1 hour, the reaction solution was concentrated under reduced pressure.

The residue was dissolved in dichloromethane (10 mL) and methanol (1 mL), manganese dioxide (200 mg) was added thereto, and the mixture was stirred at room temperature for 16 hours. The reaction solution was filtered through celite and the filtrate was concentrated under reduced pressure.

The residue was suspended in dimethylsulfoxide (5 mL), thereto was added 5-((2R)-2-amino-1-hydroxyethyl)-8-hydroxy-1H-quinolin-2-one acetate (140.1 mg, 0.5 mmol) and the mixture was stirred at 70° C. for 1 hour. To the reaction solution, sodium triacetoxyborohydride (424.0 mg, 2 mmol) was added, and the mixture was stirred at 70° C. for 1 hour. The reaction solution was, after addition of purified water (0.5 mL), purified by HPLC fractionation to obtain 4-({[5-(2-{[4-({[(2R)-2-hydroxy-2-(8-hydroxy-2-oxo-1,2-dihydroquinolin-5-yl)ethyl]amino}methyl)phenyl]formamide}ethyl)-2-phenylphenyl]carbamoyl}oxy)-1,1-dimethylpiperidin-1-ium trifluoroacetate (6.22 mg).

LC/MS: [M]+=704.3

Reference Example 59

Synthesis of (3-nitro-4-phenylphenyl)methanamine 4-(Bromoethyl)-2-nitro-1-phenylbenzene (584.3 mg, 2.0 mmol) and potassium phthalimide (555.0 mg, 3.0 mmol) were dissolved in N,N-dimethylformamide (8 mL) and the mixture was stirred at 110° C. for 3 hours. The reaction mixture was extracted with ethyl acetate and the organic layer was washed with a saturated aqueous solution of sodium chloride, dried over anhydrous magnesium sulfate, and concentrated under reduced pressure. The residue was purified by flash column chromatography to obtain 2-[(3-nitro-4-phenylphenyl)methyl]-2,3-dihydro-1H-isoindole-1,3-dione (600.8 mg).

The obtained 2-[(3-nitro-4-phenylphenyl)methyl]-2,3-dihydro-1H-isoindole-1,3-dione was dissolved in ethanol (30 mL), an aqueous solution of hydrazine monohydrate (2 mL) was added thereto, and the mixture was stirred at 70° C. for 1 hour. The reaction solution was filtered, to the filtrate was added 0.6 M hydrochloric acid and ethyl acetate, and the mixture was stirred vigorously. The aqueous layer was separated and, after being neutralized with a 5M aqueous solution of sodium hydroxide, extracted with ethyl acetate. The organic layer was washed with a saturated aqueous solution of sodium chloride, dried over anhydrous sodium sulfate, and concentrated under reduced pressure to obtain (3-nitro-4-phenylphenyl)methanamine as a crude material (305.5 mg)

Reference Example 60

Synthesis of 2-[4-(hydroxymethyl)phenoxy]-N-[(3-nitro-4-phenylphenyl)methyl]acetamide (3-Nitro-4-phenylphenyl)methanamine (152.9 mg, 0.67 mmol) obtained in Reference Example 59 was dissolved in N,N-dimethylformamide (5 mL), bromoacetic acid anhydride (346.5 mg, 1.5 mmol) was added thereto, and the mixture was stirred at room temperature for 1 hour. To the reaction solution was added water to stop the reaction and the solution was extracted with ethyl acetate. The organic layer was washed with a saturated aqueous solution of sodium bicarbonate and a saturated aqueous solution of sodium chloride, dried over anhydrous magnesium sulfate, and concentrated under reduced pressure. The residue was dissolved in N,N-dimethylformamide (5 mL) and thereto were added potassium carbonate (207.0 mg, 1.5 mmol) and 4-(hydroxymethyl)phenol (161.2 mg, 1.3 mmol). After stirring at 80° C. for 1 hour, the reaction solution was extracted with ethyl acetate. The organic layer was washed with a saturated aqueous solution of sodium chloride, dried over anhydrous magnesium sulfate, and concentrated under reduced pressure. The residue was purified by flash column chromatography to obtain 2-[4-(hydroxymethyl)phenoxy]-N-[(3-nitro-4-phenylphenyl)methyl]acetamide (212.8 mg).

Reference Example 61

Synthesis of 1-methylpiperidin-4-yl N-(5-{[(2-(4-{[(tert-butyldimethylsilyl)oxy]methyl}phenoxy)acetamide)methyl]-2-phenylphenyl}carbamate In accordance with Reference Examples 53, 11, and 12, from 2-[4-(hydroxymethyl)phenoxy]-N-[(3-nitro-4-phenylphenyl)methyl]acetamide (212.8 mg, 0.54 mmol) obtained in Reference Example 60, there was obtained 1-methylpiperidin-4-yl N-(5-{[(2-(4-{[(tert-butyldimethylsilyl)oxy]methyl}phenoxy)acetamide)methyl]-2-phenylphenyl}carbamate (254.4 mg).

Example 81

Synthesis of 4-({[5-({2-[4-({[(2R)-2-hydroxy-2-(8-hydroxy-2-oxo-1,2-dihydroquinolin-5-yl)ethyl]amino}methyl)phenoxy]acetamide}methyl)-2-phenylphenyl]carbamoyl}oxy)-1,1-dimethylpiperidin-1-ium trifluoroacetate In accordance with Example 1, from 1-methylpiperidin-4-yl N-(5-{[(2-(4-{[(tert-butyldimethylsilyl)oxy]methyl}phenoxy)acetamide)methyl]-2-phenylphenyl}carbamate (123.6 mg, 0.20 mmol) obtained in Reference Example 61, there was obtained 4-({[5-({2-[4-({[(2R)-2-hydroxy-2-(8-hydroxy-2-oxo-1,2-dihydroquinolin-5-yl)ethyl]amino}methyl)phenoxy]acetamide}methyl)-2-phenylphenyl]carbamoyl}oxy)-1,1-dimethylpiperidin-1-ium trifluoroacetate (13.5 mg)

LC/MS: [M]+=720.3 .

Example 82

Competition Binding Assays to Human M3 Muscarinic Receptor

Membrane fractions of human M3 muscarinic receptor were purchased from PerkinElmer, Inc. and stored at −80° C. until use. Phosphate buffered saline (PBS(−), Invitrogen, Co.) was used as assay buffer. The membrane fractions of human M3 muscarinic receptor (10-15 µg of membrane protein) and 1 nM L-[N-methyl-3H]scopolamine methyl chloride ([3H]—NMS) (NET636, 2.59 TBq/mmol, PerkinElmer, Inc.) were added to a final volume of 100 µL and incubated for 2 hours at room temperature (total binding). Different concentrations of test compounds (in the range of 10 pM-1 µM) were added to test the competitive inhibition of the test compounds. The amount of nonspecific binding was determined in the presence of 5 µM atropine. After the incubation was completed, the reaction was terminated by rapid filtration of the reaction liquid over GF/B glass fiber filter plates (PerkinElmer, Inc.) pre-immersed in 0.2% polyethyleneimine. The filter plates were washed three times with a washing solution (50 mM Tris hydrochloric acid pH 7.4, 0.9% sodium chloride) to remove unbound radioactivity. The plates were then dried and 40 µL Microscint-20 liquid TopCount microplate scintillation cocktail (PerkinElmer Inc.) was added and plates were counted in a Packard TopCount liquid scintillation counter (PerkinElmer, Inc.). The percentage of the binding inhibition by the test compound was calculated according to the following formula.

(%)Percentage of binding inhibition=[(Radioactivity of test compound-added sample−Amount of nonspecific binding)/(Amount of total binding−Amount of nonspecific binding)]×100

The 50% inhibitory concentrations ($IC_{50}$ values) of test compounds were analyzed by a nonlinear regression analysis for one-site competitive binding using the GraphPad Prism Software package (GraphPad Software, Inc.) for the percentage of the binding inhibition at different concentrations of the test compounds.

Exemplified compounds of the present invention tested in this assay were found to have $IC_{50}$ values of less than about 10 nM for the human M3 muscarinic receptor. For example, the compounds of Examples 1, 48 and Example 51 were found to have $IC_{50}$ values of less than 10 nM.

Example 83

Evaluation of Inhibitory Effect on Methacholine-Induced Calcium Influx Using FLIPR Assay Muscarinic receptor subtypes (M1, M3 and M5 receptors), which couple to Gq proteins, activate the phospholipase C (PLC) pathway upon agonist binding to the receptor. As a result, the activated PLC hydrolyzes phosphatidyl inositol diphosphate (PIP2) to diacyl glycerol (DAG) and phosphatidyl-1,4,5-triphosphate (IP3), which in turn generates calcium release from intracellular stores, i.e., endoplasmic and sarcoplasmic reticula. By utilizing FLIPR (Molecular Devices, Inc.) assay in which a calcium sensitive dye (Component A) is used that fluoresces when free calcium binds, the increase in intracellular calcium is measured on the basis of the change in the fluorescence intensity.

Methacholine was added to CHO-K1 cells stably expressing the human M3 muscarinic receptor to induce calcium influx and evaluate the inhibitory effect of test compounds. In the experiment, a FLIPR Calcium assay kit (Molecular Devices, Inc.) was used.

CHO-K1 cells stably expressing the human M3 muscarinic receptor suspended in Ham's F-12 media (Invitrogen, Co.) containing 10% fetal bovine serum (FBS) were seeded into 96-well FLIPR plates at a volume of 100 µL/well. Next day, 60 µL/well of Non-wash-dye solution (Hank's buffered salt solution, HBSS, containing 20 mM HEPES and 6.5 mM probenecid) was added to the cells, which were then incubated for an hour at 37° C. in the presence of 5% carbon dioxide. 20 µL of 10 concentrations of test compound solutions (HBSS containing 1% DMSO, 20 mM HEPES, 2.5 mM probenecid and 0.05% bovine serum albumin, BSA) prepared at concentrations in a range of 0.01-1000 nM with 2-fold serial dilution) were added, followed by incubation for 180 seconds. Then, 20 µL of 30 nM methacholine solution (HBSS containing 20 mM HEPES, 2.5 mM probenecid and 0.05% bovine serum albumin, BSA) was added, and fluorescence intensity was traced by the intracellular calcium influx measuring device FLIPR 96 (Molecular Devices, Inc.) for 170 seconds. The difference between the lowest and the highest values of the fluorescence intensity (FI) over the period of the measurement was used as a measured value. The percentages of inhibition by the test compounds were calculated according to the following formula from the measured value of the methacholin-added and test compound non-added sample (FIpositive), the measured value of the methacholin non-added and test compound non-added sample (FInegative), and the measured value of the methacholin-added and test compound-added sample (FItest).

(%) Percentage of inhibition by test compound=[(1−(FItest−FInegative)/(FIpositive−FInegative)]×100

The 50% inhibitory concentrations ($IC_{50}$ values) of test compounds were analyzed by a four-parameter logistic model using XLfit4 (IDBS, Ltd.) for the percentage of the inhibition by different concentrations of test compounds.

A part of the $IC_{50}$ values of the exemplified compounds of the present invention tested in this assay are shown in Activity Table A.

TABLE 1

| Activity Table A | |
|---|---|
| Example | $IC_{50}$(nM) |
| 1 | 6.4 |
| 2 | 19.3 |
| 3 | 16.2 |
| 4 | 4.9 |
| 5 | 19.2 |
| 6 | 9.0 |
| 7 | 14.5 |
| 8 | 13.5 |
| 9 | 10.1 |
| 10 | 10.5 |
| 11 | 9.7 |
| 12 | 26.4 |
| 17 | 11.4 |
| 18 | 8.9 |
| 19 | 8.7 |
| 20 | 16.8 |
| 21 | 16.8 |
| 22 | 15.8 |
| 23 | 34.3 |
| 24 | 11.7 |
| 25 | 19.0 |
| 26 | 23.2 |
| 27 | 16.1 |

TABLE 1-continued

Activity Table A

| Example | IC$_{50}$(nM) |
|---|---|
| 28 | 10.0 |
| 29 | 13.6 |
| 30 | 12.9 |
| 31 | 15.7 |
| 32 | 16.1 |
| 33 | 22.1 |
| 34 | 22.0 |
| 36 | 27.1 |
| 37 | 18.2 |
| 38 | 15.6 |
| 39 | 16.0 |
| 41 | 12.9 |
| 42 | 12.3 |
| 43 | 8.5 |
| 44 | 13.9 |
| 45 | 26.5 |
| 46 | 16.5 |
| 47 | 16.5 |
| 48 | 21.7 |
| 49 | 13.9 |
| 50 | 27.6 |
| 51 | 13.2 |
| 52 | 32.8 |
| 53 | 53.7 |
| 54 | 20.9 |
| 55 | 51.8 |
| 56 | 64.1 |
| 58 | 46.4 |
| 61 | 37.8 |
| 62 | 51.3 |
| 63 | 41.7 |
| 69 | 44.7 |
| 70 | 60.3 |
| 71 | 38.9 |
| 72 | 49.0 |
| 73 | 27.5 |
| 76 | 38.0 |
| 77 | 36.3 |
| 78 | 74.1 |
| 80 | 29.9 |
| 81 | 25.1 |

Example 84

Evaluation by Whole-Cell cAMP Flashplate Assay Using CHO-K1 Cells Stably Expressing Human β2 Adrenergic Receptor The β2 adrenergic receptor, which couples to Gs proteins, activates adenylate cyclase upon agonist binding to the receptor. As a result, cAMP is produced in cells. The activation ability of the β2 adrenergic receptor can be measured by measuring the amount of the cAMP with cAMP-Screen System (Applied Biosystems).

CHO-K1 cells expressing the human β2 adrenergic receptor suspended in Ham's F-12 media containing 10% FBS were seeded into 96-well plates at a volume of 100 μL/well. Next day, they were washed with 200 μL PBS(−), to which 80 μL of 0.5 mM IBMX solution (Ham's F-12 media containing 0.05% BSA) was then added, followed by incubation for 20 minutes at 37° C. in the presence of 5% carbon dioxide. 20 μL of 9 concentrations of test compound solutions (0.5 mM IBMX solution containing 1% DMSO) prepared at concentrations in a range of 0.01–1000 nM with 2-fold serial dilution) were added, followed by incubation for 20 minutes at 37° C. in the presence of 5% carbon dioxide. Then, 100 μL of Assay/Lysis Buffer (a reagent that comes with cAMP Screen System) was added. The cells were lysed by pipetting, further incubated for 30 minutes at 37° C., and then frozen at −80° C. After several days, samples, thawed at room temperature, were treated according to the protocol of cAMP Screen System, and then chemiluminescence was measured by EnVision (PerkinElmer, Inc.). The amount of cAMP was calculated from the standard curve for the standard attached to cAMP Screen System.

The concentrations of a test compound at which 50% of its maximal effect is reached (EC$_{50}$ values) were analyzed by a four-parameter logistic model using XLfit4 (IDBS, Ltd.) for the amounts of cAMP production at different concentrations of the test compounds.

A part of the EC$_{50}$ values of the exemplified compounds of the present invention tested in this assay are shown in Activity Table B.

TABLE 2

Activity Table B

| Example | EC$_{50}$(nM) |
|---|---|
| 1 | 1.3 |
| 2 | 1.1 |
| 3 | 9.7 |
| 4 | 4.1 |
| 5 | 8.2 |
| 6 | 1.7 |
| 7 | 5.1 |
| 8 | 5.1 |
| 9 | 1.9 |
| 10 | 3.9 |
| 11 | 3.7 |
| 12 | 4.6 |
| 17 | 5.9 |
| 18 | 0.6 |
| 19 | 1.2 |
| 20 | 2.6 |
| 21 | 3.8 |
| 22 | 2.2 |
| 23 | 2.6 |
| 24 | 6.6 |
| 25 | 0.4 |
| 26 | 0.9 |
| 27 | 1.5 |
| 28 | 0.7 |
| 29 | 4.8 |
| 30 | 0.5 |
| 31 | 25.1 |
| 32 | 8.4 |
| 33 | 4.6 |
| 34 | 1.2 |
| 35 | 2.7 |
| 36 | 4.3 |
| 37 | 4.0 |
| 38 | 10.6 |
| 39 | 4.0 |
| 40 | 3.4 |
| 41 | 6.2 |
| 42 | 0.8 |
| 43 | 3 |
| 44 | 1.7 |
| 45 | 4.1 |
| 46 | 1.4 |
| 47 | 1.9 |
| 48 | 0.4 |
| 49 | 2.3 |
| 50 | 1.7 |
| 51 | 0.3 |
| 52 | 0.4 |
| 53 | 0.6 |
| 54 | 0.9 |
| 55 | 0.2 |
| 56 | 0.9 |
| 57 | 2.7 |
| 58 | 0.6 |
| 59 | 0.2 |
| 60 | 1.2 |

TABLE 2-continued

Activity Table B

| Example | $EC_{50}$(nM) |
|---|---|
| 61 | 8.7 |
| 62 | 1.5 |
| 63 | 5.6 |
| 64 | 38 |
| 65 | 14.5 |
| 66 | 12.6 |
| 67 | 0.4 |
| 69 | 16 |
| 70 | 0.2 |
| 71 | 0.2 |
| 72 | 0.3 |
| 73 | 10 |
| 74 | 4.5 |
| 75 | 0.5 |
| 76 | 14.1 |
| 77 | 1.5 |
| 78 | 1.3 |
| 79 | 5.8 |
| 80 | 2.4 |
| 81 | 8.7 |

Example 85

Evaluation of Duration of Action in Isolated Trachea of Guinea Pigs

In this test, isolated guinea pig trachea, cut into rings, is fixed by application of constant tension in a water bath and a contractile response is induced by acetylcholine, histamine, electrical stimulation, or the like. Changes in tension are output to a portable recorder for recording, via a multi-purpose preamplifier (Nihon Kohden Corporation) and a carrier amplifier (Nihon Kohden Corporation). The intensity of the dilating action of test compounds on trachea can be evaluated by examining the suppressive action on the contractile response.

Hartley male guinea pigs (Nippon SLC, Inc.) weighing about 400-500 g were used. The animals were anesthetized with an intraperitoneal administration of 33% urethane/0.8% α-chloralose at a dose of 3 mL/kg. Then, an incision was made in their necks and they were killed with removal of the blood. After that, trachea was isolated with ablation of connective tissues and the like. The trachea was cut at two tracheal cartilages to provide bronchus ring samples in Magnus reaction liquid, i.e., Krebs-Henseleit solution (119 mM sodium chloride/25 mM sodium bicarbonate/10 mM glucose/4.7 mM potassium chloride/1.2 mM monopotassium phosphate/2.5 mM calcium chloride) containing 2.8 µM indomethacin, gassed with 95% oxygen/5% carbon dioxide. The samples were fixed by application of a tension of 1 g in a Magnus bath (UFER 5 mL chamber, Iwashiya Kishimoto Medical Instruments) filled with Magnus reaction liquid heated to 37° C. and gassed with 95% oxygen/5% carbon dioxide. They were stabilized by incubation for 60 minutes and were then washed with Magnus reaction liquid three to four times. After filling the Magnus bath with 4410 µL of Magnus reaction liquid, 90 µL of 15 µM carbamoyl chloride solution was added and the contractile response was recorded for 15 minutes. After completion of the response, they were washed with Magnus reaction liquid twice. They were used in the experiment after the return of the contractile response to baseline was confirmed.

A Magnus bath was filled with 4410 µL of Magnus reaction liquid, to which 90 µL of 150 µM acetylcholine solution or of 150 µM histamine solution was then added, followed by recording of bronchoconstrictor response for 15 minutes. After completion of the response, they were washed with Magnus reaction liquid twice, and then replaced in Magnus reaction liquid again, left until return to baseline. The Magnus bath was replaced with 4.5 mL of test compound solution prepared at 0.01-1000 nM, followed by incubation for 3 hours. In the presence of test compounds, 90 µL of 150 µM acetylcholine solution or of 150 µM histamine solution was added to 4410 µL of Magnus reaction liquid, and bronchoconstrictor response was recorded for 15 minutes (0 hours). After the completion of the response, they were washed with Magnus reaction liquid twice, and the Magnus bath was filled with Magnus reaction liquid again. The contractile response due to stimulation and the washing operation were repeated every hour for 5 hours after removal of the test compounds. The percentages of the bronchoconstriction inhibition by the test compounds at each concentration and at each time were calculated as mentioned above. The 50% inhibitory concentrations ($IC_{50}$ values) of the test compounds at each time were analyzed by a sigmoidal logistic model using XLfit4 (IDBS, Ltd.) for the percentages of the inhibition at different concentrations of the test compounds. Furthermore, the duration of action of the test compounds was evaluated by comparing the difference between the $IC_{50}$ values immediately after (0 hours) and 5 hours after the removal of the test compounds. Exemplified compounds of the present invention tested in this assay were found to retain strong suppressive action even 5 hours after the removal of the compounds, on the bronchoconstrictor response due to acetylcholine stimulation and on the bronchoconstrictor response due to histamine stimulation. For example, the compounds of Examples 2, 6, 12, 18, 19, 23, 25, 32, 33, 34, 48, 51, 77, and 78 were found to have an $IC_{50}$ value after 5 hours which is one-fiftieth or less of the $IC_{50}$ value after 0 hours.

Example 86

Effects on Acetylcholine- or Histamine-Induced Bronchoconstriction in Guinea Pigs These in vivo assays are used to evaluate the bronchoprotective effects based on the M3 muscarinic receptor antagonist activity and the β2 adrenergic receptor agonist activity of test compounds. Hartley male guinea pigs (Nippon SLC, Inc.) weighing about 400-500 g were used. The animals were anesthetized by inhalation of Fluothane (Takeda Pharmaceutical Company Limited) in a plastic box. The test compounds were dissolved in physiological saline containing DMSO, and administered through the nasal cavity into the trachea at a dose of 0.04-25 µg/kg and at a volume of 0.4 mL/kg. For control animals, solvent without a test compound was administered. In general, animals awake several minutes after completion of the administration. The animals were anesthetized with an intraperitoneal administration of 33% urethane/0.8% α-chloralose at a dose of 3 mL/kg. In order to intravenously administer acetylcholine or histamine, a catheter was inserted into the carotid artery. In order to measure artificial respiration and airway ventilation pressure, a cannula was inserted into the trachea. Artificial respiration was applied to the animals at a volume of 10 mL/kg and at a frequency of 60/minute, using a ventilator (Harvard Apparatus). The airway ventilation pressure was measured by the Konzett-Roessler method using a general respiratory function analysis system (M.I.P.S). Prior to administration of acetylcholine or histamine, the airway ventilation pressure was measured and baseline values were recorded. Then, physiological saline was administered through the carotid artery catheter at a volume of 0.4 mL/kg, and the airway ventilation pressure was measured. Bronchoconstrictor response was induced by administering acetylcholine (40 µg/kg, 0.4 mL/kg) or histamine (15 µg/kg, 0.4 mL/kg) through the carotid artery catheter one hour after the administration of the test compounds, and the airway ventilation pressure at the maximum contractile response was recorded. In addition, in order to evaluate duration of action of the test compounds, the above-mentioned dose of acetylcholine or histamine was administered, 1 hour, 6 hours, 12 hours, 18 hours, and 24 hours after the administration of test compounds, and the airway ventilation pressure was measured in the same way. The percentage of suppression by the test compounds with respect to the airway contractile response was calculated according to the following formula.

(%) Percentage of the airway constriction suppression=(Airway ventilation pressure of test compound-dosed and acetylcholine- or histamine-dosed animals−Baseline value)/(Airway ventilation pressure of acetylcholine- or histamine-dosed animals−Baseline value)×100

The 50% inhibitory doses ($ID_{50}$ values) of the test compounds were analyzed by a sigmoidal logistic model using XLfit4 (IDBS, Ltd.) for the percentage of the bronchoconstriction suppression at different doses of the test compounds.

Exemplified compounds of the present invention tested in this assay were found to have $ID_{50}$ values of less than about 5 μg/kg with respect to bronchoconstrictor response due to acetylcholine stimulation and with respect to bronchoconstrictor response due to histamine stimulation. For example, the compounds of Examples 1, 48 and Example 51 were found to have an $ID_{50}$ value of less than 1 μg/kg with respect to bronchoconstrictor response due to acetylcholine and histamine stimulation one hour after administration of the compounds.

Further, for the percentage of bronchoconstriction suppression with respect to the acetylcholine stimulation 24 hours after 25 μg/kg of the compounds were administered, it was 50% or greater, for example, for the compounds of Examples 1, 2, 6, 12, 18, 19, 20, 25, 34, 36, 46, 48, 51, 55, 57, 70, 71, and 77.

Furthermore, for the percentage of bronchoconstriction suppression with respect to the histamine stimulation 6 hours after 25 μg/kg of compounds were administered, it was 30% or greater, for example, for the compounds of Examples 1, 18, 19, 20, 23, 25, 33, 34, 35, 36, 37, 40, 41, 42, 46, 48, 51, 55, 56, and 71.

The invention claimed is:
1. A quaternary ammonium salt compound represented by general formula (I):

[Chemical Formula 1]

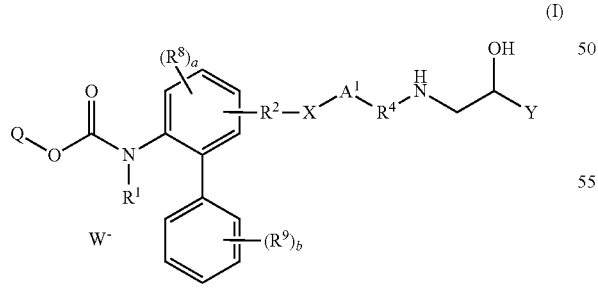

wherein
R$^1$ represents a hydrogen atom or an unsubstituted $C_{1-8}$ alkyl group;
R$^2$ represents a single bond, unsubstituted $C_{1-8}$ alkylene or $C_{1-8}$ alkylene substituted on carbon atoms by 1 to 2 oxygen atoms, unsubstituted $C_{2-4}$ alkenylene, or unsubstituted —O—$C_{1-4}$ alkylene;

X represents a single bond, —O—, —CONR$^3$—, —NR$^3$CO—, or —NR$^3$CO—CH$_2$—O—; where R$^3$ represents a hydrogen atom or an unsubstituted $C_{1-8}$ alkyl group;

A$^1$ represents a single bond, unsubstituted $C_{6-10}$ arylene or $C_{6-10}$ arylene substituted with 1 to 4 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cycloalkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, unsubstituted 5- to 10-membered heteroarylene or 5- to 10-membered heteroarylene substituted with 1 to 4 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cycloalkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl)amino group, unsubstituted $C_{1-4}$ alkylene-substituted or unsubstituted $C_{6-10}$ arylene where the substituents of $C_{6-10}$ arylene are 1 to 3 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cycloalkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl) amino group, unsubstituted $C_{1-4}$ alkylene-substituted or unsubstituted 5- to 10-membered heteroarylene where the substituents of 5- to 10-membered heteroarylene are 1 to 3 substituents selected from the group consisting of halogen atom, hydroxyl group, cyano group, nitro group, carboxyl group, trifluoromethyl group, unsubstituted $C_{1-6}$ alkyl group, unsubstituted $C_{3-8}$ cycloalkyl group, unsubstituted $C_{1-6}$ alkoxy group, unsubstituted $C_{3-8}$ cycloalkyloxy group, mercapto group, unsubstituted $C_{1-6}$ alkylthio group, unsubstituted $C_{3-8}$ cycloalkylthio group, amino group, unsubstituted mono($C_{1-6}$ alkyl)amino group and unsubstituted di($C_{1-6}$ alkyl) amino group, or unsubstituted $C_{3-8}$ cycloalkylene or $C_{3-8}$ cycloalkylene substituted with 1 to 3 substituents selected from the group consisting of halogen and unsubstituted $C_{1-6}$ alkyl group;

R$^4$ represents unsubstituted $C_{1-10}$ alkylene;

R$^8$ and R$^9$ each independently represent a halogen atom, a cyano group, an unsubstituted $C_{1-6}$ alkyl group, a nitro group, —NR$^{10}$R$^{11}$ where R$^{10}$ and R$^{11}$ each independently represent a hydrogen atom or an unsubstituted $C_{1-6}$ alkyl group, an unsubstituted $C_{1-6}$ alkoxy group, a carboxyl group, an unsubstituted $C_{1-6}$ alkoxycarbonyl group, a hydroxyl group, a trifluoromethyl group, a mercapto group, or an unsubstituted $C_{1-6}$ alkylthio group;

a and b each independently represent an integer of 0 to 3;

Y represents a group represented by formula (II):

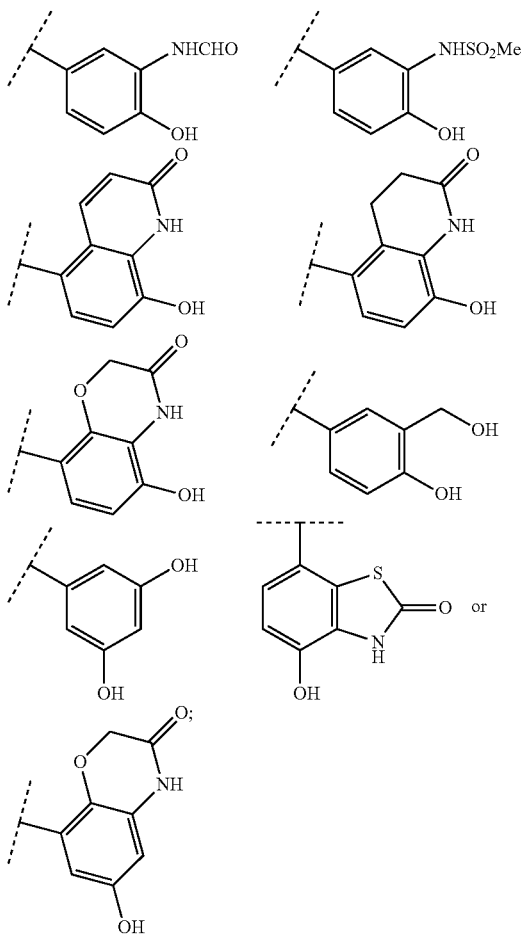

Q represents formula (III):

[Chemical Formula 3]

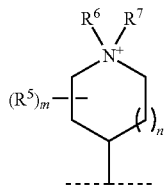

wherein
R⁶ and R⁷ each independently represent an unsubstituted $C_{1-6}$ alkyl group or a $C_{1-6}$ alkyl group substituted with 1 to 4 substituents selected from the group consisting of halogen atom, hydroxyl group and unsubstituted $C_{1-6}$ alkoxy group, or an unsubstituted $C_{8-10}$ phenoxyalkyl group or a $C_{8-10}$ phenoxyalkyl group substituted with 1 to 4 substituents selected from the group consisting of halogen atom, hydroxyl group, unsubstituted $C_{1-6}$ alkyl group and unsubstituted $C_{1-6}$ alkoxy group;

R⁵ represents an unsubstituted $C_{1-6}$ alkyl group or a $C_{1-6}$ alkyl group substituted with 1 to 4 substituents selected from the group consisting of halogen atom, hydroxyl group and unsubstituted $C_{1-6}$ alkoxy group;

n represents an integer of 1; and
m represents an integer of 0 to 3;
W⁻ represents a negative ion;
or a pharmaceutically acceptable salt thereof.

2. The quaternary ammonium salt compound or pharmaceutically acceptable salt thereof according to claim 1, wherein R², X, and A¹ are any of the following (i) to (iv):
  (i) R² represents a single bond, $C_{1-4}$ alkylene substituted on a carbon atom by an oxygen atom, unsubstituted $C_{1-8}$ alkylene, or unsubstituted —O—$C_{1-4}$ alkylene; X represents —O—; A¹ represents a single bond or unsubstituted phenylene,
  (ii) R² represents unsubstituted $C_{1-4}$ alkylene, unsubstituted $C_{2-4}$ alkenylene, or unsubstituted —O—$C_{1-4}$ alkylene; X represents —CONR³—; A¹ represents a single bond, unsubstituted phenylene, unsubstituted $C_{1-4}$ alkylene-unsubstituted phenylene, or unsubstituted $C_{6-8}$ cycloalkylene,
  (iii) R² represents unsubstituted $C_{1-4}$ alkylene; X represents —NR³CO— or —NR³CO—CH₂—O; A¹ represents unsubstituted phenylene, and
  (iv) R², X, and A¹ represent a single bond.

3. The quaternary ammonium salt compound or pharmaceutically acceptable salt thereof according to claim 1, wherein R², X, A¹, and R⁴ are any of the following (v) to (xviii):
  (v) R² represents a single bond; X represents —O—; A¹ represents a single bond; R⁴ represents unsubstituted $C_{1-10}$ alkylene,
  (vi) R² represents unsubstituted $C_{1-8}$ alkylene or $C_{1-8}$ alkylene substituted on a carbon atom by an oxygen atom; X represents —O—; A¹ represents a single bond; R⁴ represents unsubstituted $C_{1-10}$ alkylene,
  (vii) R² represents unsubstituted $C_{1-8}$ alkylene; X represents —O—; A¹ represents unsubstituted phenylene-; R⁴ represents unsubstituted $C_{1-4}$ alkylene,
  (viii) R² represents —O-unsubstituted $C_{1-4}$ alkylene; X represents —O—; A¹ represents unsubstituted phenylene; R⁴ represents unsubstituted $C_{1-4}$ alkylene,
  (ix) R² represents unsubstituted $C_{1-4}$ alkylene; X represents —CONR³—; A¹ represents a single bond; R⁴ represents unsubstituted $C_{1-8}$ alkylene,
  (x) R² represents unsubstituted $C_{1-4}$ alkylene; X represents —CONR³—; A¹ represents unsubstituted $C_{1-4}$ alkylene-unsubstituted phenylene; R⁴ represents unsubstituted $C_{1-4}$ alkylene,
  (xi) R² represents unsubstituted $C_{1-4}$ alkylene; X represents —CONR³—; A¹ represents unsubstituted $C_{6-8}$ cycloalkylene; R⁴ represents unsubstituted $C_{1-4}$ alkylene,
  (xii) R² represents unsubstituted $C_{1-4}$ alkylene; X represents —CONR³—; A¹ represents unsubstituted phenylene; R⁴ represents unsubstituted $C_{1-4}$ alkylene,
  (xiii) R² represents unsubstituted —O—$C_{1-4}$ alkylene; X represents —CONR³—; A¹ represents phenylene; R⁴ represents unsubstituted $C_{1-4}$ alkylene,
  (xiv) R² represents unsubstituted $C_{2-4}$ alkenylene; X represents —CONR³—; A¹ represents unsubstituted phenylene; R⁴ represents unsubstituted $C_{1-4}$ alkylene,
  (xv) R² represents unsubstituted $C_{2-4}$ alkenylene; X represents —CONR³—; A¹ represents unsubstituted $C_{1-4}$ alkylene-unsubstituted phenylene; R⁴ represents unsubstituted $C_{1-4}$ alkylene, (xvi) $R^2$ represents unsubstituted $C_{1-4}$ alkylene; X represents —$NR^3CO$—; $A^1$ represents unsubstituted phenylene; $R^4$ represents unsubstituted $C_{1-4}$ alkylene, (xvii) $R^2$ represents unsubstituted $C_{1-4}$ alkylene; X represents —$NR^3CO$—$CH_2$—O—; $A^1$ represents unsubstituted phenylene; $R^4$ represents unsubstituted $C_{1-4}$ alkylene, and (xviii) $R^2$ represents a single bond; X represents a single bond; $A^1$ represents a single bond; $R^4$ represents unsubstituted $C_{1-8}$ alkylene.

4. The quaternary ammonium salt compound or pharmaceutically acceptable salt thereof according to claim 1, wherein $R^2$ is unsubstituted $C_{1-6}$ alkylene or $C_{1-6}$ alkylene substituted on a carbon atom by an oxygen atom, or unsubstituted —O—$C_{1-4}$ alkylene;

X is —$CONR^3$— or —$NR^3CO$—$CH_2$—O—;

$A^1$ is unsubstituted $C_{6-10}$ arylene or 5- to 10-membered heteroarylene, or $C_{6-10}$ arylene or 5- to 10-membered heteroarylene substituted with 1 to 3 substituents selected from the group consisting of halogen atom, hydroxyl group, unsubstituted $C_{1-4}$ alkyl group, unsubstituted $C_{1-4}$ alkoxy group and trifluoromethyl group; and $R^4$ is unsubstituted $C_{1-6}$ alkylene.

5. The quaternary ammonium salt compound or pharmaceutically acceptable salt thereof according to claim 1, wherein $R^2$ is unsubstituted $C_{1-6}$ alkylene;

X is —$CONR^3$—;

$A^1$ is unsubstituted phenylene or naphthylene, or phenylene or naphthylene substituted with 1 to 4 substituents selected from the group consisting of halogen atom, hydroxyl group, unsubstituted $C_{1-4}$ alkyl group, unsubstituted $C_{1-4}$ alkoxy group and trihalomethyl group; and $R^4$ is unsubstituted $C_{1-6}$ alkylene.

6. The quaternary ammonium salt compound or pharmaceutically acceptable salt thereof according to claim 1, wherein $R^2$ is unsubstituted $C_{1-6}$ alkylene;

X is —CONH—;

$A^1$ is unsubstituted phenylene or phenylene substituted with 1 to 2 substituents selected from the group consisting of halogen and methoxy group; and $R^4$ is unsubstituted $C_{1-6}$ alkylene.

7. The quaternary ammonium salt compound or pharmaceutically acceptable salt thereof according to claim 1, wherein $R^1$ represents a hydrogen atom and a represents an integer of 0.

8. The quaternary ammonium salt compound or pharmaceutically acceptable salt thereof according to claim 7, wherein Q is a group represented by

[Chemical Formula 4]

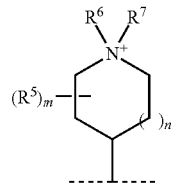

wherein $R^6$ and $R^7$ each independently represent a methyl group or a phenoxyethyl group, n represents an integer of 1, and m represents an integer of 0.

9. The quaternary ammonium salt compound or pharmaceutically acceptable salt thereof according to claim 1, wherein Y is

[Chemical Formula 6]

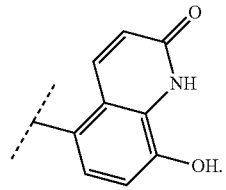

10. A composition comprising a therapeutically effective amount of a compound or a pharmaceutically acceptable salt thereof according to claim 1 and a pharmaceutically acceptable carrier.

11. A method for therapeutically treating chronic obstructive pulmonary disease or asthma comprising administering an effective amount of a compound or a pharmaceutically acceptable salt thereof according to claim 1 to a subject in need thereof.

* * * * *